United States Patent
Zaitsev et al.

(10) Patent No.: US 11,315,658 B2
(45) Date of Patent: Apr. 26, 2022

(54) SYSTEMS AND METHODS FOR DECONVOLUTION OF EXPRESSION DATA

(71) Applicant: BostonGene Corporation, Waltham, MA (US)

(72) Inventors: Aleksandr Zaitsev, Drozhzhino (RU); Maksim Chelushkin, Moscow (RU); Ilya Cheremushkin, Moscow (RU); Ekaterina Nuzhdina, Moscow (RU); Vladimir Zyrin, Moscow (RU); Daniiar Dyikanov, Moscow (RU); Alexander Bagaev, Moscow (RU); Ravshan Ataullakhanov, Moscow (RU); Boris Shpak, Krasnoyarsk (RU)

(73) Assignee: BostonGene Corporation, Waltham, MA (US)

( * ) Notice: Subject to any disclaimer, the term of this patent is extended or adjusted under 35 U.S.C. 154(b) by 0 days.

(21) Appl. No.: 17/200,492

(22) Filed: Mar. 12, 2021

(65) Prior Publication Data

US 2021/0287759 A1 Sep. 16, 2021

Related U.S. Application Data

(60) Provisional application No. 63/108,262, filed on Oct. 30, 2020, provisional application No. 62/988,700, filed on Mar. 12, 2020.

(51) Int. Cl.
  *G16B 25/10* (2019.01)
  *G16B 40/20* (2019.01)
  *G06F 17/18* (2006.01)

(52) U.S. Cl.
  CPC ............. *G16B 25/10* (2019.02); *G16B 40/20* (2019.02); *G06F 17/18* (2013.01)

(58) Field of Classification Search
  None
  See application file for complete search history.

(56) References Cited

U.S. PATENT DOCUMENTS

| 2019/0233898 A1 | 8/2019 | Newman et al. |
| 2021/0151128 A1* | 5/2021 | Abe ....................... G16B 40/00 |

FOREIGN PATENT DOCUMENTS

WO  WO 2019/018684 A1  1/2019

OTHER PUBLICATIONS

Wikipedia Nonlinear Regression retrieved from the internet on May 20, 2021 https://en.wikipedia.org/wiki/Nonlinear_regression (Year: 2021).*
Sun et al. An Efficient and Flexible Method for Deconvoluting Bulk RNA-Seq Data with Single-Cell RNA-Seq Data Cells vol. 8 article 1161 (Year: 2019).*
Newman et al. Robust enumeration of cell subsets from tissue expression profiles Nature Methods vol. 12, pp. 453-457 (Year: 2015).*
Abbas et al. Immune response in silico (IRIS): immune-specific genes identified from a compendium of microarray expression data Genes and Immunity vol. 6 pp. 319-331 (Year: 2005).*
[No Author Listed], Artyomov Lab Systems Immunology. Maxim N. Artyomov. 2013. https://artyomovlab.wustl.edu/site/index.html [last accessed Jun. 7, 2021]. 3 pages.
[No Author Listed], Deconvolution of ABsolute Immune Signal. shinyapps.io. 2021. https://giannimonaco.shinyapps.io/ABIS/ [last accessed Jun. 7, 2021]. 1 page.
[No Author Listed], MCP-counter. CIT. 2021. https://cit.ligue-cancer.net/mcp-counter/ [last accessed Jun. 7, 2021]. 2 pages.
[No Author Listed], Using EPIC to estimate the proportion of various cell types in bulk samples. EPIC. 2021. http://epic.gfellerlab.org/ [last accessed Jun. 7, 2021]. 1 page.
Altman et al., Transcriptome networks identify mechanisms of viral and nonviral asthma exacerbations in children. Nature immunology. May 2019;20(5):637-51.
Aran et al., Systematic pan-cancer analysis of tumour purity. Nature communications. Dec. 4, 2015;6(1):1-11.
Aran et al., xCell. UCSF Institute for Computational Health Sciences. 2017. https://xcell.ucsf.edu/ [last accessed Jun. 7, 2021]. 2 pages.
Aran et al., xCell: digitally portraying the tissue cellular heterogeneity landscape. Genome biology. Dec. 2017;18(1):1-14.
Becht et al., Estimating the population abundance of tissue-infiltrating immune and stromal cell populations using gene expression. Genome biology. Dec. 2016;17(1):1-20.
Ben-Moshe et al., mRNA-seq whole transcriptome profiling of fresh frozen versus archived fixed tissues. BMC genomics. Dec. 2018;19(1):11 pages.
Bray et al., Near-optimal probabilistic RNA-seq quantification. Nature biotechnology. May 2016;34(5):525-7.
Butler et al., Integrating single-cell transcriptomic data across different conditions, technologies, and species. Nature biotechnology. May 2018;36(5):411-20.
Chen et al., Profiling tumor infiltrating immune cells with CIBERSORT. Cancer systems biology. 2018:243-259.

(Continued)

*Primary Examiner* — John S Brusca
(74) *Attorney, Agent, or Firm* — Wolf, Greenfield & Sacks, P.C.

(57) ABSTRACT

Techniques for determining one or more cell composition percentages from expression data. The techniques include obtaining expression data for a biological sample, the biological sample previously obtained from a subject, the expression data including first expression data associated with a first set of genes associated with a first cell type; determining a first cell composition percentage for the first cell type using the expression data and one or more non-linear regression models including a first non-linear regression model, wherein the first cell composition percentage indicates an estimated percentage of cells of the first cell type in the biological sample, wherein determining the first cell composition percentage for the first cell type comprises: processing the first expression data with the first non-linear regression model to determine the first cell composition percentage for the first cell type; and outputting the first cell composition percentage.

15 Claims, 68 Drawing Sheets

(56) References Cited

OTHER PUBLICATIONS

Cieslik et al., The use of exome capture RNA-seq for highly degraded RNA with application to clinical cancer sequencing. Genome research. Sep. 1, 2015;25(9):1372-81.
Eisenberg et al., Human housekeeping genes, revisited. TRENDS in Genetics. Oct. 1, 2013;29(10):569-74.
Finotello et al., Molecular and pharmacological modulators of the tumor immune contexture revealed by deconvolution of RNA-seq data. Genome medicine. Dec. 2019;11(1):1-20.
Finotello et al., quanTIseq documentation. quanTIseq. Feb. 25, 2019. https://icbi.i-med.ac.at/software/quantiseq/doc/ [last accessed Jun. 7, 2021]. 9 pages.
Frankish et al., GENCODE reference annotation for the human and mouse genomes. Nucleic acids research. Jan. 8, 2019;47(D1):D766-73.
Galon et al., Type, density, and location of immune cells within human colorectal tumors predict clinical outcome. Science. Sep. 29, 2006;313(5795):1960-4.
George et al., Hemophilia B gene therapy with a high-specific-activity factor IX variant. New England Journal of Medicine. Dec. 7, 2017;377(23):2215-27.
Griffiths et al., Detection and removal of barcode swapping in single-cell RNA-seq data. Nature communications. Jul. 10, 2018;9(1):1-6.
Hao et al., Fast and robust deconvolution of tumor infiltrating lymphocyte from expression profiles using least trimmed squares. PLoS computational biology. May 6, 2019;15(5):e1006976. 21 pages.
Hirata et al., Tumor microenvironment and differential responses to therapy. Cold Spring Harbor perspectives in medicine. Jul. 1, 2017;7(7):a026781. 14 pages.
Hoek et al., A cell-based systems biology assessment of human blood to monitor immune responses after influenza vaccination. PLoS one. Feb. 23, 2015;10(2):e0118528. 24 pages.
Holik et al., RNA-seq mixology: designing realistic control experiments to compare protocols and analysis methods. Nucleic acids research. Mar. 17, 2017;45(5):e30. 18 pages.
Izar et al., A Single-Cell Landscape of High-Grade Serous Ovarian Cancer. Nature medicine. 2020;26:1271-1279. 23 pages.
Ke et al., Lightgbm: A highly efficient gradient boosting decision tree. Advances in neural information processing systems (NIPS). 2017;30:3146-54.
Lambrechts et al., Phenotype molding of stromal cells in the lung tumor microenvironment. Nature medicine. Aug. 2018;24(8):1277-89. 19 pages.
Levine et al., Data-driven phenotypic dissection of AML reveals progenitor-like cells that correlate with prognosis. Cell. Jul. 2, 2015;162(1):184-97. 31 pages.
Linsley et al., Copy number loss of the interferon gene cluster in melanomas is linked to reduced T cell infiltrate and poor patient prognosis. PLoS one. Oct. 14, 2014;9(10):e109760. 9 pages.
Lun et al., EmptyDrops: distinguishing cells from empty droplets in droplet-based single-cell RNA sequencing data. Genome biology. Dec. 2019;20(1):1-9.
Ma et al., PD1 Hi CD8+ T cells correlate with exhausted signature and poor clinical outcome in hepatocellular carcinoma. Journal for immunotherapy of cancer. Dec. 2019;7(1):331. 15 pages.
Macosko et al., Highly parallel genome-wide expression profiling of individual cells using nanoliter droplets. Cell. May 21, 2015;161(5):1202-14. 25 pages.
Marioni et al., RNA-seq: an assessment of technical reproducibility and comparison with gene expression arrays. Genome research. Sep. 1, 2008;18(9):1509-17.
Melsted et al., Modular and efficient pre-processing of single-cell RNA-seq. BioRxiv. Jun. 17, 2019:673285. 16 pages.
Monaco et al., RNA-Seq signatures normalized by mRNA abundance allow absolute deconvolution of human immune cell types. Cell reports. Feb. 5, 2019;26(6):1627-40.e7.
Neftel et al., An integrative model of cellular states, plasticity, and genetics for glioblastoma. Cell. Aug. 8, 2019;178(4):835-49.e29. 37 pages.
Newman et al., CIBERSORT. Stanford University. 2021. https://cibersort.stanford.edu/ [last accessed Jun. 7, 2021]. 1 page.
Newman et al., CIBERSORTx. Stanford University. 2021. https://cibersortx.stanford.edu/ [last accessed Jun. 7, 2021]. 1 page.
Newman et al., Determining cell type abundance and expression from bulk tissues with digital cytometry. Nature biotechnology. Jul. 2019;37(7):773-82.
Newman et al., Robust enumeration of cell subsets from tissue expression profiles. Nature methods. May 2015;12(5):453-7. 20 pages.
Norton et al., Pancreatic cancer associated fibroblasts (CAF): under-explored target for pancreatic cancer treatment. Cancers. May 2020;12(5):1347. 18 pages.
Puram et al., Single-cell transcriptomic analysis of primary and metastatic tumor ecosystems in head and neck cancer. Cell. Dec. 14, 2017;171(7):1611-24.e24. 40 pages.
Racle et al., EPIC: a tool to estimate the proportions of different cell types from bulk gene expression data. Bioinformatics for Cancer Immunotherapy. 2020:233-248.
Racle et al., Simultaneous enumeration of cancer and immune cell types from bulk tumor gene expression data. elife. Nov. 13, 2017;6:e26476. 25 pages.
Rakaee et al., Prognostic value of macrophage phenotypes in resectable non-small cell lung cancer assessed by multiplex immunohistochemistry. Neoplasia. Mar. 1, 2019;21(3):282-93.
Roider et al., Dissecting intratumour heterogeneity of nodal B-cell lymphomas at the transcriptional, genetic and drug-response levels. Nature Cell Biology. Jul. 2020;22(7):896-906. 27 pages.
Saltz et al., Spatial organization and molecular correlation of tumor-infiltrating lymphocytes using deep learning on pathology images. Cell reports. Apr. 3, 2018;23(1):181-93.e7. 21 pages.
Shin et al., Variation in RNA-Seq transcriptome profiles of peripheral whole blood from healthy individuals with and without globin depletion. PloS one. Mar. 7, 2014;9(3):e91041. 11 pages.
Stuart et al., Comprehensive integration of single-cell data. Cell. Jun. 13, 2019;177(7):1888-902.e21. 52 pages.
Sturm et al., Comprehensive evaluation of transcriptome-based cell-type quantification methods for immuno-oncology. Bioinformatics. Jul. 15, 2019;35(14):i436-45.
Tirosh et al., Dissecting the multicellular ecosystem of metastatic melanoma by single-cell RNA-seq. Science. Apr. 8, 2016;352(6282):189-96.
Van Gassen et al., FlowSOM: Using self-organizing maps for visualization and interpretation of cytometry data. Cytometry Part A. Jul. 2015;87(7):636-45.
Vivian et al., Toil enables reproducible, open source, big biomedical data analyses. Nature biotechnology. Apr. 2017;35(4):314-6.
Wagner et al., Measurement of mRNA abundance using RNA-seq data: RPKM measure is inconsistent among samples. Theory in biosciences. Dec. 1, 2012;131(4):281-5.
Wu et al., Stromal PD-L1-positive regulatory T cells and PD-1-positive CD8-positive T cells define the response of different subsets of non-small cell lung cancer to PD-1/PD-L1 blockade immunotherapy. Journal of Thoracic Oncology. Apr. 1, 2018;13(4):521-32.
Xu et al., Mapping of γ/δ T cells reveals Vδ2+ T cells resistance to senescence. EBioMedicine. Jan. 1, 2019;39:44-58.
Zaitsev et al., Complete deconvolution of cellular mixtures based on linearity of transcriptional signatures. Nature communications. May 17, 2019;10(1):2209. 16 pages.
Zheng et al., Massively parallel digital transcriptional profiling of single cells. Nature communications. Jan. 16, 2017;8(1):1-12.
Zimmermann et al., System-wide associations between DNA-methylation, gene expression, and humoral immune response to influenza vaccination. PloS one. Mar. 31, 2016;11(3):e0152034. 21 pages.
International Search Report and Written Opinion for International Application No. PCT/US2021/022155 dated Jul. 5, 2021.

* cited by examiner

FIG. 7G

Known profiles:

CD4 T cells:     NK cells:     CD8 T cells:

Unknown expression of other cell types     Observed expression

SYSTEMS AND METHODS FOR DECONVOLUTION OF EXPRESSION DATA

CROSS-REFERENCE TO RELATED APPLICATIONS

This application claims the benefit of priority under 35 U.S.C. 119(e) of U.S. provisional patent application No. 63/108,262, titled "SYSTEMS AND METHODS FOR DECONVOLUTION OF GENE EXPRESSION DATA", filed on Oct. 30, 2020, and of U.S. provisional patent application No. 62/988,700, titled, "MACHINE LEARNING SYSTEMS AND METHODS FOR DECONVOLUTION OF GENE EXPRESSION DATA", filed Mar. 12, 2020, each of which is incorporated by reference herein in its entirety.

BACKGROUND

In general, a tumor mass (or other diseased tissue) may comprise a population of malignant cells (e.g., cancer cells) and a microenvironment which may include, for example, immune cells, fibroblasts, and extracellular matrix proteins.

SUMMARY

Some embodiments provide for a method comprising using at least one computer hardware processor to perform: obtaining expression data for a biological sample, the biological sample previously obtained from a subject, the expression data including first expression data associated with a first set of genes associated with a first cell type; determining first a cell composition percentage for the first cell type using the expression data and one or more non-linear regression models including a first non-linear regression model, wherein the first cell composition percentage indicates an estimated percentage of cells of the first cell type in the biological sample, wherein determining the first cell composition percentage for the first cell type comprises: processing the first expression data with the first non-linear regression model to determine the first cell composition percentage for the first cell type; and outputting the first cell composition percentage.

Some embodiments provide for a system, comprising: at least one hardware processor; and at least one non-transitory computer-readable storage medium storing processor-executable instructions that, when executed by the at least one hardware processor, cause the at least one hardware processor to perform: obtaining expression data for a biological sample, the biological sample previously obtained from a subject, the expression data including first expression data associated with a first set of genes associated with a first cell type; determining a first cell composition percentage for the first cell type using the expression data and one or more non-linear regression models including a first non-linear regression model, wherein the first cell composition percentage indicates an estimated percentage of cells of the first cell type in the biological sample, wherein determining the first cell composition percentage for the first cell type comprises: processing the first expression data with the first non-linear regression model to determine the first cell composition percentage for the first cell type; and outputting the first cell composition percentage.

Some embodiments provide for at least one non-transitory computer-readable storage medium storing processor-executable instructions that, when executed by at least one hardware processor, cause the at least one hardware processor to perform: obtaining expression data for a biological sample, the biological sample previously obtained from a subject, the expression data including first expression data associated with a first set of genes associated with a first cell type; determining a first cell composition percentage for the first cell type using the expression data and one or more non-linear regression models including a first non-linear regression model, wherein the first cell composition percentage indicates an estimated percentage of cells of the first cell type in the biological sample, wherein determining the first cell composition percentage for the first cell type comprises: processing the first expression data with the first non-linear regression model to determine the first cell composition percentage for the first cell type; and outputting the first cell composition percentage.

Some embodiments provide for a method comprising using at least one computer hardware processor to perform: obtaining RNA expression data for a biological sample, the biological sample previously obtained from a subject having, suspected of having, or at risk of having cancer, wherein the RNA expression data includes first RNA expression data associated with a first set of genes associated with a first cell type, wherein the first RNA expression data includes expression data for at least 10 genes selected from the group of genes for the first cell type in Table 2, wherein the first cell type is selected from the group consisting of B cells, CD4+ T cells, CD8+ T cells, endothelial cells, fibroblasts, lymphocytes, macrophages, monocytes, NK cells, neutrophils, and T cells; and determining a first cell composition percentage for the first cell type, using the first RNA expression data, the first cell composition percentage indicating an estimated percentage of cells of the first cell type in the biological sample, wherein determining the first cell composition percentage for the first cell type comprises: providing the first RNA expression data as input to a first non-linear regression model to obtain a corresponding output representing an estimated percentage of RNA from the first cell type; and determining, based on the estimated percentage of RNA from the first cell type, the first cell composition percentage for the first cell type.

Some embodiments provide for a system comprising at least one hardware processor; and at least one non-transitory computer-readable storage medium storing processor-executable instructions that, when executed by the at least one hardware processor, cause the at least one hardware processor to perform obtaining RNA expression data for a biological sample, the biological sample previously obtained from a subject having, suspected of having, or at risk of having cancer, wherein the RNA expression data includes first RNA expression data associated with a first set of genes associated with a first cell type, wherein the first RNA expression data includes expression data for at least 10 genes selected from the group of genes for the first cell type in Table 2, wherein the first cell type is selected from the group consisting of B cells, CD4+ T cells, CD8+ T cells, endothelial cells, fibroblasts, lymphocytes, macrophages, monocytes, NK cells, neutrophils, and T cells; and determining a first cell composition percentage for the first cell type, using the first RNA expression data, the first cell composition percentage indicating an estimated percentage of cells of the first cell type in the biological sample, wherein determining the first cell composition percentage for the first cell type comprises: providing the first RNA expression data as input to a first non-linear regression model to obtain a corresponding output representing an estimated percentage of RNA from the first cell type; and determining, based on the estimated percentage of RNA from the first cell type, the first cell composition percentage for the first cell type.

Some embodiments provide for at least one non-transitory computer-readable storage medium storing processor-executable instructions that, when executed by at least one hardware processor, cause the at least one hardware processor to perform: obtaining RNA expression data for a biological sample, the biological sample previously obtained from a subject having, suspected of having, or at risk of having cancer, wherein the RNA expression data includes first RNA expression data associated with a first set of genes associated with a first cell type, wherein the first RNA expression data includes expression data for at least 10 genes selected from the group of genes for the first cell type in Table 2, wherein the first cell type is selected from the group consisting of B cells, CD4+ T cells, CD8+ T cells, endothelial cells, fibroblasts, lymphocytes, macrophages, monocytes, NK cells, neutrophils, and T cells; and determining a first cell composition percentage for the first cell type, using the first RNA expression data, the first cell composition percentage indicating an estimated percentage of cells of the first cell type in the biological sample, wherein determining the first cell composition percentage for the first cell type comprises: providing the first RNA expression data as input to a first non-linear regression model to obtain a corresponding output representing an estimated percentage of RNA from the first cell type; and determining, based on the estimated percentage of RNA from the first cell type, the first cell composition percentage for the first cell type.

Some embodiments provide for a method comprising: using at least one computer hardware processor to perform: obtaining training data comprising simulated RNA expression data, the simulated RNA expression data including first RNA expression data for first genes associated with a first cell type and second RNA expression data for second genes associated with a second cell type different from the first cell type; and training a plurality of non-linear regression models to estimate percentages of RNA from one or more respective cell types, the plurality of non-linear regression models comprising a first non-linear regression model for estimating percentage of RNA from the first cell type and a second non-linear regression model for estimating percentage of RNA from the second cell type, wherein training the plurality of non-linear regression models comprises training the first non-linear regression model at least in part by: generating, using the first non-linear regression model and the first RNA expression data, an estimated percentage of RNA from the first cell type; and updating parameters of the first non-linear regression model using the estimated percentage of RNA from the first cell type; and outputting the trained plurality of non-linear regression models including the first non-linear regression model and the second non-linear regression model.

Some embodiments provide for a system, comprising: at least one computer hardware processor; and at least one non-transitory computer-readable storage medium storing processor executable instructions that, when executed by the at least one computer hardware processor, cause the at least one computer hardware processor to perform: obtaining training data comprising simulated RNA expression data, the simulated RNA expression data including first RNA expression data for first genes associated with a first cell type and second RNA expression data for second genes associated with a second cell type different from the first cell type; and training a plurality of non-linear regression models to estimate percentages of RNA from one or more respective cell types, the plurality of non-linear regression models comprising a first non-linear regression model for estimating percentage of RNA from the first cell type and a second non-linear regression model for estimating percentage of RNA from the second cell type, wherein training the plurality of non-linear regression models comprises training the first non-linear regression model at least in part by: generating, using the first non-linear regression model and the first RNA expression data, an estimated percentage of RNA from the first cell type; and updating parameters of the first non-linear regression model using the estimated percentage of RNA from the first cell type; and outputting the trained plurality of non-linear regression models including the first non-linear regression model and the second non-linear regression model.

Some embodiments provide at least one non-transitory computer-readable storage medium storing processor executable instructions that, when executed by the at least one computer hardware processor, cause the at least one computer hardware processor to perform: obtaining training data comprising simulated RNA expression data, the simulated RNA expression data including first RNA expression data for first genes associated with a first cell type and second RNA expression data for second genes associated with a second cell type different from the first cell type; and training a plurality of non-linear regression models to estimate percentages of RNA from one or more respective cell types, the plurality of non-linear regression models comprising a first non-linear regression model for estimating percentage of RNA from the first cell type and a second non-linear regression model for estimating percentage of RNA from the second cell type, wherein training the plurality of non-linear regression models comprises training the first non-linear regression mode at least in part by: generating, using the first non-linear regression model and the first RNA expression data, an estimated percentage of RNA from the first cell type; and updating parameters of the first non-linear regression model using the estimated percentage of RNA from the first cell type; and outputting the trained plurality of non-linear regression models including the first non-linear regression model and the second non-linear regression model.

Some embodiments provide for a method comprising using at least one computer hardware processor to perform: obtaining expression data for a biological sample, the biological sample previously obtained from a subject having, suspected of having, or at risk of having cancer; obtaining a plurality of expression profiles for a corresponding plurality of cell types, each of the expression profiles comprising respective expression data from one or more genes associated with a respective cell type from the plurality of cell types; and determining a plurality of cell composition percentages for the plurality of cell types at least in part by optimizing a piecewise continuous error function between the expression data and the plurality of expression profiles.

Some embodiments provide for a system, comprising: at least one computer hardware processor; and at least one computer readable storage medium storing processor executable instructions that, when executed by the at least one computer hardware processor, cause the at least one computer hardware processor to perform obtaining expression data for a biological sample, the biological sample previously obtained from a subject having, suspected of having, or at risk of having cancer; obtaining a plurality of expression profiles for a corresponding plurality of cell types, each of the expression profiles comprising respective expression data from one or more genes associated with a respective cell type from the plurality of cell types; and determining a plurality of cell composition percentages for the plurality of cell types at least in part by optimizing a piecewise continuous error function between the expression data and the plurality of expression profiles.

Some embodiments provide for at least one computer-readable storage medium storing processor executable instructions that, when executed by at least one computer hardware processor, cause the at least one computer hardware processor to perform: obtaining expression data for a biological sample, the biological sample previously obtained from a subject having, suspected of having, or at risk of having cancer; obtaining a plurality of expression profiles for a corresponding plurality of cell types, each of the expression profiles comprising respective expression data from one or more genes associated with a respective cell type from the plurality of cell types; and determining a plurality of cell composition percentages for the plurality of cell types at least in part by optimizing a piecewise continuous error function between the expression data and the plurality of expression profiles.

BRIEF DESCRIPTION OF THE DRAWINGS

FIG. 7G is a chart comparing exemplary non-specificity scores for the deconvolution techniques developed by the inventors to non-specificity scores for alternative algorithms, according to some embodiments of the technology described herein.

FIGS. 13A-13J are charts and graphs depicting analysis and results from an experiment to deconvolve RNA-seq of multiple normal and cancer tissues as described in connection with Example 2.

DETAILED DESCRIPTION

Figure 1A:
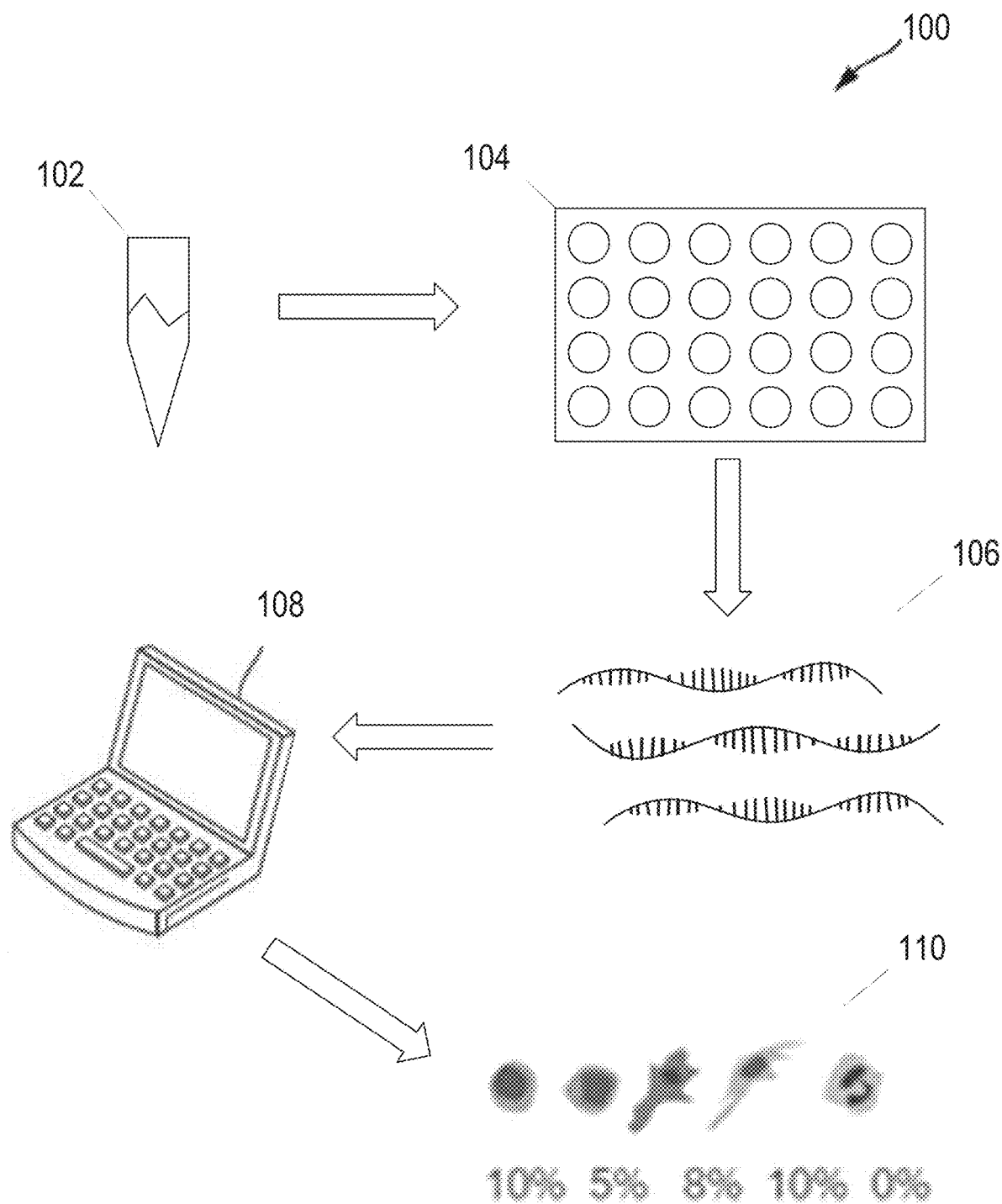
FIG. 1A is a diagram depicting a system for determining a cell composition percentage based on expression data, according to some embodiments of the technology described herein.

The inventors have developed machine learning techniques for determining cell composition percentages (e.g., percentages of cells of particular respective types) in a biological sample (e.g., such as a sample from a tumor or other diseased tissue) based on RNA expression data (e.g., data collected by processing the biological sample with a sequencing technique, such as bulk RNA-sequencing). In some embodiments, determining cell composition percentages for one or more cell types may involve using one or more non-linear regression models to estimate respective cell composition percentages for the cell types. The non-linear regression models may be trained using simulated RNA expression data, which may be generated according to the techniques described herein, such as by combining RNA expression data for a variety of malignant and/or microenvironment cell types and/or using any of the sampling, rebalancing, and noising techniques described herein.

The inventors have recognized and appreciated that the tumor microenvironment (TME) can play an important role in disease progression (e.g., whether a tumor is eradicated or metastasizes) and therapeutic responses/resistance. For example, as recognized and appreciated by the inventors, immune and non-immune components of the TME participate in tumor survival, maintenance, growth, and development using cell-to-cell contacts and different molecular signals, such as growth factors and cytokines. Furthermore, the inventors have recognized that the TME can mediate tumor survival by controlling the immune system of the host, providing immune surveillance of the tumor. The inventors have therefore appreciated that understanding the quantity and functionality of TME components is essential for cancer research and is important for therapy and understanding its clinical impact. However, despite the importance of understanding TME components, existing cancer studies have focused only upon a limited set of cell components within the TME due to the limitations of conventional methods for analyzing TME components. For example, techniques such as immunohistochemistry, flow cytometry, and CyTOF are limited due to their dependence on the availability of target-specific antibodies and unique tags such as fluorochromes.

The inventors have further recognized and appreciated that bulk RNA-sequencing (RNA-seq), which can provide information about tens of thousands of genes in a biological sample simultaneously, can allow for the detection of a signal that represents the combined contribution of multiple cell types. However, the inventors have recognized that total RNA expression data of this kind does not yield information regarding the origin of individual RNA molecules, such that there remain many challenges with determining the TME cellular composition (e.g., cell composition percentages) from bulk RNA-seq. The process of determining cell composition percentages from RNA expression data may be referred to herein as "deconvolution".

The inventors have recognized and appreciated that one significant problem with cellular deconvolution is that many genes can be expressed simultaneously by several types of cells present in a tumor and its microenvironment. This presents a particular challenge for identifying closely related cell types (e.g., such as subtypes of a particular cell type, such as CD4+ and CD8+ T cells, which may be considered subtypes of T cells), because genetic markers between closely related cell types can often be the same or similar. In some embodiments, cell types may be considered as populations of cells having distinguishable expression profiles. For example, CD4+ T cells, CD8+ T cells and NK cells tend to share the expression of a substantial amount of structural and regulatory genes, including metabolic, signaling and surface markers. In addition, monocytes express low levels of various differentiation genes that are thought to be uniquely expressed by mature dendritic cells and macrophages. Therefore, the inventors have recognized and appreciated that RNA expression data can contain both unique marker genes and genes relevant to the cell lineage. The inventors have also recognized that the ratio between marker and lineage-specific gene expression may or may not provide information about cell subtypes (for example the ratio of CD4/CD3D genes may be a marker of CD4+ T cells, but CD3D is not a unique marker for subtypes of helper T cells). Since cells of different types, even if they are closely related, can have significantly different impacts on tumor pathogenesis, the inventors have recognized that it nevertheless may be critical to distinguish cell populations even between closely related cell types.

Another challenge with cellular deconvolution recognized by the inventors is the difficulty of distinguishing between the number of cells and their state. For example, the expression of a gene specific or semi-specific to one cell type may vary depending on the activation state of the cells of that type or may differ between subtypes of that type. Although multiple studies can sequence similar cell subtypes, they may be captured in different biological states. As a result, the inventors have recognized and appreciated that the variability in biological states can play an important role in developing accurate estimate for cell composition percentages.

Additionally, the inventors have recognized and appreciated that the tumor microenvironment may make up only a relatively small fraction of the tumor as a whole. The identification of small cell populations from bulk RNA-seq data can be especially challenging because of a reduced signal-to-noise ratio. However, the inventors have recognized that identifying changes in small cell populations (e.g., NK-cells) remains important, as even small cell populations can nevertheless have significant impact on response to treatment. Moreover, the inventors have recognized and appreciated that the numeric values of RNA expression of genes can depend heavily on the specific measurement technology, library preparation protocol, and RNA enrichment method (e.g., total RNA-seq (REF), polyA enriched (REF), exome capture or 3' scRNA-seq (REF), for example) used. Even with techniques such as single cell RNA-seq (scRNA-seq), the coverage of such techniques generally does not allow for extraction of marker genes useful for the cell type identification.

As such, the inventors have recognized the need for accurate and robust cellular deconvolution techniques that account for the complexities and challenges described above. Accordingly, the inventors have developed novel systems and methods for using machine learning techniques to estimate cell composition percentages based on expression data (e.g., RNA expression data). In some embodiments a deconvolution method is provided comprising obtaining expression data (e.g., bulk RNA-seq data) for a biological sample from a subject, and determining a cell composition percentages for one or more cell types (e.g., B cells, CD4+ T cells, CD8+ T cells, endothelial cells, fibroblasts, lymphocytes, macrophages, monocytes, NK cells, neutrophils, and T cells). The cell composition percentage may indicate an estimated percentage of cells of a particular respective type in the biological sample. According to some embodiments, determining a cell composition percentage for a particular cell type may comprise obtaining expression data for a set of genes associated with the cell type (e.g., such as one or more marker genes, which may be specific or semi-specific genes for the particular cell type), and processing that expression data with a non-linear regression model to determine the cell composition percentage for the particular cell type. According to some embodiments, this process may be repeated or performed in parallel for each of multiple cell types (which may include subtypes of cell types, as described herein) in order to achieve a deconvolution across the multiple cell types. As described herein at least with respect to FIG. 7, these techniques present a significant improvement over the prior art.

In some embodiments, machine learning techniques used for determining cell composition percentages may include using multiple non-linear regression models, each trained to determine a cell composition percentage for a particular respective cell type. In some embodiments, the non-linear regression model may have multiple parameters (e.g., thousands, tens of thousands, hundreds of thousands, at least one million, millions, tens of millions, or hundreds of millions of parameters) and training the non-linear regression model may include estimating values of those parameters, computationally from expression data simulated for training. In some embodiments, generating the simulated training data may include generating many training sets (e.g., at least 25,000, at least 50,000, at least 100,000, at least 150,000, at least 200,000, at least 500,000, etc.) for each non-linear regression model, for each cell type. In some embodiments, multiple non-linear regression models may be trained respectively for multiple cells types (e.g., at least 5, at least 10, at least 20, at least 30, at least 40, etc.).

The techniques described herein and developed by the inventors offer a significant improvement in performance, accuracy, and efficiency over conventional methods for determining cell composition percentages in a robust and computational way by using machine learning techniques.

Figure 7A:
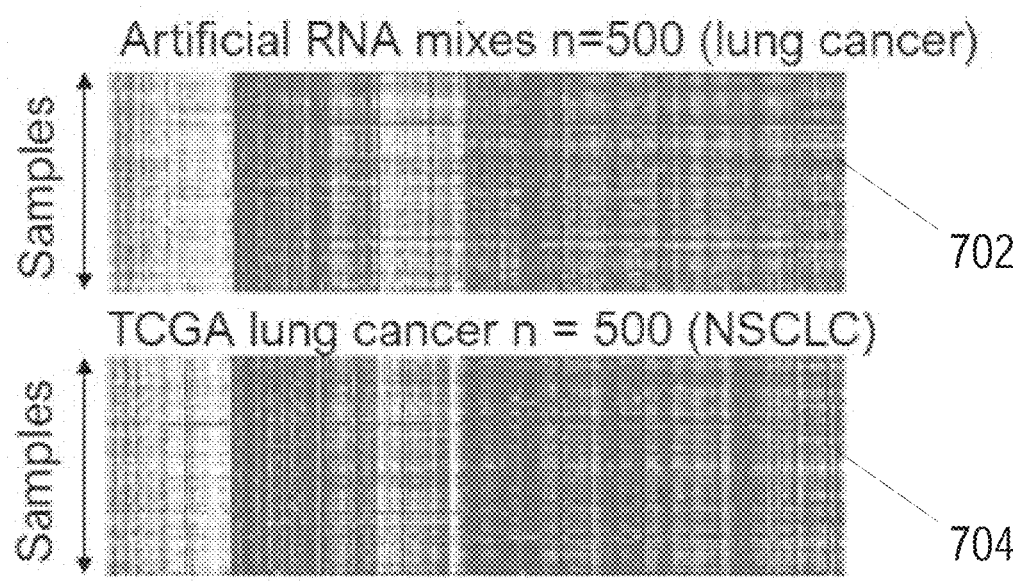
FIG. 7A is a chart comparing simulated RNA expression data to RNA expression data from a biological sample, according to some embodiments of the technology described herein.
Figure 7B:
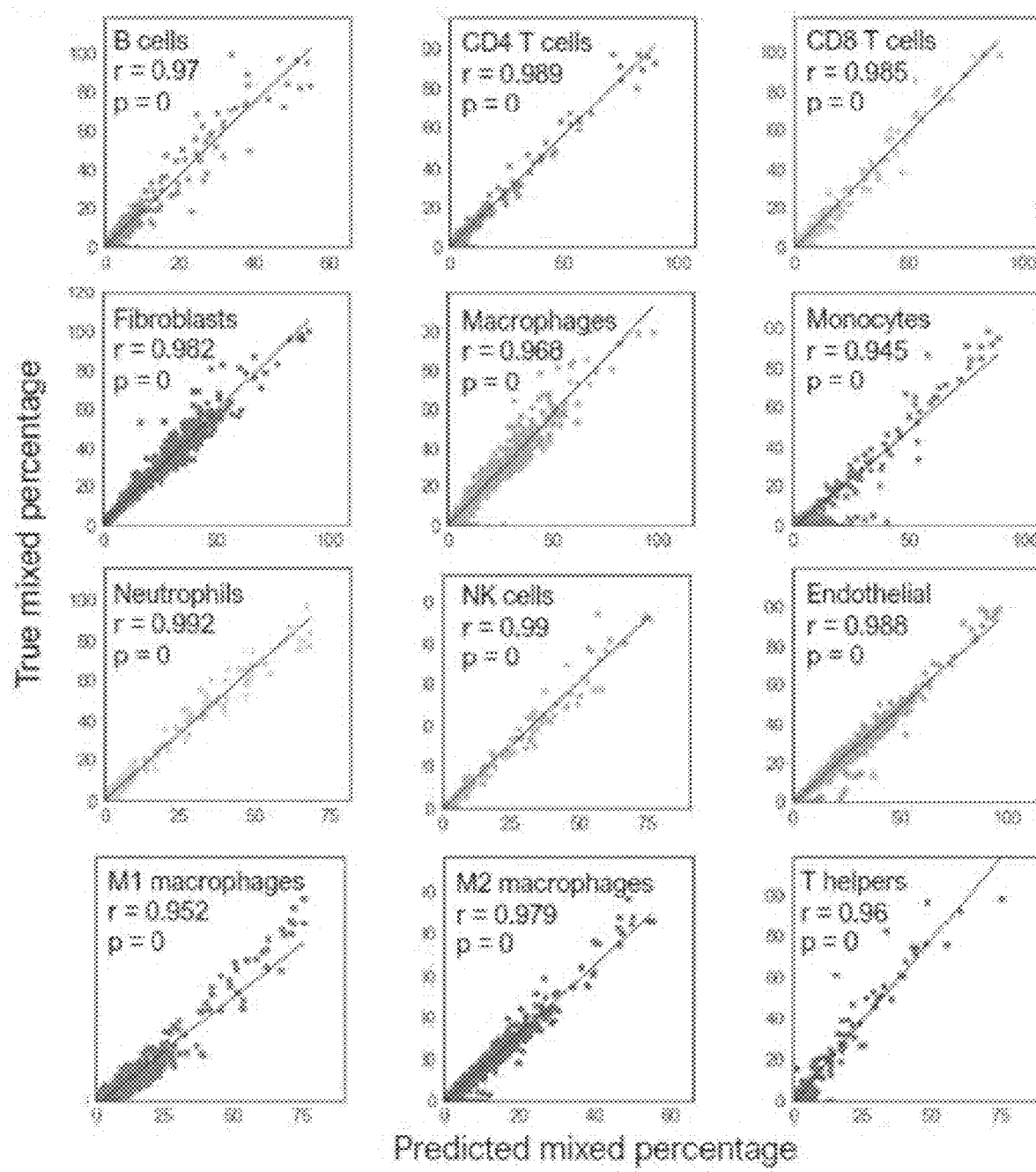
FIG. 7B is a chart depicting exemplary cell composition percentages predicted according to the deconvolution techniques developed by the inventors and corresponding true cell composition percentages, according to some embodiments of the technology described herein.
Figure 7C:
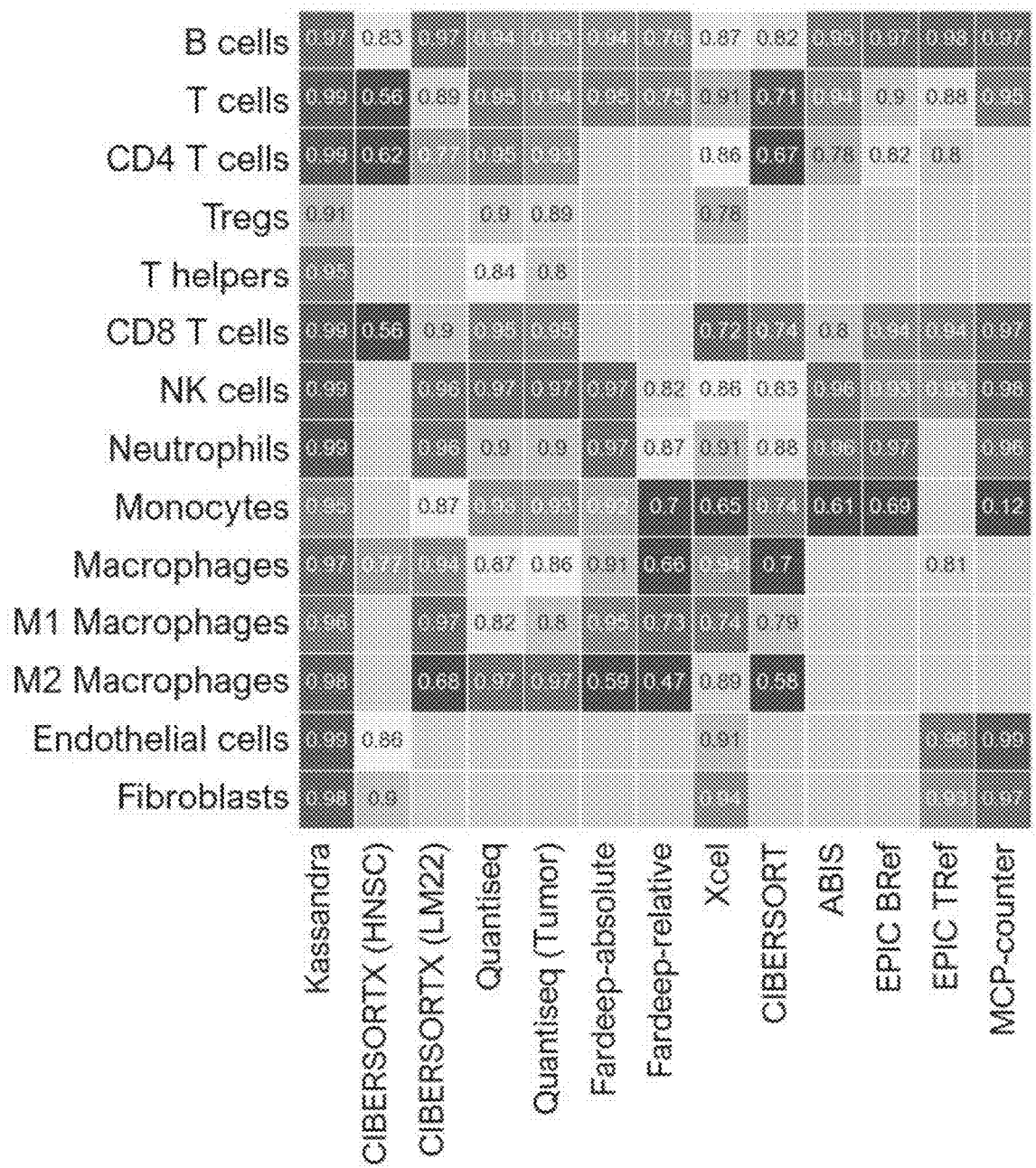
FIGS. 7C-7D are charts comparing exemplary prediction accuracy for the deconvolution techniques developed by the inventors, to prediction accuracy for alternative algorithms, according to some embodiments of the technology described herein.
Figure 7D:
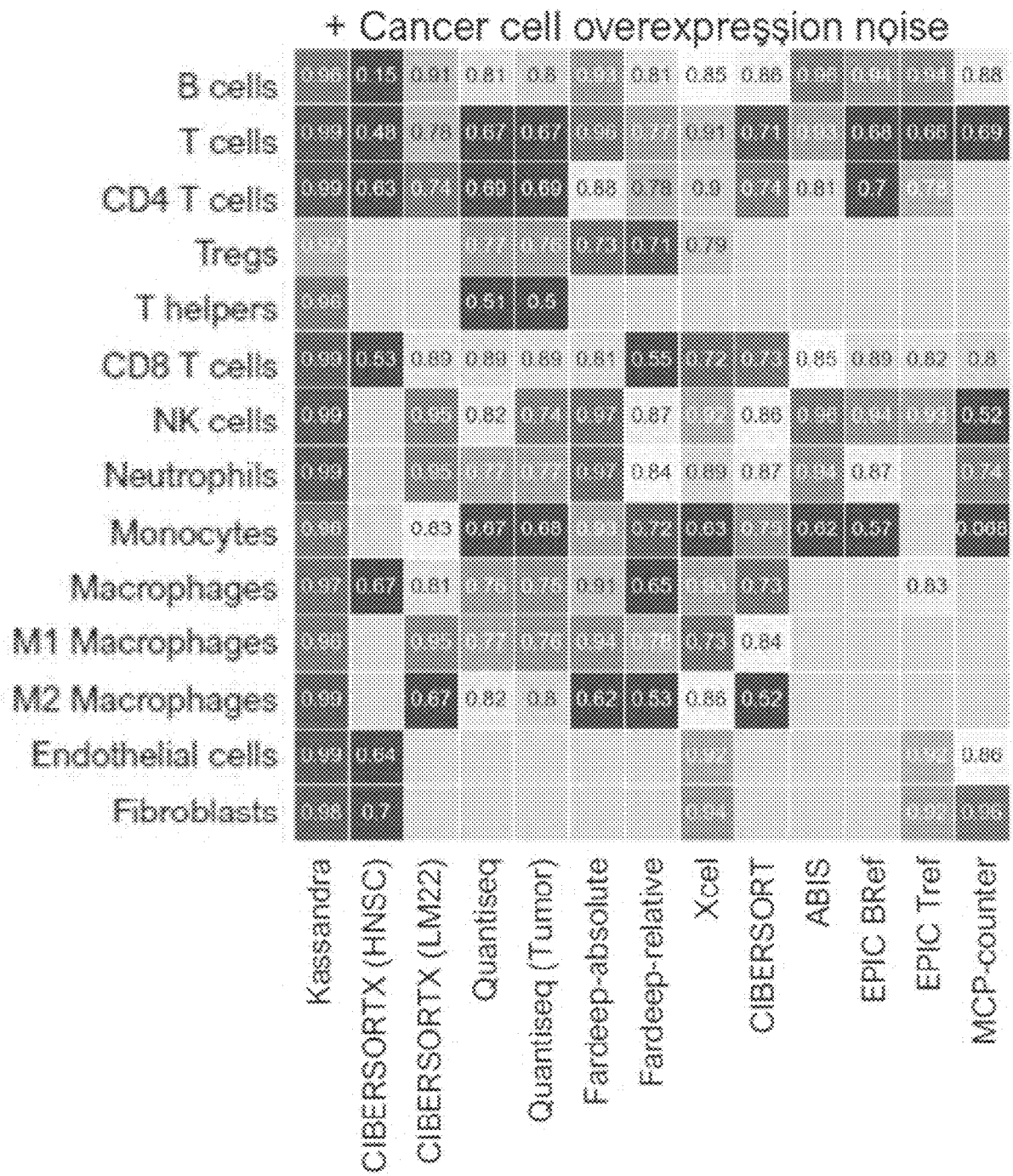

For example, FIGS. 7C and 7D show that, compared to conventional techniques, the non-linear deconvolution techniques developed by the inventors (e.g., referred to as "Kassandra") result in more accurate predictions of cell composition percentages for different cell types, even in the presence of cancer cell hyperexpression noise (e.g., as shown in FIG. 7D.) As a result, the techniques described herein constitute an improvement to bioinformatics generally and, specifically, to supporting clinical decision making and understanding tumor pathogenesis because the techniques described herein provide for improved methods of determining cell composition percentages (e.g., particularly for cell populations in the tumor microenvironment.)

For example, unlike conventional techniques, the machine learning techniques described herein can successfully identify dependencies and interconnections between genes of phenotypically closely related cell types by using expression data associated with genes that are associated (e.g., specific and/or semi-specific) with the particular subtype as input to a non-linear regression model specifically trained for that subtype, allowing for the accurate detection of cell subtypes even with similar expression patterns (FIGS. 7A, 7B). By using training data that mimics the cellular complexity and diversity of tumor biopsies and exploiting the uniqueness of expression profiles and cell population markers, the non-linear deconvolution techniques described herein are also more robust than prior algorithms, showing more consistent accuracy across a variety of cell types/subtypes, and providing significantly more accurate results than conventional techniques on realistic, noisy data (FIGS. 7C, 7D, 13F, 15G). In the context of the tumor microenvironment (e.g., analyzed in a clinical setting for a patient), these more accurate results enable improved cancer diagnosis and prognosis, as well as personalized treatment options for the patient.

One aspect of the approach developed by the inventors that contributes to its accuracy and robustness is the use of expression data particularly associated with each respective cell type to determine corresponding cell composition percentages. For example, for a given cell type, the expression data may include expression data associated with particular genes associated with the given cell type. In some embodiments, as described herein including at least with respect to FIGS. 1D-1E and Table 2, the expression data may include expression data associated with genes for a given cell type. As described herein, identifying the genes that are associated with a particular cell type may comprise processing expression data from multiple samples, which may be obtained from multiple databases, and/or with a variety of sequencing techniques, to identify genes that are only or predominantly expressed in certain cell types or subtypes. Regardless of how the genes are determined for any particular cell type, the use of expression data associated with particular genes associated with the particular cell types allows the cellular deconvolution techniques developed by the inventors to leverage domain-specific knowledge relating to which genes are expressed by which cell types, contributing to the success of the techniques described herein.

Another aspect of the approach developed by the inventors that contributes to its performance is the architecture employed both in training and using the non-linear deconvolution techniques described herein. For example, as described herein, in some embodiments a separate non-linear regression model is trained and used to estimate cell composition percentages for each respective cell type and/or subtype being analyzed in a biological sample (e.g., as described herein including at least with respect to FIG. 3A).

This may allow for cell types and/or subtypes in the biological sample to be distinguished more accurately (e.g., as shown in FIGS. 7A-7G). Moreover, in some embodiments, the model architecture may include a tiered structure (e.g., as described herein including at least with respect to FIG. 5A) which may be used as part of training and/or using the machine learning techniques described herein. For example, the model architecture may include multiple sub-models corresponding to multiple stages, in which the output of one or more previous sub-models (which may comprise, for example, initial predictions of one or more cell composition percentages for one or more cell types) may be used as part of the input for a subsequent sub-model. This allows the models to develop more accurate predictions by improving upon their initial predictions (e.g., from a first stage of training and/or using the models) in order to provide a more accurate final predictions (e.g., at a second, third, etc. stage of training and/or using the models). According to some embodiments, a tiered structure may be utilized in which outputs from the first sub-model across multiple models for multiple cell types and/or subtypes may be provided as input to subsequent sub-model(s) for each model. For example, first sub-model predictions of cell composition percentages for all cell types may be provided as input to the second sub-models (e.g., for other cell types and/or subtypes.) This may allow subsequent sub-models (e.g., the second sub-models) to account for interdependence between cell types and/or subtypes, thereby providing more accurate predictions of cell composition percentages across a variety of cell types and/or subtypes.

Another advantage of the techniques developed by the inventors is that, in some embodiments, the models described herein have been trained with data representing artificial mixtures of cell types, allowing the training process to take into account the diverse and tissue-specific expression of malignant and microenvironment cells across much larger numbers of samples of diverse composition (e.g., simulating a wide variety of tumor microenvironments) than could be practically possible by physically sampling and analyzing tumor samples. This substantially reduces the effort and computational resources associated with training the non-linear regression models for cellular deconvolution. The artificial mixes described herein can also be obtained in such a way that they replicate technical noise and capture a wide biological variability, improving the ability of a machine learning model trained using this data to identify biologically meaningful signals in the presence of such noise and variability. For example, as described herein, a quantitative noise model for technical noise was developed and may be applied to artificial mixes. Moreover, the RNA expression data used to develop these artificial mixes was derived from multiple different samples, across multiple cell populations having a variety of biological states. These artificial mixes improve the ability of the non-linear regression models to effectively estimate cell composition percentages across a variety of cell types in real tumor samples.

As described herein below including with respect to FIGS. 8 and 9A-9B, the techniques developed by the inventors also include improved linear techniques for cellular deconvolution. As described herein, one aspect of the linear techniques that contributes to their success is the use of an error function developed by the inventors. As described herein including at least with respect to FIG. 9B, the error function may be a piecewise, continuous error function. Compared to conventional methods, such as finding a square distance, the piecewise continuous error function accounts for genes that are strongly expressed in tumor cells. This may increase the accuracy for deconvolution of cells in tumor samples. The use of such an error function allows the techniques developed by the inventors to more accurately model the error associated with predicted cell composition percentages (e.g., as described herein including with respect to FIGS. 8 and 9A), providing improved results over conventional techniques.

Following below are more detailed descriptions of various concepts related to, and embodiments of, the cellular deconvolution systems and methods developed by the inventors. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

FIG. 1A depicts a system 100 for determining cell composition percentages 110. As described herein including at least with respect to FIG. 11, the illustrated system may be implemented in a clinical or laboratory setting.

As shown, the system 100 includes a biological sample 102, which may be, for example, a tumor biopsy obtained for a subject (e.g., a subject having, suspected of having, or at risk of having cancer). A subject may be at risk of having cancer, for example, if the subject has a genetic predisposition (e.g., a known genetic mutation or mutations) to cancer or may have been exposed to cancer causing agents. The biological sample 102 may be obtained by performing a biopsy, obtaining a blood sample, a salivary sample, or any other suitable biological sample from the patient. The biological sample 102 may have been previously obtained from a subject. Thus any step applied to the sample (e.g., obtaining expression data from the biological sample) may be performed in vitro. The biological sample 102 may include diseased tissue (e.g., a tumor), and/or healthy tissue. In some embodiments, the biological sample may be obtained from a physician, hospital, clinic, or other healthcare provider. In some embodiments, the origin or preparation methods of the biological sample may include any of the embodiments described with respect to the "Biological Samples" section. In some embodiments, the subject may include any of the embodiments described with the "Subjects" section.

The system 100 may further include a sequencing platform 104, which may produce sequence information 106. In some embodiments, the sequencing platform 104 may be a next generation sequencing platform (e.g., Illumina™, Roche™, Ion Torrent™, etc.), or any high-throughput or massively parallel sequencing platform. In some embodiments, the sequencing platform 104 may include any suitable sequencing device and/or any sequencing system including one or more devices. In some embodiments, these methods may be automated, in some embodiments, there may be manual intervention. In some embodiments, the sequence information 106 may be the result of non-next generation sequencing (e.g., Sanger sequencing). In some embodiments, the sample preparation may be according to manufacturer's protocols. In some embodiments, the sample preparation may be custom made protocols, or other protocols which are for research, diagnostic, prognostic, and/or clinical purposes. In some embodiments, the protocols may be experimental. In some embodiments, the origin or preparation method of the sequence information may be unknown.

Sequence information 106 can include the sequence data generated by a sequencing protocol (e.g., the series of nucleotides in a nucleic acid molecule identified by next-generation sequencing, sanger sequencing, etc.) as well as information contained therein (e.g., information indicative of source, tissue type, etc.) which may also be considered information that can be inferred or determined from the sequence data. For example, in some embodiments RNA sequence information may be analyzed to determine whether the nucleic acid was primarily polyadenylated or not. In some embodiments, sequence information 106 can include information included in a FASTA file, a description and/or quality scores included in a FASTQ file, an aligned position included in a BAM file, and/or any other suitable information obtained from any suitable file.

In some embodiments, the sequence information 106 may be generated using a nucleic acid from a sample from a subject. Reference to a nucleic acid may refer to one or more nucleic acid molecules (e.g., a plurality of nucleic acid molecules). In some embodiments, the sequence information may be a sequence data indicating a nucleotide sequence of DNA and/or RNA from a previously obtained biological sample of a subject having, suspected of having, or at risk of having a disease. In some embodiments, the nucleic acid is deoxyribonucleic acid (DNA). In some embodiments, the nucleic acid is prepared such that the whole genome is present in the nucleic acid. In some embodiments, the nucleic acid is processed such that only the protein coding regions of the genome remain (e.g., the exome). When nucleic acids are prepared such that only the exome is sequenced, it is referred to as whole exome sequencing (WES). A variety of methods are known in the art to isolate the exome for sequencing, for example, solution based isolation wherein tagged probes are used to hybridize the targeted regions (e.g., exons) which can then be further separated from the other regions (e.g., unbound oligonucleotides). These tagged fragments can then be prepared and sequenced.

In some embodiments, the nucleic acid is ribonucleic acid (RNA). In some embodiments, sequenced RNA comprises both coding and non-coding transcribed RNA found in a sample. When such RNA is used for sequencing the sequencing is said to be generated from "total RNA" and also can be referred to as whole transcriptome sequencing. Alternatively, the nucleic acids can be prepared such that the coding RNA (e.g., mRNA) is isolated and used for sequencing. This can be done through any means known in the art, for example by isolating or screening the RNA for polyadenylated sequences. This is sometimes referred to as mRNA-Seq.

In some embodiments, sequence information 106 may include raw DNA or RNA sequence data, DNA exome sequence data (e.g., from whole exome sequencing (WES), DNA genome sequence data (e.g., from whole genome sequencing (WGS)), RNA expression data, gene expression data, bias-corrected gene expression data, or any other suitable type of sequence data comprising data obtained from the sequencing platform 104 and/or comprising data derived from data obtained from sequencing platform 104. In some embodiments, the origin or preparation of the sequencing information 106 may include any of the embodiments described with respect to the "Expression Data," "Obtaining RNA expression data," "Alignment and annotation," "Removing non-coding transcripts," and "Conversion to TPM and gene aggregation" sections.

Regardless of the sequence data obtained, the sequence information 106 may be processed using computing device 108 in order to determine cell composition percentages 110. For example, the sequence information 106 may be processed by one or more software programs running on computing device 108 (e.g., as described herein with respect to FIG. 10). For example, the sequence information 106 may be processed according to the machine-learning based approach of FIGS. 2A-2C, or any other methods described herein for determining cell composition percentages (e.g., such as the non-linear deconvolution methods described at least with respect to FIGS. 2A-2C and 3A-3C and the linear deconvolution methods described at least with respect to FIGS. 8 and 9A-B). In some embodiments, the computing device 108 may be operated by a user such as a doctor, clinician, researcher, patient, or other individual. For example, the user may provide the sequence information 106 as input to the computing device 108 (e.g., by uploading a file), and/or may provide user input specifying processing or other methods to be performed using the sequence information.

Regardless of how the sequence information 106 is processed, the result may be one or more cell composition percentages 110. As described herein, each cell composition percentage may represent an estimated percentage of cells of a particular respective type in the biological sample 102. In some embodiments, the cell composition percentages are normalized so that the biological sample as a whole represents 100%. Cell types may include, for example, B-cells, Plasma B-cells, Non plasma B cells, T cells, CD4+ T-cells, CD8+ T-cells, Treg, T helpers, CD8+ PD1-high, CD8+ PD1-low, NK-cells, monocytes, macrophages, resting tumor associated macrophages (TAM), M1-like or activated macrophages, neutrophils, endothelial cells, and fibroblasts, and/or any other suitable cell types. According to some embodiments, a cell type may comprise one or more subtypes. For example, T cells may have subtypes including CD4+ T cells, CD8+ T cells, Tregs, etc. The cell composition percentages 110 may include percentages for cell subtypes as well as cell types which are not subtypes of any other cell types. According to some embodiments, the cell composition percentages may include a percentage for an "Other" cell type, which may represent an estimated percentage of cells not accounted for in the other cell composition percentages (e.g., cells of one or more types not explicitly included in the analysis).

Figure 1B:
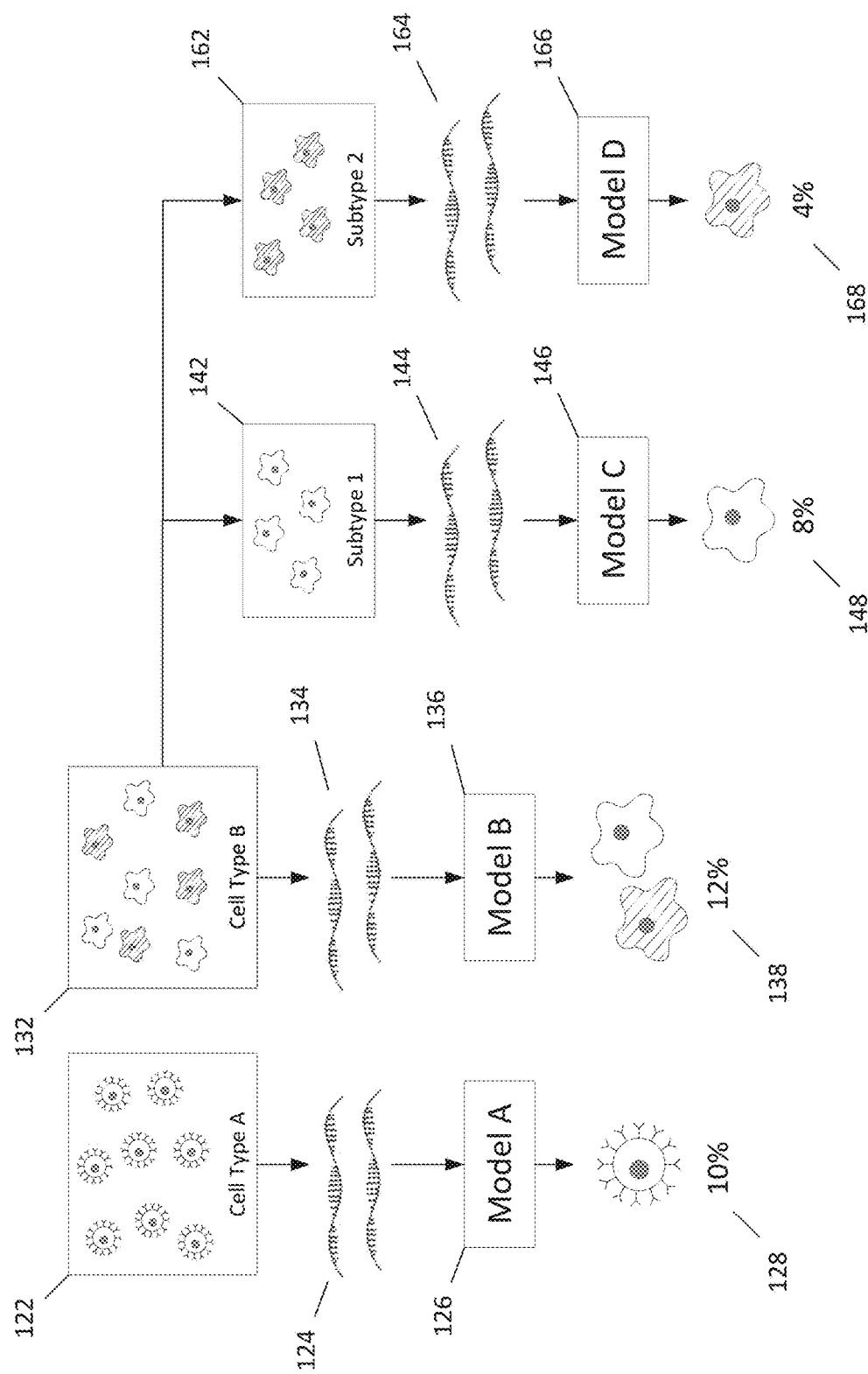
FIG. 1B is an example diagram for determining different cell composition percentages for different cell types and cell subtypes using a non-linear regression model for each respective cell type and cell sub-type, according to some embodiments of the technology described herein.

FIG. 1B is an example diagram for determining different cell composition percentages for different cell types and cell subtypes using a non-linear regression model for each respective cell type and cell sub-type, according to some embodiments of the technology described herein.

As shown in the example, a first non-linear regression model, model A 126, may be used to estimate cell composition percentage 128 for cell type A 122, using sequence information 124 associated with cell type A 122. A second non-linear regression model, model B 136, may be used to estimate cell composition percentage 138 for cell type B 132, using sequence information 134 associated with cell type B 136.

For the purpose of this example, cell type A 122 and cell type B 132 are different cell types. For example, cell type A 122 may include B-cells, while cell type B 132 may include T cells. However, cell type A and/or cell type B may be any suitable cell type, as aspects of the technology described herein are not limited in that respect.

In some embodiments, sequence information 124 and sequence information 134 may be obtained for cell type A 122 and cell type B 132, respectively. In some embodiments, sequence information may be associated with a set of genes that is specific and/or semi-specific to the cell type. For example, sequence information 124 may be associated with a first set of genes that is specific to cell type A 122, while sequence information 134 may be associated with a second set of genes that is specific to cell type B 132. Techniques for identifying genes that are specific and/or semi-specific to a particular cell type and/or subtype may include any of the embodiments described with respect to the "Gene Selection & Specificity" section.

As shown in FIG. 1B, a different non-linear regression model is used to determine cell composition percentages for different cell types. For example, model A 126 is used to estimate cell composition percentage 128 for cell type A 122, while model B 136 is used to estimate cell composition percentage 138 for cell type B 132. In some embodiments, each of the models may be trained to estimate cell composition percentages for a specific cell type, as described herein including at least with respect to FIG. 4.

In some embodiments, different cell types may include cell subtypes. As described herein, cell subtypes of close origin may share common genes (e.g., with one another and/or with the cell type from which it was differentiated.) As shown in FIG. 1B, cell type B 132 includes subtype A 142 and subtype B 162. For example, cell type B 132 may include T cells, while subtype A 142 and subtype B 162 may include subtypes of T cells (e.g., CD4+ and CD8+ T cells).

In some embodiments, a third non-linear regression model, model C 146, may be used to estimate cell composition percentage 148 for subtype A 142, using sequence information 144. A fourth non-linear regression model, model D 156 may be used to estimate cell composition percentage 158 for subtype B 162, using sequence information 164.

In some embodiments, sequence information 144 and sequence information 164 may be obtained for subtype A 142 and subtype B 162, respectively. In some embodiments, this may include obtaining sequence information associated with a gene set that includes genes specific and/or semi-specific to the subtype. For example, sequence information 144 may be associated with a first set of genes that is specific to subtype A 142, while sequence information 164 may be associated with a second set of genes that is specific to subtype B 144. Techniques for identifying genes that are specific and/or semi-specific to a particular cell type and/or subtype may include any of the embodiments described with respect to the "Gene Selection & Specificity" section.

Figure 1C:
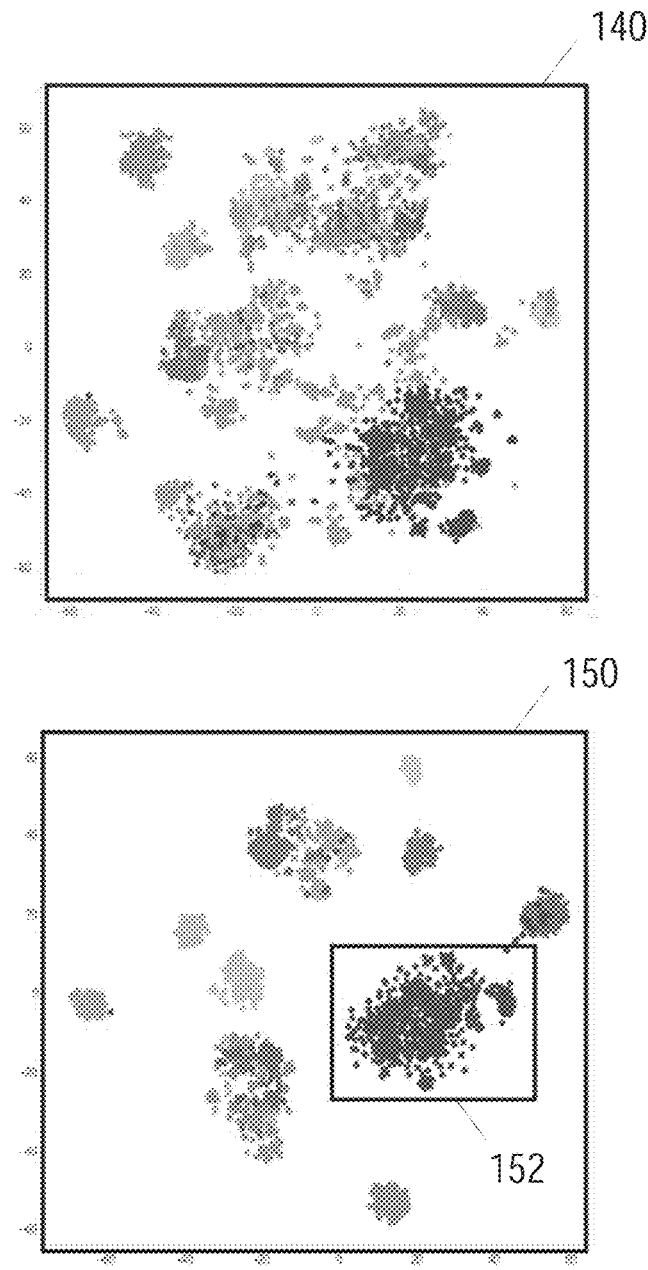
FIG. 1C is a t-SNE visualization depicting exemplary cell populations including malignant and microenvironment cells, according to some embodiments of the technology described herein.

FIG. 1C is a t-SNE visualization depicting expression data for a plurality of genes for exemplary cell populations including malignant and microenvironment cells. As indicated in the key, the cell types and/or subtypes depicted in the t-SNE plot include macrophages, M1 macrophages, M2 macrophages, B cells, B cells (non-plasma), Plasma B cells, T cells, CD8+ T cells, PD1+ CD8+ T cells, PD1− CD8+ T cells, CD4+ T cells, Tregs, T helpers, endothelium cells, monocytes, NK cells, fibroblasts, neutrophils and tumor cells (e.g., cancer cells). Malignant cells may comprise tumor cells, or any other cells associated with disease and/or diseased tissue. Microenvironment cells may comprise any non-tumor cells, including, for example, immune cells, skin cells, or any other cells not included in the tumor cells.

The t-SNE plots of FIG. 1C depict cell types/subtypes across many (e.g., at least one thousand, at least five thousand, or at least ten thousand) RNA-seq samples, which may be collected from biological samples via any of the sequencing techniques described herein. In some embodiments, the RNA-seq datasets may be combined, homogeneously annotated, and bioinformatically recalculated (e.g., expression values are bioinformatically recalculated) to obtain accurate and comparable measurements of transcript expression. For the illustrated example, RNA-seq data was available for 12,450 sorted samples (e.g., sorted by flow cytometry and magnetic-assisted sorting of cells with beads), which could be subdivided into nineteen cell populations of interest. After the removal of low coverage samples and quality checks, the selected samples were distributed between 10 major cell types and 19 cell subpopulations, listed in Table 1, below.

In the illustrated example, the t-SNE plot 140 depicts the RNA-seq samples from the listed cell types/subtypes before quality control (n=12450), while the t-SNE plot 150 depicts the RNA-seq samples from the listed cell types/subtypes after removal of samples which did not pass quality control (n=7150). The quality control techniques may include any of the embodiments described in the "Data collection, analysis, and preprocessing" section, or any other suitable quality control techniques. For example, in some embodiments, data derived from cells with abnormal physiological states may be identified (e.g., based on the annotations provided with the data) and excluded. For example, in some embodiments, all T cell samples with phorbol myristate acetate/ionomycin activation and/or induced pluripotent stem cell-derived samples were excluded. In some embodiments, samples with a low isolation purity, sequencing quality parameters, high contamination from other organisms (e.g., organisms other than the primary organism under investigation), and/or low coverage were also eliminated.

TABLE 1

This table specifies the number of samples, the number of datasets, and the average read counts for each of multiple cell types.

| Cell type | Number of samples | Number of datasets | Average read counts, millions |
|---|---|---|---|
| B cells | 39 | 7 | 14.28 |
| CD4+ T cells | 1215 | 71 | 22.37 |
| CD8+ T cells | 488 | 37 | 12.17 |
| CD8+ T cells PD1 high | 55 | 6 | 13.79 |
| CD8+ T cells PD1 low | 45 | 5 | 14.67 |
| Endothelium | 298 | 36 | 25.92 |
| Fibroblasts | 639 | 59 | 38.52 |
| Macrophages | 604 | 39 | 22.18 |
| Macrophages M1 | 538 | 13 | 28.79 |
| Macrophages M2 | 25 | 5 | 28.67 |
| Monocytes | 334 | 23 | 16.29 |
| NK Cells | 271 | 25 | 20.04 |
| Neutrophils | 219 | 18 | 19.23 |
| Non plasma B cells | 391 | 33 | 14.47 |
| Plasma B cells | 22 | 5 | 18.12 |
| T cells | 161 | 27 | 15.53 |
| T helpers | 427 | 27 | 17.19 |
| Tregs | 71 | 13 | 17.6 |
| Cancer cells | 2166 | 139 | 33.71 |
| All | 8008 | 152 | 25.25 |

As shown in plot 150, the cell populations may include tumor cells 152. The tumor cells 152 are shown in more detail in FIG. 1D, which is a t-SNE plot of cancer cell lines (n=2166), color coded by cancer type. As shown, the cancer types may include breast cancer, colorectal cancer, head and neck cancer, kidney cancer, lung cancer, melanoma, pancreatic cancer, prostate cancer, stomach cancer, and/or any other types of cancer.

Figure 1D:
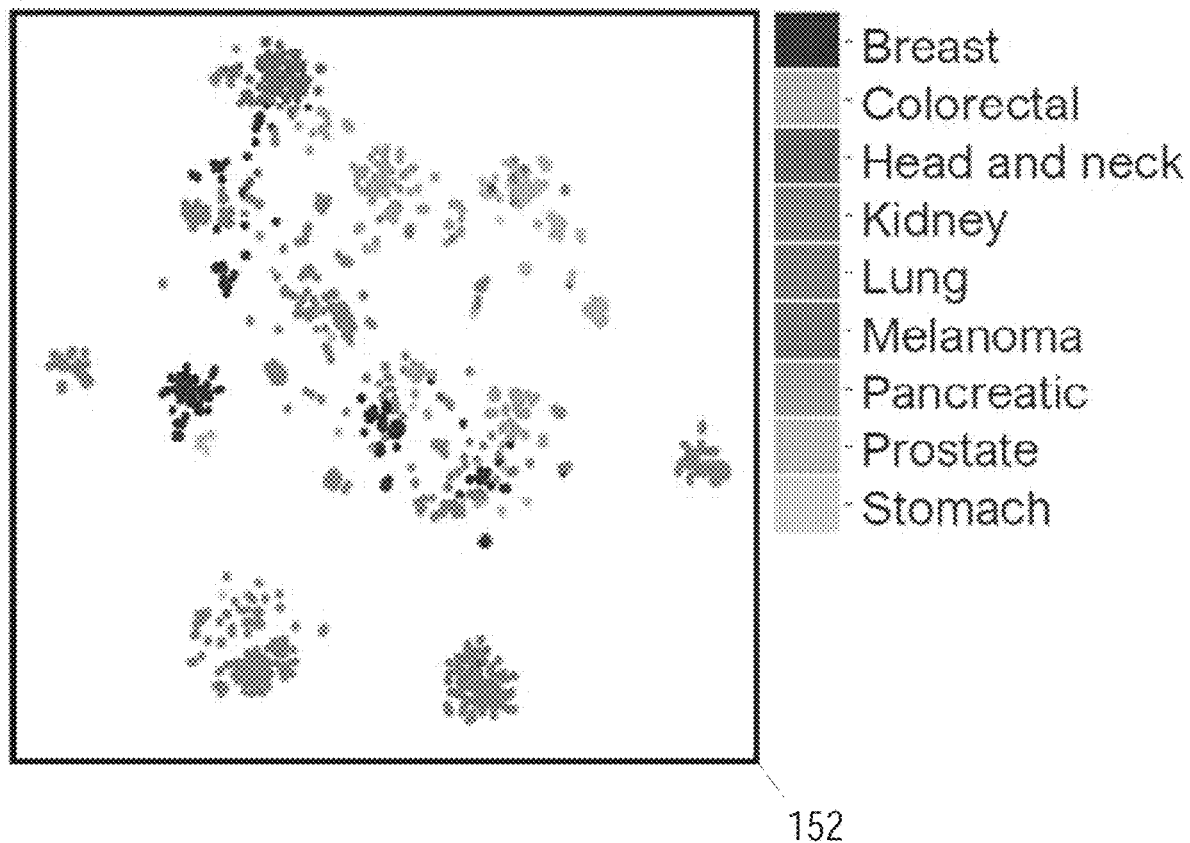
FIG. 1D is a t-SNE visualization depicting exemplary malignant cell populations, according to some embodiments of the technology described herein.
Figure 1E:
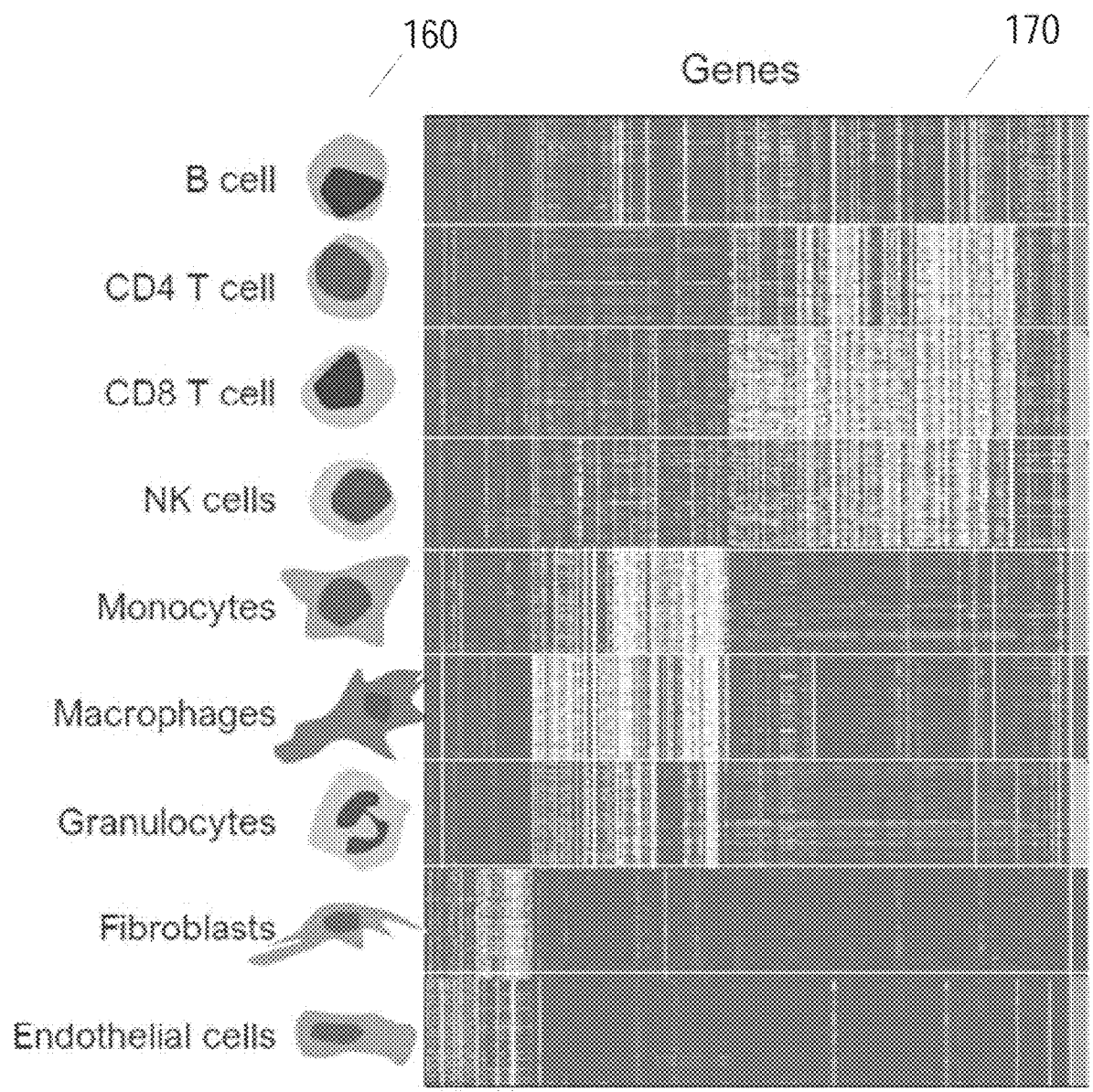
FIG. 1E is a chart depicting exemplary gene expressions for a variety of cells, according to some embodiments of the technology described herein.

According to some embodiments, some or all of the samples of RNA expression data plotted in FIGS. 1C and 1D may be used as part of selecting specific and/or semi-specific genes for particular cell types/subtypes, as described herein including at least with respect to FIG. 1E. In some embodiments, some or all of the illustrated samples of RNA expression data may be used as part of generating artificial mixes of RNA expression data, as described herein at least with respect to FIG. 6A. In some embodiments, the RNA expression data included in the data plotted in FIGS. 1C and 1D, as well as data that is similar to the RNA expression data plotted in FIGS. 1C and 1D, may be derived from public datasets and found using open source databases, such as Gene Expression Omnibus (GEO) and ArrayExpress. In some embodiments, datasets including RNA expression data that is similar to the RNA expression data plotted in FIGS. 1C and 1D can be used. For example, similar data sets that include some or all of the cell types represented in Table 1, each represented by a plurality of samples from a plurality of datasets as illustrated in Table 1, can be used.

Figure 1F:
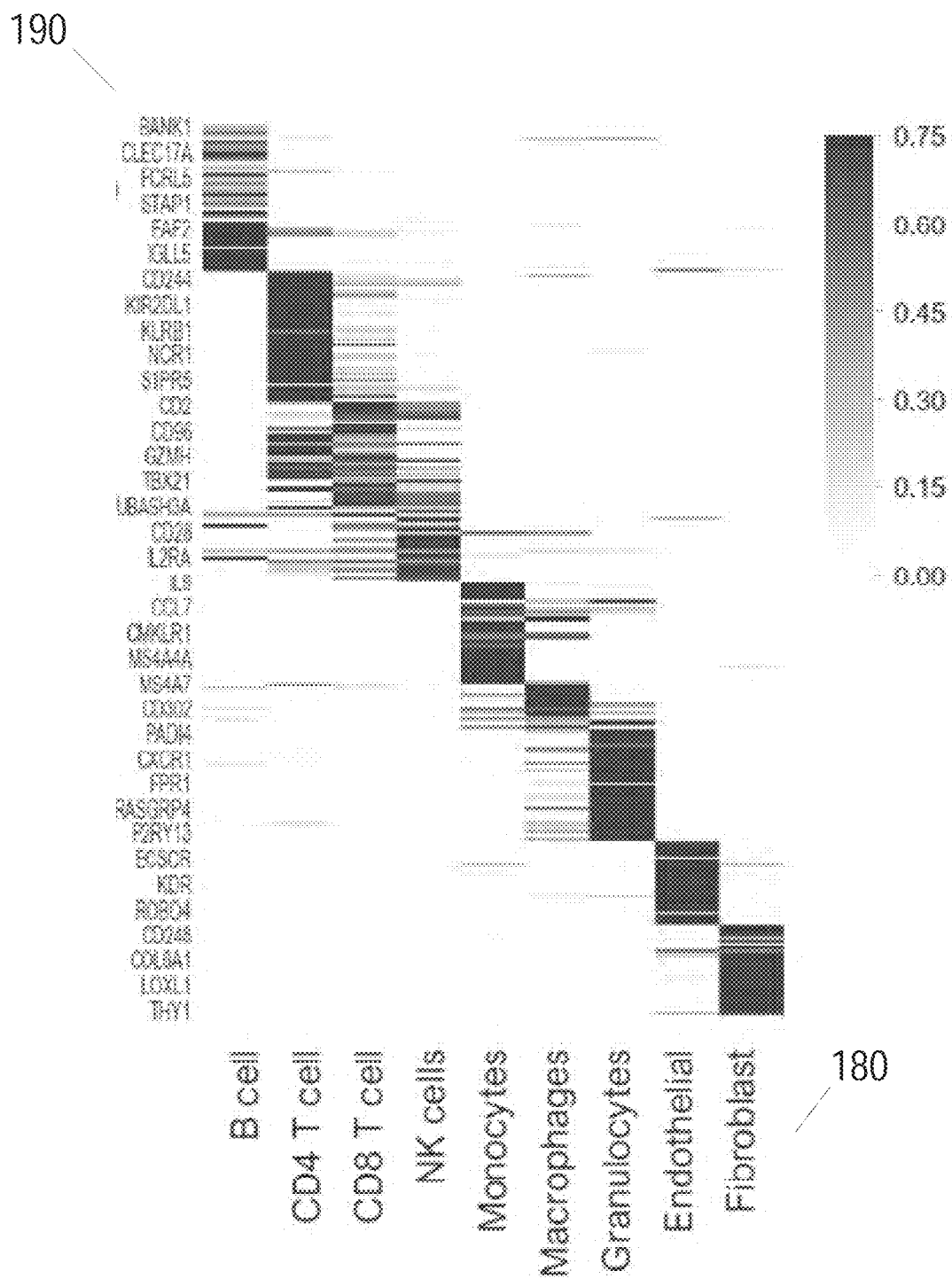
FIG. 1F is a chart depicting an exemplary correlation between genes and selected cell proportions in a sample mixture of various cell types, according to some embodiments of the technology described herein.
Figure 1G:
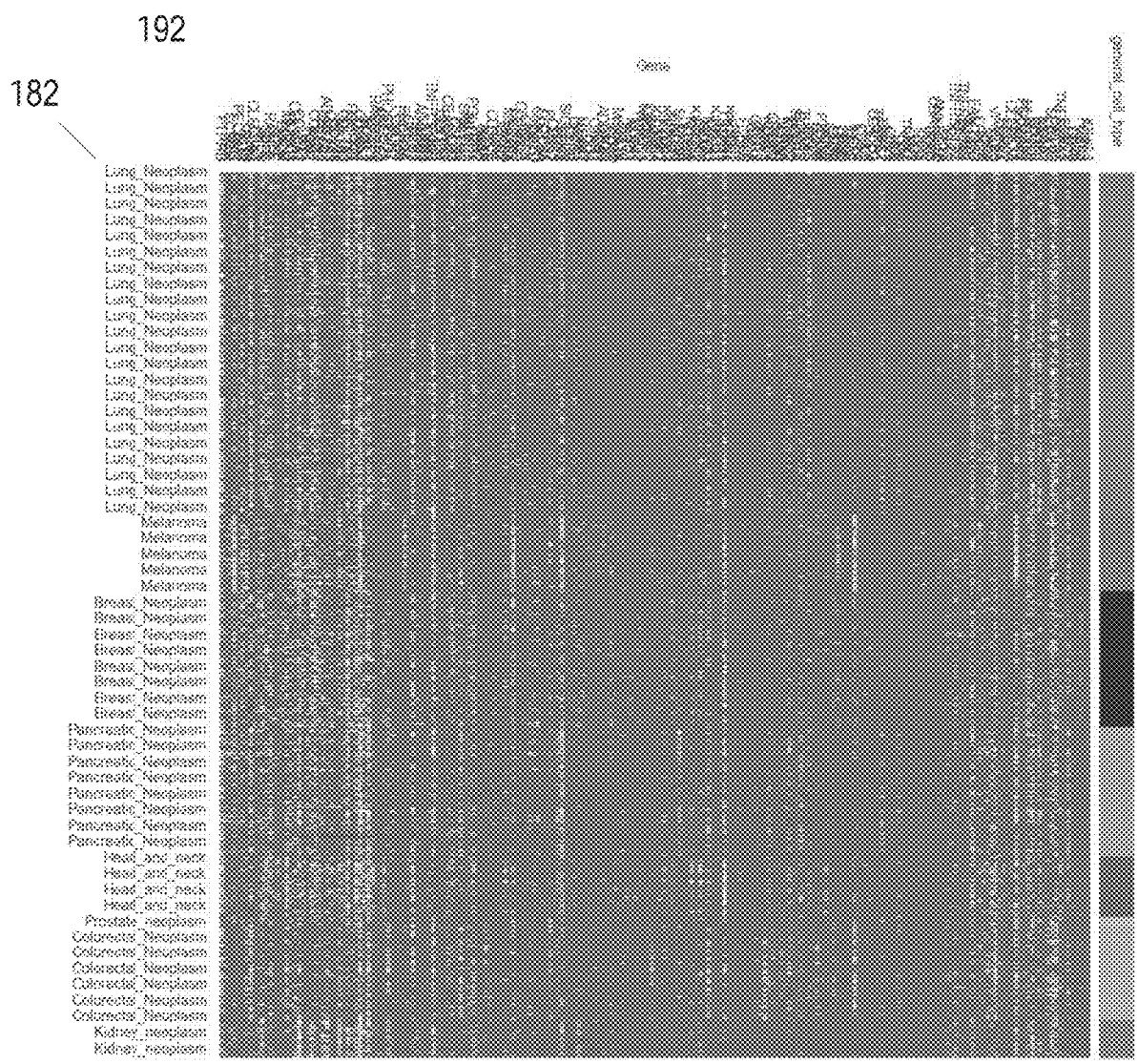
FIG. 1G is a chart depicting exemplary gene expressions for tumor cell lines, according to some embodiments of the technology described herein.

FIG. 1E is a heatmap depicting exemplary expressions of genes 170 for cell types 160. As shown, the vertical axis represents the cell types 160, and the horizontal axis represents the expression of genes 170 in transcripts per million (TPM). Each row in the heat map represents a single RNA-seq sample. As described herein, some genes may be considered specific to certain cell types. For example, as shown in the heatmap of FIG. 1F, the selected genes 190 may be correlated with the RNA percentage in corresponding sorted cell populations 180. For example, as shown in the heatmap of FIG. 1G, the selected genes 192 may have limited or no expression for tumor cell lines 182.

As shown below, Table 2 specifies, for each of multiple cell types, a set of genes which may be considered specific or semi-specific to that cell type, and/or which may be used for the deconvolution techniques described herein.

Gene Selection & Specificity

In some embodiments, the cellular deconvolution techniques developed by the inventors may involve using only certain gene expression data in order to determine cell composition percentages for a particular cell type. For example, in some embodiments, only expression data of specific and/or semi-specific genes for the particular cell type may be used, as described herein including at least with respect to FIGS. 2A-2C. In some embodiments, genes which are highly expressed in malignant cells (e.g., cancer cell lines) may be excluded (e.g., specific to tumor cells), such that the specific and/or semi-specific genes for a particular cell type (e.g., non-malignant cell types) may be uniquely expressed. In some embodiments, selecting specific and/or semi-specific genes for a particular cell type may comprise performing any or all of the following techniques: literature analysis, fold change analysis with statistical Kruskal-Wallis test (nonparametric ANOVA analogue), Conover-Iman test (nonparametric pairwise test for multiple comparisons), and/or correlation analysis using the RNA-seq data from FIGS. 1C-1D.

In some embodiments, gene sets (e.g., for a particular cell type) may be collected from various sources. In some embodiments, only genes with a known function may be used. Some genes may be similar to the labels used in CYTOF, some may be taken from literature data (which may demonstrate the specificity of certain genes), and/or some genes may be found on existing RNA-seq samples of sorted cells (e.g., after filtering experimental conditions, sequencing quality, and quality by expressions). The search for genes in samples may be carried out in several ways: using differential gene expression, using correlations of gene expression with the proportion of cells in artificial mixes (e.g., as described herein including at least with respect to FIG. 6A), using correlations of gene expression with some marker cell gene (such as CD3 for T cells) in TCGA (The Cancer Genome Atlas) samples or TCGA samples mixed with samples of sorted cells (e.g., in order to add larger percentages of cells to samples, increase the number of read counts, and reduce correlations between the presence of various cells in tumors), using linear regression methods on artificial mixes (e.g., with L1 regularization), using some metrics of feature importance for machine learning methods (such as SHAP or gain for gradient boosting trees), or using some genetic algorithm to select a combination of genes that gives the best quality of predictions of machine learning methods on artificial and/or real independent data with known cellular composition, or any combination or chain of these described methods.

A gene may be considered "specific" to a particular cell type or subtype if it is only expressed in the particular cell type or cell subtype. A gene may be considered "semi-specific" to a particular cell type or subtype when: (1) it is expressed both in the particular cell type or subtype and in one or more other cell types or subtypes; and (2) it is expressed to a greater degree in the particular cell type or subtype than in the other cell type(s) or subtype(s). For example, a gene may be considered semi-specific for a particular cell type or subtype if the average expression of the gene in the particular cell type or sub-type is at least a threshold percentage (e.g., 50%, 100%, 200%, 500%, 1000%, etc.) or threshold factor (e.g., a factor of 2, 5, 10, 15, 20, etc.) higher than the average expression of the same gene in the other cell types or sub-types. As one specific example, a gene may be considered semi-specific for a particular cell type or subtype if the average expression of the gene in the cell type or subtype is at least ten times higher than the average expression of the gene in the other cell types or subtypes. For example, there may be common genes between macrophages and monocytes, CD4+ T cells and CD8+ T cells, NK cells and CD8+ T cells. In some embodiments, the common genes may be considered semi-specific to the cell types and/or subtypes (e.g., semi-specific to both CD4+ T cells and CD8+ T cells.) In some embodiments, genes may be selected because their expression is significantly lower or absent in malignant cell (e.g., tumor) lines. In some embodiments, the specificity criterion can be evaluated when assessed on combined expression data from a plurality of datasets, as described above. In some embodiments, if several types of cells are present in the same dataset, then for each such dataset, a similar specificity analysis may also be carried out inside the datasets to control batch effects.

In some embodiments, for each set of genes, analysis may be performed to determine how these genes are expressed in TCGA (The Cancer Genome Atlas) for the desired type of tumor. For example, for a given cell type, it may be desirable that the ratios of the average TCGA expression to the average expression lie within a comparable range. In other words, if the average expression of a specific or semi-specific gene (e.g., in a specific or semi-specific set of genes) in TCGA is 70% of the average expression in the samples of the sorted cells, while the other gene expressions of this set are around 5%, then the specific or semi-specific gene is likely expressed by a tumor or other cells, or the cells in the tumor differ greatly in the expression of this gene.

Additionally or alternatively, it may be desirable for the expression of genes from the same set to correlate with one another among the TCGA samples for this type of tumor (e.g., the desired type of tumor, above.) For this, the mean among the correlations with the other genes from the set may be analyzed. The characteristic values of the expression of the considered genes in TCGA LUAD may be low (e.g., less than 10 TPM), so the correlations of these genes with each other may also be low (e.g., due to insufficient sequencing depth). In some cases, there may be especially low gene expressions of NK cells and neutrophils.

The inventors have recognized and appreciated that cells having a common origin and functions can often express the same genes. For example, hematopoietic immune cells express CD45 (PTPRC) and HCLS1. Due to their development, immune cells can be divided into lymphocytes and myeloid cells. In turn, lymphocytes can be divided into T, B, NK cells, then CD4+ and CD8+ T cells can be distinguished from among T cells. But among these cells, there are also subtypes that can play an important role both in the development of tumors and in the course of treatment. Therefore, as described herein, it may be desirable for cell composition percentages to be determined for subtypes of certain cells. However, the inventors have recognized and appreciated that isolating cell subtypes based on RNA expression data may be difficult, since fewer specific and/or semi-specific genes may be expressed in cell subtypes, and the number of such cells in the tumor microenvironment may be smaller than the combined groups of cells.

The inventors have discovered that one way to improve the accuracy of determining both cell types and subtypes may be to use information on the expression of genes specific and/or semi-specific for the combined group of cells (e.g., including cell types and cell subtypes that share common genes) in determining cell composition percentages for the cell subtypes. Such common genes can be used when determining cell composition percentages of individual cell types and subtypes, for example. Another way to use genes common to a group of cell subtypes may be to initially calculate a cell composition percentage for the combined group, then refine that calculation in order to determine cell composition percentages for individual cell types in the group, as described elsewhere herein.

TABLE 2

This table specifies, for each of multiple cell types, the list of genes which may be considered specific or semi-specific to that cell type. In some embodiments, these expression levels are used by the machine learning deconvolution techniques developed by the inventors. Exemplary NCBI Accession Numbers for genes mentioned herein are shown in Table 11 below.

| Cell group name | Gene set |
| --- | --- |
| Immune_cells | ADAP2, ADGRE3, ADGRG3, ADORA3, AIF1, AOAH, APOBEC3D, ARHGAP15, ARHGAP30, ARHGAP9, ARHGDIB, BANK1, BLK, C1QA, C1QC, C3AR1, C5AR1, CAMK4, CBLB, CCDC69, CCL5, CCL7, CCR1, CCR2, CCR3, CD14, CD160, CD163, CD19, CD1D, CD2, CD22, CD226, CD244, CD247, CD27, CD300A, CD300C, CD300E, CD300LB, CD302, CD33, CD37, CD3D, CD3E, CD3G, CD4, CD48, CD5, CD53, CD6, CD68, CD69, CD7, CD79A, CD79B, CD86, CEACAM8, CECR1, CELF2, CLDND2, CLEC17A, CLEC2D, CLEC5A, CLEC7A, CMKLR1, CORO1A, CPNE5, CR2, CSF1R, CSF2RA, CSF3R, CTSS, CTSW, CXCR1, CXCR2, CXCR5, CYBB, CYFIP2, CYTH4, CYTIP, DENND1C, DERL3, DOCK2, EAF2, ELF1, ELMO1, EVI2B, FAM129C, FAM78A, FCER1G, FCGR1A, FCGR1B, FCGR2A, FCGR3B, FCMR, FCN1, FCRL1, FCRL2, FCRL3, FCRL5, FCRLA, FERMT3, FFAR2, FGR, FKBP11, FLT3LG, FMNL1, FNBP1, FPR1, FPR2, FPR3, GLCCI1, GLT1D1, GPR174, GZMM, HCK, HCLS1, HLA-DOB, HMHA1, ICAM3, IFI30, IFITM2, IGFLR1, IGHG1, IGHG3, IGHM, IGKC, IGLL5, IKZF1, IKZF3, IL10, IL16, IL2RB, IL2RG, IL4I1, INPP5D, IRF5, ITGAL, ITGAX, ITGB2, ITGB7, ITK, KCNA3, KCNAB2, KCNJ15, KIR2DL1, KIR2DL2, KIR2DL3, KIR2DL4, KIR2DS2, KIR3DL1, KIR3DL2, KLRB1, KLRC2, KLRC3, KLRD1, KLRF1, KLRK1, LAG3, LAIR1, LAPTM5, LAT, LAX1, LCK, LCP1, LIM2, LRRC25, LSP1, LTA, LY9, MAP4K1, MEFV, MMP25, MNDA, MRC1, MS4A1, MS4A4A, MS4A6A, MSR1, MYO1F, MYO1G, MZB1, NCAM1, NCF2, NCKAP1L, NCR1, NCR3, NFATC2, NKG7, NLRC3, NMUR1, P2RY10, P2RY13, P2RY8, PADI2, PADI4, PARVG, PAX5, PGLYRP1, PHOSPHO1, PIK3AP1, PILRA, PLA2G7, PLCB2, POU2AF1, PPP1R16B, PRF1, PRKCB, PTGDR, PTPN22, PTPN6, PTPRC, PTPRCAP, PVRIG, PYHIN1, RAB7B, RAC2, RASGRP1, RASGRP2, RASGRP4, RASSF5, RCSD1, RHOH, RLTPR, S1PR5, SAMD3, SAMSN1, SASH3, SEC11C, SH2D1B, SIGLEC1, SIGLEC5, SIGLEC7, SIGLEC9, SIRPB2, SIRPG, SIT1, SLA2, SLAMF6, SNX20, SP140, SPI1, SPIB, SPN, SSR4, STAP1, STAT5A, STK4, TAGAP, TBC1D10C, TBX21, TCF7, TESPA1, TLR2, TMC8, TMIGD2, TNFAIP8, TNFAIP8L2, TNFRSF10C, TNFRSF13B, TNFRSF13C, TNFRSF17, TRAC, TRAF3IP3, TRAT1, TRBC2, TRDC, TREM2, TRGC1, TRGC2, TXNDC11, TXNDC5, TYROBP, UBASH3A, VAV1, VNN2, VNN3, VPREB3, VSIG4, WAS, XCL2, ZBED2 |
| B_cells | BANK1, BLK, CD19, CD22, CD37, CD79A, CD79B, CLEC17A, CPNE5, CR2, CXCR5, DERL3, EAF2, FAM129C, FCRL1, FCRL2, FCRL3, FCRL5, FCRLA, FKBP11, GLCCI1, HLA-DOB, IGHG1, IGHG3, IGHM, IGKC, IGLL5, MS4A1, MZB1, PAX5, POU2AF1, SEC11C, SPIB, SSR4, STAP1, TNFRSF13B, TNFRSF13C, TNFRSF17, TXNDC11, TXNDC5, VPREB3 |

TABLE 2-continued

This table specifies, for each of multiple cell types, the list of genes which may be considered specific or semi-specific to that cell type. In some embodiments, these expression levels are used by the machine learning deconvolution techniques developed by the inventors. Exemplary NCBI Accession Numbers for genes mentioned herein are shown in Table 11 below.

| Cell group name | Gene set |
|---|---|
| Plasma_B_cells | BANK1, BLK, CD19, CD22, CD37, CD79A, CD79B, CLEC17A, CPNE5, CR2, DERL3, EAF2, FAM129C, FCRL1, FCRL2, FCRL3, FCRL5, FCRLA, FKBP11, GLCCI1, HLA-DOB, IGHG1, IGHG3, IGHM, IGKC, IGLL5, MZB1, POU2AF1, SEC11C, SPIB, SSR4, STAP1, TNFRSF13B, TNFRSF13C, TNFRSF17, TXNDC11, TXNDC5 |
| Non_plasma_B_cells | ADAM28, BANK1, BCL11A, BLK, CD19, CD22, CD37, CD72, CD79A, CD79B, CLEC17A, CPNE5, CR2, CXCR5, FAM129C, FCER2, FCRL1, FCRL2, FCRL3, FCRL5, FCRLA, HLA-DOB, MS4A1, PAX5, POU2AF1, RALGPS2, SPIB, STAP1, TNFRSF13B, TNFRSF13C, VPREB3 |
| T_cells | CAMK4, CBLB, CD2, CD226, CD3D, CD3E, CD3G, CD48, CD5, CD6, CD7, FLT3LG, ITK, KCNA3, KLRB1, LAG3, LAT, LCK, LTA, SIRPG, srrl, SLA2, TBX21, TCF7, TESPA1, TRAC, TRAF3l133, TRAT1, TRBC2, TRDC, TRGC1, TRGC2, UBASH3A, ZBED2 |
| CD4_T_cells | ANKRD55, CCR4, CD2, CD27, CD28, CD3D, CD3E, CD3G, CD4, CD4OLG, CD5, CD6, FHIT, FLT3LG, ICOS, IKZFl, IL2RA, IL9, IRF4, ITK, LCK, LEF1, LTA, TESPA1, TNFRSF4, TRAC, TRAT1, TRBC2, UBASH3A |
| Tregs | CCR4, CCR8, CD2, CD27, CD4, CTLA4, ENTPD1, FOXP3, HAVCR2, IKZF2, IKZF4, IL21R, IL2RA, IL2RB, IL2RG, ITGAE, ITK, LAG3, LTB, SIRPG, TIGIT, TNFRSF18, TNFRSF4, TNFRSF8, TNFRSF9, TRAC |
| T_helpers | ANKRD55, CD2, CD28, CD4OLG, CD5, CD6, FHIT, FLT3LG, IL7R, ITK, ITM2A, KLRB1, LCK, LEF1, LRRN3, NELL2, P2RY8, TCF7, TESPA1, THEMIS, TRAF3IP3, TRAT1 |
| CD8_T_cells | CCL5, CD2, CD3D, CD3E, CD3G, CD6, CD7, CD8A, CD8B, CD96, CRTAM, CXCR3, EOMES, FCRL6, FLT3LG, GZMA, GZMB, GZMH, GZMK, ITK, KLRC2, KLRC4, KLRK1, PRF1, PRKCQ, PTGDR, PVRIG, SH2D1A, TBX21, TCF7, THEMIS, TIGIT, TRAC, TRAT1, TRBC2, UBASH3A, XCL2, ZAP70, ZBED2 |
| CD8_T_cells_PD1_low | CCR7, CD160, CD28, CD5, CD8A, CD8B, CRTAM, EOMES, FCRL6, FGFBP2, GZMK, GZMM, IL7R, KCNA3, KLRF1, KLRG1, KLRK1, PRKCQ, PTGDR, PVRIG, S1PR5, SH2D1A, TCF7, ZAP70 |
| CD8_T_cells_PD1_high | CBLB, CD2, CD226, CD244, CD27, CD38, CD8A, CD8B, CRTAM, CTLA4, ENTPD1, FASLG, HAVCR2, ICOS, IL2RA, IL2RB, IRF4, ITGAE, KLRC1, KLRK1, LAG3, LTA, PDCD1, PRDM1, PRKCQ, PVRIG, SH2D1A, SIRPG, TIGIT, TMIGD2, TNFRSF9 |
| NK_cells | CCL5, CD160, CD244, CD247, CD7, CLDND2, CTSW, GZMM, IL2RB, KIR2DL1, KIR2DL2, KIR2DL3, KIR2DL4, KIR2DS2, KIR3DL1, KIR3DL2, KLRB1, KLRC2, KLRC3, KLRD1, KLRF1, KLRK1, LIM2, NCAM1, NCR1, NCR3, NKG7, NMUR1, PRF1, PTGDR, PYHIN1, S1PR5, SAMD3, SH2D1B, TMIGD2, XCL2 |
| Monocytes | AOAH, CCR1, CCR2, CD1D, CD300C, CD300E, CD300LB, CD302, CD33, CECR1, CSF1R, CTSS, CYBB, FCN1, IRF5, MEFV, MS4A6A, PADI4 |
| Macrophages | ADAP2, ADORA3, C1QA, C1QC, C3AR1, C5AR1, CCL7, CCR1, CD14, CD163, CD33, CD4, CD68, CLEC5A, CMKLR1, CSF1R, CYBB, FPR3, IL10, IL4I1, MRC1, MS4A4A, MS4A7, MSR1, PLA2G7, RAB7B, SIGLEC1, TREM2, VSIG4 |
| Macrophages_M1 | C15orf48, C1QC, C3AR1, CCL3, CCL3L3, CCL4L2, CCL7, CD14, CD68, CLEC5A, CSF1R, CXCL3, CYBB, GADD45G, GRAMD1A, IL10, IL12B, IL15RA, IL1RN, IL27, IL4I1, LILRB4, MMP19, PFKFB3, PLA2G7, SIGLEC1, SLAMF7, SOCS3, SOD2, SPHK1, TNF, TNFAIP6, TNIP3, VSIG4 |
| Macrophages_M2 | ADAP2, C1QC, CCR1, CD14, CD163, CD209, CD4, CD68, CLEC5A, CMKLR1, CSF1R, CYBB, FKBP15, FPR3, GPNMB, LACC1, LIPA, MRC1, MS4A4A, MSR1, NPL, PLA2G7, RAB42, SIGLEC1, SLC38A6, STAB1, TREM2, VSIG4 |
| Neutrophils | ADGRE3, ADGRG3, C5AR1, CCR3, CEACAM8, CLEC7A, CSF3R, CXCR1, CXCR2, EVI2B, FCGR2A, FCGR3B, FFAR2, FPR1, FPR2, GLT1D1, IFITM2, KCNJ15, LILRB3, MEFV, MMP25, MNDA, P2RY13, PADI2, PADI4, PGLYRP1, PHOSPHO1, RASGRP4, SIGLEC5, TNFRSF10C, VNN2, VNN3, WAS |
| Fibroblasts | ACTA2, ADAMTS2, CD248, COL16A1, COL1A1, COL1A2, COL3A1, COL4A1, COL5A1, COL6A1, COL6A2, COL6A3, |

TABLE 2-continued

This table specifies, for each of multiple cell types, the list of genes which may be considered specific or semi-specific to that cell type. In some embodiments, these expression levels are used by the machine learning deconvolution techniques developed by the inventors. Exemplary NCBI Accession Numbers for genes mentioned herein are shown in Table 11 below.

| Cell group name | Gene set |
| --- | --- |
| Endothelium | FAP, FBLN2, FBN1, FGF2, LOXL1, MFAP5, PCOLCE, PDGFRA, PDGFRB, TAGLN, THBS2, THY1, VEGFC ANGPT2, APLN, CDH5, CLEC14A, ECSCR, EMCN, ENG, ESAM, ESM1, FLT1, HHIP, KDR, MMRN1, MMRN2, NOS3, PECAM1, PTPRB, RASIP1, ROBO4, SELE, TEK, TIE1, VWF |
| Myeloid_cells | ACRBP, ADAP2, ADGRE2, ADGRE3, ADGRG3, ADORA3, AIF1, AOAH, C1QA, C1QC, C3AR1, C5AR1, CCL7, CCR1, CCR2, CCR3, CD14, CD163, CD1D, CD300A, CD300C, CD300E, CD300LB, CD302, CD33, CD4, CD68, CD86, CEACAM8, CECR1, CLEC5A, CLEC7A, CMKLR1, CSF1R, CSF2RA, CSF3R, CTSS, CXCR1, CXCR2, CYBB, EMILIN2, EVI2B, FCER1G, FCGR1A, FCGR1B, FCGR2A, FCGR3B, FCN1, FFAR2, FGL2, FPR1, FPR2, FPR3, GLT1D1, HCK, HK3, IFI30, IFITM2, IGSF6, IL10, IL4I1, IRF5, ITGAM, ITGAX, KCNJ15, LILRA3, LILRA5, LILRA6, LILRB2, LRRC25, LYN, LYZ, MAFB, MEFV, MMP25, MNDA, MPP1, MRC1, MS4A4A, MS4A6A, MSR1, NCF2, NINJ1, OSCAR, P2RX1, P2RY13, PADI2, PADI4, PGLYRP1, PHOSPHO1, PILRA, PLA2G7, PLEK, PRKCD, PSAP, RAB7B, RASGRP4, RNASE6, RP2, SIGLEC1, SIGLEC14, SIGLEC5, SIGLEC9, SIRPB2, SPI1, STX11, TLR2, TNFRSF10C, TNFSF13, TREM2, TYROBP, VNN2, VNN3, VSIG4, WAS |
| Lymphocytes | ACAP1, ANXA2R, APOBEC3D, APOBEC3G, BANK1, BLK, CAMK4, CARD11, CBLB, CCL5, CD160, CD19, CD2, CD22, CD226, CD244, CD247, CD27, CD37, CD3D, CD3E, CD3G, CD48, CD5, CD6, CD69, CD7, CD79A, CD79B, CLDND2, CLEC17A, CLEC2D, CPNE5, CR2, CTSW, CXCR5, CYFIP2, DEF6, DERL3, EAF2, ETS1, EVL, FAM129C, FCMR, FCRL1, FCRL2, FCRL3, FCRL5, FCRLA, FKBP11, FLT3LG, GLCCI1, GPR174, GPR18, GRAP2, GZMM, HLA-DOB, IGHG1, IGHG3, IGHM, IGKC, IGLL5, IKZF1, IKZF3, IL16, IL2RB, IL2RG, ITGB7, ITK, KCNA3, KIR2DL1, KIR2DL2, KIR2DL3, KIR2DL4, KIR2DS2, KIR3DL1, KIR3DL2, KLRB1, KLRC2, KLRC3, KLRD1, KLRF1, KLRK1, LAG3, LAT, LAX1, LCK, LIM2, LTA, LY9, MAP4K1, MS4A1, MZB1, NCAM1, NCR1, NCR3, NFATC2, NKG7, NLRC3, NMUR1, P2RY10, P2RY8, PARP15, PAX5, PIK3IP1, POU2AF1, PPP1R16B, PPP3CC, PRF1, PTGDR, PTPRCAP, PVRIG, PYHIN1, RASAL3, RASGRP1, RASGRP2, RHOH, RLTPR, S1PR5, SAMD3, SEC11C, SH2D1B, SIRPG, SIT1, SKAP1, SLA2, SLAMF6, SP140, SPIB, SSR4, STAP1, TBC1D10C, TBX21, TCF7, TESPA1, TMC6, TMC8, TMIGD2, TNFRSF13B, TNFRSF13C, TNFRSF17, TRAC, TRAF3IP3, TRAT1, TRBC2, TRDC, TRGC1, TRGC2, TXNDC11, TXNDC5, UBASH3A, VPREB3, XCL2, ZBED2, ZNF101 |

Figure 2A:
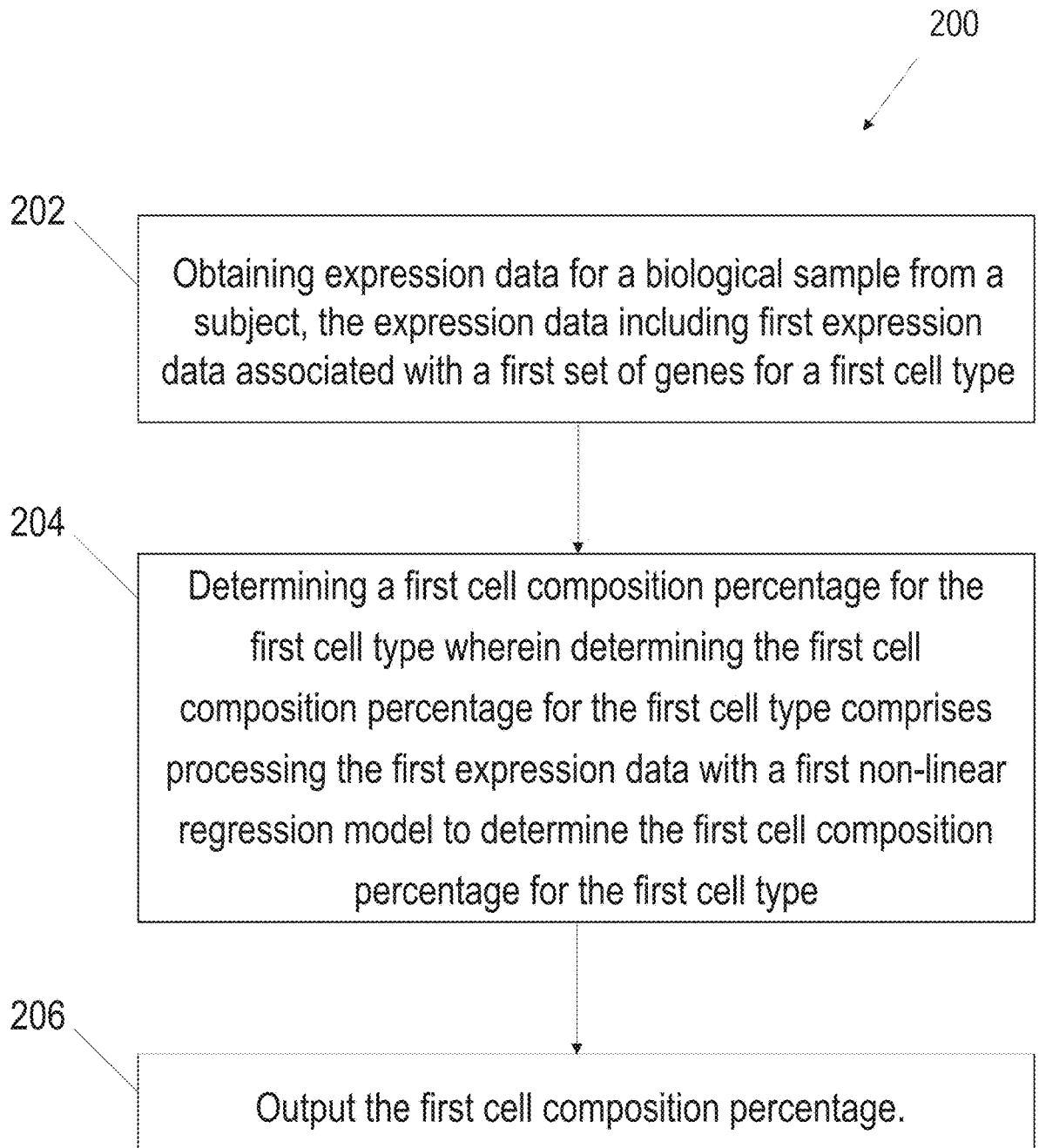
FIG. 2A is a flowchart depicting an exemplary non-linear method for determining a cell composition percentage based on expression data, according to some embodiments of the technology described herein.

FIG. 2A is a flowchart depicting a method 200 for determining a cell composition percentage for at least one cell type. In some embodiments, the method 200 may be carried out on a computing device (e.g., as described herein including at least with respect to FIG. 10). For example, the computing device may include at least one processor, and at least one non-transitory storage medium storing processor-executable instructions which, when executed, perform the acts of method 200. The method 200 may be carried out, for example, in a system such as system 100 (which may include, for example, a clinical setting or a laboratory setting), by one or more computing devices such as by computing device 108.

At act 202, the method 200 begins with obtaining expression data for a biological sample from a subject. In some embodiments, obtaining expression data may include obtaining expression data from a biological sample that has been previously obtained from a subject using any suitable techniques. In some embodiments, obtaining the expression data may include obtaining expression data that has been previously obtained from a biological sample (e.g., obtaining the expression data by accessing a database.) In some embodiments, the expression data is RNA expression data. Examples of RNA expression data are provided herein. In some embodiments, the subject may have, be suspected of having, or be at risk of having cancer. As described herein including with respect to FIG. 1A, the biological sample may comprise a biopsy (e.g., of a tumor or other diseased tissue of the subject), any of the embodiments described herein including with respect to the "Biological Samples" section, or any other suitable type of biological sample. In some embodiments, the origin or preparation of the expression data may include any of the embodiments described with respect to the "Expression Data" and "Obtaining RNA expression data" sections. For example, the expression data may be RNA expression data extracted using any suitable techniques. As another example, the expression data obtained at act 202 may comprise RNA expression data measured in TPM.

In some embodiments, the expression data may be stored on at least one storage medium and accessed as part of act 202. For example, the expression data may be stored in one or more files or in a database, then read. In some embodiments, the at least one storage medium storing the RNA expression data may be local to the computing device (e.g., stored on the same at least one non-transitory storage medium), or may be external to the computing device (e.g., stored in a remote database or a cloud storage environment). The expression data may be stored on a single storage medium or may be distributed across multiple storage mediums.

In some embodiments, the expression data of act 202 may include first expression data associated with a first set of genes associated with a first cell type (e.g., a cell type of the cell types and/or subtypes being analyzed in the biological sample). In some embodiments, the first set of genes may comprise genes that are specific and/or semi-specific to the first cell type, as described herein at least with respect to FIG. 1E. For example, for the endothelium cell type, the set of genes may comprise: ANGPT2, APLN, CDH5, CLEC14A, ECSCR, EMCN, ENG, ESAM, ESM1, FLT1, HHIP, KDR, MMRN1, MMRN2, NOS3, PECAM1, PTPRB, RAWL ROBO4, SELE, TEK, TIE1, and/or VWF. In some embodiments, the first set of genes may be the same as a set of genes, or a subset of a set of genes, used as part of training a corresponding non-linear regression model for the cell type, as described herein including at least with respect to FIGS. 4-6.

At act 204, the method 200 proceeds with determining a first cell composition percentage for at least the first cell type. As shown, determining a first cell composition percentage for the first cell type may comprise processing first expression data associated with a first set of genes for the first cell type with a first non-linear regression model (e.g., of the one or more non-linear regression models) to determine the first cell composition percentage for the first cell type. For example, the first expression data may be provided as input to the first non-linear regression model. In some embodiments, other information may be provided as part of the input to the non-linear regression model. For example, a median of the expression data may be included as part of the input to the non-linear regression model. In some embodiments, any other suitable information may additionally or alternatively be provided as part of the input (e.g., an average of the expression data, a median or average of a subset of the expression data, or any other suitable statistics derived from or otherwise relating to the expression data).

In some embodiments, parts of act 204 may be repeated and/or performed in parallel for each cell type and/or subtype being analyzed. For example, a subset of the expression data may be provided as input to each non-linear regression model for each respective cell type and/or subtype.

In some embodiments, the output of the non-linear regression model may comprise information representing an estimated percentage of RNA from the first cell type in the sample. As described herein including at least with respect to FIG. 2C and FIG. 3C, the estimate percentage of RNA from the first cell type may be used to calculate a corresponding cell composition percentage for the first cell type. In some embodiments, the techniques described herein including at least with respect to FIG. 3C may be applied as part of processing the non-linear regression model, such that the output of the non-linear regression model may be an estimated cell composition percentage for the first cell type rather than an estimated percentage of RNA.

In some embodiments, process 200 then proceeds to act 206 for outputting the first cell composition percentage. Regardless of the architecture or input(s) to the non-linear regression models, including the non-linear regression model for the first cell type, the output(s) of the one or more non-linear regression models may be combined, stored, or otherwise post-processed as part of method 200. For example, the cell composition percentages for each cell type may be stored locally on the computing device used to perform method 200 (e.g., on the non-transitory storage medium). In some embodiments, the cell composition percentages may be stored in one or more external storage mediums (e.g., such as a remote database or cloud storage environment).

Figure 2B:
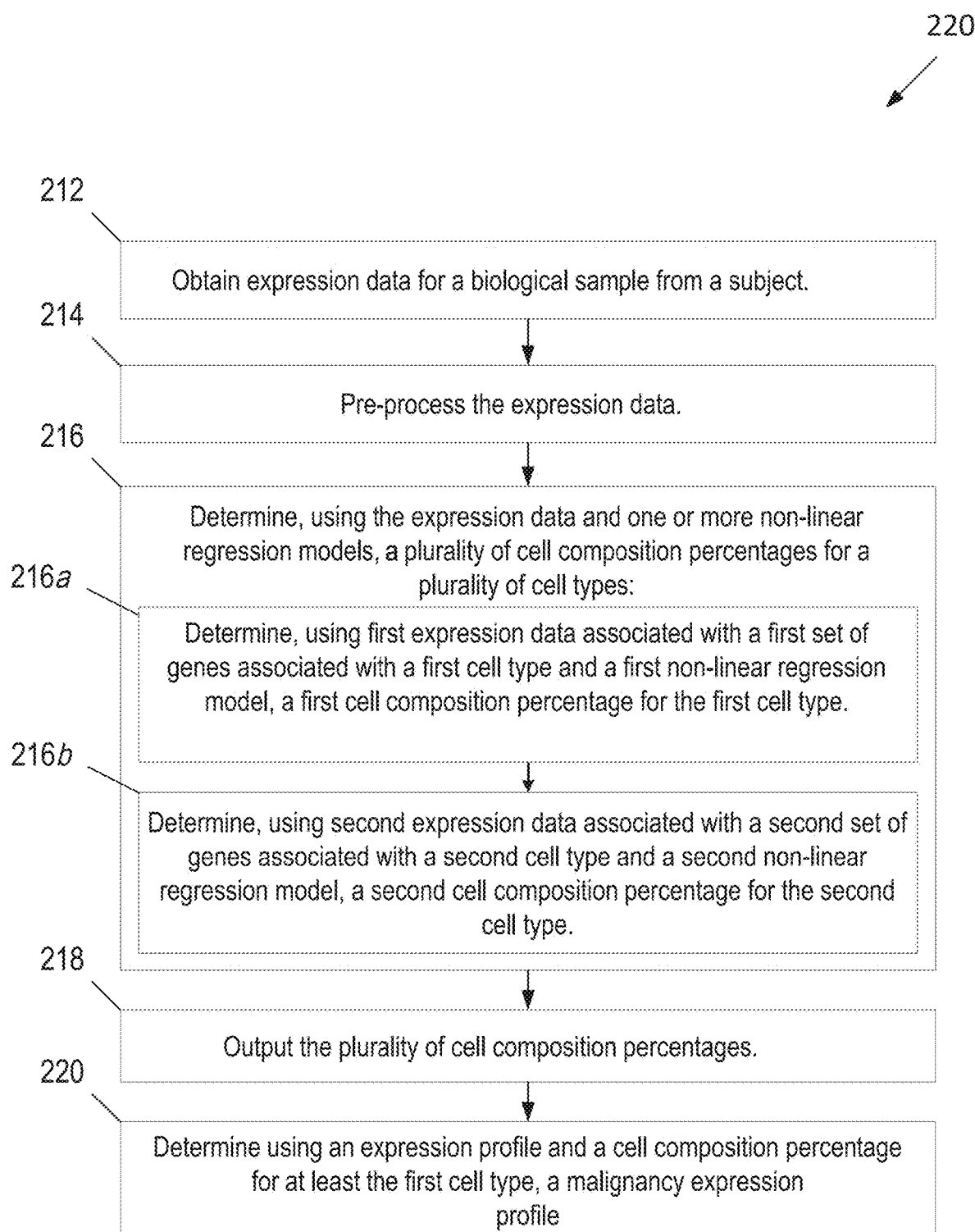
FIG. 2B is a flowchart illustrating an example implementation of method 200 for determining a cell composition percentage based on expression data, according to some embodiments of the technology described herein.

FIG. 2B is an example implementation of method 200 for determining a cell composition percentage based on expression data. In some embodiments, implementing method 200 may include any suitable combination of acts included in the example flowchart of FIG. 2B. In some embodiments, implementing method 200 may include additional or alternative steps that are not shown in FIG. 2B. For example, executing method 200 may include every act included in the example flowchart. Alternatively, method 200 may include only a subset of the acts included in the example flowchart (e.g., acts 212 and 216, acts 212, 214, 216, and 218, acts 212, 216, and 220, etc.).

In some embodiments, the example implementation 220 begins at act 212, where expression data is obtained for a biological sample from a subject. Obtaining expression data for a biological sample from a subject is described herein above including with respect to act 202 of FIG. 2A.

In some embodiments, act 212 may include obtaining first expression data and second expression data. The first expression data may be associated with a first set of genes that is associated with a first cell type, while the second expression data may be associated with a second set of genes that is associated with a second cell type. For example, the first expression data may be associated with a first set of genes that is associated with B cells, while the second expression data may be associated with a second set of genes that is associated with T cells. Additionally or alternatively, the first expression data may be associated with a first set of genes associated with a first cell subtype, while the second expression data may be associated with a second set of genes associated with a second cell subtype. For example, the first expression data may be associated with a first set of genes associated with CD4+ cells, while the second expression data may be associated with a second set of genes associated with CD8+ cells. Techniques for identifying genes associated with different cell type and/or subtypes are described herein including with respect to the "Gene Selection & Specificity" section.

In some embodiments, the example method 220 proceeds to act 214, where the expression data is pre-processed. In some embodiments, the pre-processing may make the expression data suitable to be processed using the one or more non-linear regression models. For example, the expression data may be sorted, combined, organized into batches, filtered, or pre-processed with any other suitable techniques. In some embodiments, techniques for processing the expression data may include any of the embodiments described with respect to the "Alignment and annotation," "Removing non-coding transcripts," and "Conversion to TPM and gene aggregation" sections.

After the expression data is pre-processed, example method 220 proceeds to act 216, where a plurality of cell composition percentages may be determined for a plurality of cell types using the expression data and one or more non-linear regression models (e.g., at least five, at least ten, at least fifteen, models.) In some embodiments, each nonlinear regression model may be trained according to the techniques described herein including at least with respect to FIGS. 4-6.

In some embodiments, a separate non-linear regression model may be used to estimate a cell composition percentage for each cell type and/or subtype. For example, act 216 may include act 216a and act 216b, each of which includes using a separate non-linear regression model trained for determining cell composition percentages for the first and second cell types and/or subtypes, respectively. Act 216a includes determining a first cell composition percentage for the first cell type using the first expression data and a first non-linear regression model. Act 216b includes determining a second cell composition percentage for the second cell type using the second expression data and a second non-linear regression model. In some embodiments, act 216 may include only one of acts 216a and 216b. In some embodiments, act 216 may include using one or more additional non-linear regression models for determining cell composition percentages for one or more other cell types (e.g., a third cell type or subtype). An example implementation of act 216a is described herein including with respect to FIG. 2C.

In some embodiments, example method 220 proceeds to act 218 for outputting the plurality of cell composition percentages. In some embodiments, the plurality of cell composition percentages may be output through a graphical user interface, saved to memory, transmitted to one or more other computing devices and/or output in any other suitable way.

In some embodiments, techniques may be used to post-process the plurality of cell composition percentages output at act 218 and/or the expression data obtained at act 212. As described herein, post-processing techniques may include using the cell composition percentages and expression data to determine a malignancy expression profile for the biological sample at act 220. A malignancy expression profile may include information indicative of the expression of malignant cells included in the biological sample. For example, this may include the expression of different genes associated with the malignant cells. In some embodiments, determining the malignancy expression profile may include (a) estimating the expression profile for TME cells in the biological sample and (b) subtracting the expression of the TME cells from the total expression (e.g., bulk expression data, expression data obtained at act 212, etc.) of the biological sample. An example method for determining a malignancy expression profile is described herein including with respect to FIG. 3D.

Figure 2C:
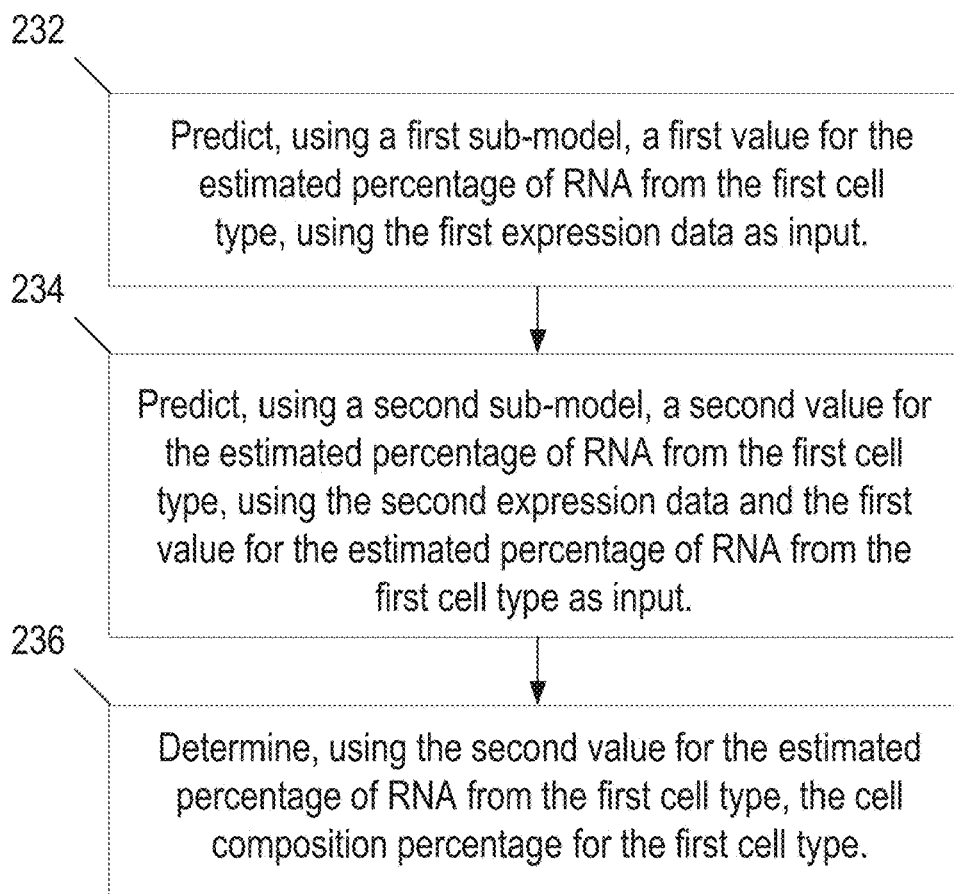
FIG. 2C is a flowchart illustrating an example implementation of act 216a of method 200, according to some of the embodiments of the technology described herein.

FIG. 2C shows an example implementation of act 216a for determining, using the first expression data and the first non-linear regression model, a first cell composition percentage for the first cell type. As shown, in some embodiments, the first non-linear regression model may include a first sub-model and/or a second sub-model for processing the first expression data (e.g., as shown in FIG. 3C).

In some embodiments, the first expression data may include first expression data associated with a first set of genes associated with the first cell type, as well as second expression data associated with a second set of genes associated with the first cell type.

In some embodiments, the example implementation begins at act 232, for predicting a first value for the estimated percentage of RNA from the first cell type, using a first sub-model. In some embodiments, the first expression data associated with the first set of genes and/or any other input information may be provided as input to the first sub-model of the non-linear regression model, and the output may be a predicted percentage of RNA from the first cell type.

In some embodiments, after predicting the first value, the example implementation proceeds to act 234, for predicting a second value for the estimated percentage of RNA from the first cell type, using a second sub-model. In some embodiments, the second expression data associated with the second set of genes may be provided as input to the second sub-model of the non-linear expression model in addition to the prediction from the first sub-model and/or any other input information provided at the first sub-model. Additionally or alternatively, the first expression data associated with the first set of genes may be provided as input to the second sub-model. According to some embodiments, predictions from multiple non-linear regression models (e.g., the output of the first sub-model of each non-linear regression model for each cell type) may be provided as input to the second sub-model of the non-linear regression model for the first cell type. Regardless of the input to the second sub-model, the output of the second sub-model of the non-linear regression model may be an estimated percentage of RNA from the first cell type in the sample. The output of the second sub-model may comprise the output of the non-linear regression model for the first cell type, in some embodiments.

In some embodiments, the non-linear regression model may comprise more than two sub-models. For example, the second sub-model may be repeated any number of times, with the predictions from one or more of the prior sub-models being included as input each time.

In some embodiments, the example implementation then proceeds to act 236 for determining, using the second value for the estimated percentage of RNA from the first cell type, the cell composition percentage for the first cell type. In some embodiments, determining the estimated percentage of RNA from the first cell type may include (a) estimating the number of cells of the first type included in the biological sample and (b) estimating the total number of cells included in the biological sample (e.g., using equation 350.) Estimating the number of cells of the first type may include comparing the estimated percentage of RNA (e.g., $R_{cell}$ of equation 350) to an RNA per cell coefficient (e.g., $A_{cell}$ of equation 350.) Estimating the total number of cells may include estimating the number of cells of each cell type, then summing those values. Techniques for estimating cell composition percentages are described herein including with respect to FIG. 3C.

Figure 3A:
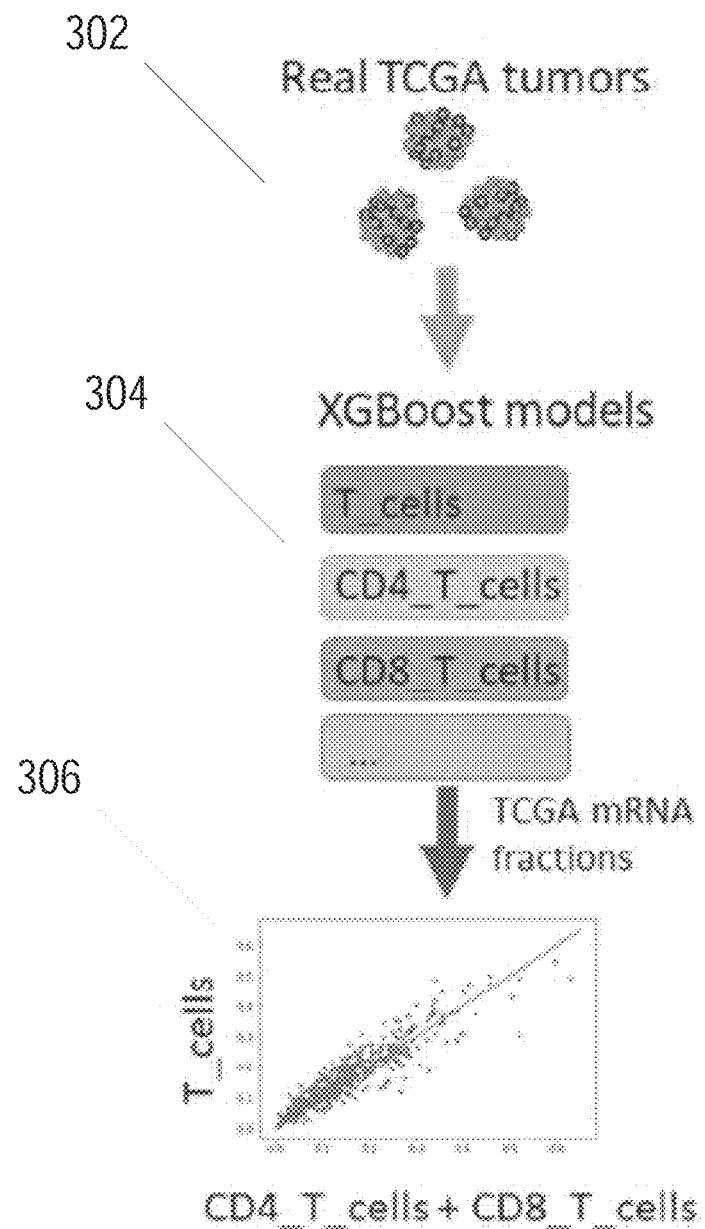
FIG. 3A is a diagram depicting use of a machine learning method for determining RNA percentages based on RNA expression data, according to some embodiments of the technology described herein.

FIG. 3A is a diagram depicting an illustrative use of a machine learning method for determining RNA percentages based on RNA expression data. In the illustrated example, RNA expression data from primary tumor samples 302 available on the TCGA database is processed according to the machine learning techniques described herein including at least with respect to FIGS. 2A-2C, in order to arrive at corresponding estimated RNA percentages 306 for T cells, CD4+ T cells, CD8+ T cells.

In the illustrated example, the RNA expression data for the tumor samples 302 is obtained from an online database of RNA expression data (e.g., from The Cancer Genome Atlas (TCGA) database, in this example). In some embodiments, the RNA expression data may be obtained from any suitable source, including one or more databases such as TCGA, or directly from a biological sample (e.g., as described herein including at least with respect to FIG. 1A).

Regardless of how the RNA expression data is obtained from tumor samples 302, the RNA expression data may be processed using non-linear regression models 304. According to some embodiments, the non-linear regression models 304 may be implemented using a gradient boosting technique (e.g., as implemented in XGBoost) as described herein including at least with respect to FIGS. 4-6. According to some embodiments, as described herein including with respect to FIGS. 2A-2C, non-linear regression models 304 may comprise separate non-linear regression model for each of multiple cell types. In the illustrated example, the non-linear regression models 304 include a non-linear regression model for T cells, a non-linear regression model for CD4+ T cells, and a non-linear regression model for CD8+ T cells. As shown, additional non-linear regression models for one or more additional cell types and/or subtypes may be provided, in some embodiments.

In some embodiments, the input to the non-linear regression models 304 may comprise a select subset of the RNA expression data for each non-linear regression model. For example, as described herein including with respect to FIGS. 2A-2C, the input to a non-linear regression model for a particular cell type may comprise RNA expression data for specific and/or semi-specific genes for that cell type. For instance, in the illustrated example, the non-linear regression model for T cells may take as input RNA expression data for genes: CAMK4, CBLB, CD2, CD226, CD3D, CD3E, CD3G, CD48, CD5, CD6, CD7, FLT3LG, ITK, KCNA3, KLRB1, LAGS, LAT, LCK, LTA, SIRPG, SIT1, SLA2, TBX21, TCF7, TESPA1, TRAC, TRAF3IP3, TRAT1, TRBC2, TRDC, TRGC1, TRGC2, UBASH3A, ZBED2. In some embodiments, other information about the RNA expression data (e.g., a median of the RNA expression data, or any other suitable statistics) may be additionally or alternatively provided as input to the non-linear regression models.

In some embodiments, the output of non-linear regression models 304 may be RNA percentages 306 for respective cell types and/or subtypes. For example, the non-linear regression model for T cells may produce as its output a predicted percentage of RNA from T cells in the input RNA expression data. Similarly, the non-linear regression model for CD 4 T cells may produce as its output a predicted percentage of RNA from CD 4 T cells, and the non-linear regression model for CD 8 T cells may produce as its output a predicted percentage of RNA from CD 8 T cells. As described herein with respect to FIG. 3C, the predicted percentages of RNA may be used to calculate corresponding cell composition percentages for some or all of the cell types and/or subtypes being analyzed.

In the illustrated example, a plot comparing the predictions for T cells and the predictions for CD 4 T cells+CD 8 T cells is shown. In some embodiments, the sum of the predictions for the subtypes may or may not be equal to the prediction for the type comprising those subtypes. For example, the sum of predictions for CD 4 T cells and CD 8 T cells may exceed the prediction for T cells, or the sum of predictions for CD 4 T cells and CD 8 T cells may be lower than the prediction for T cells. In some embodiments, the sum of the subtype predictions may be equal to the total type prediction, and/or the subtype predictions may be normalized or adjusted so that their sum is equal to the total type prediction.

Figure 3B:
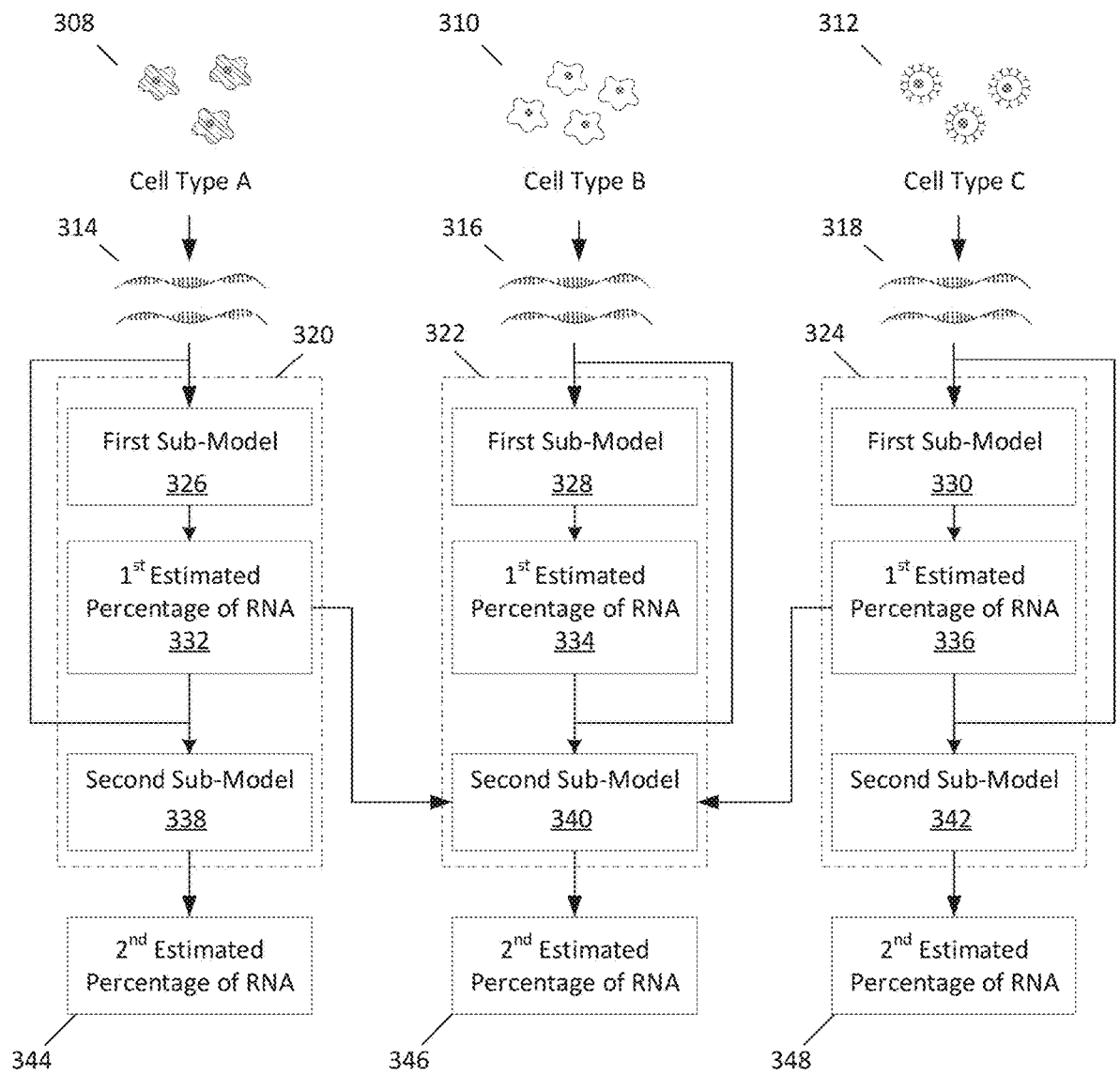
FIG. 3B is a diagram depicting use of a non-linear regression model comprising sub-models for determining RNA percentages based on RNA expression data, according to some embodiments of the technology described herein.
Figure 3C:
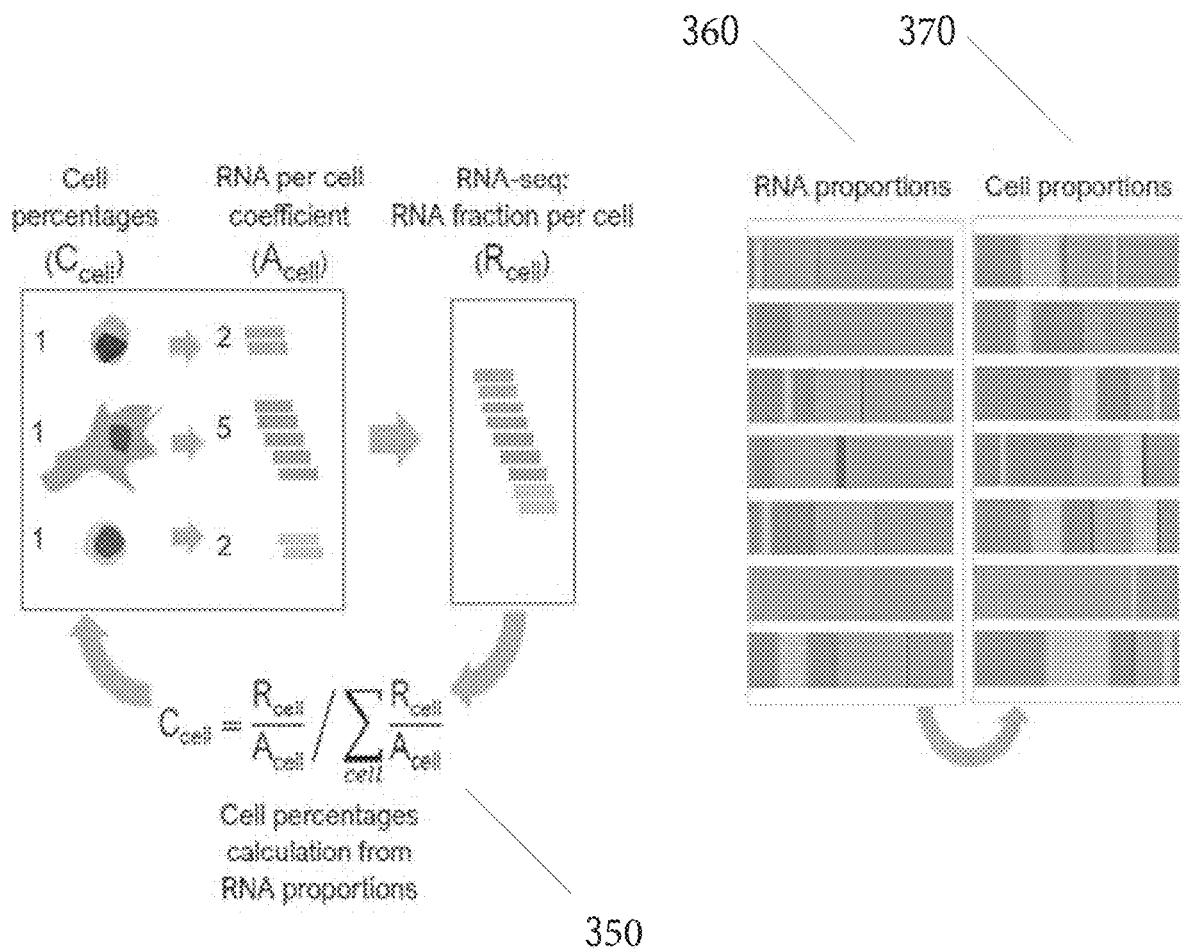
FIG. 3C is a diagram depicting a method for determining cell composition percentages based on RNA percentages, according to some embodiments of the technology described herein.

FIG. 3B is a diagram depicting use of non-linear regression models 320, 322, 324 comprising first sub-models 326, 328, 330 and second sub-models 338, 340, 342 for determining RNA percentages based on RNA expression data.

As shown in the illustrative embodiment of FIG. 3B, a different non-linear regression model 320, 322, 324 is used to process expression data 314, 316, 318 for genes associated with each cell type: cell type A 308, cell type B 310, and cell type C 312. In some embodiments, each example non-linear regression model includes a first sub-model 326, 328, 330, for generating a first value 332, 334, 336 for the estimated percentage of RNA from each cell type, and a second sub-model 338, 340, 342 for generating a second value 344, 346, 348 for the estimated percentage of RNA from each cell type.

As a non-limiting example for using a non-linear regression model that includes one or more sub-models, consider the non-linear regression model 322 trained to estimate an RNA percentage for cell type B 310. In some embodiments, expression data 316 may be obtained from a set of genes associated with cell type B 310 and used as input to the non-linear regression model 322. For example, cell type B 310 may include immune cells and the expression data 316 may include expression data for the genes ADAP2, ADGRE3, ADGRG3, C1QA, C1QC, and C3AR1 (e.g., from the gene set associated with immune cells listed in Table 2.) In some embodiments, at least some of the expression data 316 (e.g., expression data associated with a subset of genes, expression data associated with all the genes, etc.) is used as input to the first sub-model 328. For example, a subset of the expression data 316 including expression data for the genes ADAP2, ADGRE3, and ADGRG3 may be used input. The first sub-model may then process the input expression data to determine a first value 334 of the estimated percentage of RNA from cell type B 310.

In some embodiments, the example non-linear regression model 322 may include a second sub-model 340 to generate a second value 346 of the estimated percentage of RNA from cell type B 310. In some embodiments, the second sub-model 340 may use one or more inputs to generate the second value 340. For example, in some embodiments, at least some of the expression data 316 may be used as input. In some embodiments the expression data may include the same expression data input to the first sub-model 328 (e.g., expression data for the genes ADAP2, ADGRE3, and ADGRG3.) In some embodiments, the expression data may include the same expression data input to the first sub-model, as well as additional expression data (e.g., expression data for the genes ADAP2, ADGRE3, ADGRG3, C1QA, and C3AR1.) In some embodiments, the expression data may include expression data different from the expression data input to the first sub-model (e.g., expression data for the genes C1QA, C1QC, and C3AR1.)

Additionally or alternatively, in some embodiments, the second sub-model 340 may take as input estimate percentages of RNA output by the first sub-models 326, 330 of non-linear regression models 320, 324 for other cell types 308, 312. As shown, the second sub-model 340 for cell type B 310 takes as input the first value 332 for the estimate percentage of RNA from cell type A 308 and the first value 336 for the estimate percentage of RNA from cell type C 312. This type of input may be informative when trying to determine the percentage of RNA from a cell type that is associated with a same gene or same set of genes as another cell type(s). For example, if cell type B 310 is associated with a same gene, gene X, as cell type C 312, then expression data obtained for gene X may not be highly informative about which of the two cell types is present in the biological sample, since it may be unclear which cell type generated the expression data. However, consider a scenario where the first sub-model 330 outputs 0% as the first value 336 of the estimated percentage of RNA determined for cell type C. This indicates that there are no cells of cell type C 312 in the biological sample. As a result, any expression data obtained for gene X must have been expressed by cell type B 310. In some embodiments, the second sub-model 340 can use the first values 332, 336 to make such inferences.

In some embodiments, the output of the second sub-model 340 is a second value 346 for the estimated percentage of RNA from cell type B 310. As described herein including with respect to FIG. 3D, the estimated RNA percentages may be processed to determine cell composition percentages for each of the cell types.

FIG. 3C is a diagram depicting a method for determining cell composition percentages 370 based on RNA percentages 360. For example, the method of FIG. 3C may be applied to RNA percentages predicted according to the techniques described herein including with respect to FIGS. 2 and 3A, in order to arrive at predictions for cell composition percentages for some or all of the cell types and/or subtypes being analyzed.

As shown in the figure, obtaining cell composition percentages based on RNA percentages may comprise applying equation 350 to the RNA percentages for each cell type. In some embodiments, equation 350 may be applied independently to each RNA percentage (e.g., in sequence), or may be applied to some or all of the RNA percentages together (e.g., in parallel) in some embodiments. In some embodiments, equation 350 may be applied initially to RNA percentages for cell types which are not subsets of one another. In some embodiments, equation 350 may subsequently be applied to RNA percentages for cell types that are a subtype of one or more initially used cell types. In some embodiments, the calculation of cell composition percentages for cell subtypes may be modified based on the initially calculated cell composition percentages. For example, in some embodiments, subsequently calculated cell composition percentages for cell subtypes may be normalized or otherwise adjusted such that they sum to the cell composition percentage for the total cell type (i.e., the initially-calculated cell type of which they are subtypes).

For a given cell type cell, equation 350 is:

$$C_{cell} = \frac{R_{cell}}{A_{cell}} \bigg/ \sum_{cells} \frac{R_{cell}}{A_{cell}}$$

Where $C_{cell}$ is the cell composition percentage for the cell type, $R_{cell}$ is the RNA percentage for the cell type, and $A_{cell}$ is an RNA per cell coefficient. As shown in equation 350, the denominator may comprise a sum over all cell types and/or subtypes being analyzed (cells). As such, the expression $$\frac{R_{cell}}{A_{cell}}$$

may be initially computed for all cell types and/or subtypes, then used to compute individual $C_{cell}$ values for each cell type and/or subtype.

According to some embodiments, an RNA percentage for a cell type may be represented as a fraction or decimal (e.g., for purposes of calculation with equation 350). In some embodiments, the RNA percentages used with equation 350 may sum to one (e.g., $\Sigma_{cells} R_{cell} = 1$). In some embodiments, if the sum of the RNA percentages is less than one, then an $R_{other}$ expression may be introduced, which may be equal to $1 - \Sigma_{cells} R_{cell}$. In some embodiments, if the sum of the RNA percentages is greater than one, then $R_{other} = 0$ and the RNA percentages may be normalized such that they sum to one.

In some embodiments, equation 350 includes an RNA per cell coefficient $A_{cell}$, which may represent an RNA concentration per cell. The inventors have recognized and appreciated that the abundance of RNA per cell may depend on the cellular size and/or other factors. As such, different cell types may contribute a different amount of RNA to the bulk sample. The RNA per cell coefficient can be used to allow the conversion of RNA percentages to corresponding cell composition percentages. In some embodiments, the RNA per cell coefficient $A_{cell}$ may be determined as part of a model training process (e.g., from simulated or artificial data with known percentages of the different cell types.) In some embodiments, the RNA per cell coefficient $A_{cell}$ may be determined experimentally for some or all cell types. For example, RNA per cell coefficients may be obtained by accessing data relating to RNA expression for each cell type (e.g., from available scientific literature, such as PMID: 29130882, PMID: 30726743, or estimated from single cell data, using average or non-linearly transformed UMI count per cell type) and using that data to determine a corresponding RNA per cell coefficient (e.g., by analyzing purity and/or histological TCGA lymphocyte data, for example) for each cell type.

In some embodiments, the RNA per cell coefficients may be tissue specific, and could vary based on the disease being analyzed (e.g., from cancer to cancer). In some embodiments, the RNA per cell coefficient may be tissue agnostic, and may not vary based on a disease being analyzed (e.g., because non-malignant microenvironment cells may be represented by the same or substantially similar cellular phenotypes even across different cancers, tissues, or diseases). In the latter case, data from multiple types of cancers, tissues, diseases, etc. may be combined in order to calculate the RNA per cell coefficients. For example, in some embodiments, more than 10,000 different cancer tissues samples from TCGA were analyzed as part of determining RNA per cell coefficients for cell types. The inventors have recognized and appreciated that non-malignant cell composition percentages may correspond to the tumor cellularity defined by histology and WES analysis. As such, in some embodiments, determining RNA per cell coefficients may comprise aligning non-malignant cell composition percentages obtained from RNA to cell composition percentages obtained from DNA in order to develop coefficients for RNA per cell type.

It should be appreciated that the techniques described herein are not limited to be applied only to RNA-seq data. For example, some embodiments of the technology described herein may be applied to microarray data. To this end, the expression values may be normalized to lie in a range similar to the values of the transcripts per million (TPM) for RNA-seq (for example, make the sum of the expressions be 1 million) and optionally use a linear scale.

Figure 3D:
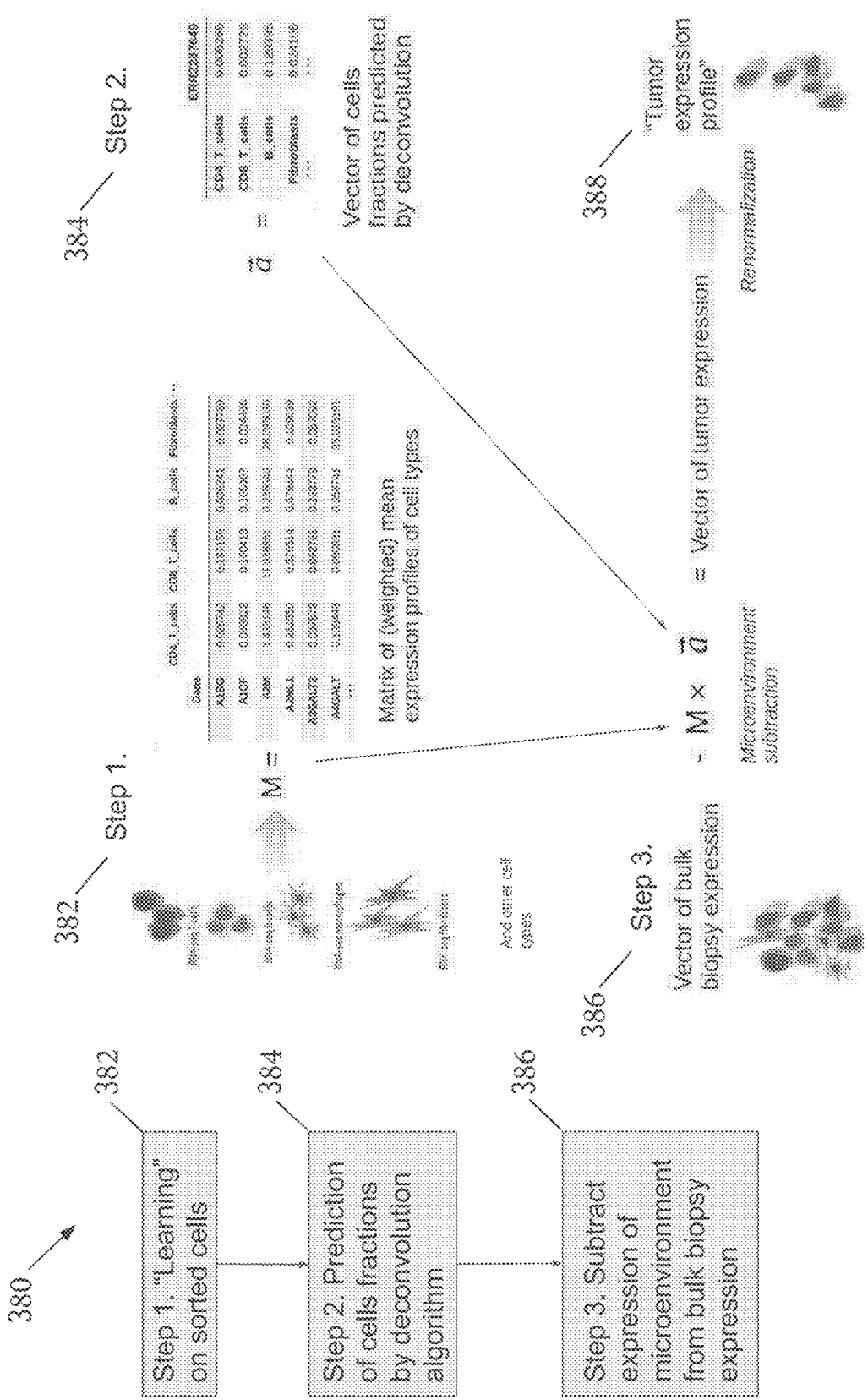
FIG. 3D is a diagram depicting an example method for determining malignancy expression profiles based on cell composition percentages, according to some embodiments of the technology described herein.

FIG. 3D is a diagram depicting an example method 380 for determining malignancy expression profiles based on cell composition percentages, according to some embodiments of the technology described herein. This may include obtaining a biological sample (e.g., a biopsy) and determining the expression (e.g., the expression of individual genes) of malignant cells included in the biological sample. In some embodiments, this may include removing the expression of TME cells from the overall expression of the biological sample (e.g., bulk biopsy expression).

As shown, the example method includes three steps. The first step 382 includes determining mean expression profiles of different, non-malignant cell types. In some embodiments, this may include using expression data from sorted cell types. For example, this may include obtaining and using RNA-seq data from T cells, B cells, macrophages, fibroblasts, and any other suitable cell type that may be included in a TME. In some embodiments, the cell types may exclude tumor (e.g., malignant) cells. A mean expression profile may include the mean expression of a set of genes for each cell type.

The example method then proceeds to the second step 384 for predicting the cell composition fractions using cellular deconvolution techniques. The cell composition fractions may be indicative of the fraction of each cell type in a biological sample (e.g., a biopsy.) As shown, this may include generating a vector of cell composition fractions. Using cellular deconvolution techniques may include any of the embodiments described herein, including with respect to FIGS. 1-3C.

The mean expression profiles of different cell types included in the TME (e.g., first step 382) and the fraction of each of those cell types in the biological sample (e.g., second step 384) may be used to estimate the expression of each cell type in the biological sample. As shown, the third step 386 may include determining the product of the matrix of expression profiles and the vector of cell fractions. The resulting vector is an estimate expression profile of the TME cells in the biological sample.

In some embodiments, determining the tumor expression profile may include subtracting the TME expression profile from the bulk expression of the biological sample (e.g., the bulk biopsy expression). As shown, this may include subtracting the vector generated for the expression profile of the TME cells from the vector of bulk expression.

Figure 4:
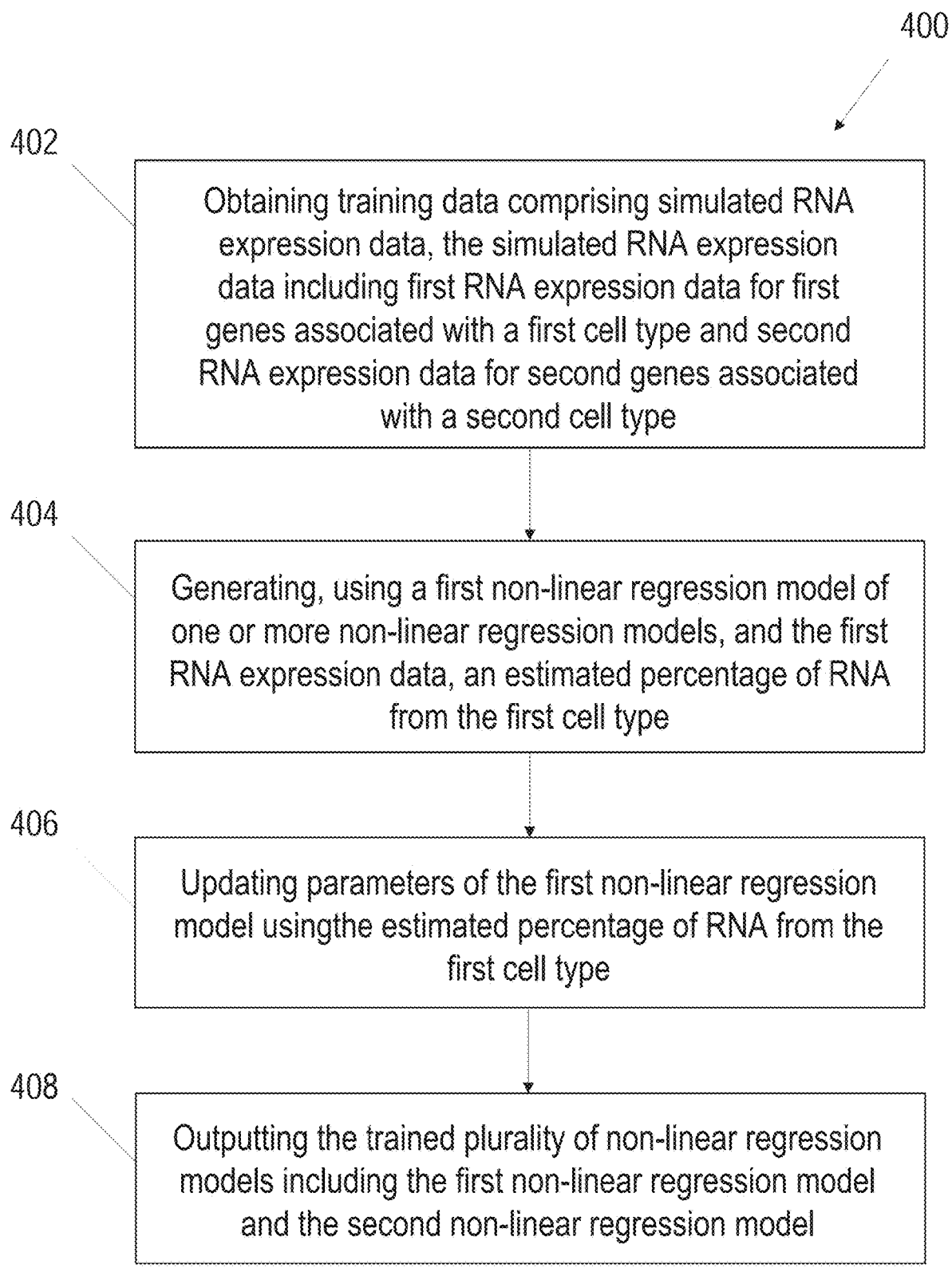
FIG. 4 is a flowchart depicting an exemplary method for training one or more non-linear regression models to determine cell composition percentages based on RNA expression data, according to some embodiments of the technology described herein.

FIG. 4 is a flowchart depicting a method 400 for training one or more non-linear regression models to determine cell composition percentages based on RNA expression data. As described herein, the method 400 may comprise training one or more non-linear regression models (e.g., at least five, at least ten, at least fifteen non-linear regression models) to estimate cell composition percentages for a corresponding one or more cell types in a biological sample. In some embodiments, a separate non-linear regression model may be trained for each cell type and/or subtype, such that each non-linear regression model is trained to estimate cell composition percentages for a particular cell type in the biological sample.

Figure 10:
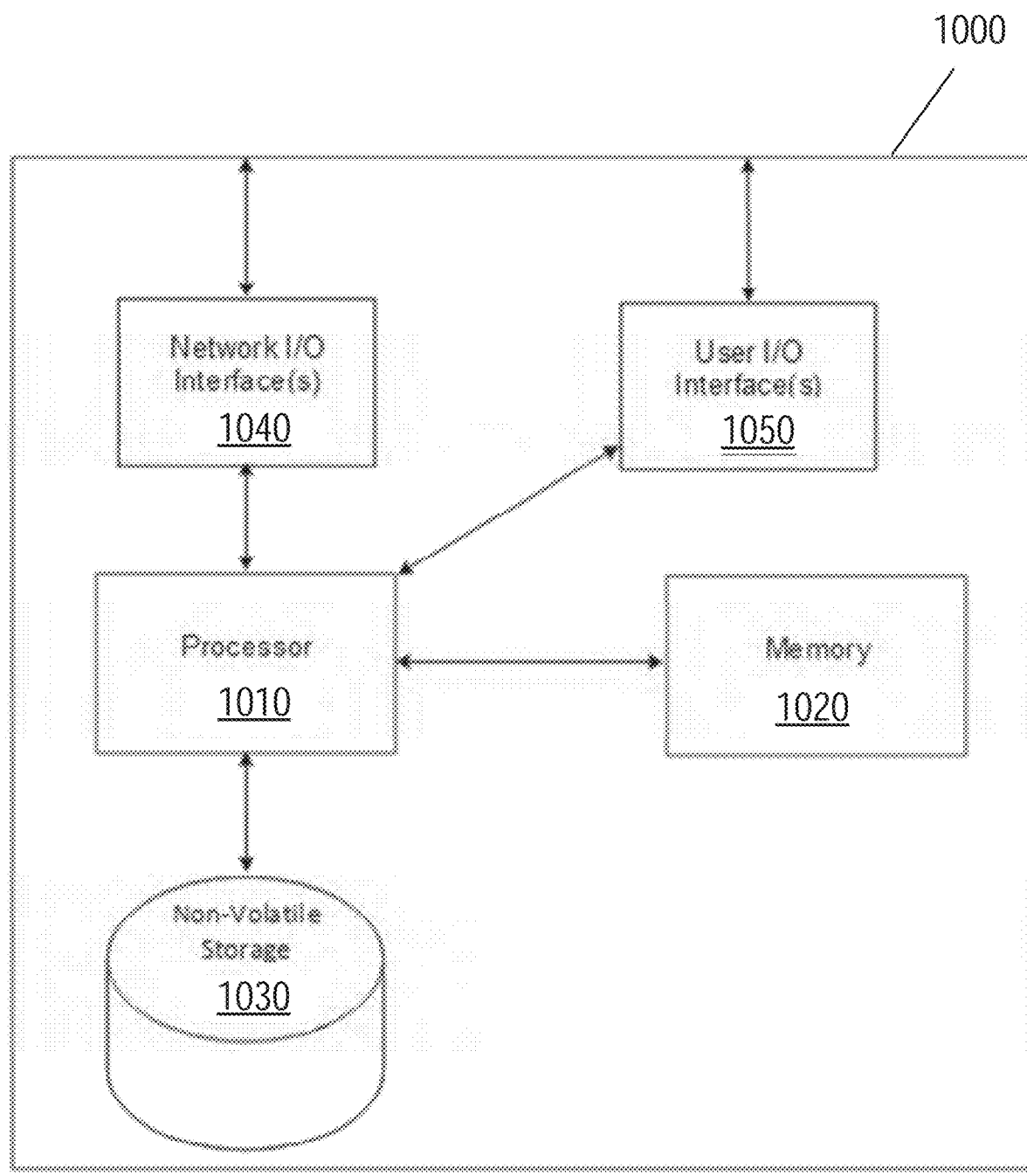
FIG. 10 depicts an illustrative implementation of a computer system that may be used in connection with some embodiments of the technology described herein.

In some embodiments, the method 400 may be carried out on a computing device (e.g., as described herein including at least with respect to FIG. 10). For example, the computing device may include at least one processor, and at least one non-transitory storage medium storing processor-executable instructions which, when executed, perform the acts of method 400.

At act 402, the method 400 may begin with obtaining training data comprising simulated RNA expression data. In some embodiments, the "simulated" RNA expression data may include RNA expression data that is generated partially in silico. For example, the simulated RNA expression data may include data that was obtained by sampling reads from multiple expression data sets from purified cell type samples. In some embodiments, the RNA expression data may comprise expression data measured in TPM. In the illustrated example, the RNA expression data includes first RNA expression data for first genes associated with a first cell type and second RNA expression data for second genes associated with a second cell type. The first genes may be, for example, the specific and/or semi-specific genes for the first cell type, while the second genes may be specific and/or semi-specific genes for the second cell type. In some embodiments, the training data may comprise RNA expression data of genes associated with each cell type and/or subtype being analyzed, and/or other cell types.

In some embodiments, the training data may be generated as part of act 402. As described herein including at least with respect to FIG. 6A, in some embodiments the simulated RNA expression data may be generated by combining RNA expression data from malignant cells (e.g., cancer cells) with RNA expression data from microenvironment cells (e.g., immune cells, skin cells, etc.) to produce a plurality of simulated RNA mixtures (which may be referred to herein as "artificial mixtures" or "mixes") for training. In some embodiments, at least a thousand, at least ten thousand, at least one hundred thousand, or at least one million mixes may be generated and/or accessed as part of act 402.

The training data may be obtained in any suitable manner at act 402. For example, the training data may be stored on at least one storage medium (e.g., in one or more files, or in a database). In some embodiments, the at least one storage medium storing the training data may be local to the computing device (e.g., stored on the same at least one non-transitory storage medium), or may be external to the computing device (e.g., stored in a remote database or a cloud storage environment). The training data may be stored on a single storage medium, or may be distributed across multiple storage mediums.

In some embodiments, act 402 may further comprise pre-processing the training data in any suitable manner. For example, the training data may be sorted, combined, organized into batches, filtered, or pre-processed with any other suitable techniques. The pre-processing may make the training data suitable to be processed using the one or more non-linear regression models, for example. In some embodiments, the training data may be split into separate training, validation, and holdout datasets, as described herein including at least with respect to FIG. 5A.

In acts 404 to 408, the method 400 may proceed with training the one or more non-linear regression models using the training data. In particular, acts 404 to 408 describe training a first model of the non-linear regression models to estimate cell composition percentages for a corresponding first cell type. Acts 404 and 406 may be referred to herein as a training step. According to some embodiments, each model of the non-linear regression models may be trained at least in part separately for each cell type (e.g., with corresponding different input data, and different learned parameters, for each non-linear regression model). In some embodiments, each non-linear regression model of the one or more non-linear regression models may be trained, mutatis mutandis, according to the techniques described herein including with respect to acts 404 to 406, and/or stored according to act 408.

At act 404, training the first model of the non-linear regression models may proceed with generating an estimated percentage of RNA for the first cell type, using the first model and the first RNA expression data. As described herein, the first RNA expression data may comprise first genes associated with the first cell type (e.g., only specific and/or semi-specific genes for the first cell type). In some embodiments, the first RNA expression data may be provided as input to the first model. In some embodiments, other input may additionally or alternatively be provided to the first model. For example, a median, average, or any other suitable information relating the some or all of the RNA expression data may be provided as part of the input to the first model.

At act 406, training the first model of the non-linear regression models may proceed with updating parameters using the estimated percentage of RNA from the first cell type. In some embodiments, the estimated percentage of RNA from the first cell type may be compared to a known value for the percentage of RNA from the first cell type as part of act 406. For example, a loss function may be applied to the estimated value and the known value in order to determine a loss associated with the estimated value. In some embodiments, the loss may be used to update the parameters of the model. For example, a gradient descent, or any other suitable optimization technique, may be applied in order to update the parameters of the model so as to minimize the loss.

The first model may process its input using any suitable techniques, including non-linear regression techniques, as described herein. In some embodiments, the first model may use a gradient boosting machine learning technique. For example, the first model may comprise an ensemble of weak prediction models, such as decision trees, or any other suitable prediction models, which may be combined in an iterative fashion using a gradient boosting algorithm. In some embodiments, a gradient boosting framework such as XGBoost or LightGBM may be used as part of training the first model. In some embodiments, a random forest model may be used as part of training the first model.

In some embodiments, for a given non-linear regression model, acts 404 to 406 may be repeated multiple times (e.g., at least one hundred, at least one thousand, at least ten thousand, at least one hundred thousand, or at least one million times). In some embodiments, acts 404 to 406 may be repeated for a set number of iterations, or may be repeated until a threshold is surpassed (e.g., until loss decreases below a threshold value). In some embodiments, the non-linear regression models may be trained in two or more stages, as described herein including at least with respect to FIG. 5A.

At act 408, the method 400 may proceed with outputting the trained plurality of non-linear regression models including the first non-linear regression model and the second non-linear regression model. In some embodiments, outputting the trained plurality of non-linear regression models may comprise: storing one or more of the models in at least one non-transitory computer-readable storage medium (e.g., memory) for subsequent access, providing the model(s) to a recipient (e.g., transmitting data associated with the model(s) to a recipient using any suitable communication network or other means), displaying information associate with the model(s) to a user via a graphical user interface, and/or any other suitable manner of outputting the trained models, as aspects of the technology described herein are not limited in this respect.

Figure 5A:
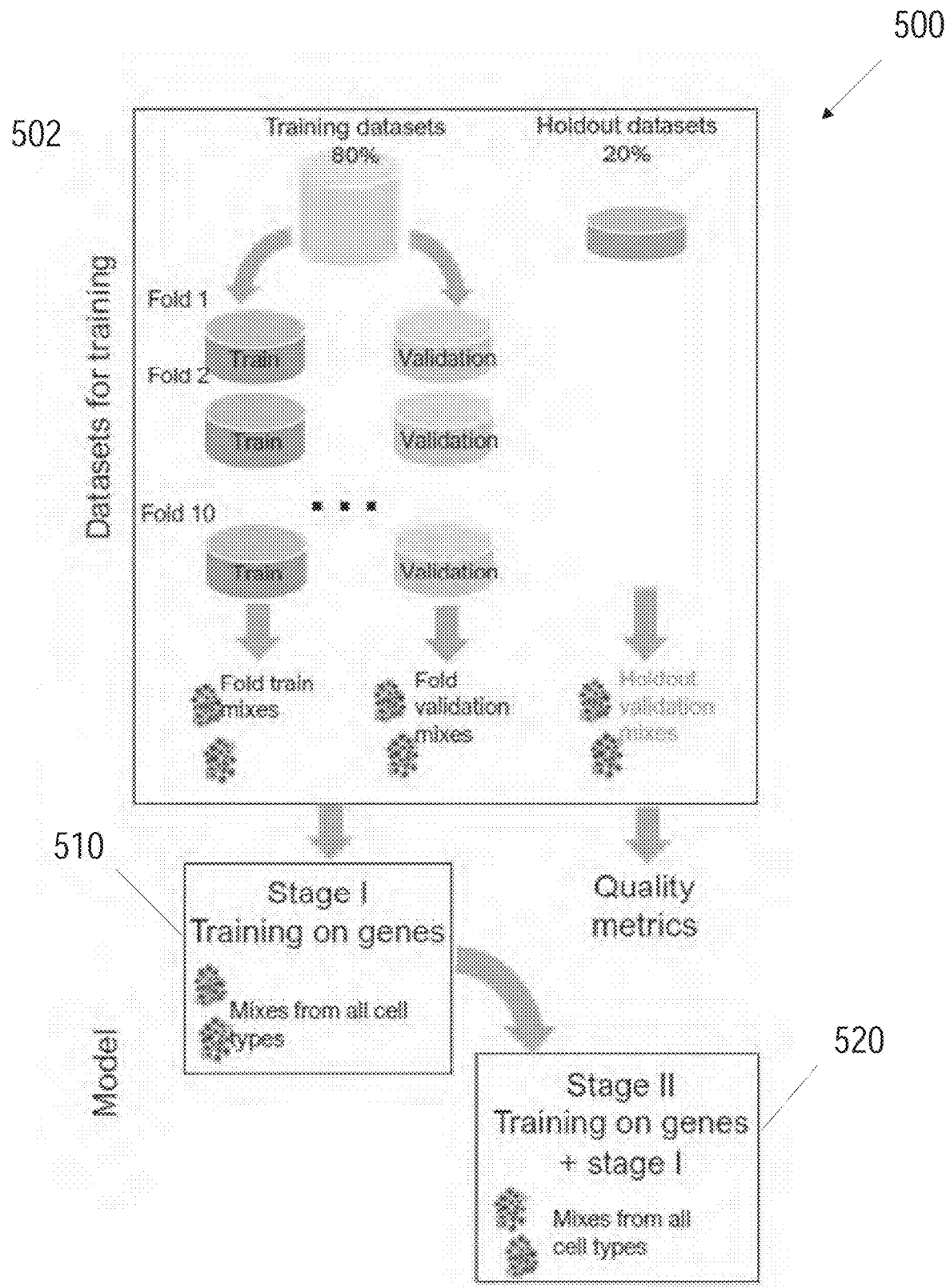
FIG. 5A-5B are diagrams depicting an exemplary method for training one or more machine learning models including validation and multiple stages of training, according to some embodiments of the technology described herein.

FIG. 5A depicts an exemplary method 500 for training one or more non-linear regression models, according to the techniques developed by the inventors. The illustrated techniques may be used in conjunction with any of the other techniques described herein, including at least with respect to FIGS. 2 and 4.

As shown in the figure, the method 500 may begin at act 502 with preparing one or more datasets for training. In some embodiments, the datasets may be generated (e.g., according to the techniques described herein including at least with respect to FIG. 6A) and/or accessed (e.g., from one or more databases) as part of act 502. As described herein in further detail including with respect to FIG. 6A, the datasets may comprise a plurality of artificial mixes of RNA expression data, which may comprise RNA expression data from a variety of malignant (e.g., tumor) and/or microenvironment cells. In some embodiments, the datasets may comprise at least one thousand, at least ten thousand, at least one hundred thousand, or at least one million artificial mixes.

In some embodiments, the datasets may be separated into training datasets and holdout datasets. For example, the datasets may be separated into the training and holdout datasets at random in some embodiments, with a set percentage of the datasets to be used for training and holdout, respectively. For instance, in the illustrated example, 80% of the datasets are used as training datasets, while the remaining 20% are retained as holdout datasets.

As shown in the figure, the holdout datasets may be used to develop quality metrics (e.g., as described herein including at least with respect to FIG. 7B). In some embodiments, there may be no holdout datasets, such that all the datasets may be used for training. As shown in the figure at act 502, the training datasets may be further subdivided into one or more (e.g., ten) folds each containing a respective training and validation set. According to some embodiments, the training datasets may be divided into folds at random. In some embodiments, cross-fold validation may be performed as part of training.

Regardless of how the datasets are prepared at act 502, the method 500 may continue at acts 510 and 520 with training a plurality of non-linear regression models using the training datasets. As described herein including at least with respect to FIG. 4, each non-linear regression model may be trained to estimate, based on input RNA expression data, a corresponding percentage of RNA from a particular cell type. As shown in the illustrated example, the non-linear regression models may be trained in two stages, the first stage corresponding to training a first sub-model of the non-linear regression model, the second stage corresponding to training a second sub-model of the non-linear regression model.

In the first stage, at act 510, the first sub-model of each non-linear regression model may be trained to generate an initial prediction for the percentage of RNA from its respective cell type. For each first sub-model of each non-linear regression model, the input may comprise RNA expression data of specific and/or semi-specific genes for the corresponding cell type. In some embodiments, only the RNA expression data of the specific and/or semi-specific genes for the cell type may be provided as input. In some embodiments, other information, such as a median of the expression data, may be provided. Regardless of the input provided at the first stage, the output of the first stage may be initial predictions for the percentages of RNA from each cell type, with each first sub-model of each non-linear regression model providing a prediction for its respective cell type.

In the second stage, at act 520, the second sub-model of each non-linear regression model may be trained to generate a second prediction for the percentage of RNA from its respective cell type. For each second sub-model of each non-linear regression model, the input may comprise RNA expression data of specific and/or semi-specific genes for the corresponding cell type, and the predictions from the first stage. In some embodiments, the RNA expression data used at the second stage may be different from the RNA expression data used at the first stage. For example, in some embodiments, some or all of the training data may be regenerated (e.g., according to the techniques described herein including with respect to FIGS. 5B and 6) for the purposes of training the non-linear regression models in the second stage. In some embodiments, the training data for the first stage and the second stage may be generated in parallel (e.g., at the same time) but independently, such that the training data for each stage is different. In addition to the RNA expression data, the predictions from the first stage may be provided as input at the second stage. According to some embodiments, the initial predictions for all cell types may be provided as input to the second stage. This may allow the second stage to effectively correct the predictions from the first stage, and may increase the consistency and/or accuracy of the final model.

Regardless of the input provided at the second stage, the output at the second stage may be second predictions for the percentages of RNA from each cell type, with the second sub-model of each non-linear regression model providing a prediction for its respective cell type. In some embodiments, the second predictions may be the final output of the non-linear regression models (e.g., as described herein including with respect to FIGS. 2 and 4). In some embodiments, additional stages of training (e.g., additional sub-models) may be performed (e.g., a third stage, a fourth stage, etc.), with each stage taking as input new training data (e.g., RNA expression data), and the predictions from the previous stage.

Providing the predictions from the previous stage as part of the input to the next stage may allow a model for a particular cell type to use the information about estimated proportions of other cell types and adapt to them (e.g., by knowing that the total number of T cells equals 10 and number of CD4+ T cells is 8, the number of CD8+ T cells could not exceed 2). A multi-stage training procedure, as described herein, may allow the model to account for this. This procedure may allow for information from different cell types and subtypes to be used for each individual cell type model.

Figure 5B:
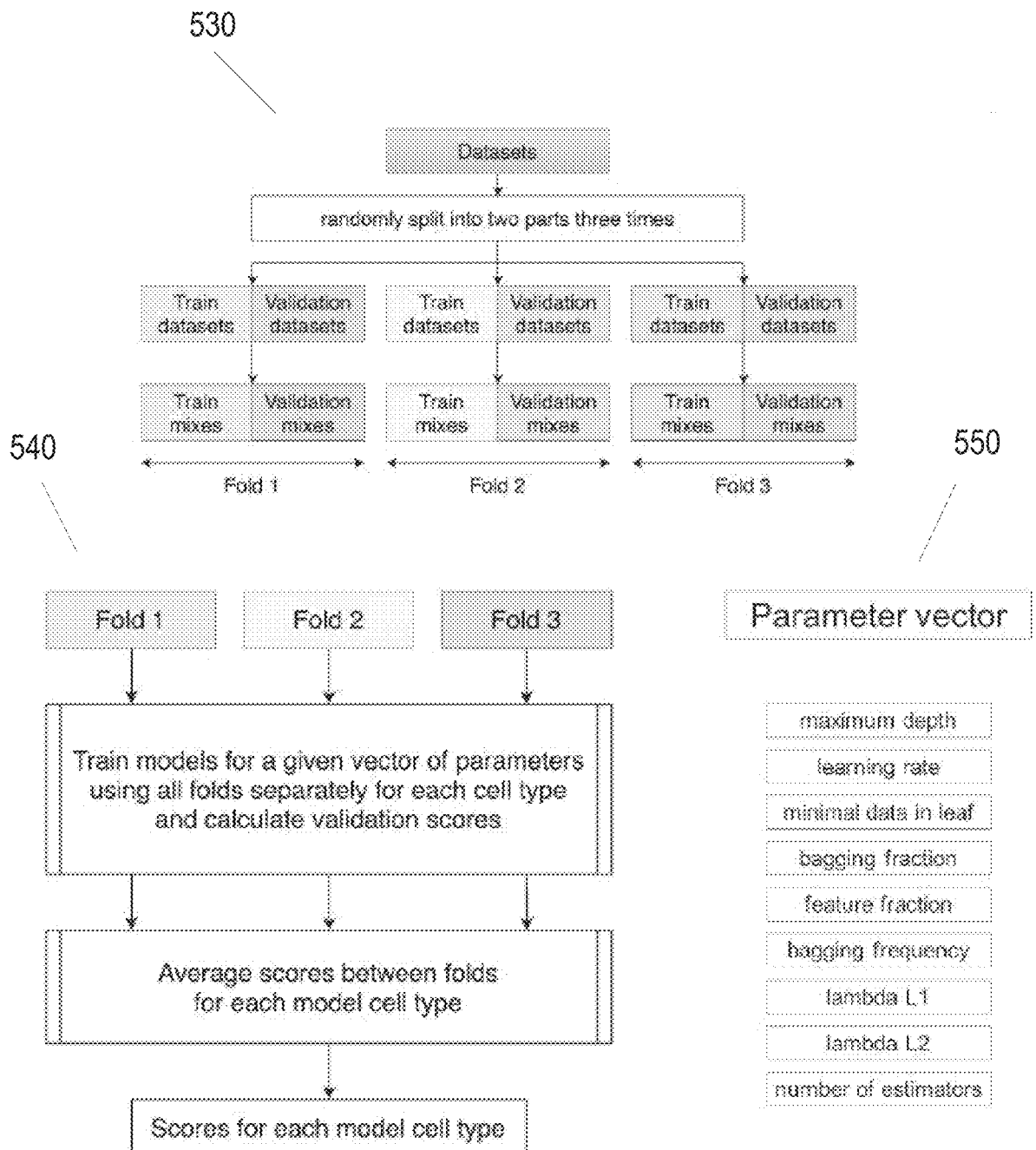

FIG. 5B is an exemplary, non-limiting illustration for training a machine learning model, in accordance with some embodiments of the technology described herein. The illustrated techniques may be used in conjunction with any of the other techniques described herein, including at least with respect to FIGS. 2 and 4.

As shown in the figure, diagram 530 illustrates the division of the datasets into one or more folds, as described herein including with respect to FIG. 5A. For example, the datasets may be randomly split into three folds, with each of the three folds being further divided into a training dataset and a validation dataset. In some embodiments, datasets may be used to generate artificial mixes, as described herein including with respect to FIG. 6A.

In some embodiments, as shown in diagram 540, the folds may then be used to train one or more models for a given set of parameters (e.g., parameters 550). The parameters may be generated (e.g., at random) based on a set of predetermined ranges shown in Table 3. In some embodiments, at least some of the (e.g., all) folds may be used to train each cell type model separately. Subsequently, in some embodiments, validation mixes may be used to evaluate each parameter set and generate associated evaluation data. In some embodiments, as described herein including with respect to FIG. 4, parameters may be updated with each stage of training and/or used as input to subsequent training stages. For example, a first fold may be used as input for a first stage of training to generate a first set of parameters. A second fold may then be used as input for a second stage of training to generate an updated set of parameters. Tables 4 and 5 show example parameters for one or more cell type models after a first stage and a second stage of training, respectively.

TABLE 3

This table lists exemplary model parameters and specifies example values that define a range for each parameter.

| Parameter | Min | Max | Type |
|---|---|---|---|
| max_depth | 2 | 17 | Int |
| learning_rate | 0.005 | 0.15 | Float |
| min_data_in_leaf | 1 | 1000 | Int |
| bagging_fraction | 0.01 | 1 | Float |
| feature_fraction | 0.01 | 1 | Float |

TABLE 4

This table specifies example values for the mode parameters for each cell type model as a result of a first stage of training.

| Cell | bagging_fraction | bagging_freq | feature_fraction | lambda_l1 | lambda_l2 | learning_rate | max_depth | min_data_in_leaf | num_leaves | n_estimators |
|---|---|---|---|---|---|---|---|---|---|---|
| B_cells | 0.816699982 | 0 | 0.823000014 | 1.185199976 | 0.933099985 | 0.105999999 | 11 | 171 | 1161 | 1100 |
| CD4_T_cells | 0.781599998 | 7 | 0.957499981 | 2.525300026 | 0.005 | 0.027899999 | 7 | 80 | 73 | 1200 |
| CD8_T_cells | 0.688099998 | 7 | 0.741999984 | 1.042199969 | 2.052599907 | 0.0348 | 9 | 34 | 462 | 1400 |
| CD8_T_cells_PD1_high | 0.64319998 | 1 | 0.082999997 | 3.191699982 | 1.98239994 | 0.017100001 | 3 | 304 | 5 | 1100 |
| CD8_T_cells_PD1_low | 0.086199999 | 2 | 0.785399973 | 4.72149992 | 3.551500082 | 0.0241 | 14 | 68 | 12762 | 1100 |
| Immune_general | 0.848699987 | 5 | 0.111100003 | 0.302300006 | 0.813799977 | 0.0295 | 9 | 420 | 460 | 3900 |
| Lymphocytes | 0.848699987 | 5 | 0.111100003 | 0.302300006 | 0.813799977 | 0.0295 | 9 | 420 | 460 | 4000 |
| Macrophages | 0.848699987 | 5 | 0.111100003 | 0.302300006 | 0.813799977 | 0.0295 | 9 | 420 | 460 | 4000 |
| Macrophages_M1 | 0.980099976 | 9 | 0.620000005 | 0.0121 | 0.661499977 | 0.114299998 | 11 | 144 | 1642 | 1100 |
| Macrophages_M2 | 0.123199999 | 3 | 0.71390003 | 2.701800108 | 1.988800049 | 0.098399997 | 2 | 754 | 2 | 3800 |
| Monocytes | 0.26879999 | 0 | 0.978500009 | 0.0942 | 4.521699905 | 0.105800003 | 11 | 219 | 1974 | 3900 |
| Myeloid_cells | 0.848699987 | 5 | 0.111100003 | 0.302300006 | 0.813799977 | 0.0295 | 9 | 420 | 460 | 4000 |
| NK_cells | 0.718900025 | 4 | 0.543900013 | 0.0041 | 1.568199992 | 0.0462 | 16 | 120 | 58504 | 3900 |
| Neutrophils | 0.26879999 | 0 | 0.978500009 | 0.0942 | 4.521699905 | 0.105800003 | 11 | 219 | 1974 | 3900 |
| Non_plasma_B_cells | 0.220500007 | 0 | 0.286599994 | 0.482199997 | 1.171300054 | 0.0142 | 12 | 169 | 2103 | 4000 |
| Plasma_B_cells | 0.733500004 | 8 | 0.079700001 | 0.728999972 | 0.400099993 | 0.082599998 | 8 | 135 | 138 | 1800 |
| T_cells | 0.26879999 | 0 | 0.978500009 | 0.0942 | 4.521699905 | 0.105800003 | 11 | 219 | 1974 | 1800 |
| T_helpers | 0.781599998 | 7 | 0.957499981 | 2.525300026 | 0.005 | 0.027899999 | 7 | 80 | 73 | 1200 |
| Tregs | 0.505800009 | 6 | 0.310099989 | 0.754499972 | 2.318599939 | 0.081500001 | 10 | 22 | 896 | 3900 |
| Endothelium | 0.9607 | 9 | 0.2933 | 3.9006 | 2.938 | 0.0149 | 14 | 271 | 9419 | 4000 |
| Fibroblasts | 0.8669 | 0 | 0.2166 | 0.2936 | 3.1764 | 0.0088 | 14 | 77 | 8582 | 3900 |

TABLE 5

This table specifies example values for the model parameters for each cell type model as a result of a second stage of training.

| Cell | bagging_fraction | bagging_freq | feature_fraction | lambda_l1 | lambda_l2 | learning_rate | max_depth | min_data_in_leaf | num_leaves | n_estimators |
|---|---|---|---|---|---|---|---|---|---|---|
| B_cells | 3200 | 481 | 0.94 | 0 | 2 | 4.2994 | 1 | 9 | 0.1018 | 193 |
| CD4_T_cells | 4000 | 3491 | 0.7865 | 0.2936 | 9 | 3.5040195 | 0.9199 | 12 | 0.02061331 | 77 |
| CD8_T_cells | 1100 | 2320 | 0.8003279 | 0.2936 | 0 | 1.3659 | 0.9199 | 12 | 0.0449 | 77 |
| CD8_T_cells_PD1_high | 1100 | 446 | 1 | 4.9709 | 7 | 0 | 0.32803038 | 9 | 0.005 | 55 |
| CD8_T_cells_PD1_low | 1400 | 9 | 0.8047 | 3.2544096 | 3 | 2.1213 | 0.9167 | 4 | 0.005 | 732 |
| Immune_general | 2700 | 2107 | 0.8300869 | 0.2936 | 0 | 3.871263 | 0.9199 | 12 | 0.03894949 | 77 |
| Lymphocytes | 2900 | 192 | 0.94 | 0.3183 | 3 | 5 | 0.9845639 | 8 | 0.1018 | 281 |
| Macrophages | 1100 | 121 | 0.92891896 | 0.3183 | 3 | 3.6479895 | 1 | 7 | 0.1018 | 193 |
| Macrophages_M1 | 4000 | 8 | 0.3423854 | 0.106176496 | 0 | 0 | 0.8538462 | 4 | 0.1479 | 171 |
| Macrophages_M2 | 4000 | 14 | 0.7785 | 0 | 7 | 0.262 | 0.9844 | 4 | 0.11388969 | 183 |
| Monocytes | 1900 | 192 | 0.94 | 0.3183 | 3 | 5 | 0.9845639 | 8 | 0.1018 | 281 |
| Myeloid_cells | 4000 | 375 | 0.80310357 | 0.2936 | 9 | 5 | 0.8633423 | 9 | 0.0348 | 77 |
| NK_cells | 2000 | 192 | 0.94 | 0.3183 | 3 | 5 | 0.9845639 | 8 | 0.1018 | 281 |
| Neutrophils | 4000 | 14952 | 0.80310357 | 0.2936 | 6 | 1.9707032 | 0.9415555 | 14 | 0.0348 | 77 |
| Non_plasma_B_cells | 1800 | 219 | 0.9575 | 2.079026 | 7 | 4.7449 | 0.8669 | 8 | 0.00833594 | 1 |
| Plasma_B_cells | 4000 | 153 | 0.9716 | 0.1056 | 4 | 2.7129 | 0.85468626 | 8 | 0.1092 | 387 |
| T_cells | 4000 | 10097 | 0.7865 | 0.2936 | 9 | 1.8597416 | 0.9199 | 14 | 0.0348 | 77 |
| T_helpers | 3400 | 14952 | 0.8031035 | 0.2936 | 6 | 1.9707 | 0.9415555 | 14 | 0.0348 | 77 |
| Tregs | 3300 | 61781 | 0.8762 | 0.3017 | 3 | 3.688625 | 0.8080787 | 16 | 0.0532 | 56 |
| Endothelium | 1300 | 698 | 0.742 | 0.4822 | 0 | 1.1887 | 0.6881 | 10 | 0.0348 | 1 |

Figure 6A:
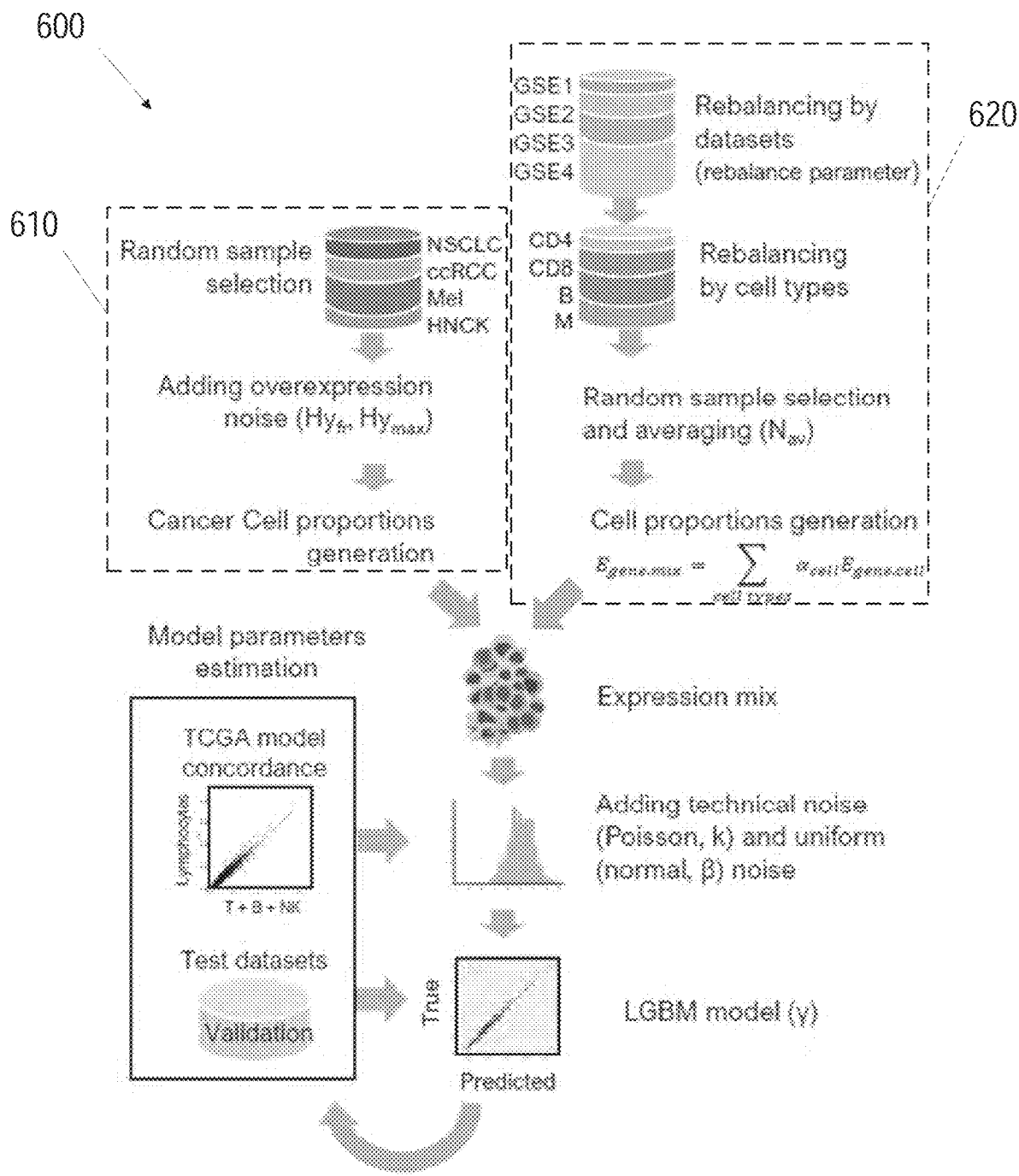
FIG. 6A is a diagram depicting an exemplary method for training one or more non-linear regression models including generating simulated RNA expression data, according to some embodiments of the technology described herein.

FIG. 6A is a diagram depicting an exemplary method 600 for training one or more non-linear regression models, including generating simulated RNA expression data (e.g., to use as training data, as described herein including at least with respect to FIGS. 4-5). In some embodiments, the simulated RNA expression data may be generated by combining samples of RNA expression data from malignant cells (e.g., cancer cells) and microenvironment cells (e.g., immune cells, stromal cells, etc.), as shown in branches 610 and 620 of the method 600. An exemplary process for generating artificial mixes of RNA expression data is described herein below with respect to FIG. 6A.

Figure 6B:
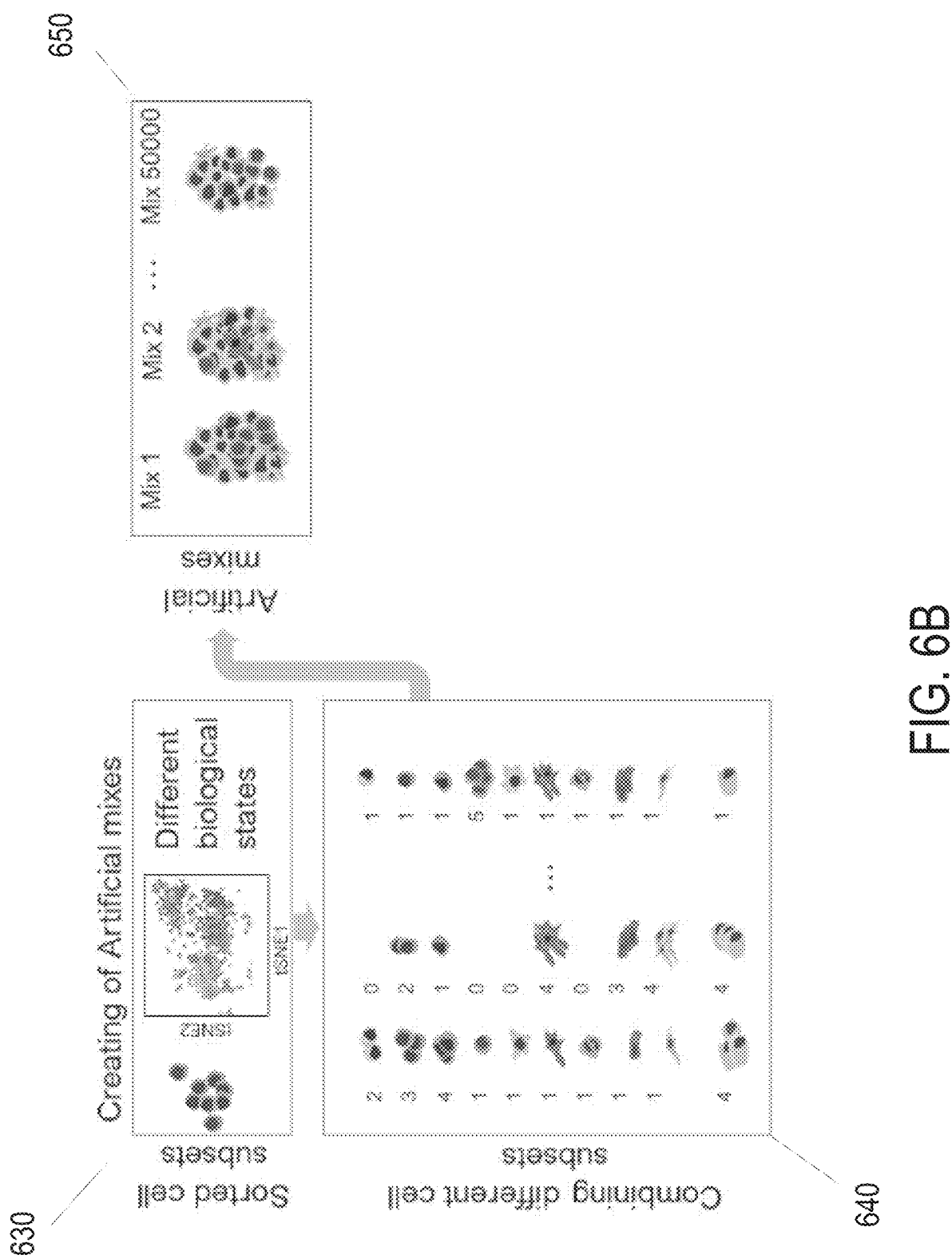
FIG. 6B is an exemplary diagram for generating artificial mixes of RNA expression data to imitate real tissue, according to some embodiments of the technology described herein.

FIG. 6B is a diagram depicting an example of generating artificial mixes of RNA expression data to imitate real tissue, according to some embodiments of the technology described herein. In some embodiments, the RNA expression data is derived from one or more sorted cell types/subtypes representing one or more biological states (e.g., positive gene regulation, negative gene regulation, etc.), as shown in branch 630. In some embodiments, the one or more cell types/subtypes are mixed in different proportions to generate artificial mixes, as shown in branches 640 and 650.

Figure 6C:
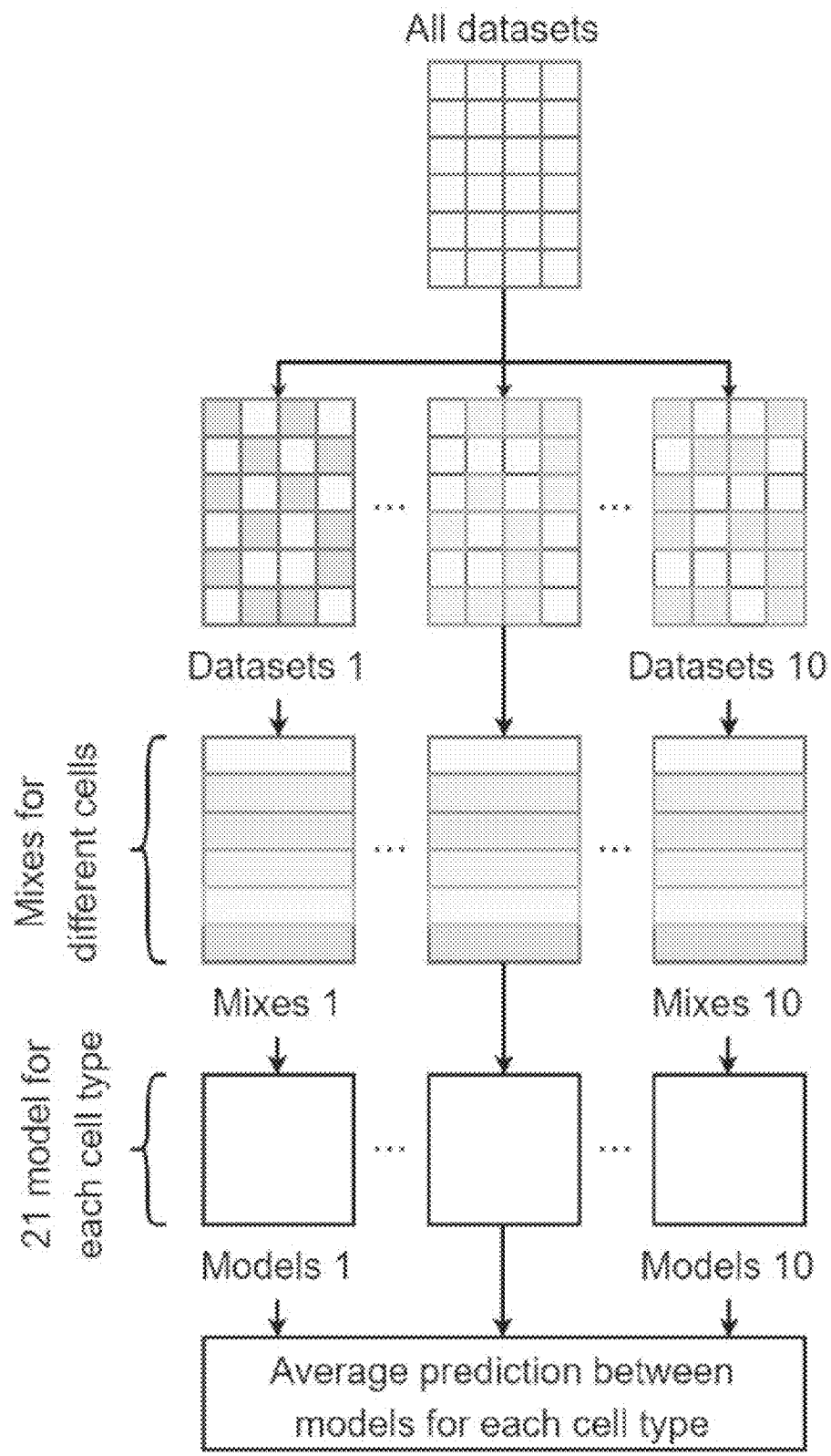
FIG. 6C is an exemplary diagram for generating and using artificial mixes to train cell type models, according to some embodiments of the technology described herein.

FIG. 6C is an exemplary diagram for generating and using artificial mixes to train cell type models, according to some embodiments of the technology described herein. In some embodiments, as described herein including with respect to FIG. 5A, the dataset is divided into folds. In some embodiments, the resultant datasets are used to create artificial mixes. Subsequently, in some embodiments, the artificial mixes are used to train and validate each of one or more non-linear regression models that is specific to one or more cell type/subtype. In some embodiments, the resultant models from each of the folds may be considered together or independently, as described with respect to FIG. 5A.

Figure 6D:
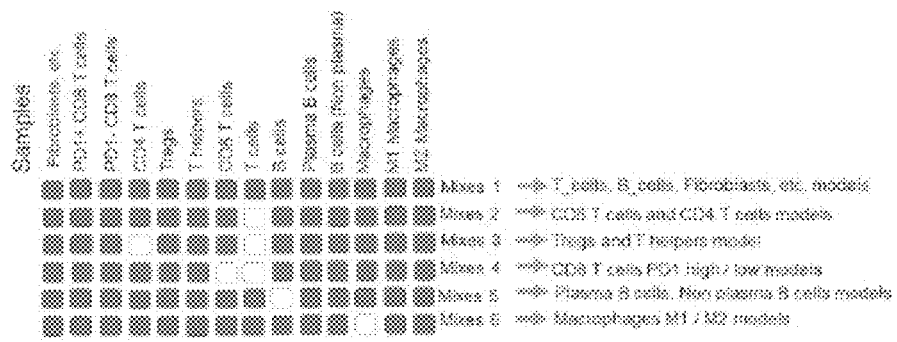
FIG. 6D-E are exemplary illustrations for generating specific artificial mixes for training particular cell type/subtype models, according to some embodiments of the technology described herein.
Figure 6E:
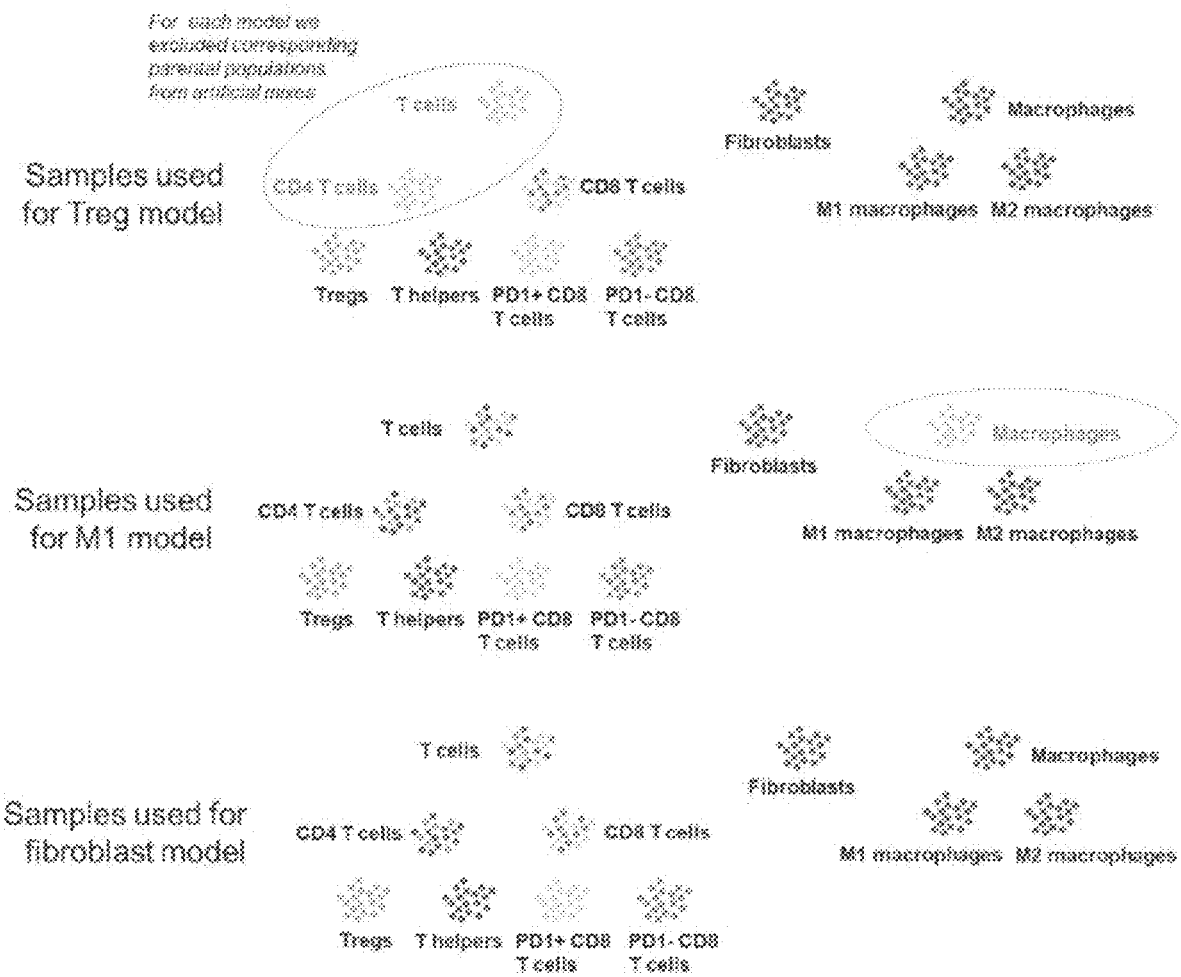

FIGS. 6D and 6E are exemplary illustrations for generating specific artificial mixes for training particular cell type/subtype models, according to some embodiments of the technology described herein. In some embodiments, one or more datasets may be excluded for training a specific cell type/subtype model, as described herein including with respect to Table 6.

Figure 6F:
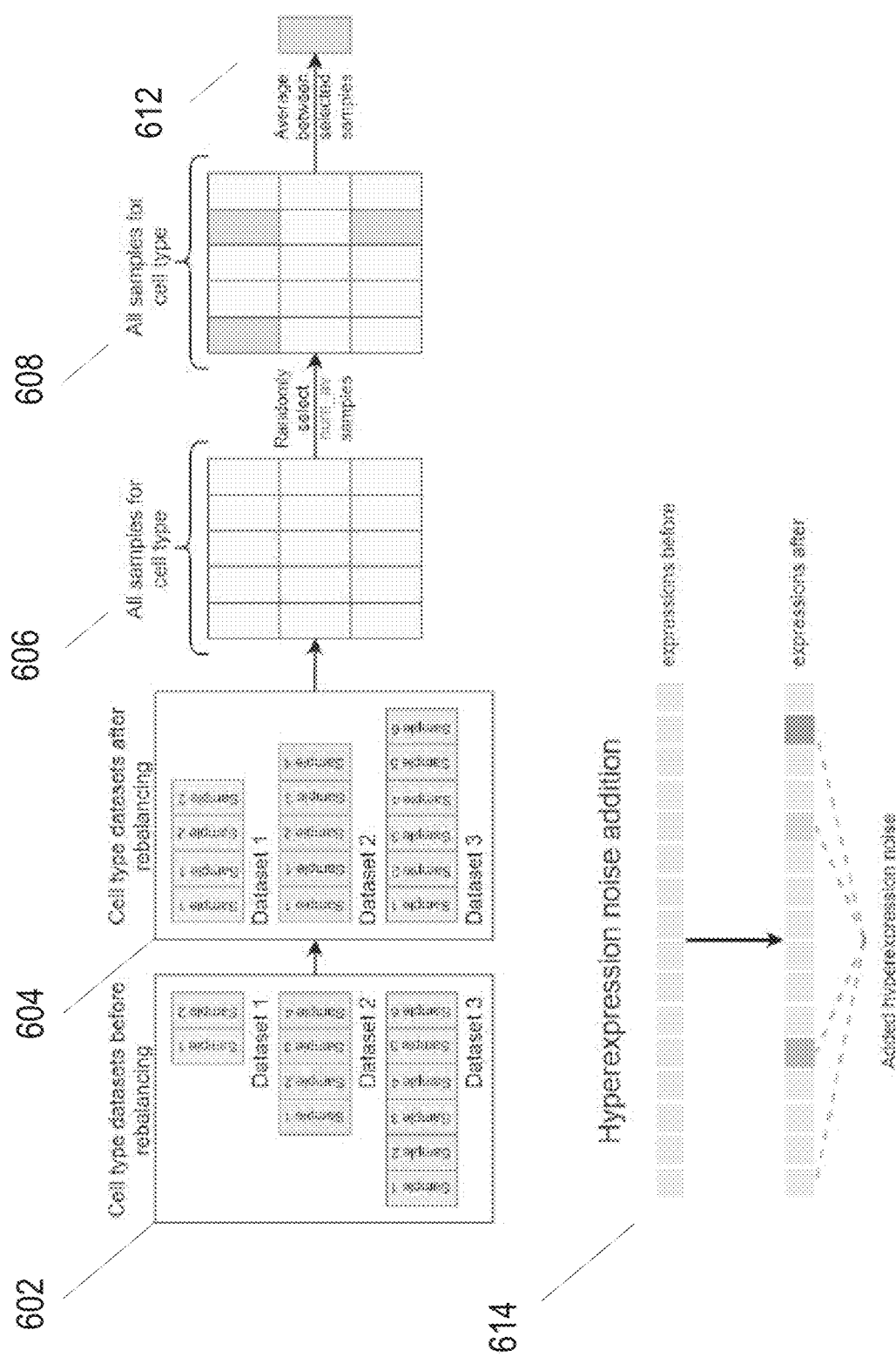
FIG. 6F is an exemplary diagram illustrating techniques for processing datasets and generating artificial mixes, according to some embodiments of the technology described herein.

FIG. 6F is an exemplary diagram illustrating techniques for processing datasets and generating artificial mixes, according to some embodiments of the technology described herein. As shown in the figure, act 602 illustrates datasets for a cell type, prior to rebalancing (e.g., resampling large datasets to avoid overtraining models.) In some embodiments, as described herein below including with respect to FIG. 6A, datasets may be rebalanced 604 and combined into a total set of samples for a specific cell type. Further, as described herein, samples may then be randomly selected in act 608 and averaged in act 612. In some embodiments, in accordance with the techniques described herein, hyperexpression noise may be added to the expression of the cell type, as illustrated in 614.

Data Collection, Analysis and Preprocessing

According to some embodiments, the samples of RNA expression data may be obtained as described herein including at least with respect to FIGS. 1C-1D. For example, a large number of samples of sorted malignant and microenvironment cells may be used to construct the artificial mixes of RNA expression data. In some embodiments, the number of samples may be on the order of the number of samples included in Table 1. In some embodiments, the number of samples may be at least 5,000, at least 10,000, at least 15,000, at least 20,000, at least 30,000, at least 50,000, at least 100,000, or any number of suitable samples. In some embodiments, open source datasets such as Gene Expression Omnibus (GEO) and ArrayExpress may be used. In some embodiments, the datasets used may be selected so as to satisfy the following criteria: only *Homo sapiens*, standard RNA-seq (without polyA depletion, targeted panel, etc.) with read length higher 31 bp. In some embodiments, for constructing artificial mixtures, only relevant cell types for the particular disease being analyzed (e.g., particular type of tumor) may be used. In contrast, for the analysis of gene expression specificity, as described herein including at least with respect to FIG. 1E, data for all cell types may instead be used.

In some embodiments, selection of datasets may be based on both biological and bioinformatic parameters. For example, datasets with samples cultivated in conditions close to normal physiological conditions may be used. In some embodiments, datasets with abnormal stimulation were excluded, like datasets of CD4+ T-cells hyper stimulated with phorbol 12-myristate 13-acetate and ionomycin activation or macrophages co-cultured with an excessive number of bacterial cultures. In some embodiments, only those samples having at least 4 million coding read counts were used.

In some embodiments, quality control may be performed on the RNA expression data prior to construction of the artificial mixes (e.g., to exclude strange or unreliable datasets). For example, if some samples of CD4+ T cells show no or very low expression of CD45, CD4 or CD3 genes, they may be excluded. The same may done for other cell types, in some embodiments. For example, samples for some cell types may be excluded if they significantly express genes that are not typical for that type of cell (e.g., if in a sample of T cells, CD19, CD33, MS4A1, etc. were expressed in significant amounts, while in most other T cell samples these expressions were low). In some embodiments, samples of CD4+ T cells may be removed if they express significant amounts of CD8 genes. In some embodiments, several methods of expression analysis like t-SNE or PCA with different gene sets may be used to visualize the similarities and differences between datasets (e.g., as shown in FIGS. 1C and 1D). If a particular cell type from one dataset fails to cluster with the same cell type in the other datasets (e.g., in a t-SNE, PCA, or other plot), then the one dataset may be further analyzed as part of quality control, and some or all of the data from that dataset may be excluded.

Mixes Construction

According to some embodiments, a variety of artificial mixes of RNA expression data (e.g., representing simulated tumor tissue) may be constructed using samples prepared as described herein above. Artificial mixes may be generated using sample expressions in TPM (transcripts per million) units, such that the gene expressions for an overall sample are formed as a linear combination of the expressions of individual cells from that sample. In some embodiments, RNA expression data from samples of various cell types may be mixed in predetermined proportions, as described herein below. As shown in FIG. 6A, simulated RNA expression data for malignant cells (e.g., generated as shown in branch 610) may be combined with simulated RNA expression data for microenvironment cells (e.g., generated as shown in branch 620).

Referring now to branch 620, an exemplary process for generating simulated microenvironment cell RNA expression data is shown. In the illustrated example, samples of each cell type (e.g., samples of RNA expression data, such as of genes GSE1, GSE2, GSE3, or GSE4, as shown) may be rebalanced by datasets (e.g., reducing the weight of datasets with a large number of samples) and subtypes (e.g., changing the proportions of subtypes of a sample). Techniques for rebalancing are described herein including with respect to the "Rebalancing by datasets" and "Rebalancing by subtypes" sections. For each cell type, multiple samples may then be randomly selected and averaged. Then, for some or all of the cell types being used, the rebalanced/averaged samples may be mixed together in particular proportions (e.g., so as to simulate a real tumor microenvironment).

Referring now to branch 610, an exemplary process for generating simulated malignant cell RNA expression data is shown. In the illustrated example, random samples of cancer cells (e.g., NSCLC, ccRCC, Mel, HNCK, etc.) may be selected. Then, hyperexpression noise may be added to the resulting RNA expression data to account for abnormal expression of genes by malignant cells. For example, tumor cells sometimes express genes which are ordinarily absent in the parental cell type. When this is the case for specific, semi-specific, or marker genes that are linked to immune or stromal cells within the TME, the overexpressed genes may interfere with the deconvolution techniques described herein. Regardless of whether hyperexpression noise is included, the result of branch 610 may be simulated malignant cell RNA expression data.

As shown in the figure, the simulated RNA expression data for the malignant cells (e.g., generated as shown in branch 610) and the simulated RNA expression data for the microenvironment cells (e.g., generated as shown in branch 620) may be combined into an artificial mix (referred to in FIG. 6A as an "expression mix"). In some embodiments, the simulated RNA expression data for the malignant cells and the simulated RNA expression data for the microenvironment cells may be mixed together in a random proportion based on a given distribution for cancer cells. In some embodiments, noise may then be added to the mix to mimic technical noise and noise resulting from biological variability. Each type of noise may be specified according to one or more suitable distributions. For example, as shown in FIG. 6A, the technical noise may be specified by a Poisson distribution, while the noise resulting from biological variability may be specified according to a normal distribution. However, in some embodiments, technical noise may have multiple components, which may be specified by other distributions. For example, another component of technical noise may be specified by a non-Poisson distribution. Regardless of how the artificial mix is generated, in some embodiments the artificial mix may be representative of an artificial tumor, including the tumor microenvironment (TME).

The inventors have recognized and appreciated that, when creating artificial mixes, it may be desirable to use different cells of the same type from different samples. Using a small number of samples for the mixes, or even just one sample for each cell type, would provide poor performance on real tumor samples (e.g., due to the variability of cell states and their expressions, as well as noise due to limited numbers of read counts for different expressions, alignment errors and other causes of technical noise). Therefore, when creating artificial mixtures, the inventors have recognized that is may be desirable to use as many available cell samples as possible.

Accordingly, for this example, a large number of RNA-seq samples (e.g., at least one hundred, at least five hundred, at least one thousand, at least two thousand, or at least five thousand samples) of various cell types were collected. In some embodiments, a number of datasets of malignant cells (e.g., pure cancer cells for various diagnoses, cancer cell lines or sorted from tumors) may also be collected. For each cell type, there may be a corresponding number of samples from different datasets. Table 7 lists the quantities of samples remaining after quality control for a number of cell types.

In some embodiments, as described herein including with respect to FIG. 5A, the artificial mixes may be used as training datasets for training one or more non-linear regression models. In some embodiments, the non-linear regression models may be specific to a cell type/subtype. Accordingly, in some embodiments many (e.g., 150,000) artificial mixes may be generated to train models for each specific cell type model. The sets of mixes used for each model may include or exclude specific datasets that allow for differentiation between particular cell types/subtypes, as illustrated in FIGS. 6D and 6E. For example, to train a model for CD4+ T cells, datasets that include unspecified T cells may be excluded to avoid uncertainty about the proportions of CD4+ T cells within the datasets. As an example, Table 6 specifies the mixes used to train one or more corresponding cell type/subtype models.

TABLE 6

This table specifies, as an example, the samples included in the artificial mixes used to train particular cell type models.

| Mixes set | Trained models |
|---|---|
| All available samples | Immune cells, Myeloid cells, Lymphocytes, Monocytes, Fibroblasts, Endothelium, Neutrophils, NK cells, T cells, Macrophages, B cells |
| Without T cell samples | CD4+ T cells, CD8+ T cells |
| Without T cells, CD8+ T cells samples | CD8+ T cells PD1 high, CD8 + T cells PD1 low |
| Without T cells, CD4+ T cells samples | Tregs, T helpers |
| Without Macrophages samples | Macrophages M1, Macrophages M2 |
| Without B cells samples | Plasma B cells, Non plasma B cells |

Averaging of Samples

In some embodiments, multiple samples for each cell type may be averaged in any suitable manner (e.g., to improve the quality of samples before adding artificial noise). For example, in some embodiments, averaging may be performed in groups of two, such that an averaged sample of 4 million reads may contain information on 8 million reads. In some embodiments, averaging across multiple samples may reduce the noise in the expression caused by technical factors during sequencing.

In some embodiments, for each cell type, $num_{av}$ samples are selected, the expressions of which are averaged (the value of $num_{av}$ is indicated in the parameter table, Table 9). As samples of a more general cell type, any subtype samples may be used at this stage. So, for example, Tregs may be processed along with T cells in some embodiments. Since this approach creates greater subtype diversity for artificial samples but can decrease the biological variability of gene expression within cell type or subtype if too many samples are averaged, the degree of averaging employed may affect the learning outcome. Therefore, the number of samples for averaging may appear as a parameter, which, together with other parameters, may be selected during training (e.g., so as to increase or maximize quality).

Samples Rebalancing

Since different datasets and cell subtypes can vary significantly in the number of available cell samples, in some embodiments the number of samples may be rebalanced. As described herein below, in one example, the samples may be rebalanced by datasets, then by cell subtypes. Then $num_{av}$ samples may be selected from the rebalanced number of samples.

Rebalancing by Datasets

In some embodiments, the number of samples of sorted cells in datasets may range from one to several hundred (e.g., at least five, at least ten, at least 50, or at least 100 samples). Typically, each dataset may contain samples of one or two cell types, sorted and sequenced in the same way. Cell samples within the same dataset may also have specific conditions, such as a specific set of markers for sorting or a specific disease of patients from whom the cells were taken. Datasets with a large number of samples can lead to overtraining of models for such datasets. To reduce the weight of datasets with a large number of samples, samples of all datasets are resampled in order to rebalance by datasets.

For example, in some embodiments, for each dataset the number of samples are resampled with replacement to number $N_{dataset,new}$:

$$N_{dataset,new} = N_{max} * \left(\frac{N_{dataset,old}}{N_{max}}\right)^{1-rebalance\ parameter}$$

Where $N_{max}$ is number of samples in the largest dataset (e.g., for the particular cell type) and $N_{dataset,old}$ is the original number of samples in the dataset. The rebalance parameter in the equation is a value in the range [0, 1], where 0 means there is no change in the number of samples, and 1 means that for each dataset there will be the same number of samples. In some embodiments, the rebalancing parameter may be selected during training.

Rebalancing by Cell Subtypes

For a number of cell types, in addition to samples of this type, there may also be samples of more specific subtypes. The number of available subtype samples may not coincide with those ratios that are specified during the formation of mixes with these subtypes, in some cases. Therefore, when creating mixes for the cell type, samples of its subtypes may be rebalanced.

For example, in some embodiments, there may be significantly more CD4+ T cells (and T helpers with Tregs) samples available than CD8+ T cells. In this case, to form an average T cells sample, proportions of CD4+ and CD8+ T cells samples may be changed before the random selection of samples. For example, the proportions may be chosen similar to the ratios of the predicted average RNA fractions for the TCGA or PBMC samples for these cell types. In some embodiments, the predictions may be obtained using one or more linear models trained on mixes with equal cell proportions.

The subtype rebalancing algorithm may be as follows. To rebalance each subtype for a given type, resample with replacement a number of samples equal to:

$$P_{subtype} * msize/\min_P + 1$$

Where $P_{subtype}$ is a number reflecting the proportion of a given subtype (e.g., the proportion of this subtype among all subtypes for the given type, which may be represented as the number of samples for the subtype divided by the total number of samples for the type); msize is the maximum number of samples among all the subtypes for the given type, and $\min_P$ is the minimum number $P_{subtype}$ between all subtypes. According to some embodiments, the rebalancing operation may be performed recursively for all nested subtypes (e.g., subtypes which themselves have subtypes).

Microenvironment Cells Proportions Generation

According to some embodiments, the resulting samples of different cell types may be mixed with one another in random ratios in order to generate the simulated microenvironment cell RNA expression data. For example, a first set of artificial mixes may be generated using random proportions of each cell type:

$$f_{cell} = \frac{R_{cell}K_{cell}}{\sum_{cell} R_{cell}K_{cell}}$$

Wherein $R_{cell}$ is a random number distributed uniformly from 0 to 1 and $K_{cell}$ is the coefficient for the particular cell type.

According to some embodiments, the coefficient $K_{cell}$ in the above equations may be chosen so that the most likely ratios of cells mRNA are close to what is observed in TCGA or PBMC samples. These approximate ratios may be calculated from the TCGA or PBMC samples, using models trained without using such ratios. For example, a vector of numbers may be used, reflecting approximate proportions for a given type of tissue. Each number of the vector is multiplied by a random number from 0 to 1. The resulting coefficients are normalized to the sum and used in a linear combination. In some embodiments, $K_{cell}$ may be selected from Table 7, which specifies, for each of multiple cell types, the most likely proportion of the cell type based on tumor tissue and blood (PBMC).

The inventors have recognized and appreciated that it may be desirable for the deconvolution algorithm to work in any cell range. For example, the preparation of a cell suspension from a tumor sample may lead to a dramatic increase in the proportion of lymphocytes—and it may be desirable for the algorithm to work on the sequencing data of such a suspension. However, the inventors have recognized and appreciated that the formation of cell ratios by the method described may generate practically no samples where there is a large proportion (e.g., 70-100%) of a certain cell type, such as NK cells. Therefore, in some embodiments, additional mixtures are created in which proportions are generated from the Dirichlet distribution with parameter 1/number_of_types for each dimension. This parameter may be selected along with other parameters for creating mixtures. The number of samples in a dataset formed in this way may be controlled by a parameter dirichlet_samples_proportion (Table 9). This parameter may also be selected as a parameter for creating mixtures. Thus, in the final dataset, each cell type may be found in proportions from 0 to 100 percent. However, there most of the characteristic quantities may reflect cell populations that mimic real tumors.

In some embodiments, expressions of artificial tissue may be generated based on expression vectors of each cell type and the randomly selected proportion of RNA of those cells.

For example, as described herein, expression vectors are added up with random coefficients that reflect the proportion of RNA of those cells:

$$T_i^{mix_{before}} = \sum_{cell\ types} \alpha_{cell} T_i^{cell}$$

$$\sum_{cell\ types} \alpha_{cell} = 1$$

where α is the random coefficient that reflects the random proportion of RNA of the cells for each cell type, $T_i^{cell}$ represents the RNA expression data of a particular gene for the cell, and $T_i^{mix_{before}}$ represents the RNA expression data of the particular gene for the mix.

TABLE 7

This table specifies, for each of multiple cell types, the most likely proportion of the cell type based on tumor tissue and blood (PBMC).

| Cell type | Solid tumors | PBMC |
| --- | --- | --- |
| B_cells | 11 | 20 |
| Plasma_B_cells | 6 | 3 |
| Non_plasma_B_cells | 5 | 17 |
| T_cells | 15 | 100 |
| CD4_T_cells | 7 | 50 |
| Tregs | 4 | 2 |
| CD8_T_cells | 8 | 50 |
| CD8_T_cells_PD1_low | 4 | 48 |
| CD8_T_cells_PD1_high | 4 | 2 |
| NK_cells | 2 | 16 |
| Monocytes | 2 | 80 |
| Macrophages | 40 | 1 |
| Neutrophils | 2 | 10 |
| Fibroblasts | 50 | 1 |
| Endothelium | 36 | 1 |
| T_helpers | 3 | 48 |
| Macrophages_M1 | 12 | 0.5 |
| Macrophages_M2 | 28 | 0.5 |

Noise Generation

As shown in FIG. 6A, after the artificial mixes have been generated, noise (e.g., technical noise, uniform noise, or any suitable form of noise) may be added to the RNA expression data. For example, noise may be generated and added to the RNA expression data according to the process described herein below:

$$T_i^{mix_{after}} = T_i^{mix_{before}} + \text{Noise}(T_i^{mix_{before}})$$

In some embodiments, expression of each gene may contribute noise to the overall tissue expression. For example, the expression of a single gene ($T_i^j$) could be represented as a sum:

$$T_i^j = \mu_{T_i} + P_i^j + N_{prep_i} + N_{bio_i}$$

Wherein $u_{T_i}$ represents the true expression of the gene, $P_i^j$ represents Poisson technical noise, $N_{prep_i}$ represents normally distributed noise derived from sequencing library preparation, and $N_{bio_i}$ represents variable biological noise.

In some embodiments, a relative standard deviation of Poisson technical noise ($\delta_{P_i}$) and a relative standard deviation of the normally distributed noise ($\delta_{N_i}$) are used to calculate a quantitative relative standard deviation:

$$\delta_i = \sqrt{\delta_{P_i}^2 + \delta_{N_i}^2}$$

Technical variability may result from differences in sample and library preparation (non-Poisson noise) and random transcript selection on the sequencer track due to limited coverage (Poisson noise). Many cell types of the microenvironment may typically occupy a small fraction in tumor samples. Therefore, the inventors have recognized and appreciated that it may be important to consider different levels of variability or noise for different genes, depending on the level of their expression. For example, in some embodiments, a TPM-based mathematical noise model is provided, which accounts for technical noise (both Poisson and non-Poisson). In some embodiments, this model of variability may be added to the artificial mixes generated to train the non-linear regression models, as described herein. In some embodiments, technical non-Poisson noise is assumed to be normally distributed. These may account for variability in the library preparation, alignment or variations in human handling of different samples. In contrast, Poisson noise is a type of technical noise which may be associated with the sequencing coverage or number of read counts and may not be normally distributed. The resulting dependence of technical noise on coverage and gene expression could be expressed by a formula:

$$\delta_{P_i} = \alpha \sqrt{\frac{1}{\ell_i T_i R}}$$

Where $l_i$ is an effective gene length, $T_i$ is a mean TPM in technical replicates, R is read counts, and α is an estimated proportional coefficient. According to this equation, the lower the coverage the higher the variability. According to this equation, genes with a low expression will present with a high level of Poisson noise.

Figure 12A:
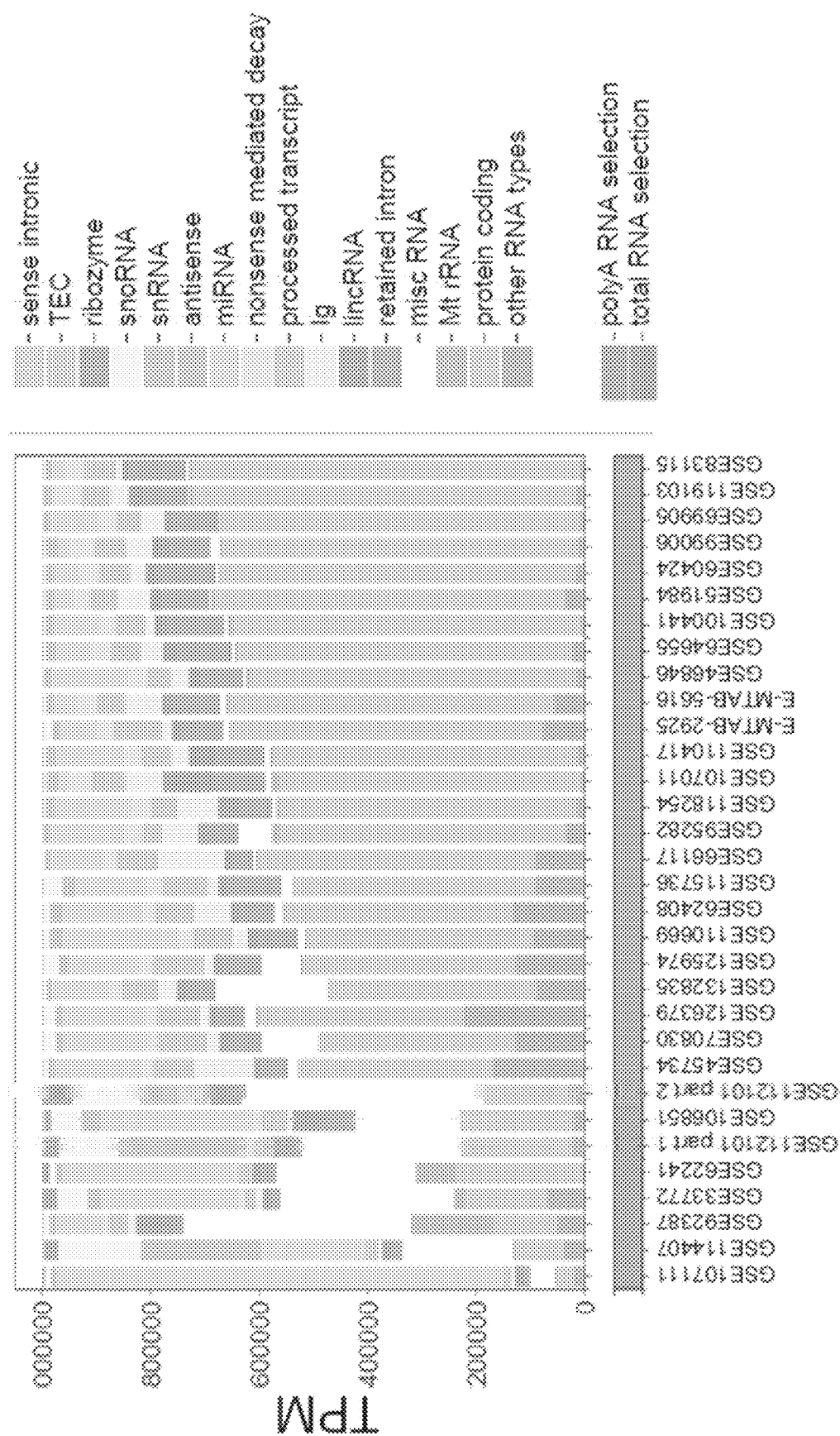
FIGS. 12A-12K are charts and graphs depicting analysis and results from an experiment to establish RNA transcript normalization, and analyze sequencing technical noise as described in connection with Example 1.
Figure 12B:
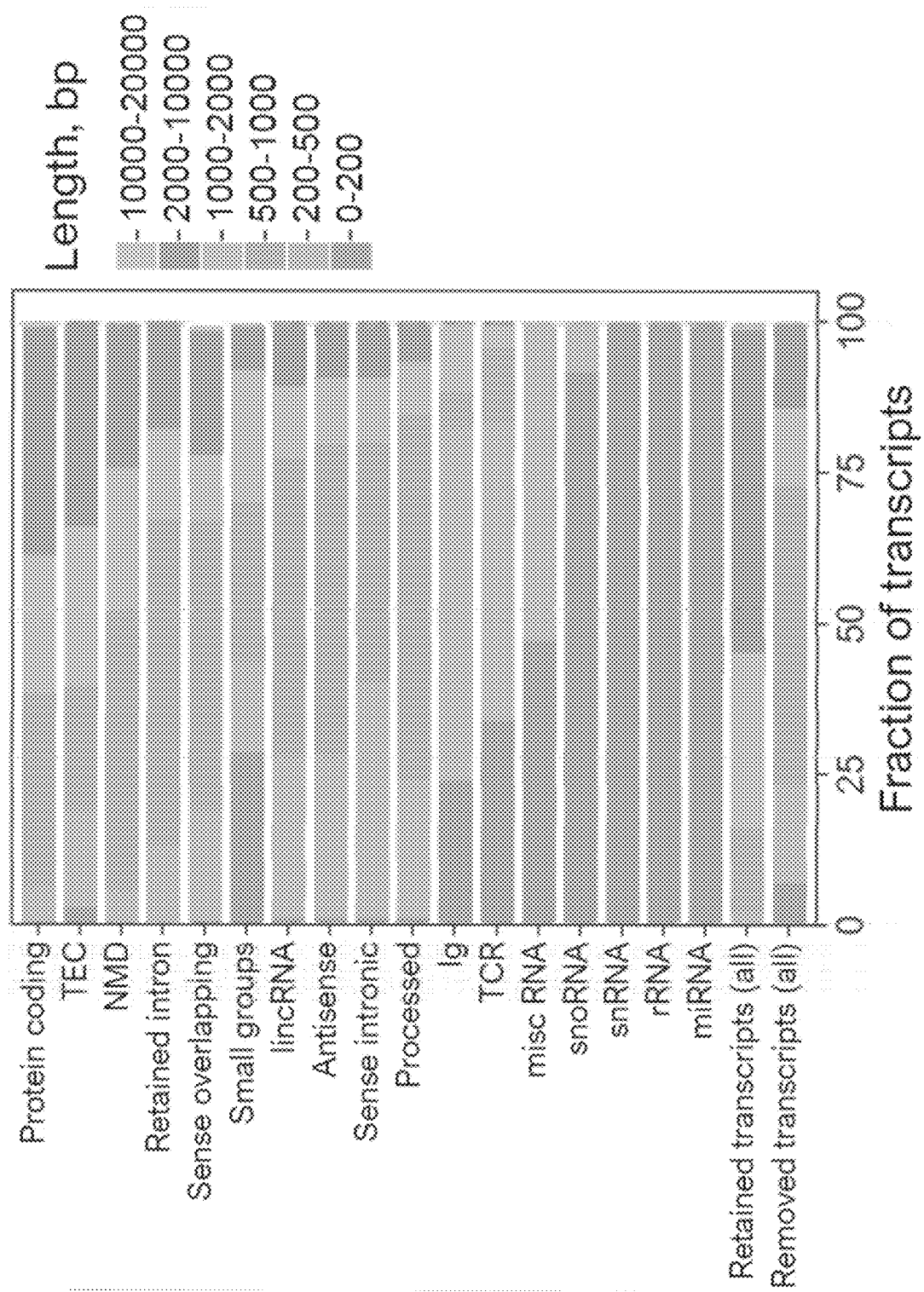
Figure 12C:
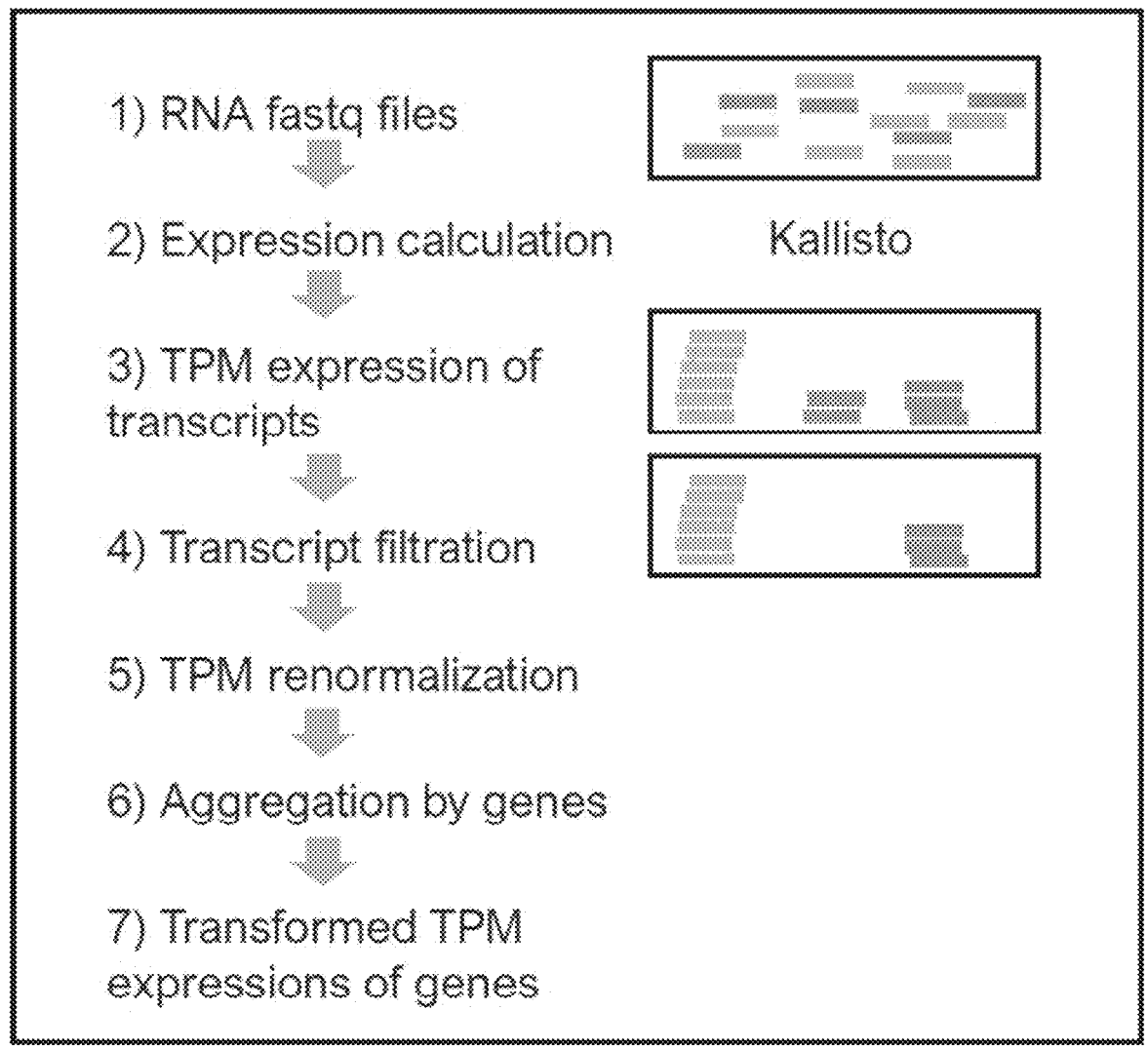
Figure 12D:
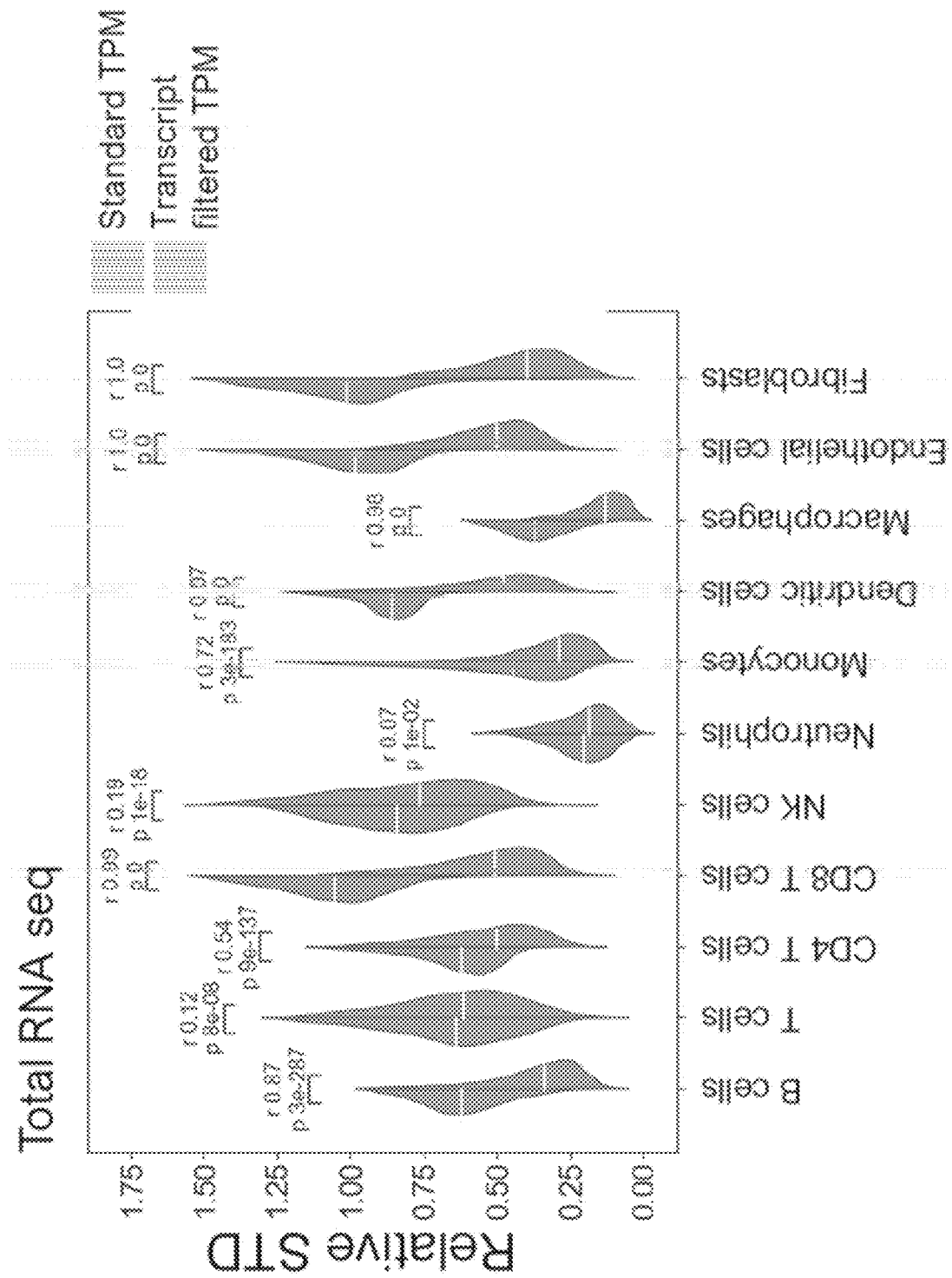
Figure 12E:
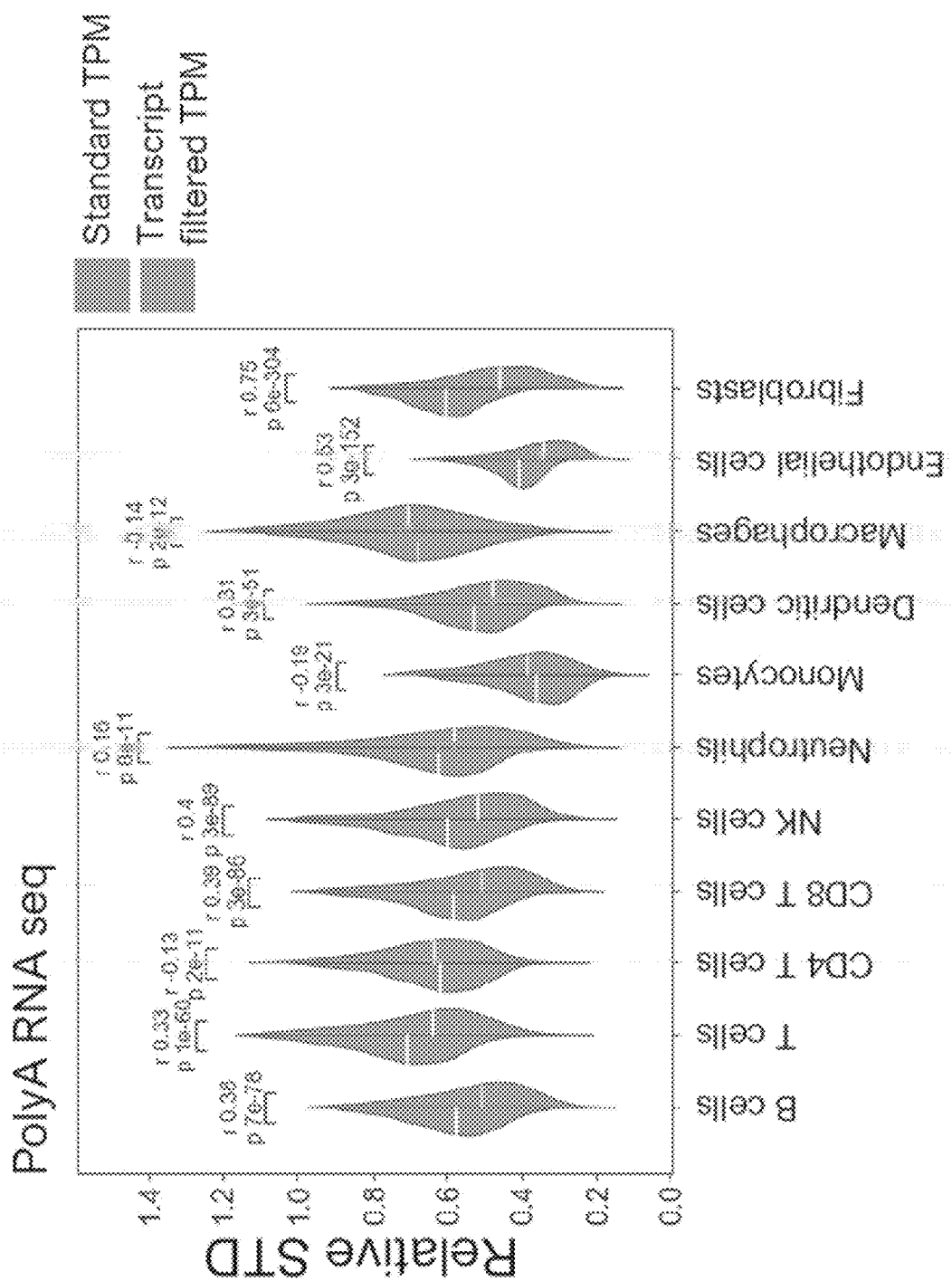
Figure 12F:
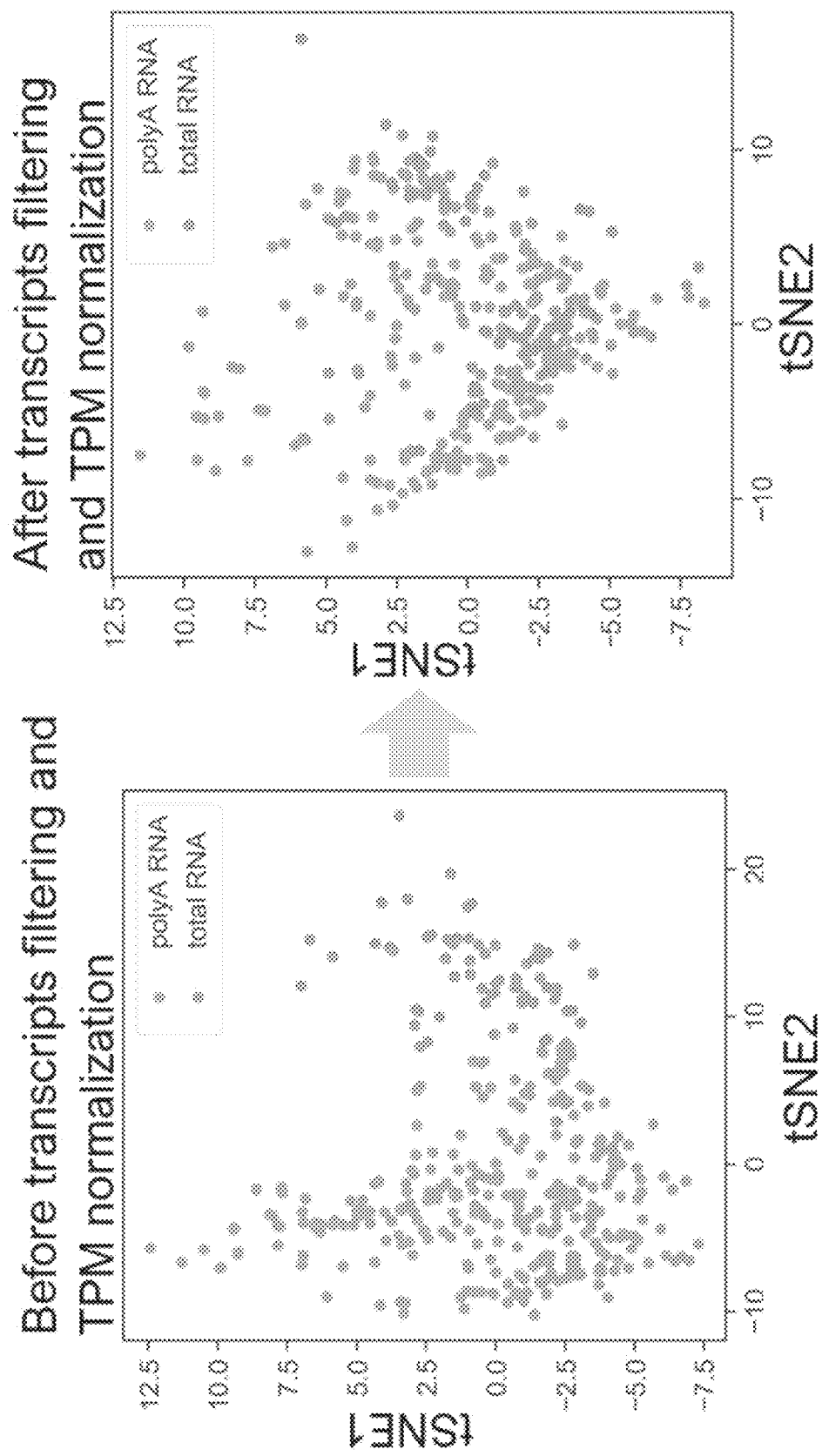
Figure 12G:
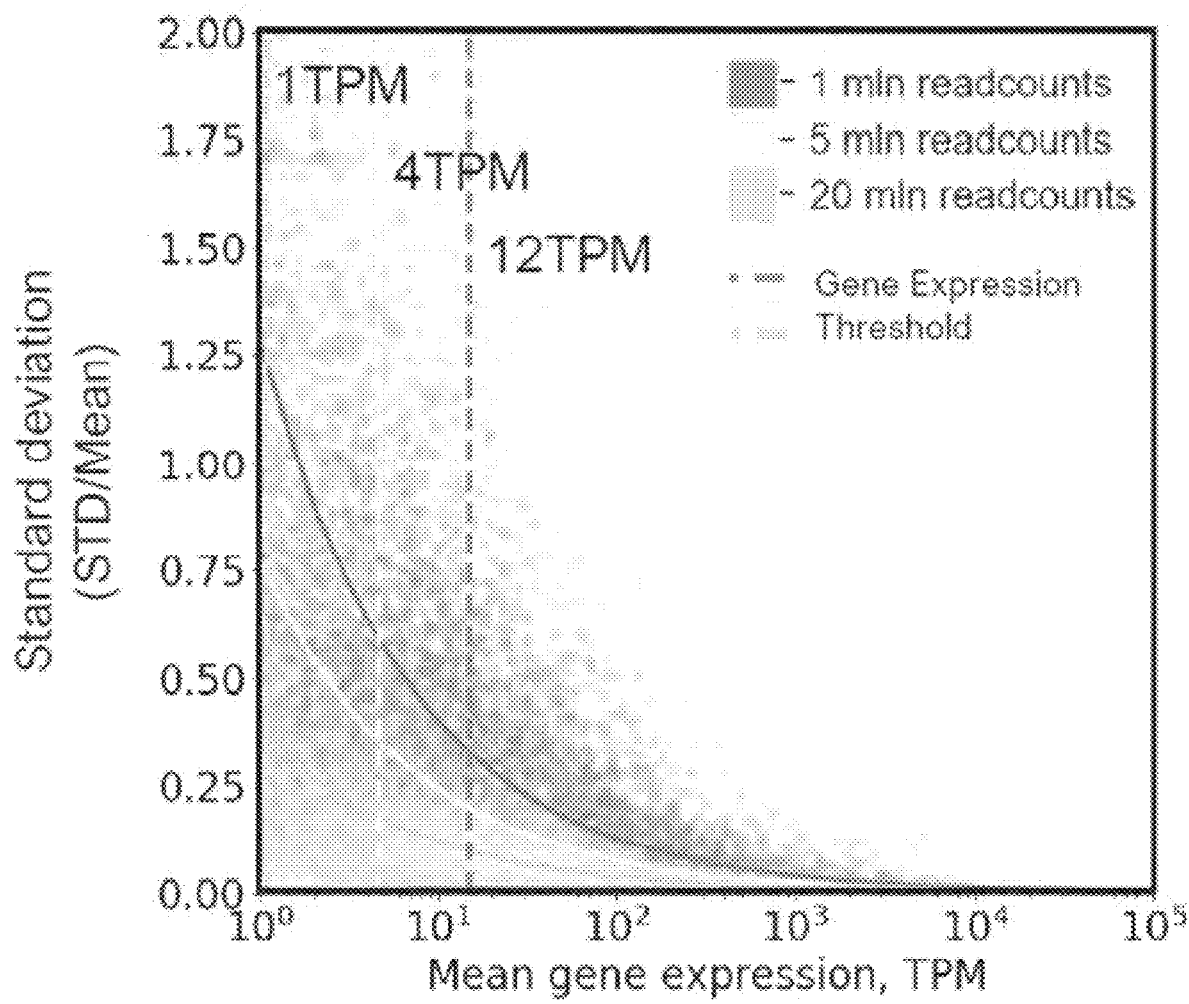
Figure 12H:
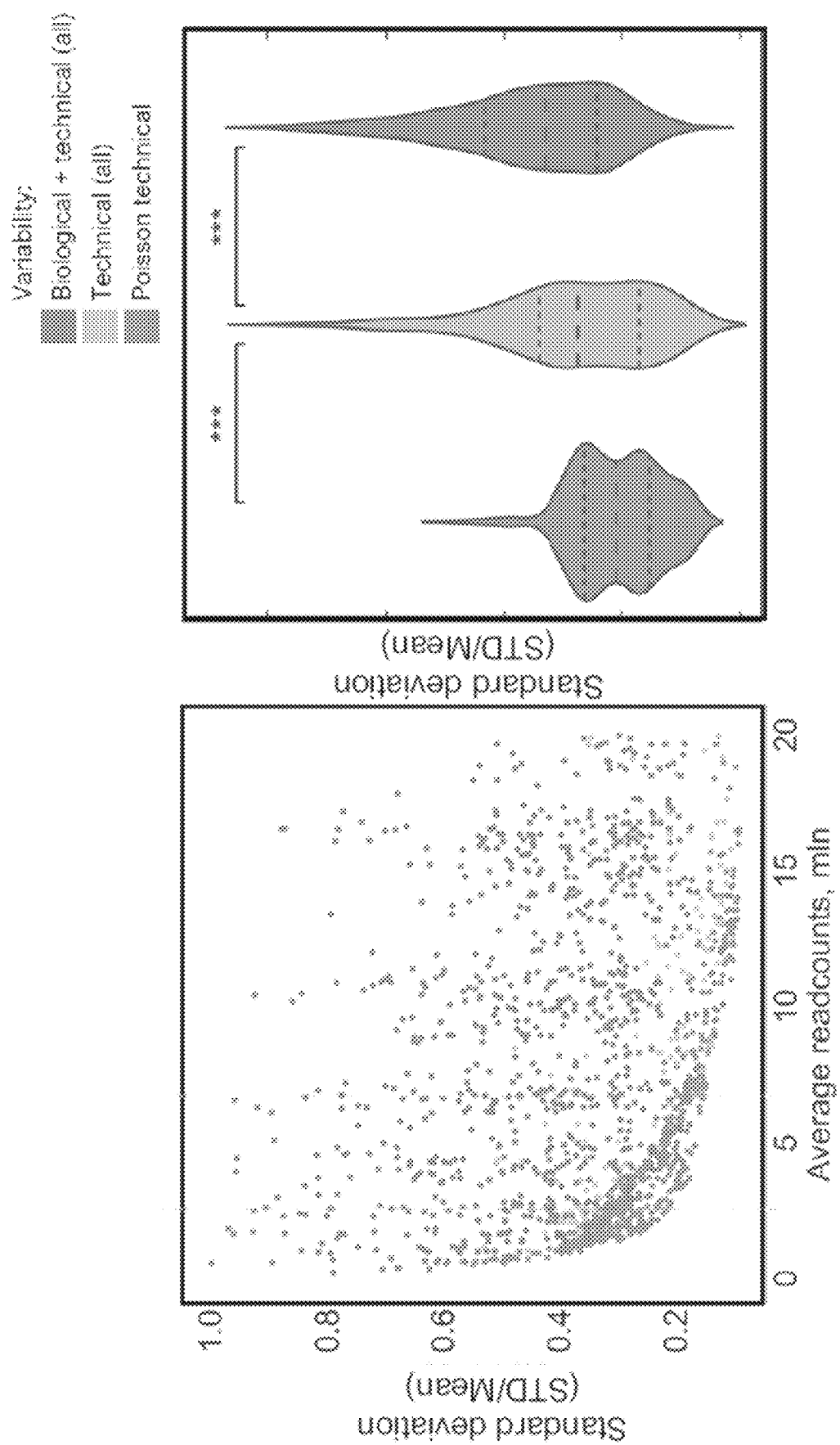
Figure 12I:
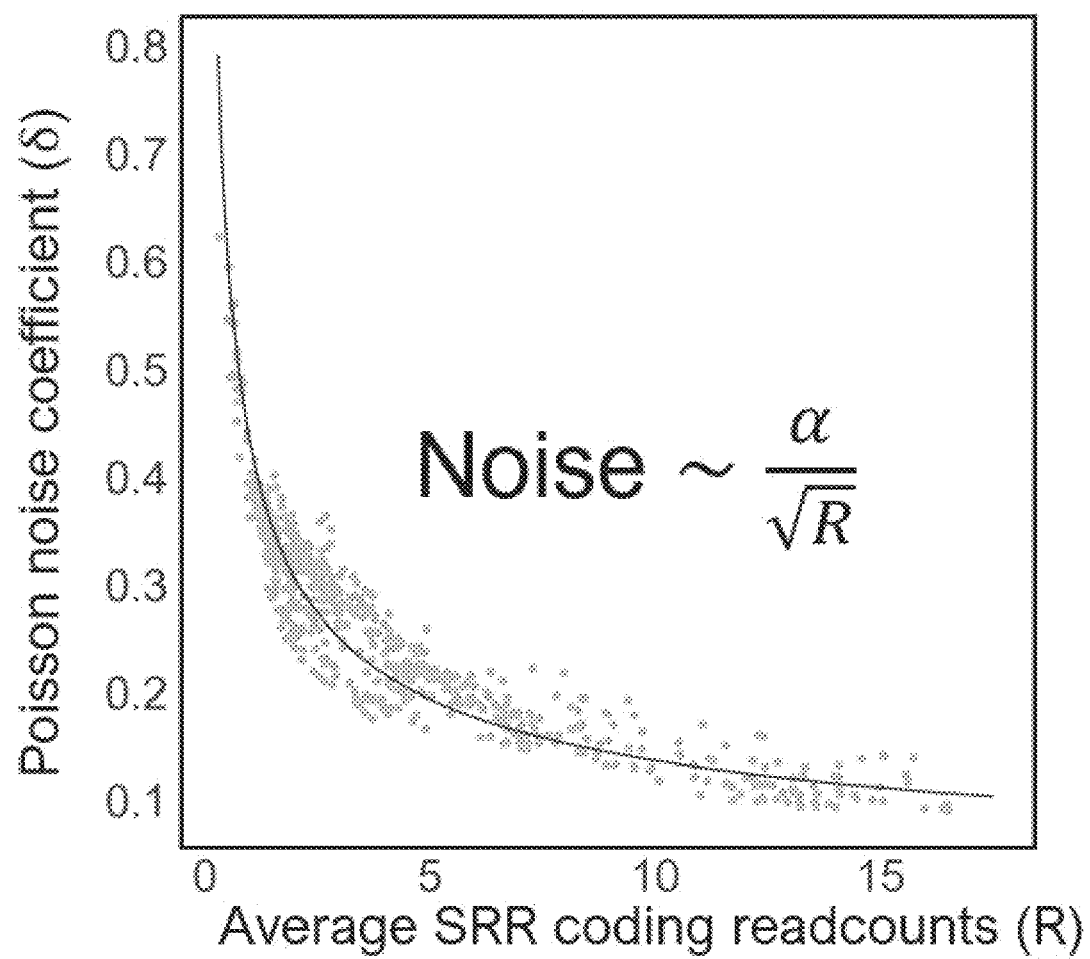
Figure 12J:
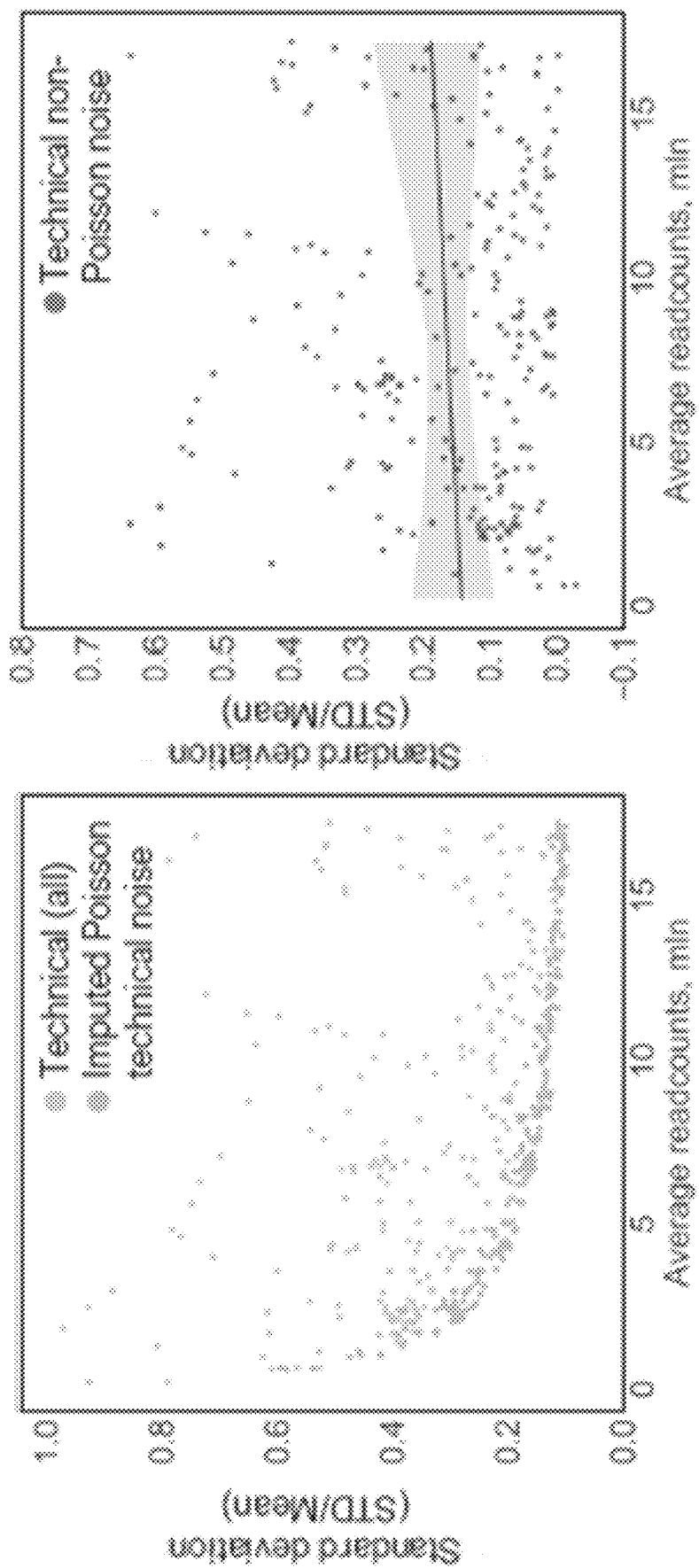
Figure 12K:
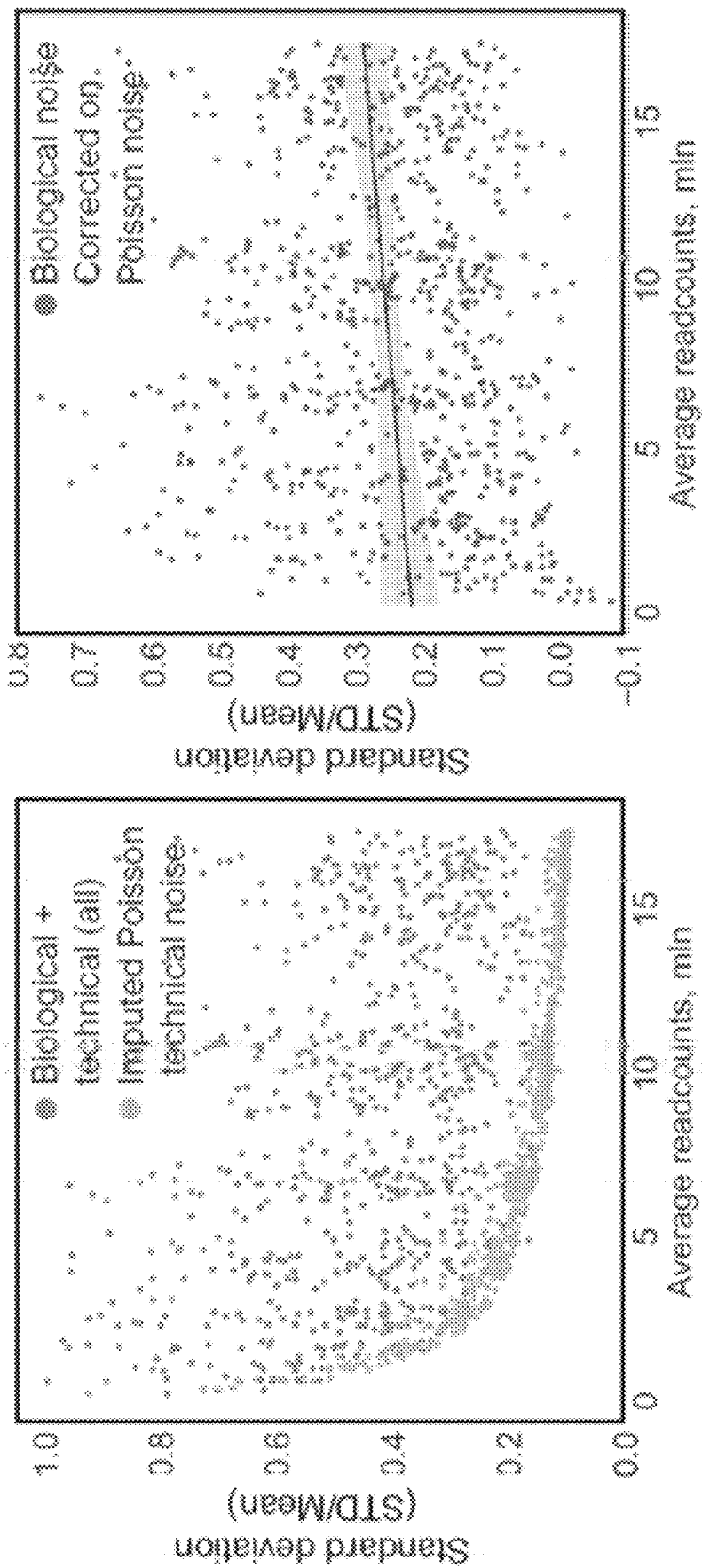

As described herein below with respect to Example 1, this model may correctly represent the gene expression variability as a result of expression levels and coverage, as shown using technical replicates of purified cell populations (FIG. 12I). As shown, in this case the limit of detection of gene expression varied from 1TPM at a coverage of 20 million total reads to 12 TPM at a coverage of 1 million reads per sample Therefore, the ability to assess gene expression may be influenced by the amount of material which is available. By plotting replicate values in function of read counts, the noise coefficient (a) can be calculated for Poisson noise (FIG. 12K). By calculating this coefficient, the technical noise for each sample and each gene can be inferred according to the deduced formula.

In addition to technical noise, biological noise, which may be associated with different activated states of a cell, can contribute to the overall variance in an RNA-seq sample. In some embodiments, there may be no need to add biological noise to artificial mixes, as this noise may already be present through the use of RNA-seq data derived from cell subsets representing a variation of biological states. As described herein below with respect to Example 1, this overall variance can be assessed, in one example, by plotting data for the same cell types, obtained by different experiments (FIG. 12J). An example of the dependence of technical noise, both Poisson and non-Poisson, and biological variability on the average sequencing coverage is presented in FIG. 12J. In this example, on average the noise increases from 10% to 26% from technical to biological replicates for certain cell types (FIG. 12J, right).

In some embodiments, the analysis of noise contribution due to single gene expression, as described herein, may be applied to simulate technical and biological noise in artificial mixes. For example, noise may be added to total gene expression in two summands:

$$T_i^{mix_{after}} = T_i^{mix_{before}} + \beta\sqrt{\frac{T_i^{mix_{before}}}{l_i}}\xi_P + \gamma T_i^{mix_{before}}\xi_N$$

Wherein $\xi_P, \xi_N \sim N(0,1)$, $\beta$ is the coefficient of Poisson noise level coefficient, and $\gamma$ is the coefficient of uniform level non-Poisson noise (Table 9).

As described herein below with respect to Example 1, the above-describe approach may be validated by excluding the technical Poisson noise from the technical non-Poisson and biological noise. In the example of FIGS. 12L-12M, an average variance at about 16% was obtained, which was subsequently used in mixes. In this example, after technical correction the noise lost the dependence on the sequencing coverage. This may be expected, since the technical non-Poisson and biological variability do not depend on the measurement method.

The noise model described herein may be used to add technical (both Poisson and non-Poisson) variation to artificial mixes. This results in artificial mixes which better mimic real tissues. Improved artificial mixes may subsequently be used to train the deconvolution algorithm (e.g., as described herein including with respect to FIGS. 4-6) to ensure model stability when encountering real sequencing variability.

Hyperparameter Estimation

As shown in FIG. 6A, training a non-linear regression model according to the techniques developed by the inventors may comprise estimating and/or updating parameters for the model, in some embodiments. As described herein, the parameters for the model may include some parameters, which may be referred to herein as hyperparameters, other than the learned weights for the model (e.g., as described herein at least with respect to FIG. 4). An exemplary list of such hyperparameters and their values is shown in Table 9.

In some embodiments, values for the hyperparameters may be estimated as the non-linear regression models are trained. For example, some or all of the hyperparameters may be updated based on one or more validation sets of the training data (e.g., with each fold of the model training). In some embodiments, the hyperparameters may be estimated based on TCGA data. For example, the results for a particular setting of the hyperparameters may be checked for consistency against TCGA data, such that TCGA model concordance may be achieved. In the illustrated example, for instance, it is confirmed that, for a given cell type (e.g., lymphocytes), the sum of results across the cell subtypes (e.g., T cells, B cells, and NK cells) is equal (or close) to the overall result for the cell type.

In some embodiments, a parameter search may be performed as part of estimating the hyperparameters. Any suitable parameter search technique may be used, including a random search, a grid search, or a genetic algorithm. In some embodiments, the parameter search may be performed using Bayesian optimization, gradient-based optimization, or evolutionary optimization, for example. In some embodiments, a parameter search may select one or more hyperparameter values from a predetermined range associated with the hyperparameter.

Tables 8 and 9 list example hyperparameters: number of samples for averaging (Nav), uniform noise level ($\gamma$), Dirichlet samples proportion (Dp), rebalance parameter (r), hyperexpression fraction (Hf), and maximum hyperexpression level (Mhl).

As described above, including with respect to the "Averaging of samples" section, "Nav" samples are selected for each cell type, the expressions of which are averaged.

As described above, including with respect to the "Microenvironment cells proportions generation" section, a number of artificial mixes "Dp" may be created in which proportion are generated from the Dirichlet distribution.

As described above, including with respect to the "Rebalance by dataset section," the rebalance parameter "r" may be used in an equation to determine a new number of samples in the dataset. As described, "r" is a value in the range [0, 1], where 0 means there is no change in the number of samples, and 1 means that for each dataset there will be the same number of samples. In some embodiments, the rebalancing parameter may be selected during training.

As described above, including with respect to the "Mixes construction" section, to imitate abnormal amplification of genes' expression in tumor cells, hyperexpression noise may be added to each of the artificial mixes. In some embodiments, random values are added to the genes' expression of a selected tumor sample with a small probability for creating each mix. For example, with a probability of "Hf" a random number from a uniform distribution from zero to "Mhl" may be added to the expression of each gene.

TABLE 8

This table specifies, for each of multiple hyperparameters, example values that define a range for each hyperparameter.

| Mixing parameter | Min | Max | Type |
|---|---|---|---|
| Nav | 2 | 14 | Int |
| γ | 0.05 | 0.6 | Float |
| Dp | 0.05 | 0.45 | Float |
| r | 0.05 | 0.6 | Float |
| Hf | 0.2 | 6 | Float |
| Mhl | 100 | 15000 | Float |

TABLE 9

This table specifies, for each of multiple hyperparameters, example values for the hyperparameter

| Mixing parameter | Letter | Value |
|---|---|---|
| num_av | Nav | 9 |
| Poisson_noise_level | β | 0.35 |
| uniform_noise_level | γ | 0.168618 |
| dirichlet_samples_proportion | Dp | .334754 |
| tumor_width | Tw | 1 |
| tumor_level | Tl | 0.5 |
| rebalance_parameter | r | 0.432012 |
| hyperexpression_fraction | Hf | 0.03 |
| max_hyperexpression_level | Mhl | 3428 |

Computational Complexity

It should be appreciated that the machine learning models described herein may include tens of thousands, hundreds of thousands, or millions of parameters. For example, the non-linear regression models 304, as described herein including at least with respect to FIGS. 2-6, may include at least ten thousand parameters, at least one hundred thousand parameters, or at least one million parameters. As such, processing data with machine learning models like the non-linear regression models 304, even after they have been trained, requires millions of calculations to be performed, which cannot be done practically in the human mind and without computers.

The algorithms for training such the machine learning models described herein may require an even greater amount of computational resources, as such models are trained using tens of thousands, hundreds of thousands, or millions of artificial mixes (e.g., as described herein including at least with respect to FIG. 6A). In one specific example, three million artificial mixes may be generated for training the non-linear regression models across two stages (e.g., as described herein including at least with respect to FIG. 5A). Neither the training algorithms nor the use of the trained models may be performed without computing resources.

Results

Described herein below with respect to FIGS. 7A-7G are a variety of results achieved using the techniques developed by the inventors. As described herein, the techniques developed by the inventors substantially outperform conventional techniques for cellular deconvolution. In the figures, the cellular deconvolution techniques developed by the inventors may be referred to as "Kassandra".

FIG. 7A is a chart comparing simulated RNA expression data 702 (e.g., a plurality of artificial mixes generated according to the techniques of FIG. 6A) to RNA expression data 704 from a plurality of biological samples (e.g., tumor). In the illustrated example, the RNA expression data 702 is obtained from five hundred artificial lung cancer samples, developed using the techniques described herein including with respect to FIG. 6A. In comparison, the RNA expression data 704 comprises gene expression patterns from RNA-seq data of five hundred non-small-cell lung carcinomas from TCGA. As shown in the illustrated example, the gene expression patterns for the artificial mixes and real tumors are substantially similar. Across all samples, the correlation between real and artificial tumors reached 0.9 (p=0.001).

FIG. 7B is a chart depicting exemplary cell composition percentages predicted according to the deconvolution techniques developed by the inventors, and corresponding true cell composition percentages. In the illustrated example, the performance of the deconvolution techniques developed by the inventors is measured as a Pearson correlation on the holdout artificial mixes (e.g., as described herein including with respect to FIG. 5A). As shown, the correlation is above 0.94 for all cell types, with multiple cell types exhibiting correlation above 0.98 (p=0).

FIGS. 7C and 7D are exemplary charts representing the Pearson correlation for different cell types between predicted and true artificial mix values (e.g., prediction accuracy.) The graphs compare exemplary prediction accuracy for the deconvolution techniques developed by the inventors, and the prediction accuracy for alternative algorithms. In FIG. 7C, the prediction accuracy without cancer cell hyperexpression noise is presented. In FIG. 7D, the prediction accuracy with cancer cell hyperexpression is presented.

Figure 7E:
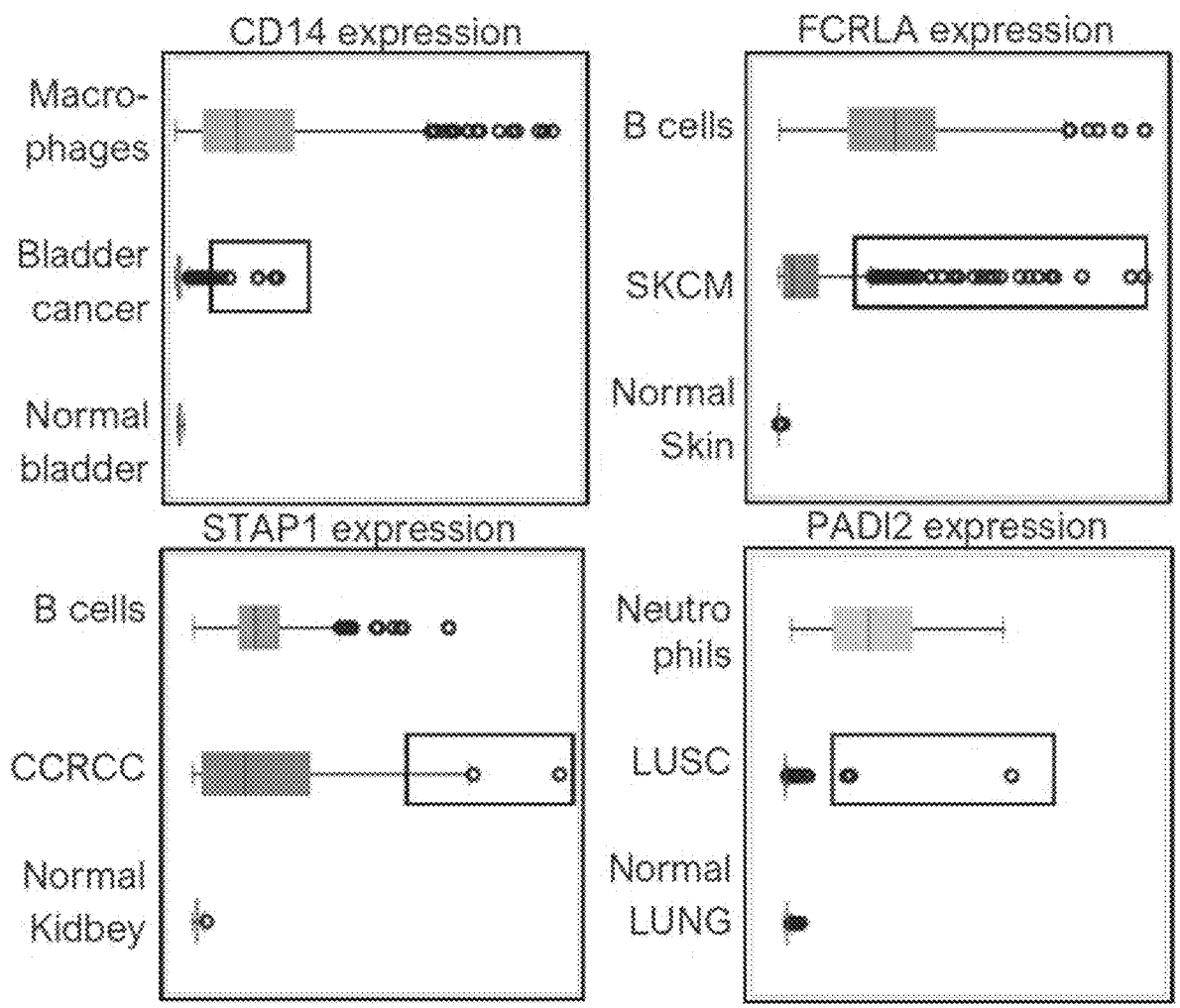
FIG. 7E is a graph depicting expression of four selected genes in normal tissue, immune cell types, and cancerous tissue, according to some embodiments of the technology described herein.

As described herein including at least with respect to FIG. 6A, random hyperexpression noise may be added to artificial mixes (e.g., to allow the deconvolution techniques developed by the inventors to ignore aberrant expressions from malignant cells in the samples). In order to create accurate hyperexpression noise, four example gene markers in TCGA data derived from four different cancer types were analyzed: CD14 in bladder cancer, FCRLA in skin cutaneous melanoma, STAP1 in clear cell renal cell carcinoma, and PAD12 in lung squamous cell carcinoma. Each of these markers were found to be overexpressed in the corresponding cancer type. While these markers are not expressed in the corresponding normal tissue, they are found to be expressed in immune cells (FIG. 7E).

As a result, the deconvolution techniques developed by the inventors are stable to aberrant high expression present in the data. As shown in FIGS. 7C-7D, the techniques developed by the inventors produce accurate predictions across cell types, even when hyperexpression noise is present (FIG. 7D). Furthermore, FIG. 7D indicates that the performance of the alternative algorithms is significantly reduced in the presence of overexpression noise, while the techniques developed by the inventors retained high correlation scores on the validation dataset.

The alternative algorithms include CIBERSORT, CIBERSORTx, QuanTIseq, FARDEEP, Xcell, ABIS, EPIC, MCP-counter, Scaden, and MuSiC. Newman et al. ("Robust enumeration of cell subsets from tissue expression profiles." Nat. Methods 12, 453-457, (2015)) describes CIBERSORT. Newman et al. ("Determining cell type abundance and expression from bulk tissues with digital cytometry." Nat Biotechnol 37, 773-782 (2019)), describes CIBERSORTx. Finotello et al. ("Molecular and pharmacological modulators of the tumor immune contexture revealed by deconvolution of RNA-seq data." Genome Med 11, 34 (2019).) describes QuanTIseq. Hao et al. ("Fast and Robust Deconvolution of Tumor Infiltrating Lymphocyte from Expression Profiles using Least Trimmed Squares." bioRxiv 358366; doi: https://doi.org/10.1101/358366) describes FARDEEP. Aran at al. ("xCell: digitally portraying the tissue cellular heterogeneity landscape." Genome Biol. 18, 220, (2017)) describes X cell. Monaco et al. ("RNA-Seq signatures normalized by mRNA abundance allow absolute deconvolution of human immune cell types." Cell Rep. 26, 1627-1640.e1627 (2019)) describes ABIS.

Figure 7F:
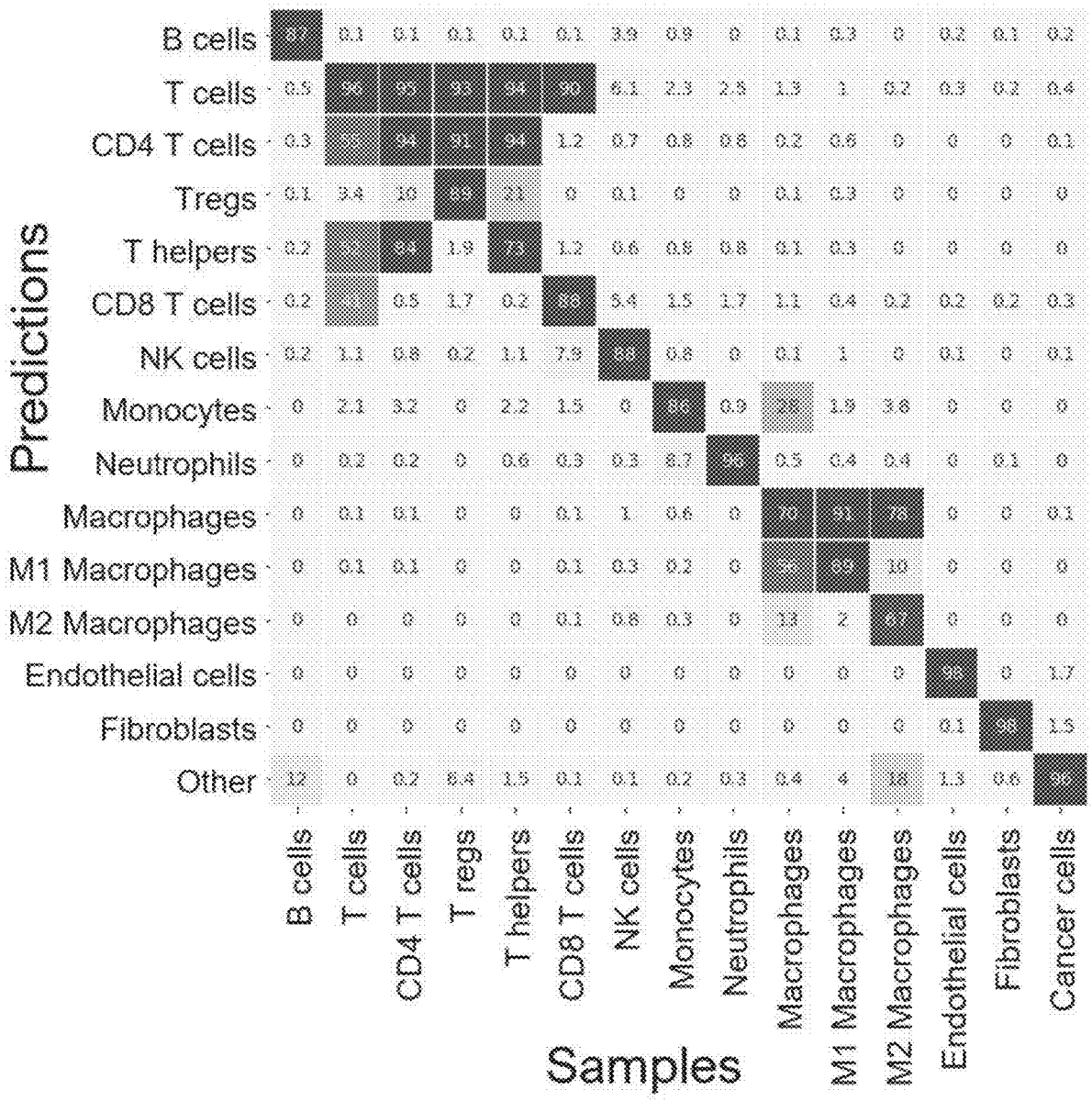
FIG. 7F is a chart depicting exemplary prediction specificity for the deconvolution techniques developed by the inventors, according to some embodiments of the technology described herein.

FIG. 7F is a heatmap representing the Pearson correlation for different cell types between predicted and true artificial mix values (e.g., prediction accuracy) for the deconvolution techniques developed by the inventors. Predicted cell percentages for different cell types are shown for data from sorted samples, derived from holdout datasets. As shown, the deconvolution techniques developed by the inventors achieved high prediction accuracy scores across cell types, including closely related cell types.

Figure 7G:
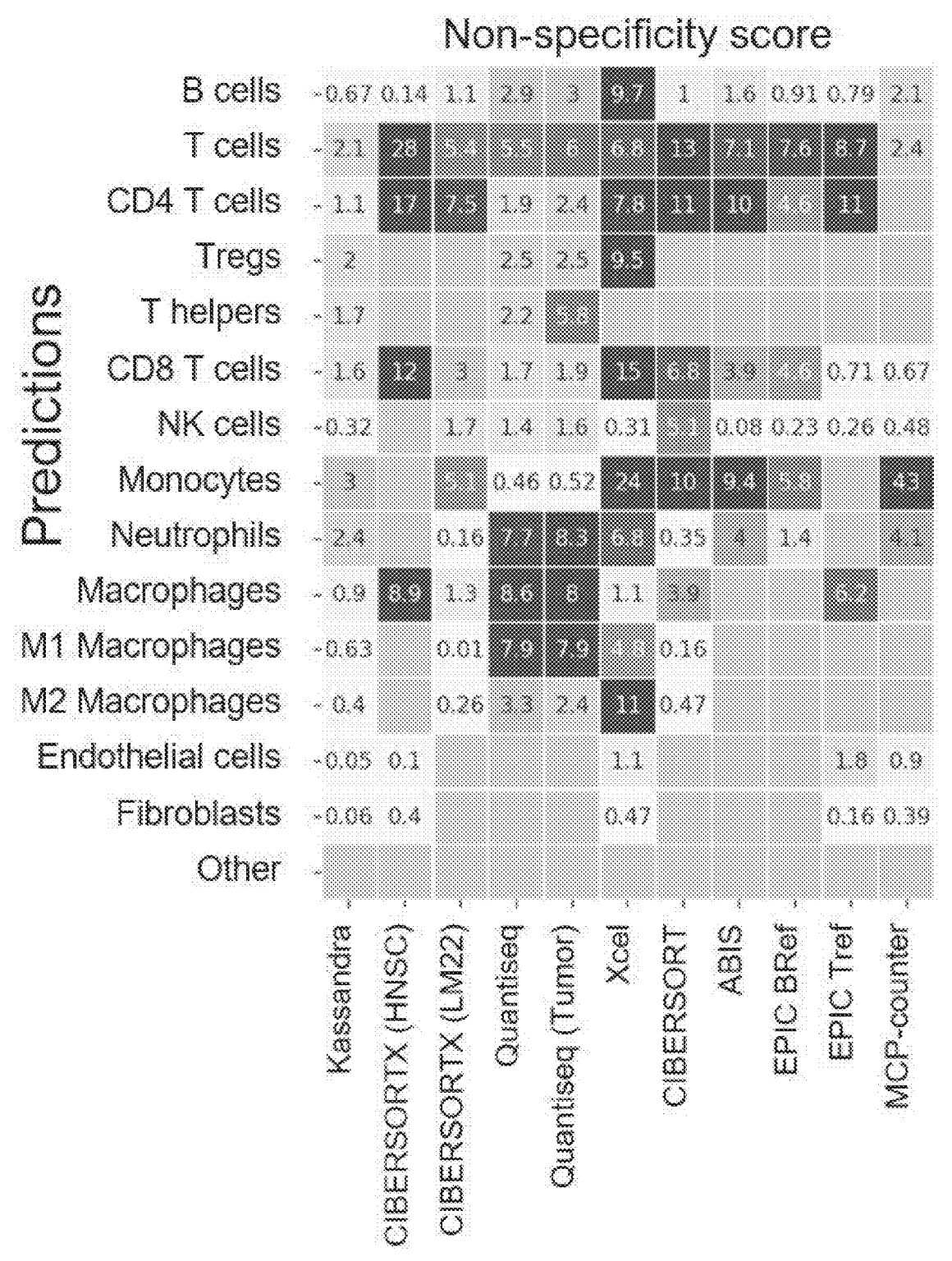

FIG. 7G is a chart comparing exemplary non-specificity scores for the deconvolution techniques developed by the inventors to non-specificity scores for alternative algorithms. In the illustrated example, non-specificity scores for eleven alternative algorithms are shown. The values in the chart of FIG. 7G represent percentages of non-specific (false positive) predictions relative to specific (true positive) predictions for different cell types. A low non-specificity score indicates a lower percentage of false positives predictions (e.g., indicating a more specific model). Specifically, the detection of signals for each cell type in pure populations was assessed, and B-cells, T-cells, and macrophages were further subdivided, with each subclass clearly distinguished from the others.

Linear Methods for Deconvolution

According to some embodiments of the techniques developed by the inventors, a linear method of cellular deconvolution may be provided. An exemplary linear deconvolution technique is described herein below with respect to FIGS. 8 and 9A-9C.

Figure 8:
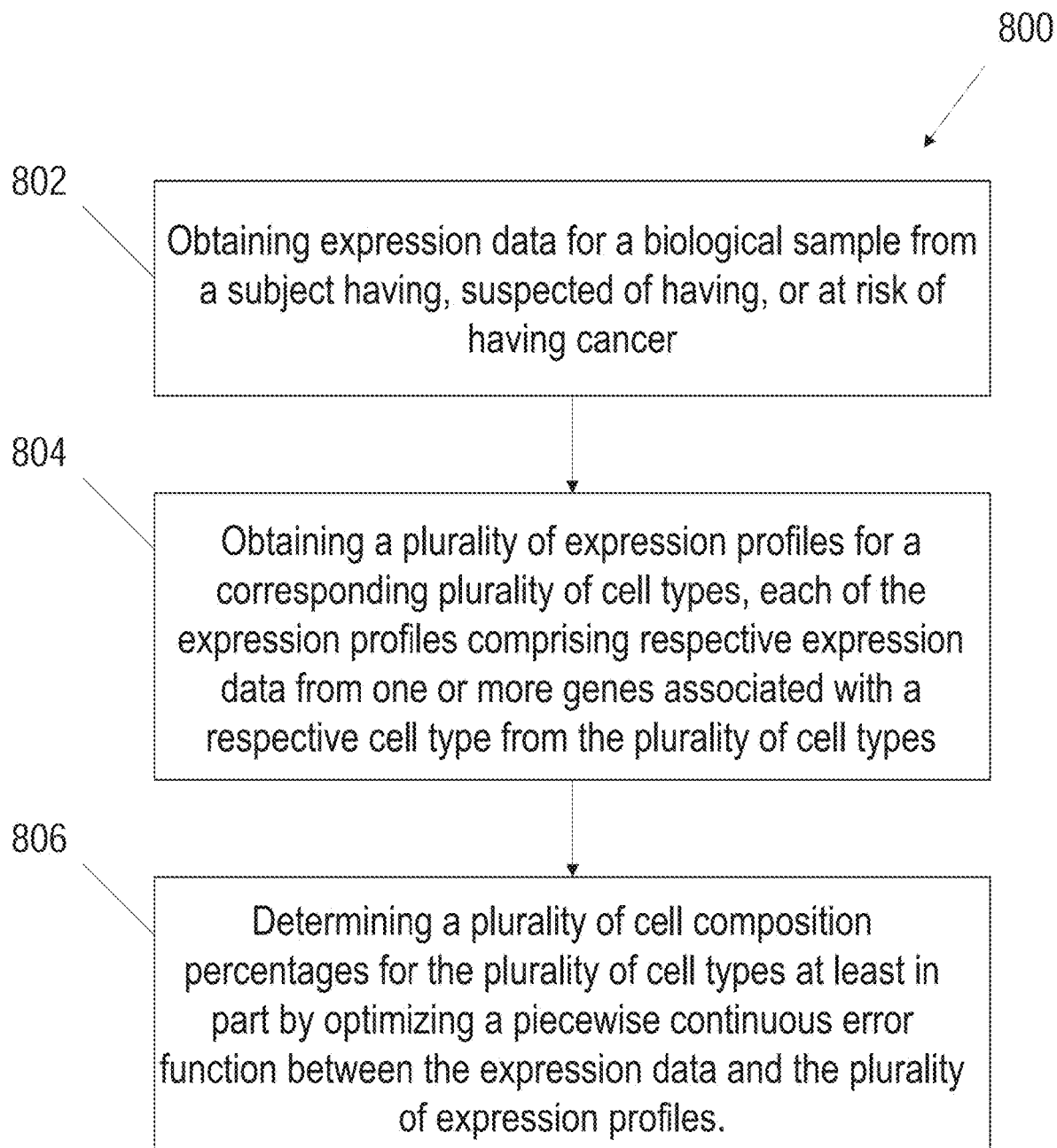
FIG. 8 is a flowchart depicting an exemplary linear method for determining cell composition percentages based on RNA expression data, according to some embodiments of the technology described herein.

FIG. 8 is a flowchart depicting an exemplary linear method 800 for determining cell composition percentages based on expression data (e.g., RNA expression data). As described herein, the method 800 may comprise estimating cell composition percentages for one or more cell types in a biological sample, using an expression profile (e.g., an RNA expression, and/or an expression profile as shown in FIG. 9A) for each cell type.

In some embodiments, the method 800 may be carried out on a computing device (e.g., as described herein including at least with respect to FIG. 10). For example, the computing device may include at least one processor, and at least one non-transitory storage medium storing processor-executable instructions which, when executed, perform the acts of method 800. The method 800 may be carried out, for example, in a system such as system 100 (which may include, for example, a clinical setting or a laboratory setting), by one or more computing devices such as by computing device 108.

At act 802, the method 800 may begin with obtaining RNA expression data for a biological sample from a subject. In some embodiments, act 802 may include accessing RNA expression data that was previously obtained from a biological sample. As described herein including with respect to FIG. 1A, the biological sample may comprise a biopsy (e.g., of a tumor or other diseased tissue of the subject) or any other suitable type of biological sample, and the expression data may be extracted using any suitable techniques. The expression obtained at act 802 may comprise RNA expression data measured in TPM. In some embodiments, the origin or preparation methods of the biological sample may include any of the embodiments described with respect to the "Biological Samples" section. In some embodiments, the origin or preparation methods of the expression data may include any of the embodiments described with respect to the "Expression Data" and "Obtaining RNA expression data" sections.

In some embodiments, the expression data may be stored on at least one storage medium and accessed as part of act 802. For example, the expression data may be stored in one or more files or in a database, which may be read as part of act 802. In some embodiments, the at least one storage medium storing the expression data may be local to the computing device (e.g., stored on the same at least one non-transitory storage medium), or may be external to the computing device (e.g., stored in a remote database or a cloud storage environment). The expression data may be stored on a single storage medium or may be distributed across multiple storage mediums.

In some embodiments, act 802 may further comprise pre-processing the expression data in any suitable manner. For example, the expression data may be sorted, combined, organized into batches, filtered, or pre-processed with any other suitable techniques. The pre-processing may make the expression data suitable to be processed using the linear regression technique described herein with respect to acts 804-806. In some embodiments, pre-processing the RNA may include any of the embodiments described with respect to the "Alignment and annotation," "Removing non-coding transcripts," and "Conversion to TPM and gene aggregation" sections.

As described herein with respect to acts 804 to 806, the method 800 may proceed with processing the RNA expression data using a linear regression technique in order to determine one or more corresponding cell composition percentages for the cell types.

At act 804, the method 800 may proceed with obtaining a plurality of expression profiles (e.g., as described herein including with respect to FIG. 9A) for a corresponding plurality of cell types. For example, if CD4+ T cells, NK cells, and CD8+ T cells are being analyzed using method 800, then an expression profile for CD4+ T cells, an expression profile for NK cells, and an expression profile for CD8+ T cells may be obtained at act 802. Each of the expression profiles (e.g., RNA expression profiles) may comprise respective expression data (e.g., RNA expression data) from one or more genes associated with a respective cell type from the plurality of cell types. In some embodiments, the genes associated with each respective cell type may be specific and/or semi-specific genes for the cell type. For example, the genes associated with each respective cell type may comprise corresponding genes listed in Table 2. In some embodiments, the corresponding genes may include at least 2 genes, at least 4 genes, at least 6 genes, at least 8 genes, at least 10 genes, at least 12 genes, at least 14 genes, or at least 16 genes included in Table 2. In some embodiments, the corresponding genes may include fewer than 10,000, fewer than 5,000, fewer than 2,000, fewer than 1,000, fewer than 500, fewer than 250, or fewer than 100 genes.

The expression profile may be obtained in any suitable manner. For example, the expression profile may be stored in one or more files or in a database, which may be read as part of act 804. In some embodiments, the at least one storage medium storing the expression profile may be local to the computing device (e.g., stored on the same at least one non-transitory storage medium), or may be external to the computing device (e.g., stored in a remote database or a cloud storage environment). The expression profile may be stored on a single storage medium, or may be distributed across multiple storage mediums.

Figure 9A:
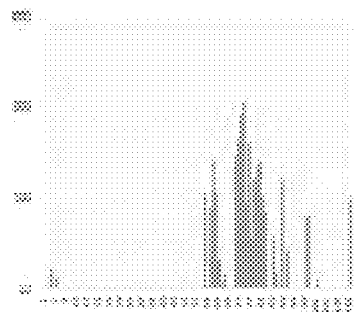
FIG. 9A is a diagram depicting exemplary RNA expression profiles and overall RNA expression data, according to some embodiments of the technology described herein.
Figure 9A:
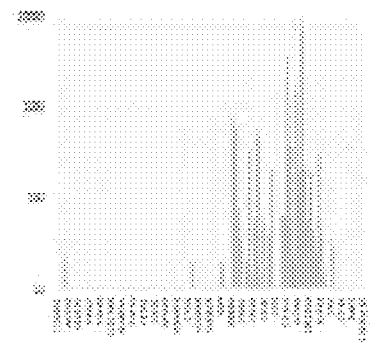
Figure 9A:
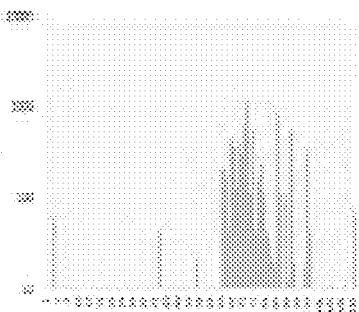
Figure 9A:
Figure 9A:
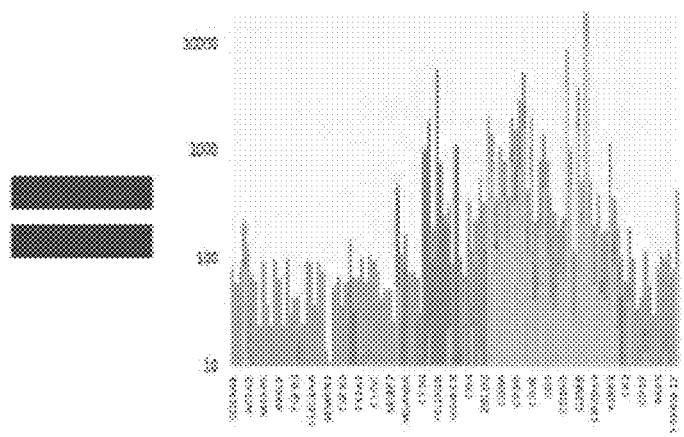

At act 806, the method 800 may proceed with determining a plurality of cell composition percentages for the plurality of cell types at least in part by optimizing a piecewise continuous error function (e.g., the example piecewise continuous error function described with respect to FIG. 9A) between the expression data and the plurality of expression profiles. Act 806 may be performed simultaneously or iteratively across the plurality of cell types, and may be repeated (e.g., for a set number of iterations, or until a measurement of error is below a threshold) in some embodiments.

According to some embodiments, act 806 may comprise performing a linear regression using the expression data, the plurality of expression profiles, and the piecewise continuous error function. This may include, in some embodiments, optimizing the piecewise continuous error function. In some embodiments, optimizing the piecewise continuous error function is not limited to finding a global maximum or minimum of the piecewise continuous error function, but may also encompass finding a local maximum or minimum within a threshold distance of a global maximum or minimum. For example, act 806 may involve determining a combination (e.g., a weighted sum) of the expression profiles that has a lowest error or an error below a threshold (e.g., with the error measured using the piecewise continuous error function) relative to the expression data.

For a particular cell type, act 806 may comprise determining, for each gene associated with the cell type, a corresponding output of a piecewise continuous error function (e.g., such as the error function of FIG. 9C). The piecewise continuous error function may serve to compare an actual measured expression value from real data (e.g., RNA-seq data), against a predicted expression value which may be computed using the gene's expression in the expression profile for the cell type (e.g., as obtained at act 804). For example, the predicted expression value may be computed as a product of the expression of the gene in the expression profile, and a coefficient α for the cell type.

For a given gene and cell type, the input to the error function may be the coefficient α, the expression g of the gene in the input expression data, and the expression p of the gene in the expression profile for the cell type. The error function may have coefficients a, b, k, as described herein including with respect to FIG. 9C, which may be updated as part of act 806. According to some embodiments, act 806 may be performed iteratively or in parallel for some or all of the genes. For example, act 806 may be performed repeatedly across the plurality of cell types until a coefficient α is found for each cell type such that the piecewise continuous error function is below a threshold or minimized. According to some embodiments, for a given cell type, the value of coefficient α may be determined by finding the coefficient value that minimizes the weighted error sum across all of the genes (e.g., the piecewise error function as described herein including with respect to act 806 and FIG. 9C, summed across all genes).

In some embodiments, the coefficient α may represent the cell composition percentage for the corresponding cell type (e.g., because α defines the weight of each expression profile in the weighted sum for the expression data). For example, determining the plurality of cell composition percentages for the plurality of cell types may comprise processing the coefficients, such as by normalizing them, in order to obtain corresponding cell composition percentages for each of the plurality of cell types.

FIG. 9A is a diagram depicting exemplary RNA expression profiles and overall RNA expression data. In the illustrated example, known RNA expression profiles are shown for CD4+ T cells, NK cells, and CD8+ T cells. Each RNA expression profile is illustrated as a bar graph, with the horizontal axis representing genes, and the vertical axis representing the expression of those genes. As shown in the figure, each RNA expression profile may be unique for a given cell type.

As shown in the illustrated example, the overall observed expression for a biological sample may be considered as a sum of expression profiles for cell types comprising the biological sample. Although not shown, each RNA expression profile may be weighted by a coefficient α, such that the biological sample may be considered as a weighted sum of the RNA expression profiles. According to some embodiments, the sum may further include a term for unknown expression of other cell types. This term may represent expression data that is not accounted for with the weighted sum of RNA expression profiles (e.g., as shown in gray in the observed expression for the biological sample).

Figure 9B:
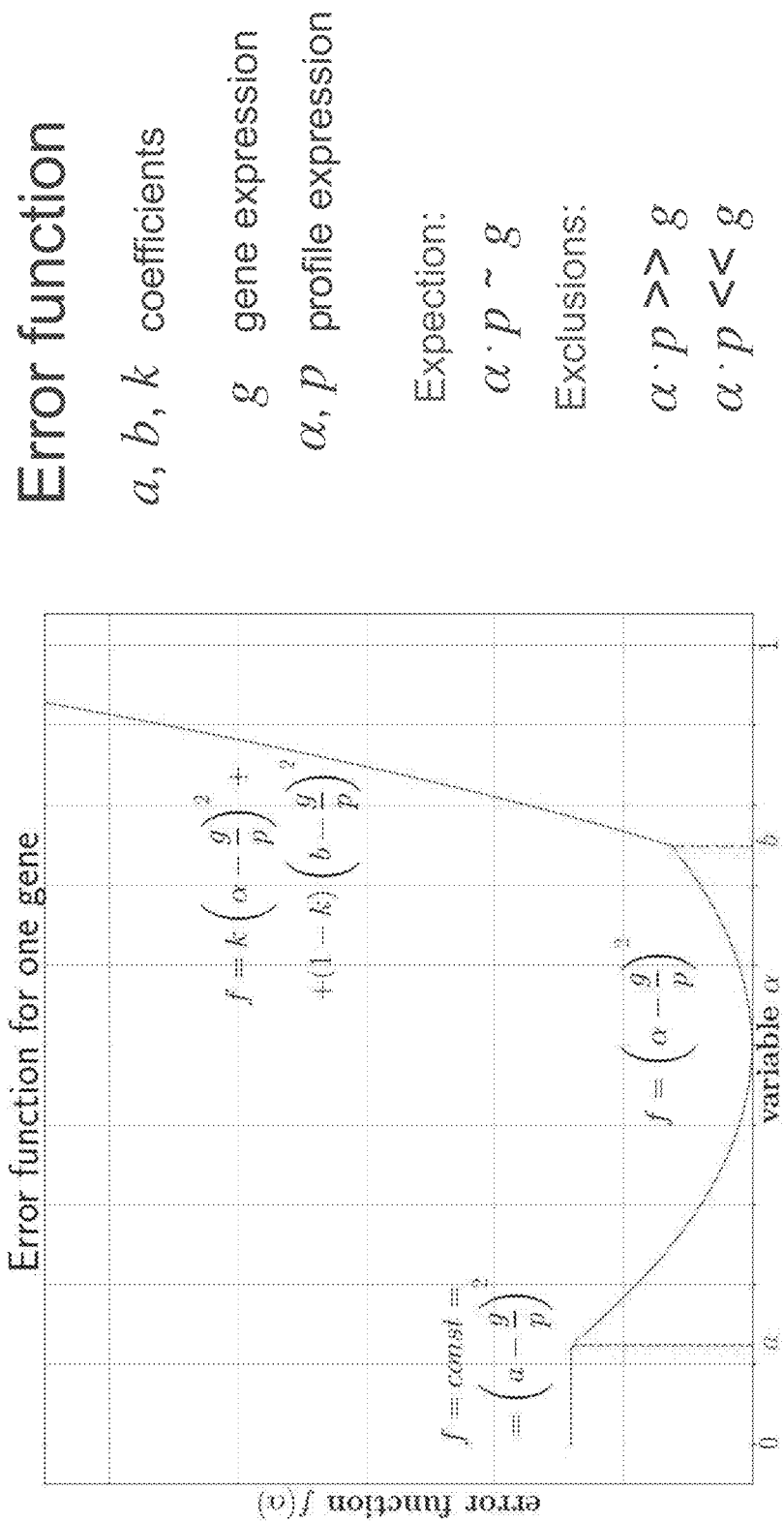
FIG. 9B depicts an exemplary piecewise continuous error function, according to some embodiments of the technology described herein.

FIG. 9B depicts an exemplary piecewise continuous error function for use with the method of FIG. 8. As shown in the illustrated plot, the error function f is piecewise, with the coefficients a and b dividing the function into three sections, and coefficient k affecting the shape of the rightmost section of the error function. For each section of the function, the error may be computed according the illustrated expression.

Biological Samples

Any of the methods, systems, or other claimed elements may use or be used to analyze a biological sample from a subject. In some embodiments, a biological sample is obtained from a subject having, suspected of having cancer, or at risk of having cancer. The biological sample may be any type of biological sample including, for example, a biological sample of a bodily fluid (e.g., blood, urine or cerebrospinal fluid), one or more cells (e.g., from a scraping or brushing such as a cheek swab or tracheal brushing), a piece of tissue (cheek tissue, muscle tissue, lung tissue, heart tissue, brain tissue, or skin tissue), or some or all of an organ (e.g., brain, lung, liver, bladder, kidney, pancreas, intestines, or muscle), or other types of biological samples (e.g., feces or hair).

In some embodiments, the biological sample is a sample of a tumor from a subject. In some embodiments, the biological sample is a sample of blood from a subject. In some embodiments, the biological sample is a sample of tissue from a subject.

A sample of a tumor, in some embodiments, refers to a sample comprising cells from a tumor. In some embodiments, the sample of the tumor comprises cells from a benign tumor, e.g., non-cancerous cells. In some embodiments, the sample of the tumor comprises cells from a premalignant tumor, e.g., precancerous cells. In some embodiments, the sample of the tumor comprises cells from a malignant tumor, e.g., cancerous cells.

Examples of tumors include, but are not limited to, adenomas, fibromas, hemangiomas, lipomas, cervical dysplasia, metaplasia of the lung, leukoplakia, carcinoma, sarcoma, germ cell tumors, and blastoma.

A sample of blood, in some embodiments, refers to a sample comprising cells, e.g., cells from a blood sample. In some embodiments, the sample of blood comprises non-cancerous cells. In some embodiments, the sample of blood comprises precancerous cells. In some embodiments, the sample of blood comprises cancerous cells. In some embodiments, the sample of blood comprises blood cells. In some embodiments, the sample of blood comprises red blood cells. In some embodiments, the sample of blood comprises white blood cells. In some embodiments, the sample of blood comprises platelets. Examples of cancerous blood cells include, but are not limited to, leukemia, lymphoma, and myeloma. In some embodiments, a sample of blood is collected to obtain the cell-free nucleic acid (e.g., cell-free DNA) in the blood.

A sample of blood may be a sample of whole blood or a sample of fractionated blood. In some embodiments, the sample of blood comprises whole blood. In some embodiments, the sample of blood comprises fractionated blood. In some embodiments, the sample of blood comprises buffy coat. In some embodiments, the sample of blood comprises serum. In some embodiments, the sample of blood comprises plasma. In some embodiments, the sample of blood comprises a blood clot.

A sample of a tissue, in some embodiments, refers to a sample comprising cells from a tissue. In some embodiments, the sample of the tumor comprises non-cancerous cells from a tissue. In some embodiments, the sample of the tumor comprises precancerous cells from a tissue.

Methods of the present disclosure encompass a variety of tissue including organ tissue or non-organ tissue, including but not limited to, muscle tissue, brain tissue, lung tissue, liver tissue, epithelial tissue, connective tissue, and nervous tissue. In some embodiments, the tissue may be normal tissue or it may be diseased tissue or it may be tissue suspected of being diseased. In some embodiments, the tissue may be sectioned tissue or whole intact tissue. In some embodiments, the tissue may be animal tissue or human tissue. Animal tissue includes, but is not limited to, tissues obtained from rodents (e.g., rats or mice), primates (e.g., monkeys), dogs, cats, and farm animals.

The biological sample may be from any source in the subject's body including, but not limited to, any fluid [such as blood (e.g., whole blood, blood serum, or blood plasma), saliva, tears, synovial fluid, cerebrospinal fluid, pleural fluid, pericardial fluid, ascitic fluid, and/or urine], hair, skin (including portions of the epidermis, dermis, and/or hypodermis), oropharynx, laryngopharynx, esophagus, stomach, bronchus, salivary gland, tongue, oral cavity, nasal cavity, vaginal cavity, anal cavity, bone, bone marrow, brain, thymus, spleen, small intestine, appendix, colon, rectum, anus, liver, biliary tract, pancreas, kidney, ureter, bladder, urethra, uterus, vagina, vulva, ovary, cervix, scrotum, penis, prostate, testicle, seminal vesicles, and/or any type of tissue (e.g., muscle tissue, epithelial tissue, connective tissue, or nervous tissue).

Any of the biological samples described herein may be obtained from the subject using any known technique. See, for example, the following publications on collecting, processing, and storing biological samples, each of which are incorporated herein in its entirety: Biospecimens and biorepositories: from afterthought to science by Vaught et al. (Cancer Epidemiol Biomarkers Prev. 2012 February; 21(2): 253-5), and Biological sample collection, processing, storage and information management by Vaught and Henderson (IARC Sci Publ. 2011; (163):23-42).

In some embodiments, the biological sample may be obtained from a surgical procedure (e.g., laparoscopic surgery, microscopically controlled surgery, or endoscopy), bone marrow biopsy, punch biopsy, endoscopic biopsy, or needle biopsy (e.g., a fine-needle aspiration, core needle biopsy, vacuum-assisted biopsy, or image-guided biopsy).

In some embodiments, one or more than one cell (i.e., a cell biological sample) may be obtained from a subject using a scrape or brush method. The cell biological sample may be obtained from any area in or from the body of a subject including, for example, from one or more of the following areas: the cervix, esophagus, stomach, bronchus, or oral cavity. In some embodiments, one or more than one piece of tissue (e.g., a tissue biopsy) from a subject may be used. In certain embodiments, the tissue biopsy may comprise one or more than one (e.g., 2, 3, 4, 5, 6, 7, 8, 9, 10, or more than 10) biological samples from one or more tumors or tissues known or suspected of having cancerous cells.

Any of the biological samples from a subject described herein may be stored using any method that preserves stability of the biological sample. In some embodiments, preserving the stability of the biological sample means inhibiting components (e.g., DNA, RNA, protein, or tissue structure or morphology) of the biological sample from degrading until they are measured so that when measured, the measurements represents the state of the sample at the time of obtaining it from the subject. In some embodiments, a biological sample is stored in a composition that is able to penetrate the same and protect components (e.g., DNA, RNA, protein, or tissue structure or morphology) of the biological sample from degrading. As used herein, degradation is the transformation of a component from one from to another such that the first form is no longer detected at the same level as before degradation.

In some embodiments, a biological sample (e.g., tissue sample) is fixed. As used herein, a "fixed" sample relates to a sample that has been treated with one or more agents or processes in order to prevent or reduce decay or degradation, such as autolysis or putrefaction, of the sample. Examples of fixative processes include but are not limited to heat fixation, immersion fixation, and perfusion. In some embodiments a fixed sample is treated with one or more fixative agents. Examples of fixative agents include but are not limited to cross-linking agents (e.g., aldehydes, such as formaldehyde, formalin, glutaraldehyde, etc.), precipitating agents (e.g., alcohols, such as ethanol, methanol, acetone, xylene, etc.), mercurials (e.g., B-5, Zenker's fixative, etc.), picrates, and Hepes-glutamic acid buffer-mediated organic solvent protection effect (HOPE) fixatuve. In some embodiments, a biological sample (e.g., tissue sample) is treated with a cross-linking agent. In some embodiments, the cross-linking agent comprises formalin. In some embodiments, a formalin-fixed biological sample is embedded in a solid substrate, for example paraffin wax. In some embodiments, the biological sample is a formalin-fixed paraffin-embedded (FFPE) sample. Methods of preparing FFPE samples are known, for example as described by Li et al. JCO Precis Oncol. 2018; 2: PO.17.00091.

In some embodiments, the biological sample is stored using cryopreservation. Non-limiting examples of cryopreservation include, but are not limited to, step-down freezing, blast freezing, direct plunge freezing, snap freezing, slow freezing using a programmable freezer, and vitrification. In some embodiments, the biological sample is stored using lyophilization. In some embodiments, a biological sample is placed into a container that already contains a preservant (e.g., RNALater to preserve RNA) and then frozen (e.g., by snap-freezing), after the collection of the biological sample from the subject. In some embodiments, such storage in frozen state is done immediately after collection of the biological sample. In some embodiments, a biological sample may be kept at either room temperature or 4° C. for some time (e.g., up to an hour, up to 8 h, or up to 1 day, or a few days) in a preservant or in a buffer without a preservant, before being frozen.

Non-limiting examples of preservants include formalin solutions, formaldehyde solutions, RNALater or other equivalent solutions, TriZol or other equivalent solutions, DNA/RNA Shield or equivalent solutions, EDTA (e.g., Buffer AE (10 mM Tris.Cl; 0.5 mM EDTA, pH 9.0)) and other coagulants, and Acids Citrate Dextronse (e.g., for blood specimens). In some embodiments, special containers may be used for collecting and/or storing a biological sample. For example, a vacutainer may be used to store blood. In some embodiments, a vacutainer may comprise a preservant (e.g., a coagulant, or an anticoagulant). In some embodiments, a container in which a biological sample is preserved may be contained in a secondary container, for the purpose of better preservation, or for the purpose of avoid contamination.

Any of the biological samples from a subject described herein may be stored under any condition that preserves stability of the biological sample. In some embodiments, the biological sample is stored at a temperature that preserves stability of the biological sample. In some embodiments, the sample is stored at room temperature (e.g., 25° C.). In some embodiments, the sample is stored under refrigeration (e.g., 4° C.). In some embodiments, the sample is stored under freezing conditions (e.g., −20° C.). In some embodiments, the sample is stored under ultralow temperature conditions (e.g., −50° C. to −800° C.). In some embodiments, the sample is stored under liquid nitrogen (e.g., −1700° C.). In some embodiments, a biological sample is stored at −60° C. to −80° C. (e.g., −70° C.) for up to 5 years (e.g., up to 1 month, up to 2 months, up to 3 months, up to 4 months, up to 5 months, up to 6 months, up to 7 months, up to 8 months, up to 9 months, up to 10 months, up to 11 months, up to 1 year, up to 2 years, up to 3 years, up to 4 years, or up to 5 years). In some embodiments, a biological sample is stored as described by any of the methods described herein for up to 20 years (e.g., up to 5 years, up to 10 years, up to 15 years, or up to 20 years).

Methods of the present disclosure encompass obtaining one or more biological samples from a subject for analysis. In some embodiments, one biological sample is collected from a subject for analysis. In some embodiments, more than one (e.g., 2, 3, 4, 5, 6, 7, 8, 9, 10, 11, 12, 13, 14, 15, 16, 17, 18, 19, 20, or more) biological samples are collected from a subject for analysis. In some embodiments, one biological sample from a subject will be analyzed. In some embodiments, more than one (e.g., 2, 3, 4, 5, 6, 7, 8, 9, 10, 11, 12, 13, 14, 15, 16, 17, 18, 19, 20, or more) biological samples may be analyzed. If more than one biological sample from a subject is analyzed, the biological samples may be procured at the same time (e.g., more than one biological sample may be taken in the same procedure), or the biological samples may be taken at different times (e.g., during a different procedure including a procedure 1, 2, 3, 4, 5, 6, 7, 8, 9, 10 days; 1, 2, 3, 4, 5, 6, 7, 8, 9, 10 weeks; 1, 2, 3, 4, 5, 6, 7, 8, 9, 10 months, 1, 2, 3, 4, 5, 6, 7, 8, 9, 10 years, or 1, 2, 3, 4, 5, 6, 7, 8, 9, 10 decades after a first procedure).

A second or subsequent biological sample may be taken or obtained from the same region (e.g., from the same tumor or area of tissue) or a different region (including, e.g., a different tumor). A second or subsequent biological sample may be taken or obtained from the subject after one or more treatments and may be taken from the same region or a different region. As a non-limiting example, the second or subsequent biological sample may be useful in determining whether the cancer in each biological sample has different characteristics (e.g., in the case of biological samples taken from two physically separate tumors in a patient) or whether the cancer has responded to one or more treatments (e.g., in the case of two or more biological samples from the same tumor or different tumors prior to and subsequent to a treatment). In some embodiments, each of the at least one biological sample is a bodily fluid sample, a cell sample, or a tissue biopsy sample.

In some embodiments, one or more biological specimens are combined (e.g., placed in the same container for preservation) before further processing. For example, a first sample of a first tumor obtained from a subject may be combined with a second sample of a second tumor from the subject, wherein the first and second tumors may or may not be the same tumor. In some embodiments, a first tumor and a second tumor are similar but not the same (e.g., two tumors in the brain of a subject). In some embodiments, a first biological sample and a second biological sample from a subject are sample of different types of tumors (e.g., a tumor in muscle tissue and brain tissue).

In some embodiments, a sample from which RNA and/or DNA is extracted (e.g., a sample of tumor, or a blood sample) is sufficiently large such that at least 2 µg (e.g., at least 2 µg, at least 2.5 µg, at least 3 µg, at least 3.5 µg or more) of RNA can be extracted from it. In some embodiments, the sample from which RNA and/or DNA is extracted can be peripheral blood mononuclear cells (PBMCs). In some embodiments, the sample from which RNA and/or DNA is extracted can be any type of cell suspension. In some embodiments, a sample from which RNA and/or DNA is extracted (e.g., a sample of tumor, or a blood sample) is sufficiently large such that at least 1.8 µg RNA can be extracted from it. In some embodiments, at least 50 mg (e.g., at least 1 mg, at least 2 mg, at least 3 mg, at least 4 mg, at least 5 mg, at least 10 mg, at least 12 mg, at least 15 mg, at least 18 mg, at least 20 mg, at least 22 mg, at least 25 mg, at least 30 mg, at least 35 mg, at least 40 mg, at least 45 mg, or at least 50 mg) of tissue sample is collected from which RNA and/or DNA is extracted. In some embodiments, at least 20 mg of tissue sample is collected from which RNA and/or DNA is extracted. In some embodiments, at least 30 mg of tissue sample is collected. In some embodiments, at least 10-50 mg (e.g., 10-50 mg, 10-15 mg, 10-30 mg, 10-40 mg, 20-30 mg, 20-40 mg, 20-50 mg, or 30-50 mg) of tissue sample is collected from which RNA and/or DNA is extracted. In some embodiments, at least 30 mg of tissue sample is collected. In some embodiments, at least 20-30 mg of tissue sample is collected from which RNA and/or DNA is extracted. In some embodiments, a sample from which RNA and/or DNA is extracted (e.g., a sample of tumor, or a blood sample) is sufficiently large such that at least 0.2 µg (e.g., at least 200 ng, at least 300 ng, at least 400 ng, at least 500 ng, at least 600 ng, at least 700 ng, at least 800 ng, at least 900 ng, at least 1 µg, at least 1.1 µg, at least 1.2 µg, at least 1.3 µg, at least 1.4 µg, at least 1.5 µg, at least 1.6 µg, at least 1.7 µg, at least 1.8 µg, at least 1.9 µg, or at least 2 µg) of RNA can be extracted from it. In some embodiments, a sample from which RNA and/or DNA is extracted (e.g., a sample of tumor, or a blood sample) is sufficiently large such that at least 0.1 µg (e.g., at least 100 ng, at least 200 ng, at least 300 ng, at least 400 ng, at least 500 ng, at least 600 ng, at least 700 ng, at least 800 ng, at least 900 ng, at least 1 µg, at least 1.1 µg, at least 1.2 µg, at least 1.3 µg, at least 1.4 µg, at least 1.5 µg, at least 1.6 µg, at least 1.7 µg, at least 1.8 µg, at least 1.9 µg, or at least 2 µg) of RNA can be extracted from it.

Subjects

Aspects of this disclosure relate to a biological sample that has been obtained from a subject. In some embodiments, a subject is a mammal (e.g., a human, a mouse, a cat, a dog, a horse, a hamster, a cow, a pig, or other domesticated animal). In some embodiments, a subject is a human. In some embodiments, a subject is an adult human (e.g., of 18 years of age or older). In some embodiments, a subject is a child (e.g., less than 18 years of age). In some embodiments, a human subject is one who has or has been diagnosed with at least one form of cancer. In some embodiments, a cancer from which a subject suffers is a carcinoma, a sarcoma, a myeloma, a leukemia, a lymphoma, or a mixed type of cancer that comprises more than one of a carcinoma, a sarcoma, a myeloma, a leukemia, and a lymphoma. Carcinoma refers to a malignant neoplasm of epithelial origin or cancer of the internal or external lining of the body. Sarcoma refers to cancer that originates in supportive and connective tissues such as bones, tendons, cartilage, muscle, and fat. Myeloma is cancer that originates in the plasma cells of bone marrow. Leukemias ("liquid cancers" or "blood cancers") are cancers of the bone marrow (the site of blood cell production). Lymphomas develop in the glands or nodes of the lymphatic system, a network of vessels, nodes, and organs (specifically the spleen, tonsils, and thymus) that purify bodily fluids and produce infection-fighting white blood cells, or lymphocytes. Non-limiting examples of a mixed type of cancer include adenosquamous carcinoma, mixed mesodermal tumor, carcinosarcoma, and teratocarcinoma. In some embodiments, a subject has a tumor. A tumor may be benign or malignant. In some embodiments, a cancer is any one of the following: skin cancer, lung cancer, breast cancer, prostate cancer, colon cancer, rectal cancer, cervical cancer, and cancer of the uterus. In some embodiments, a subject is at risk for developing cancer, e.g., because the subject has one or more genetic risk factors, or has been exposed to or is being exposed to one or more carcinogens (e.g., cigarette smoke, or chewing tobacco).

Expression Data

Expression data (e.g., indicating expression levels) for a plurality of genes may be used for any of the methods or compositions described herein. The number of genes which may be examined may be up to and inclusive of all the genes of the subject. In some embodiments, expression levels may be examined for all of the genes of a subject. As a non-limiting example, four or more, five or more, six or more, seven or more, eight or more, nine or more, ten or more, eleven or more, twelve or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 35 or more, 40 or more, 50 or more, 60 or more, 70 or more, 80 or more, 90 or more, 100 or more, 125 or more, 150 or more, 175 or more, 200 or more, 225 or more, 250 or more, 275 or more, or 300 or more genes may be used for any evaluation described herein. As another set of non-limiting examples, the expression data may include, for each cell type listed in Table 2, expression data for at least 5, at least 10, at least 15, at least 20, at least 25, at least 35, at least 50, at least 75, at least 100 genes selected from the group of genes for that cell type in Table 2.

Any method may be used on a sample from a subject in order to acquire expression data (e.g., indicating expression levels) for the plurality of genes. As a set of non-limiting examples, the expression data may be RNA expression data, DNA expression data, or protein expression data.

DNA expression data, in some embodiments, refers to a level of DNA in a sample from a subject. The level of DNA in a sample from a subject having cancer may be elevated compared to the level of DNA in a sample from a subject not having cancer, e.g., a gene duplication in a cancer patient's sample. The level of DNA in a sample from a subject having cancer may be reduced compared to the level of DNA in a sample from a subject not having cancer, e.g., a gene deletion in a cancer patient's sample.

DNA expression data, in some embodiments, refers to data for DNA (or gene) expressed in a sample, for example, sequencing data for a gene that is expressed in a patient's sample. Such data may be useful, in some embodiments, to determine whether the patient has one or more mutations associated with a particular cancer.

RNA expression data may be acquired using any method known in the art including, but not limited to: whole transcriptome sequencing, total RNA sequencing, mRNA sequencing, targeted RNA sequencing, small RNA sequencing, ribosome profiling, RNA exome capture sequencing, and/or deep RNA sequencing. DNA expression data may be acquired using any method known in the art including any known method of DNA sequencing. For example, DNA sequencing may be used to identify one or more mutations in the DNA of a subject. Any technique used in the art to sequence DNA may be used with the methods and compositions described herein. As a set of non-limiting examples, the DNA may be sequenced through single-molecule real-time sequencing, ion torrent sequencing, pyrosequencing, sequencing by synthesis, sequencing by ligation (SOLiD sequencing), nanopore sequencing, or Sanger sequencing (chain termination sequencing). Protein expression data may be acquired using any method known in the art including, but not limited to: N-terminal amino acid analysis, C-terminal amino acid analysis, Edman degradation (including though use of a machine such as a protein sequenator), or mass spectrometry.

In some embodiments, the expression data is acquired through bulk RNA sequencing. Bulk RNA sequencing may include obtaining expression levels for one or more genes across RNA extracted from a population of multiple input cells, which population may include multiple different cell types. In some embodiments, the expression data is acquired through single cell sequencing (e.g., scRNA-seq). Single cell sequencing may include sequencing individual cells.

In some embodiments, the expression data comprises whole exome sequencing (WES) data. In some embodiments, the expression data comprises whole genome sequencing (WGS) data. In some embodiments, the expression data comprises next-generation sequencing (NGS) data. In some embodiments, the expression data comprises microarray data.

Obtaining RNA Expression Data

In some embodiments, a method to process RNA expression data (e.g., data obtained from RNA sequencing (also referred to herein as RNA-seq data)) comprises obtaining RNA expression data for a subject (e.g., a subject who has or has been diagnosed with a cancer). In some embodiments, obtaining RNA expression data comprises obtaining a biological sample and processing it to perform RNA sequencing using any one of the RNA sequencing methods described herein. In some embodiments, RNA expression data is obtained from a lab or center that has performed experiments to obtain RNA expression data (e.g., a lab or center that has performed RNA-seq). In some embodiments, a lab or center is a medical lab or center.

In some embodiments, RNA expression data is obtained by obtaining a computer storage medium (e.g., a data storage drive) on which the data exists. In some embodiments, RNA expression data is obtained via a secured server (e.g., a SFTP server, or Illumina BaseSpace). In some embodiments, data is obtained in the form of a text-based filed (e.g., a FASTQ file). In some embodiments, a file in which sequencing data is stored also contains quality scores of the sequencing data). In some embodiments, a file in which sequencing data is stored also contains sequence identifier information.

Alignment and Annotation

In some embodiments, a method to process RNA expression data (e.g., data obtained from RNA sequencing (also referred to herein as RNA-seq data)) comprises aligning and annotating genes in the RNA expression data with known sequences of the human genome to obtain annotated RNA expression data.

In some embodiments, alignment of RNA expression data comprises aligning the data to a known assembled genome for a particular species of subject (e.g., the genome of a human) or to a transcriptome database. Various sequence alignment software are available and can be used to align data to an assembled genome or a transcriptome database. Non-limiting examples of alignment software includes short (unspliced) aligners (e.g., BLAT; BFAST, Bowtie, Burrows-Wheeler Aligner, Short Oligonucleotide Analysis package, or Mosaik), spliced aligners, aligners based on known splice junctions (e.g., Errange, IsoformEx, or Splice Seq), or de novo splice aligner (e.g., ABMapper, BBMap, CRAC, or HiSAT). In some embodiments, any suitable tool can be used for aligning and annotating data. For example, Kallisto (github.com/pachterlab/kallisto) is used to align and annotate data. In some embodiments, a known genome is referred to as a reference genome. A reference genome (also known as a reference assembly) is a digital nucleic acid sequence database, assembled as a representative example of a species' set of genes. In some embodiments, human and mouse reference genomes used in any one of the methods described herein are maintained and improved by the Genome Reference Consortium (GRC). Non-limiting examples of human reference releases are GRCh38, GRCh37, NCBI Build 36.1, NCBI Build 35, and NCBI Build 34. A non-limiting example of transcriptome databased include Transcriptome Shotgun Assembly (TSA).

In some embodiments, annotating RNA expression data comprises identifying the locations of genes and/or coding regions in the data to be processed by comparing it to assembled genomes or transcriptome databases. Non-limiting examples of data sources for annotation include GENCODE (www.gencodegenes.org), RefSeq (see e.g., www.ncbi.nlm.nih.gov/refseq/), and Ensembl. In some embodiments, annotating genes in RNA expression data is based on a GENCODE database (e.g., GENCODE V23 annotation; www.gencodegenes.org).

Consea et al. (A survey of best practices for RNA-seq data analysis; Genome Biology201617:13) provides best practices for analyzing RNA-seq data, which are applicable to any one of the methods described herein and is incorporated herein by reference in its entirety. Pereira and Rueda (bio-informatics-core-shpaed-training.github.io/cruk-bioinf-sschool/Day2/rnaSeq_align.pdf) also describe methods for analyzing RNA sequencing data, which are applicable to any one of the methods described herein, and is incorporated herein by reference in its entirety.

Removing Non-Coding Transcripts

In some embodiments, a method to process RNA expression data (e.g., data obtained from RNA sequencing (also referred to herein as RNA-seq data)) comprises removing non-coding transcripts from annotated RNA expression data. Aligning and annotating RNA expression data allows identification of coding and non-coding reads. In some embodiments, non-coding reads for transcripts are removed so as to concentrate analysis effort on expression of proteins (e.g., those that may be involved in pathology of cancer). In some embodiments, removing reads for non-coding transcripts from the data reduces the variance in the data, e.g., in replicates of the same or similar sample (e.g., nucleic acid from the same cells or cell-type). In some embodiments, non-limiting examples of expression data that is removed include one or more non-coding transcripts (e.g., 10-50, 50-100, 100-1,000, 1,000-2,500, 2,500-5,000 or more non-coding transcripts) that belong to one or more gene groups selected from the list consisting of: pseudogenes, polymorphic pseudogenes, processed pseudogenes, transcribed processed pseudogenes, unitary pseudogenes, unprocessed pseudogenes, transcribed unitary pseudogenes, constant chain immunoglobulin (IG C) pseudogenes, joining chain immunoglobulin (IG J) pseudogenes, variable chain immunoglobulin (IG V) pseudogenes, transcribed unprocessed pseudogenes, translated unprocessed pseudogenes, joining chain T cell receptor (TR J) pseudogenes, variable chain T cell receptor (TR V) pseudogenes, small nuclear RNAs (snRNA), small nucleolar RNAs (snoRNA), microRNAs (miRNA), ribozymes, ribosomal RNA (rRNA), mitochondrial tRNAs (Mt tRNA), mitochondrial rRNAs (Mt rRNA), small Cajal body-specific RNAs (scaRNA), retained introns, sense intronic RNA, sense overlapping RNA, nonsense-mediated decay RNA, non-stop decay RNA, antisense RNA, long intervening noncoding RNAs (lincRNA), macro long non-coding RNA (macro lncRNA), processed transcripts, 3prime overlapping non-coding RNA (3prime overlapping ncrna), small RNAs (sRNA), miscellaneous RNA (misc RNA), vault RNA (vaultRNA), and TEC RNA.

In some embodiments, information (e.g., sequence information) for one or more transcripts for one of more of these types of transcripts can be obtained in a nucleic acid database (e.g., a Gencode database, for example Gencode V23, Genbank database, EMBL database, or other database). In some embodiments, a fraction (e.g., 10%, 20% 30%, 40%, 50%, 60%, 70%, 80%, 90%, 95%, 98%, 99%, or 99.5% or more) of the non-coding transcripts, histone-encoding gene, mitochondrial genes, interleukin-encoding genes, collagen-encoding genes, and/or T cell receptor-encoding genes as described herein are removed from aligned and annotated RNA expression data.

Conversion to TPM and Gene Aggregation

In some embodiments, a method to process RNA expression data (e.g., data obtained from RNA sequencing (also referred to herein as RNA-seq data)) comprises normalizing RNA expression data per length of transcript (e.g., to transcripts per kilobase million (TPM) format) that is read. In some embodiments, RNA expression data that is normalized per length of transcript is first aligned and annotated. Conversion of data to TPM allows presentation of expression in the form of concentration, rather than counts, which in turn allows comparison of samples with different total read counts and/or length of reads.

In some embodiments, RNA expression data that is normalized per length of transcript read is then analyzed to obtain gene expression data (expression data per gene). This is also referred to as gene aggregation. Gene aggregation comprises combining expression data in reads for transcripts for all isoforms of a gene to obtain expression data for that gene. In some embodiments, gene aggregation to obtain gene expression data is performed after TPM normalization but before identifying genes that introduce bias. In some embodiments, gene aggregation is performed before conversion of the data to TPM.

Wagner et al (Theory Biosci. (2012) 131:281-285) provides an explanation of how TPM can be calculated and is incorporated herein by reference in its entirety. In some embodiments, the following formula is used to calculate TPM:

$$A \cdot \frac{1}{\sum(A)} \cdot 10^6$$

$$\text{Where } A = \frac{\text{total reads mapped to gene} \cdot 10^3}{\text{gene length in bp}}$$

Computer Implementation & Sample Processing Environment

An illustrative implementation of a computer system 1000 that may be used in connection with any of the embodiments of the technology described herein (e.g., such as the method of FIGS. 2, 4, and 6) is shown in FIG. 10. The computer system 1000 includes one or more processors 1010 and one or more articles of manufacture that comprise non-transitory computer-readable storage media (e.g., memory 1020 and one or more non-volatile storage media 1030). The processor 1010 may control writing data to and reading data from the memory 1020 and the non-volatile storage device 1030 in any suitable manner, as the aspects of the technology described herein are not limited in this respect. To perform any of the functionality described herein, the processor 1010 may execute one or more processor-executable instructions stored in one or more non-transitory computer-readable storage media (e.g., the memory 1020), which may serve as non-transitory computer-readable storage media storing processor-executable instructions for execution by the processor 1010.

Computing device 1000 may also include a network input/output (I/O) interface 1040 via which the computing device may communicate with other computing devices (e.g., over a network), and may also include one or more user I/O interfaces 1050, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

Figure 11:
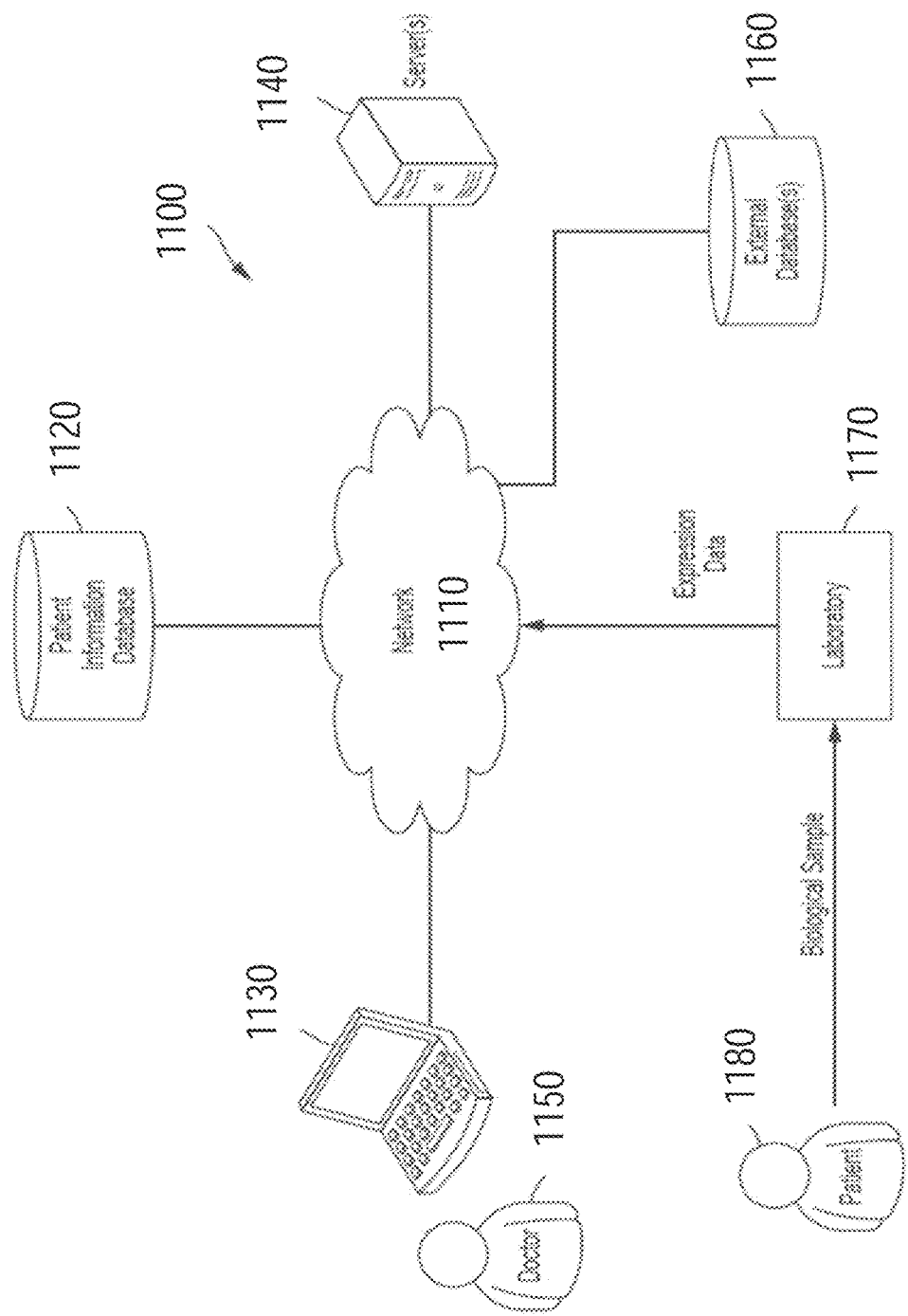
FIG. 11 is a block diagram of an illustrative environment in which one or more embodiments of the technology described herein may be implemented.

In some embodiments, the techniques described herein may be implemented in the illustrative environment 1100 shown in FIG. 11. As shown in FIG. 11, within illustrative environment 1100, one or more biological samples of a subject 1180 may be provided to a laboratory 1170. Laboratory 1170 may process the biological sample(s) to obtain expression data (e.g., DNA, RNA, and/or protein expression data) and/or sequence information and provide it, via network 1110, to at least one database 1160 that stores information about subject (e.g., patient) 1180.

Network 1110 may be a wide area network (e.g., the Internet), a local area network (e.g., a corporate Intranet), and/or any other suitable type of network. Any of the devices shown in FIG. 11 may connect to the network 1110 using one or more wired links, one or more wireless links, and/or any suitable combination thereof.

In the illustrated embodiment of FIG. 11, the at least one database 1120 may store expression data and or sequence information for the subject (e.g., patient), medical history data for the subject (e.g., patient), test result data for the subject (e.g., patient), and/or any other suitable information about the subject 1180. Examples of stored test result data for the subject (e.g., patient) include biopsy test results, imaging test results (e.g., MRI results), and blood test results. The information stored in at least one database 1120 may be stored in any suitable format and/or using any suitable data structure(s), as aspects of the technology described herein are not limited in this respect. The at least one database 1120 may store data in any suitable way (e.g., one or more databases, one or more files). The at least one database 1120 may be a single database or multiple databases.

As shown in FIG. 11, illustrative environment 1100 includes one or more external databases 1120, which may store information for patients other than patient 1180. For example, external databases 1160 may store expression data and/or sequence information (of any suitable type) for one or more patients, medical history data for one or more patients, test result data (e.g., imaging results, biopsy results, blood test results) for one or more patients, demographic and/or biographic information for one or more patients, and/or any other suitable type of information. In some embodiments, external database(s) 1160 may store information available in one or more publicly accessible databases such as TCGA (The Cancer Genome Atlas), one or more databases of clinical trial information, and/or one or more databases maintained by commercial sequencing suppliers. The external database(s) 1160 may store such information in any suitable way using any suitable hardware, as aspects of the technology described herein are not limited in this respect.

In some embodiments, the at least one database 1120 and the external database(s) 1160 may be the same database, may be part of the same database system, or may be physically co-located, as aspects of the technology described herein are not limited in this respect.

For example, in some embodiments, server(s) 1140 may access information stored in database(s) 1120 and/or 1160 and use this information to perform processes described herein for determining one or more characteristics of a biological sample (e.g., determining cell composition percentages thereof) and/or of the sequence information.

In some embodiments, server(s) 1140 may include one or multiple computing devices. When server(s) 1140 include multiple computing devices, the device(s) may be physically co-located (e.g., in a single room) or distributed across multi-physical locations. In some embodiments, server(s) 1140 may be part of a cloud computing infrastructure. In some embodiments, one or more server(s) 1140 may be co-located in a facility operated by an entity (e.g., a hospital, research institution) with which doctor 1150 is affiliated. In such embodiments, it may be easier to allow server(s) 1140 to access private medical data for the patient 1180.

As shown in FIG. 11, in some embodiments, the results of the analysis performed by server(s) 640 may be provided to doctor 1150 through a computing device 1130 (which may be a portable computing device, such as a laptop or smartphone, or a fixed computing device such as a desktop computer). The results may be provided in a written report, an e-mail, a graphical user interface, and/or any other suitable way. It should be appreciated that although in the embodiment of FIG. 11, the results are provided to a doctor 1150, in other embodiments, the results of the analysis may be provided to patient 1180 or a caretaker of patient 1180, a healthcare provider such as a nurse, or a person involved with a clinical trial.

In some embodiments, the results may be part of a graphical user interface (GUI) presented to the doctor 1150 via the computing device 1130. In some embodiments, the GUI may be presented to the user as part of a webpage displayed by a web browser executing on the computing device 1130. In some embodiments, the GUI may be presented to the user using an application program (different from a web-browser) executing on the computing device 1130. For example, in some embodiments, the computing device 1130 may be a mobile device (e.g., a smartphone) and the GUI may be presented to the user via an application program (e.g., "an app") executing on the mobile device.

EXAMPLES

Example 1—Establishment of RNA Transcript Normalization and Analysis of Sequencing Technical Noise An experiment was undertaken to establish an exemplary process for RNA transcript normalization, and to analyze sequencing technical noise, as described herein.

FIG. 12A shows the proportions of Transcripts Per Million (TPM) covering transcripts of different biological types calculated in the different samples of purified B cells sequenced in different laboratories (as an example for a cell type). GEO and ArrayExpress IDs of the different datasets of sorted B cells are shown as labels on the X axis. The transcript biological type is indicated in the legend (according to GENCODE annotation, version 23). As shown, variability in total expression belonging to short RNA transcripts strongly skews TPM value distribution of genes of interest due to increased variation resulting from length normalization of short transcripts. As described above including with respect to the "Removing non-coding transcripts" section, reads for non-coding transcripts from the data may reduce the variance in the data.

FIG. 12B shows transcripts distribution by transcript biotype and length, as shown in the legend, of a reference human transcriptome (GENCODE, v23). Proportions of transcript numbers of different length for each biotype in the reference transcriptome are shown (with additional categories of all retained and all removed transcripts in FIG. 12C). In addition to non-coding transcripts, a substantial amount of noise was derived from short transcripts of TCR- and BCR-coding genes, annotated in the transcriptome as corresponding to V, D, or J regions. While T- and B-cells produce long transcripts after VDJ recombination, these short transcripts are never synthesized; therefore, different TCR and BCR variants (TCR and BCR repertoires) could not be correctly measured without specific realignment. Ultimately, in addition to filtering out short non-coding RNA sequences, these TCR and BCR protein-coding transcripts were excluded from TPM normalization. Excluding non-coding transcripts and transcripts of TCR- and BCR-transcripts may reduce the variance in the data, as shown in FIG. 12B.

FIG. 12C is a schematic representation of an exemplary process for expression quantification and TPM renormalization. TPM expressions of transcripts were calculated by Kallisto (Bray et al. 2016). Next non-coding transcripts, transcripts coding for TCR/BCR associated with short V, D or J segments and other transcripts according to their biological properties and quality/evidence information are filtered. Finally, transcripts are aggregated by genes and normalized on 1 million TPM.

TABLE 10

This table specifies example transcript groups that may be filtered and excluded from TPM normalization.

| | |
|---|---|
| All non-coding transcript biological types according to the GENCODE (Frankish et al. 2019) annotation v23 | Transcripts of GENCODE biotypes: pseudogene, polymorphic_pseudogene, processed_pseudogene, transcribed_processed_pseudogene, unitary_pseudogene, unprocessed_pseudogene, transcribed_unitary_pseudogene, IG_C_pseudogene, IG_J_pseudogene, IG_V_pseudogene, transcribed_unprocessed_pseudogene, translated_unprocessed_pseudogene, TR_J_pseudogene, TR_V_pseudogene, snRNA, snoRNA, miRNA, ribozyme, rRNA, Mt_tRNA, Mt_rRNA, scaRNA, retained_intron, sense_intronic, sense_overlapping, nonsense_mediated_decay, non_stop_decay, antisense, lincRNA, macro_lncRNA, processed_transcript, 3prime_overlapping_ncrna, sRNA, misc_RNA, vaultRNA, TEC |
| Transcripts of V, D and J regions of immunoglobulins and TCR genes | Transcripts of GENCODE biotypes: IG_V_gene, IG_D_gene, IG_J_gene, TR_V_gene, TR_D_gene, TR_J_gene |
| Transcripts of particular genes according to their biological family | Transcripts of GENCODE biotypes: IG_V_gene, IG_D_gene, IG_J_gene, TR_V_gene, TR_D_gene, TR_J_gene |
| Major groups of transcripts with low annotation quality | Transcripts which coding region start or end could not be confirmed (annotation tags "cds_start_NF", "cds_end_NF"), transcripts with "bad" Transcript Support Level (TSL, which is intended to highlight the well-supported and poorly-supported transcript models) i.e. TSL:4, TSL:5, TSL:NA except for those transcript categories which always have TSL:NA-single-exon transcripts and immunoglobulin, TCR and HLA transcripts. |

TABLE 10-continued

This table specifies example transcript groups that may be filtered and excluded from TPM normalization.

| | |
|---|---|
| Minor groups of transcripts with low annotation or reference sequence quality | Transcripts with GENCODE tags: fragmented_locus, inferred_exon_combination, low_sequence_quality, non_canonical_genome_sequence_error, non_canonical_TEC, not_best_in_genome_evidence, not_organism_supported, reference_genome_error, sequence_error |

FIGS. 12D-12E are violin plots showing the relative standard deviations in expression of 3515 housekeeping genes (Eisenberg and Levanon 2013) for different cell types before (red) and after (blue) transcript filtration and TPM renormalization. Data is grouped based on the library preparation type, using either total RNA-seq (FIG. 12D) or polyA RNA-seq (FIG. 12E). The indicated P-values are calculated by the two-sided Wilcoxon test. Medians of distributions and rank-biserial correlation coefficients are shown.

FIG. 12F is a PCA projection of RNA expression of sorted B cells obtained from experiments using either total RNA-seq (green) or polyA RNA-seq (red), before (left) and after (right) proposed transcript filtration and renormalization. As shown, there is a decrease in unwanted batch effects between expression profiles, after the procedure of TPM renormalization described herein. Techniques for TPM normalization are described herein including with respect to the "Conversion to TPM and gene aggregation" section.

FIG. 12G shows the dependence of relative standard deviation of technical replicates on gene expression levels (TPM). RNA-seq experiments with a total coverage of 1 (pink), 5 (yellow) and 10 (green) million readcounts are presented.

FIG. 12H (left) shows the dependence of mean standard deviation of gene expression on the total coverage of read counts in RNA-seq. The illustrated graph shows samples with sequential additions of noise level: Technical Poisson noise only (blue), all technical noise (yellow), and both technical and biological noise (red). FIG. 12H (right) is a violin plot showing the distribution of the same standard deviations of gene expression calculated within samples having different types of noise. As described above, including with respect to FIG. 6, a component of technical noise may specified by a Poisson distribution, another component of technical noise may be specified by non-Poisson noise, and biological noise may be specified by a normal distribution.

FIG. 12I is a plot showing measured Poisson noise coefficients for technical replicates of RNA-seq experiments with different total readcount coverage. Poisson noise is inversely proportional to the square root of the total readcount coverage of RNA-seq data.

FIG. 12J (left) shows the dependence of mean standard deviation of gene expression on the total coverage of read counts in RNA-seq. The illustrated graph shows gene expression with imputed Poisson noise (green) and data for the same samples with all technical noise (yellow). FIG. 12J (right) shows the dependence of mean standard deviation of gene expression on the total coverage of read counts in RNA-seq. The illustrated graph shows the same data as presented in the left graph after subtraction of the imputed Poisson noise, revealing the non-Poisson addition to the technical noise. This non-Poisson technical noise does not show any dependence to sequencing coverage.

FIG. 12K (left) shows the dependence of mean standard deviation of gene expression on the total coverage of read counts in RNA-seq. The illustrated graph shows gene expression for one cell line across various laboratories and experiments, accounting for both biological and technical noise. Imputed Poisson technical noise calculated for the same samples is represented in green. FIG. 12K (right) shows the dependence of mean standard deviation of gene expression on the total coverage of read counts in RNA-seq. The illustrated graph shows gene expression as shown on the left after subtraction of the imputed Poisson noise, revealing the pure biological noise in the samples, which did not depend on sequencing coverage.

Example 2—Deconvolution of Microenvironment from RNA-Seq of Multiple Normal and Cancer Tissues An experiment was undertaken to perform cellular deconvolution according to the techniques described herein using RNA-seq data from multiple normal and cancer tissues. In the figures, the cellular deconvolution techniques developed by the inventors may be referred to as "Kassandra". Specifically, techniques for selecting specific and/or semi-specific genes for cell types and/or subtypes, generating artificial mixes, training multiple non-linear regression models to determine a plurality of cell composition percentages for a plurality of cell types, using the trained non-linear regression models to determine the cell composition percentages, and other pre-processing and post-processing techniques described herein.

Figure 13A:
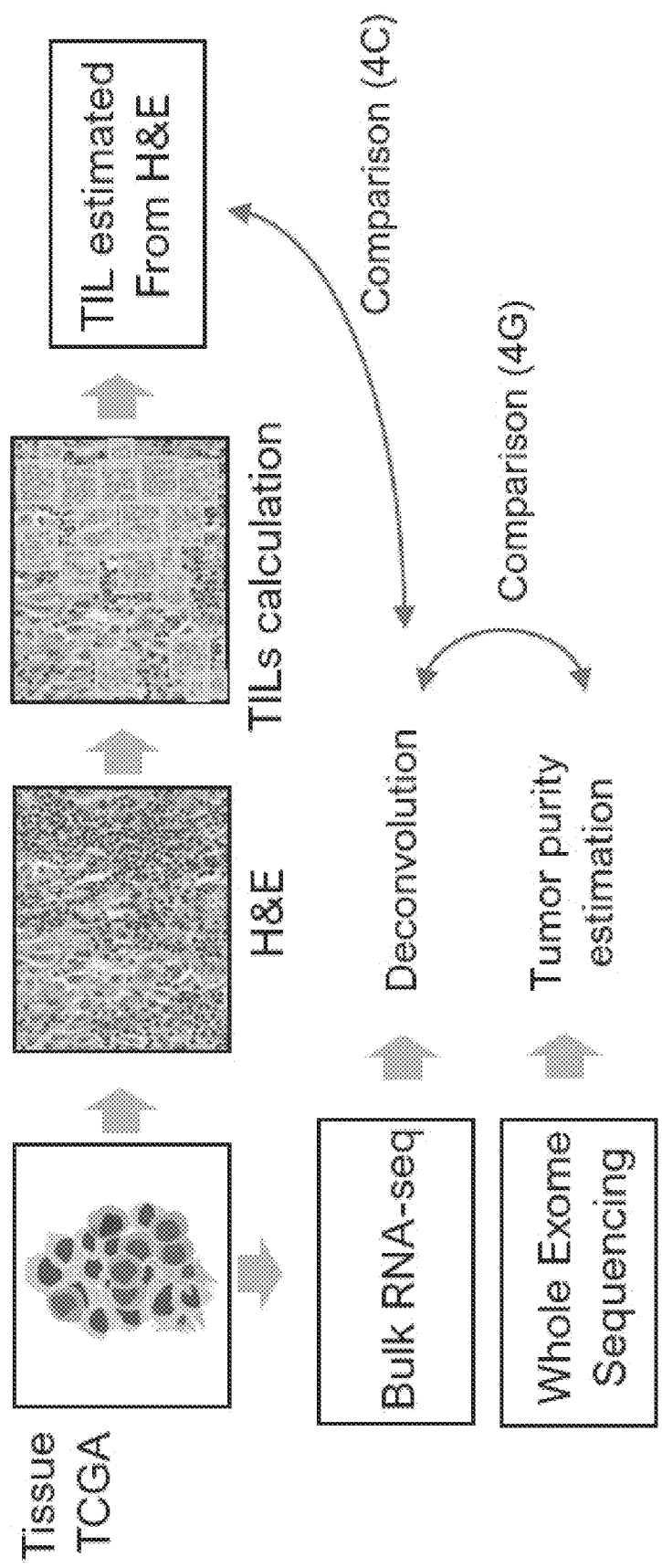

FIG. 13A is a schematic representation of a validation experiment for deconvolution based on TCGA data. Data on the number of cells obtained by other methods from hematoxylin and eosin (H&E) slides and whole exome sequencing (WES) are used.

Figure 13B:
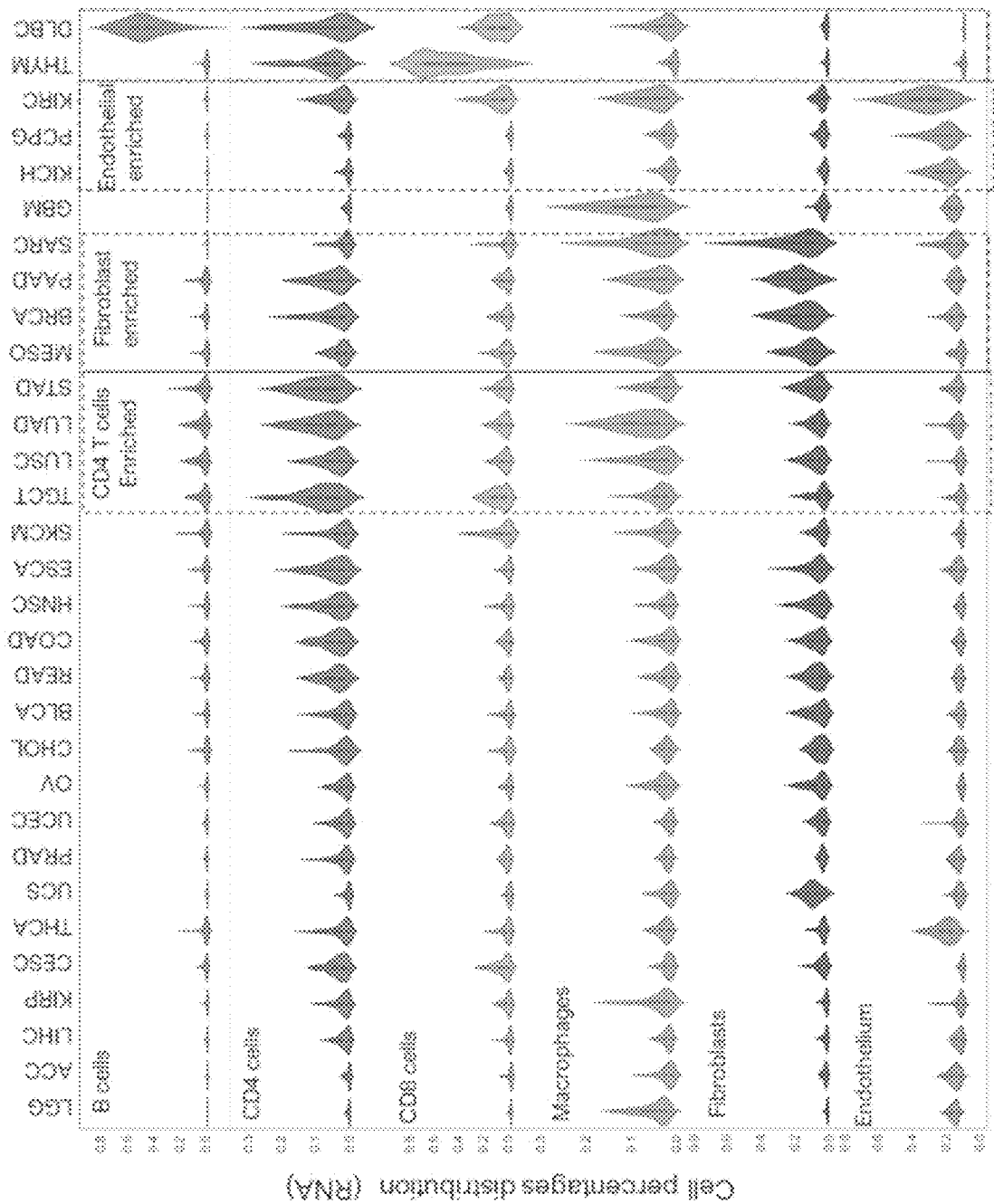

FIG. 13B are violin plots showing distributions of cell composition percentages estimated using the deconvolution techniques (e.g., using trained non-linear regression models) described herein for B-cells, CD4+, CD8+, macrophage, fibroblasts, and endothelium cells in 10,489 tumor biopsies from TCGA. As shown, tumor tissues are split by cancer type in the illustrated example.

Figure 13C:
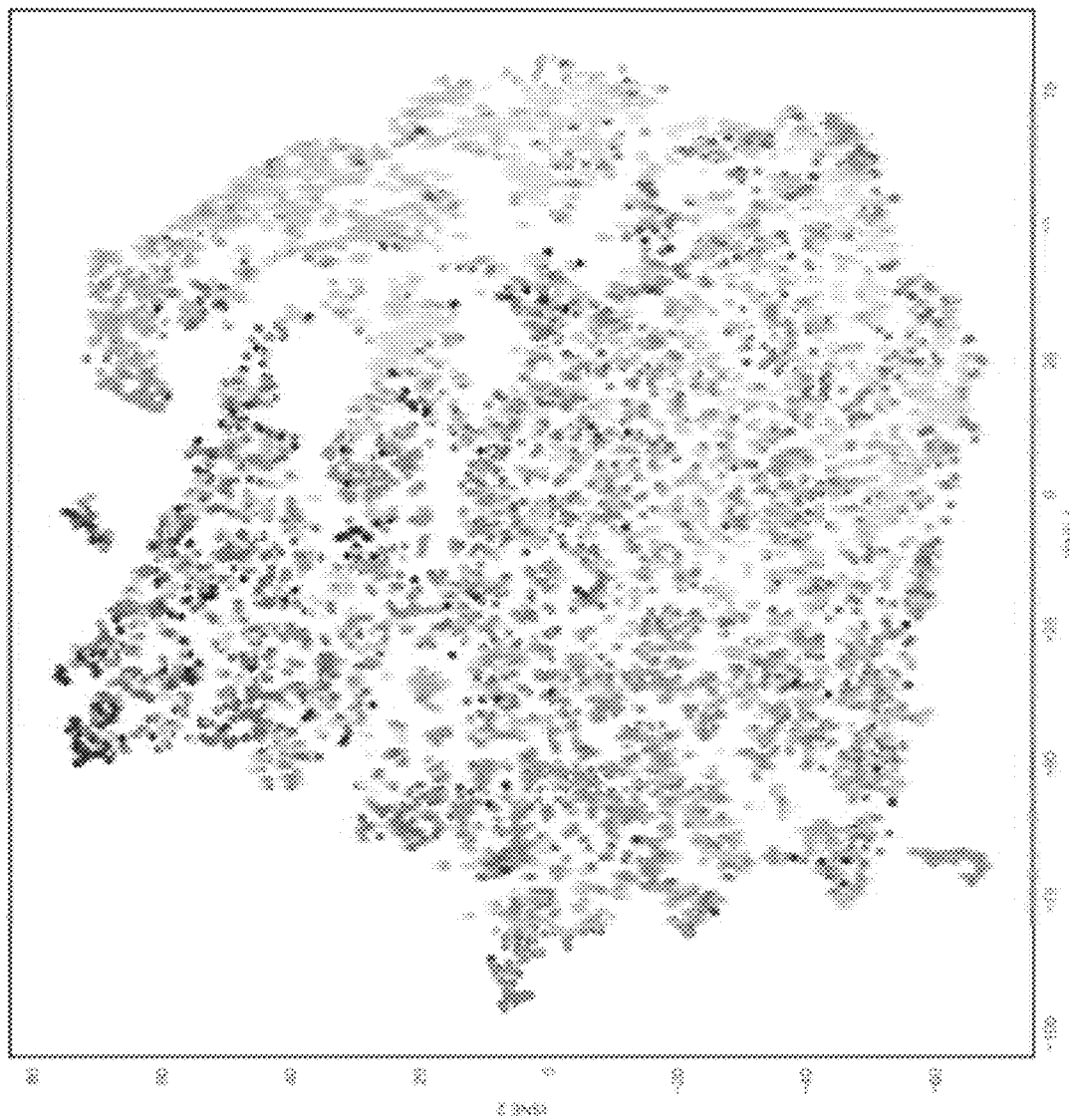

FIG. 13C is a t-SNE plot showing TCGA and GTEX samples calculated based on deconvolved cell percentages.

Figure 13D:
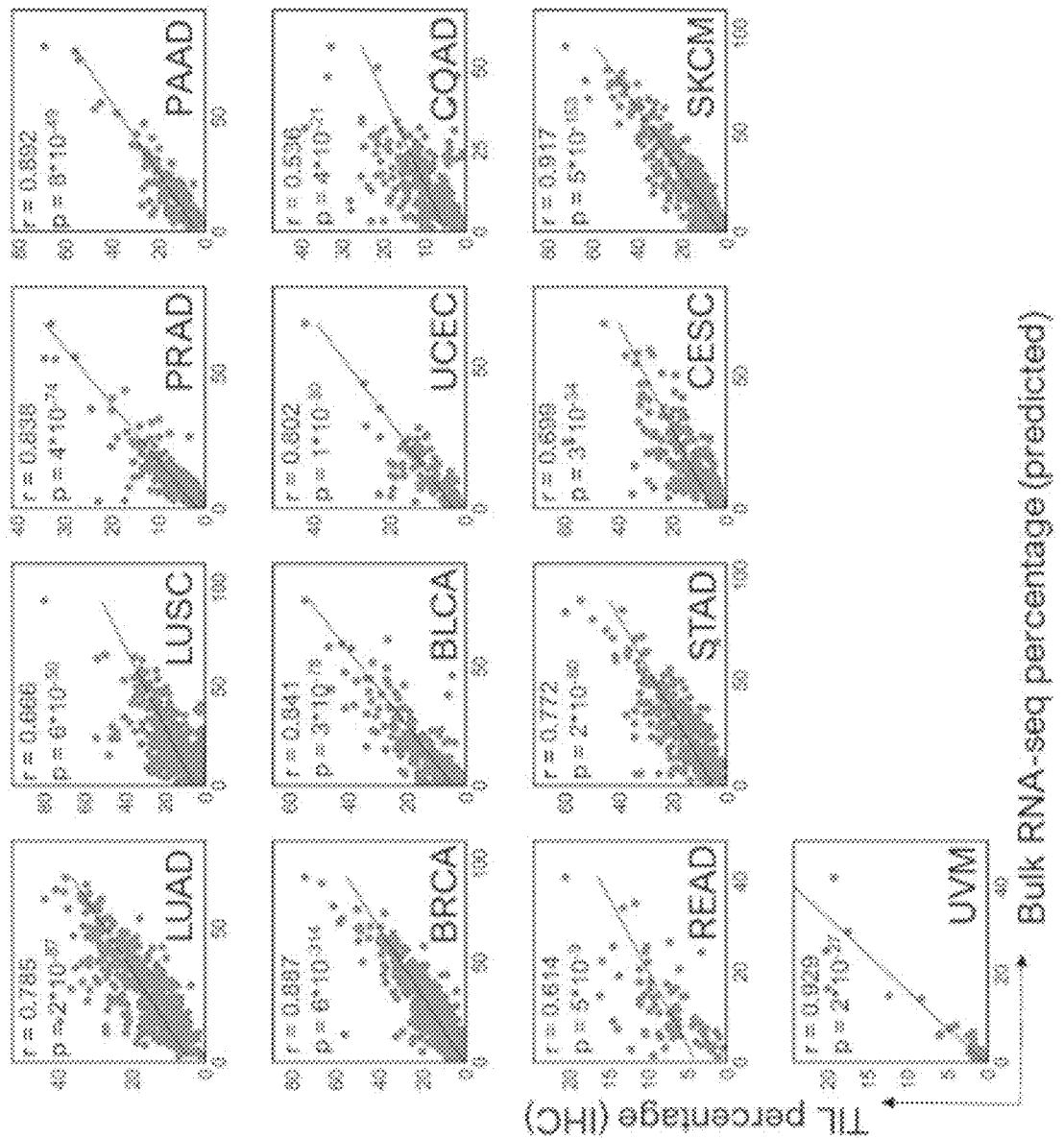

FIG. 13D is a graph showing the Pearson correlation between percentages of lymphocytes predicted by the techniques described herein on TCGA RNA-seq data and predicted by machine analysis of histological TCGA data by (Saltz et al. 2018).

Figure 13E:
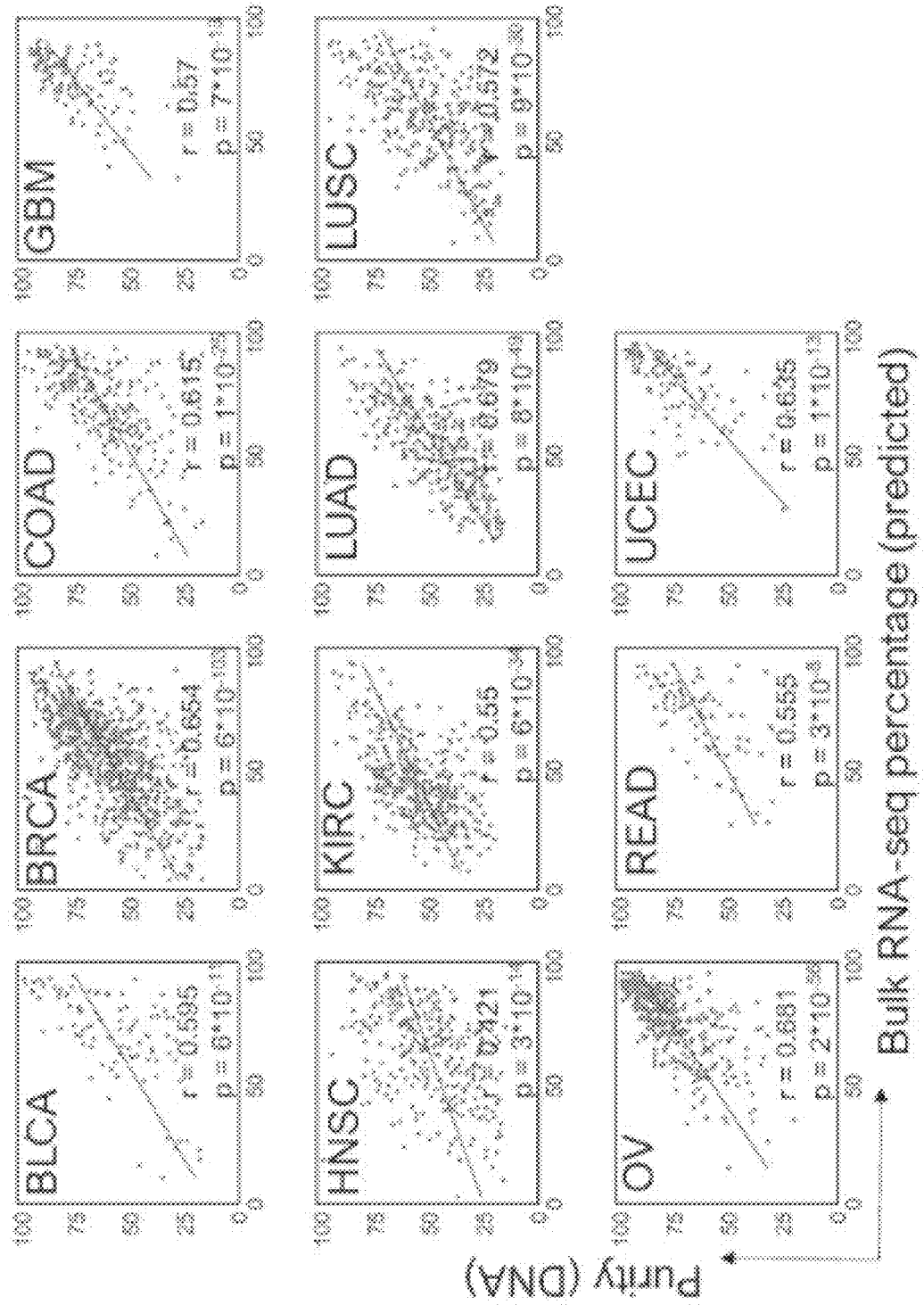

FIG. 13E is a plot showing the correlation of predicted percentages of malignant cells from RNA-seq by the techniques described herein, with tumor purity estimated from WES for 11 TCGA cancer types.

Figure 13F:
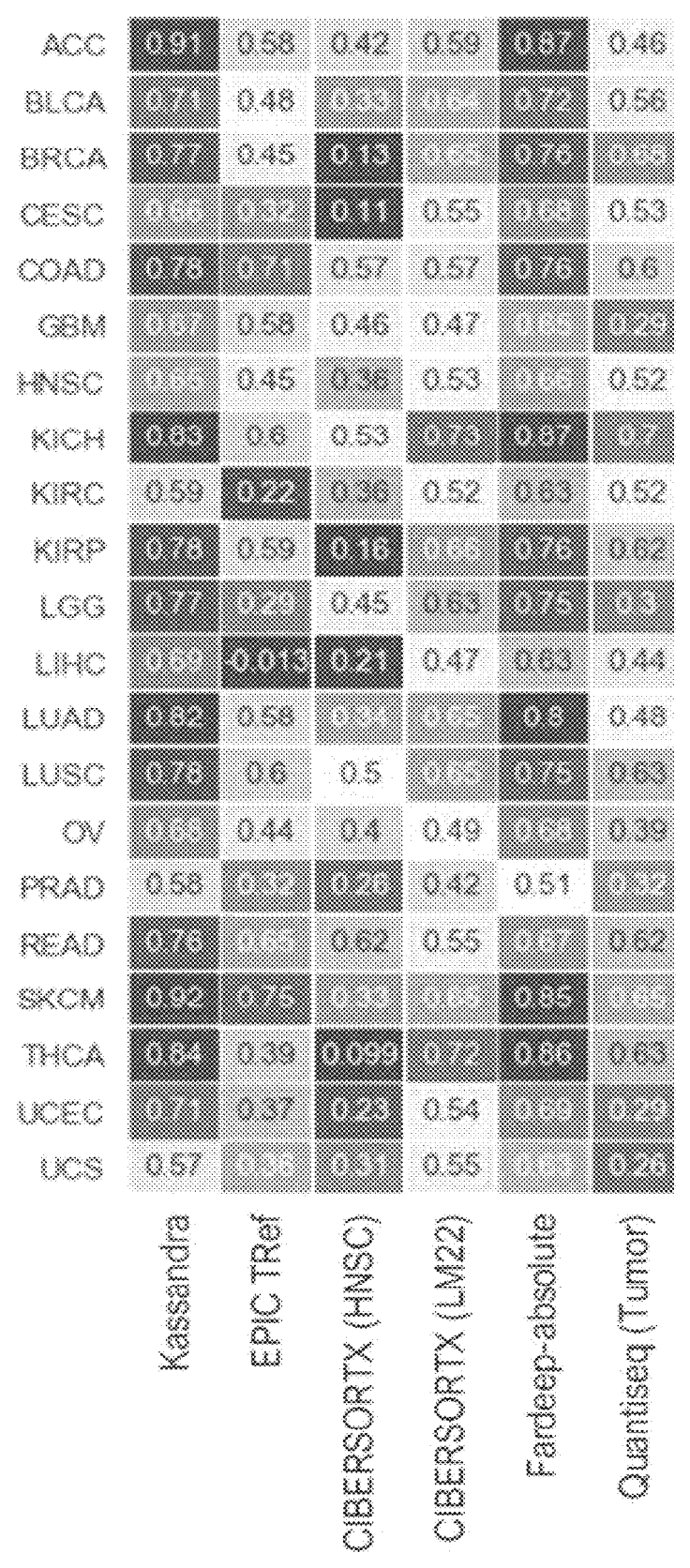

FIG. 13F is a graph showing Pearson correlations between tumor purity and predicted percentages of malignant cells based on RNA-seq data. Tumor data was derived from TCGA. The graph shows Pearson correlations for predictions by the techniques described herein, as well as Pearson correlations for predictions by various alternative algorithms. Compared to other algorithms, the non-linear deconvolution techniques developed by the inventors more accurately predicted the percentage of malignant cells, demonstrating an improvement over conventional techniques.

Figure 13H:
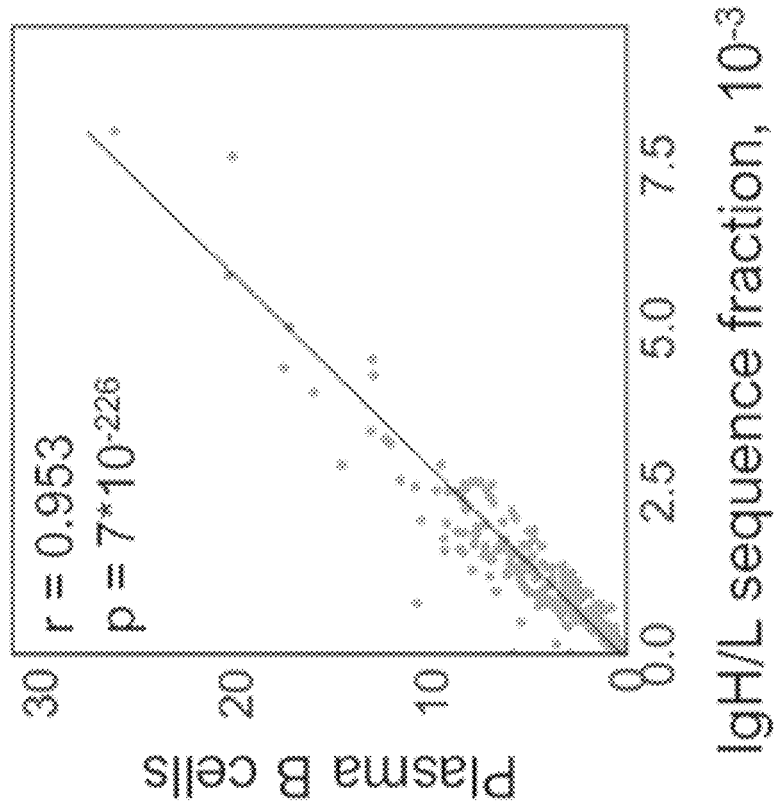
Figure 13G:
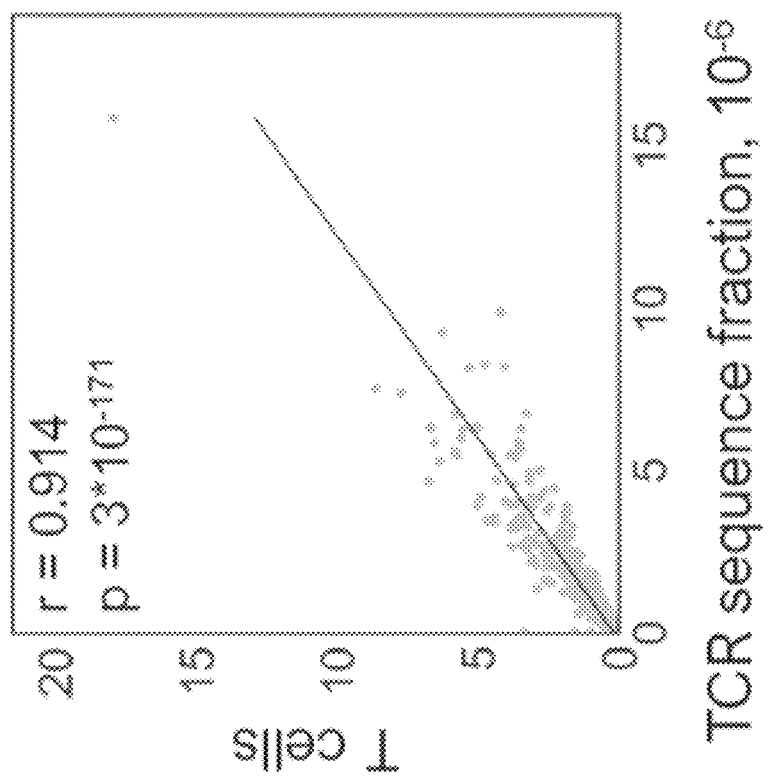

FIG. 13G is a graph showing Pearson correlations of predicted T cell RNA percentages by the techniques described herein with T cell receptor (CDR3 region of TCR) reads by MiXCR in LUSC TCGA data.

FIG. 13H is a graph showing Pearson correlations of predicted Plasma B cell RNA percentages by the techniques described herein with B cell receptor (CDR3 region of IgH) reads by MiXCR in LUSC TCGA data.

Figure 13J:
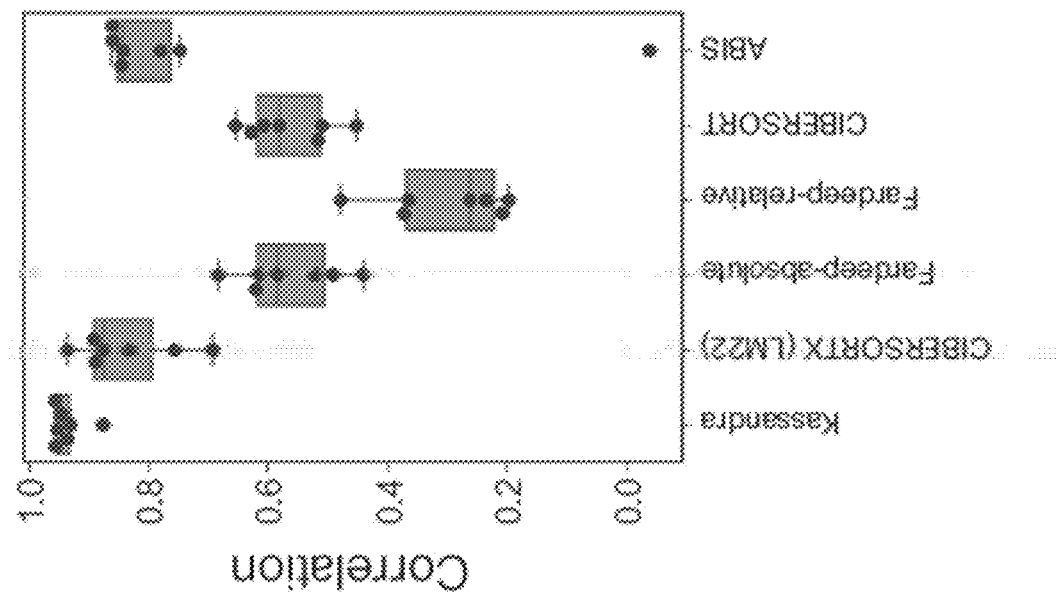
Figure 13I:
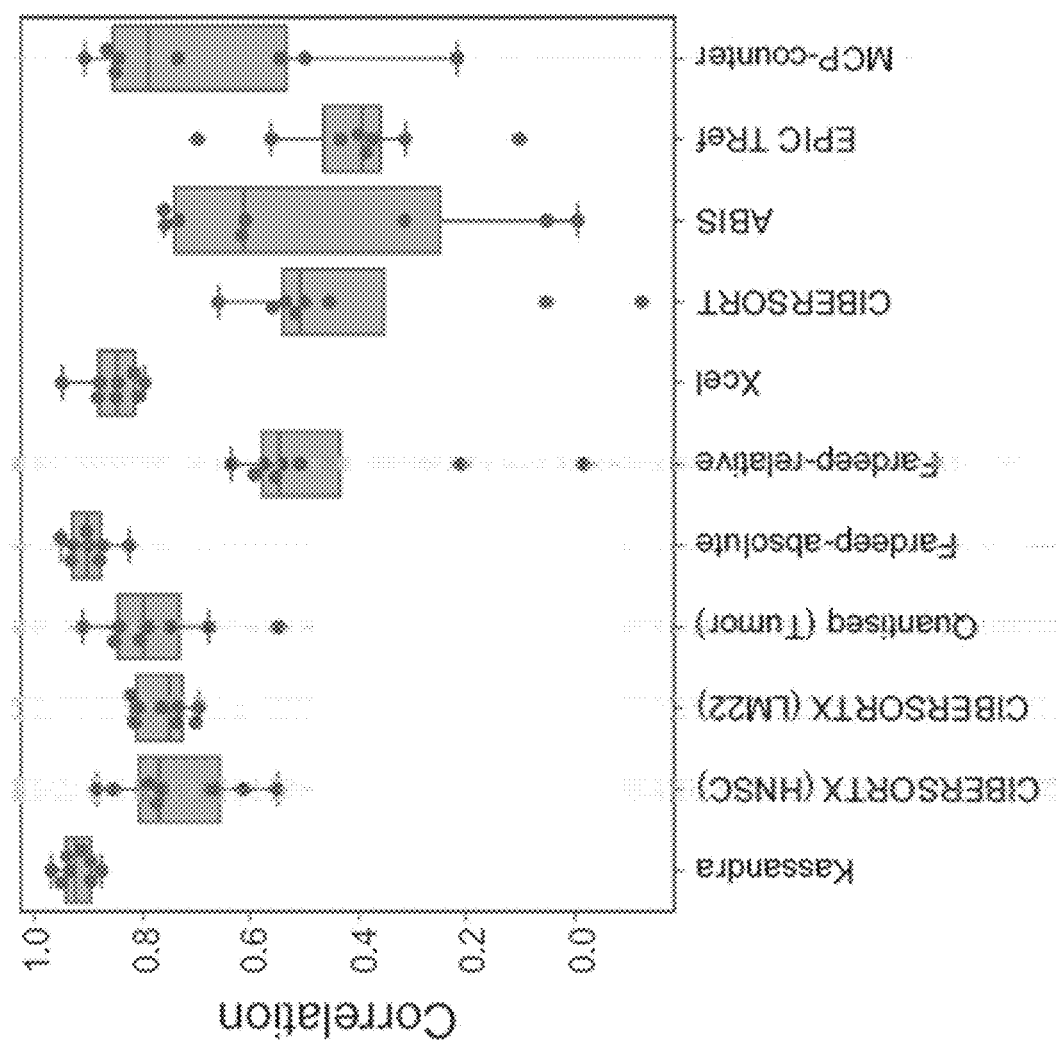

FIG. 13I is a graph showing Pearson correlation values for predicted T cell RNA percentages with T cell receptor (CDR3 region of TCR) reads in different cancer types from TCGA data. Predictions by the techniques described herein and predictions by various alternative algorithms are shown. Each data point corresponds to a different cancer type (COAD, KIRC, LUAD, LUSC, READ, SKCM, TNBC).

FIG. 13J is a graph showing Pearson correlation values for predicted Plasma B cell RNA percentages with B cell receptor (CDR3 region of IgH) reads in different cancer types from TCGA. Predictions by the techniques described herein and predictions by various alternative algorithms are shown. Each data point corresponds to a different cancer type (COAD, KIRC, LUAD, LUSC, READ, SKCM, TNBC).

In this experiment, the inventors analyzed the cellular composition of TCGA samples of different tumor types and healthy tissues (FIG. 13B). Five major cell populations were quantified including: B-cells, CD4+ T-cells, CD8+ T-cells, Macrophages, Fibroblasts, and Endothelial cells (FIG. 13C). These values agreed with what has been reported. For example, DLBC RNA-seq data showed a strong enrichment for B-cells. Next, the correlation between predicted tumor purity values by the techniques described herein and other deconvolution algorithms was compared using an established purity algorithm (FIG. 13E-F). This analysis supports the ability of the techniques described herein to accurately predict cell population from bulk RNAseq data.

In this example, the proportion of expressed T-cell receptor (TCR) and IgH/L (B cell receptor) sequences in the RNA-seq data correlates with the presence of T or plasma B cells actively producing immunoglobulins. The sequences were realigned using MIXCR to measure the abundance and diversity of CDR3 transcripts, associated with different T and plasma B cell clones. As shown, only the techniques described herein among alternative algorithms provided a strong correlation of predicted T cells percentages with the number of found TCR within the sample, and plasma B cells percentages with IgH/L transcripts fraction (FIGS. 13G-J).

Example 3—Deconvolution of Single Cell RNA-Seq and Bulk RNA-Seq of Blood

An experiment was undertaken to perform cellular deconvolution according to the techniques described herein using single cell RNA-seq data and bulk RNA-seq of blood data. In the figures, the cellular deconvolution techniques developed by the inventors may be referred to as "Kassandra". Specifically, techniques for generating artificial mixes, selecting specific and/or semi-specific genes for cell types and/or subtypes, training multiple non-linear regression models to determine a plurality of cell composition percentages for a plurality of cell types, using the trained non-linear regression models to determine the cell composition percentages, and other pre-processing and post-processing techniques described herein.

Figure 14A:
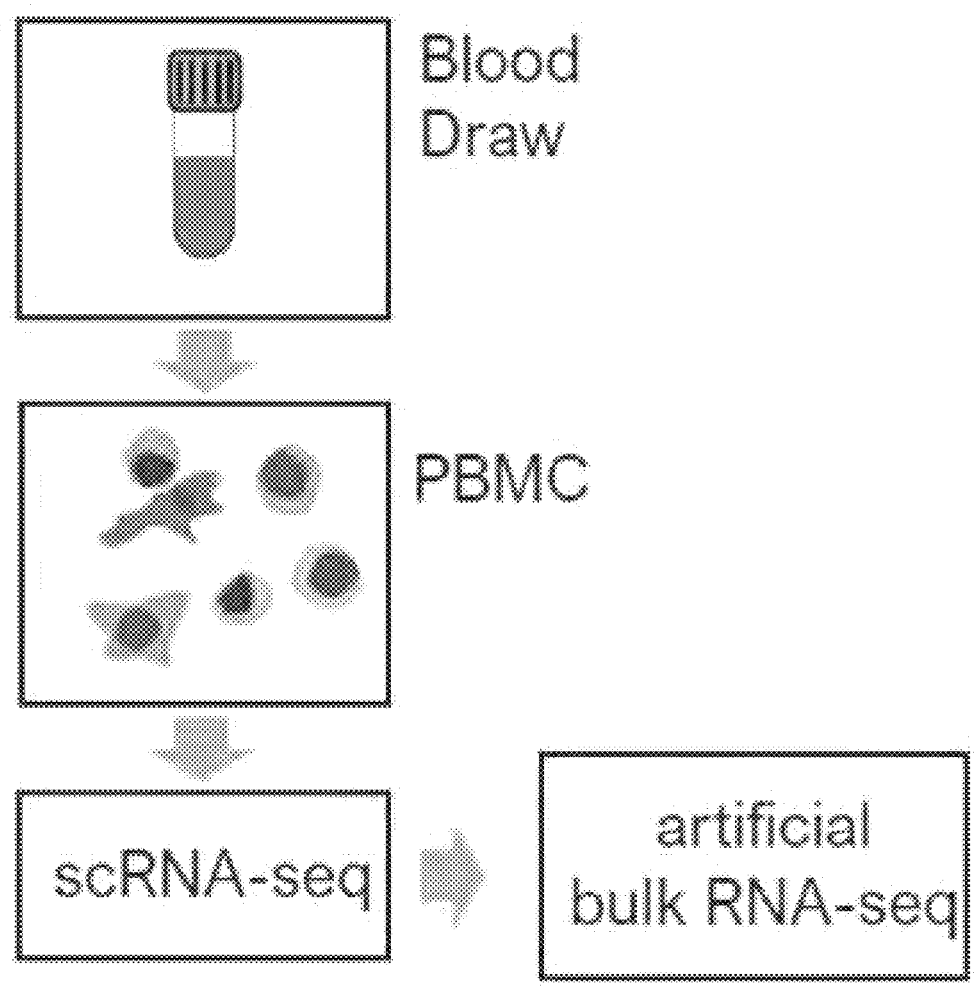
FIGS. 14A-14G are charts and graphs depicting analysis and results from an experiment to deconvolve single cell RNA-seq data and bulk RNA-seq of blood as described in connection with Example 3.

FIG. 14A is a schematic representation of a validation experiment for deconvolution using scRNA-seq samples from PBMC. The scRNA-seq data was artificially mixed to create a bulk RNA-seq dataset.

Figure 14C:
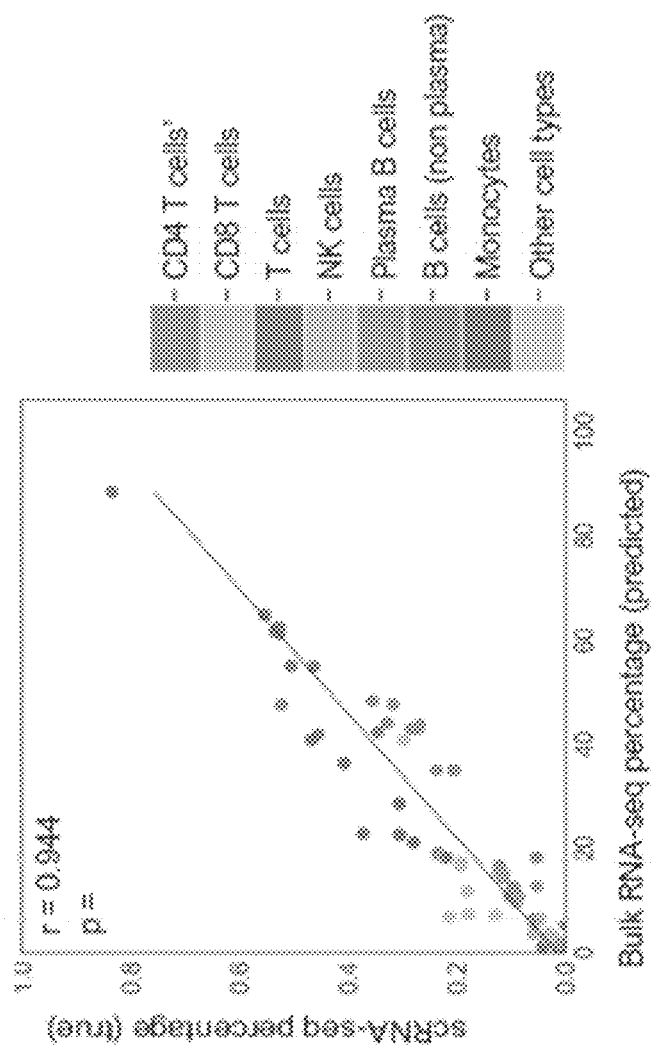
Figure 14B:
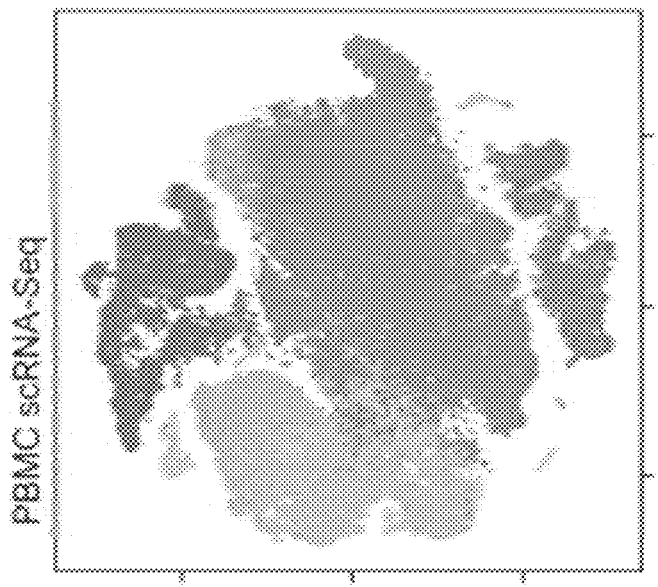

FIG. 14B is a t-SNE plot of cell phenotyping across 9 single-cell PBMC datasets provided by 10× Genomics. The joined plot was obtained by the Seurat pipeline including SCTransform normalization, batch correction and preceding PCA (Butler et al. 2018; Stuart et al. 2019). As shown, different cell types and/or subtypes express key cell markers (e.g., specific and/or semi-specific genes) that distinguish them.

FIG. 14C is a graph showing the correlation between true cell percentages from scRNA-seq of PBMC, and predictions made with the techniques described herein for the bulk RNA-seq mixture.

Figure 14D:
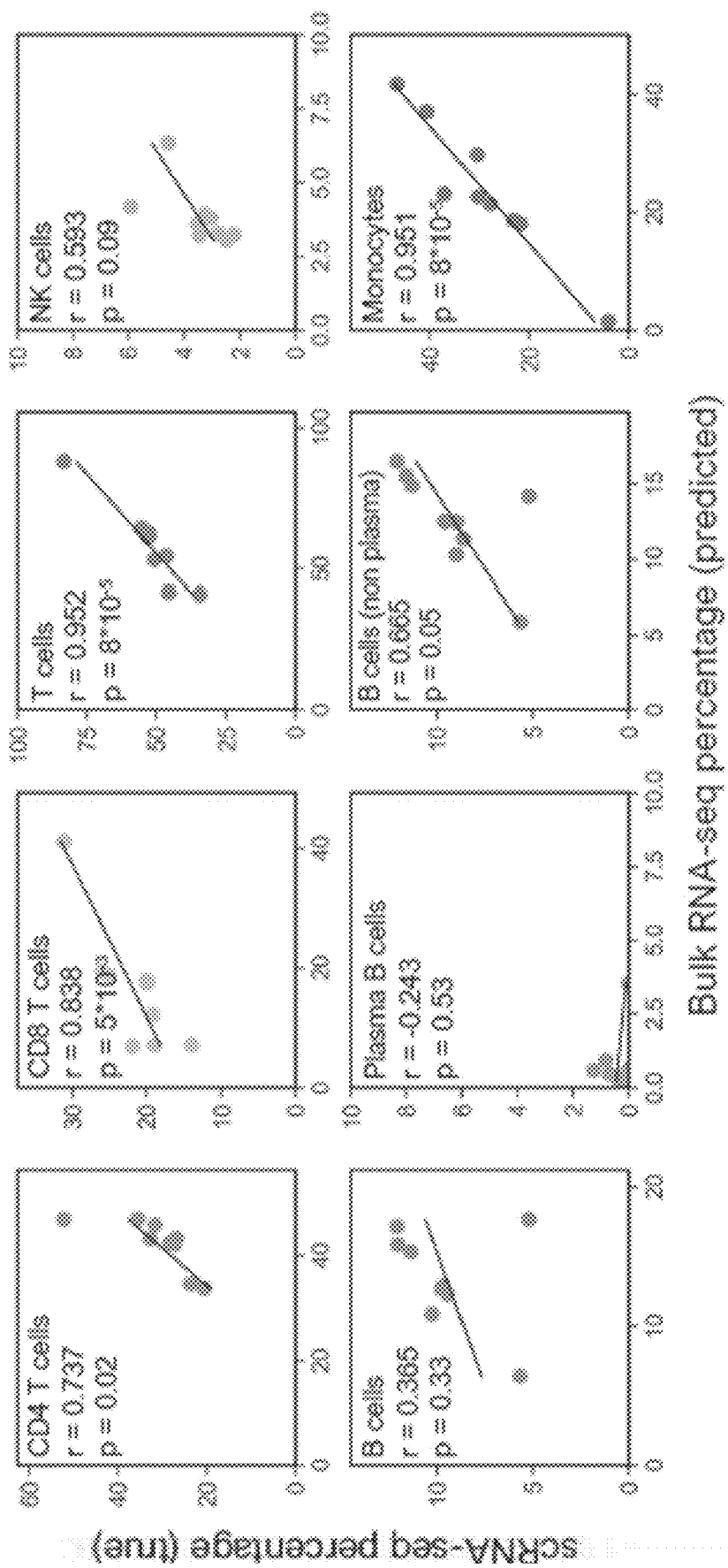

FIG. 14D are plots showing correlation of true percentages from scRNA-seq of PBMC and predictions made with the techniques described herein (e.g., using non-linear regression models to determine cell composition percentages) for eight cell subtypes.

Figure 14E:
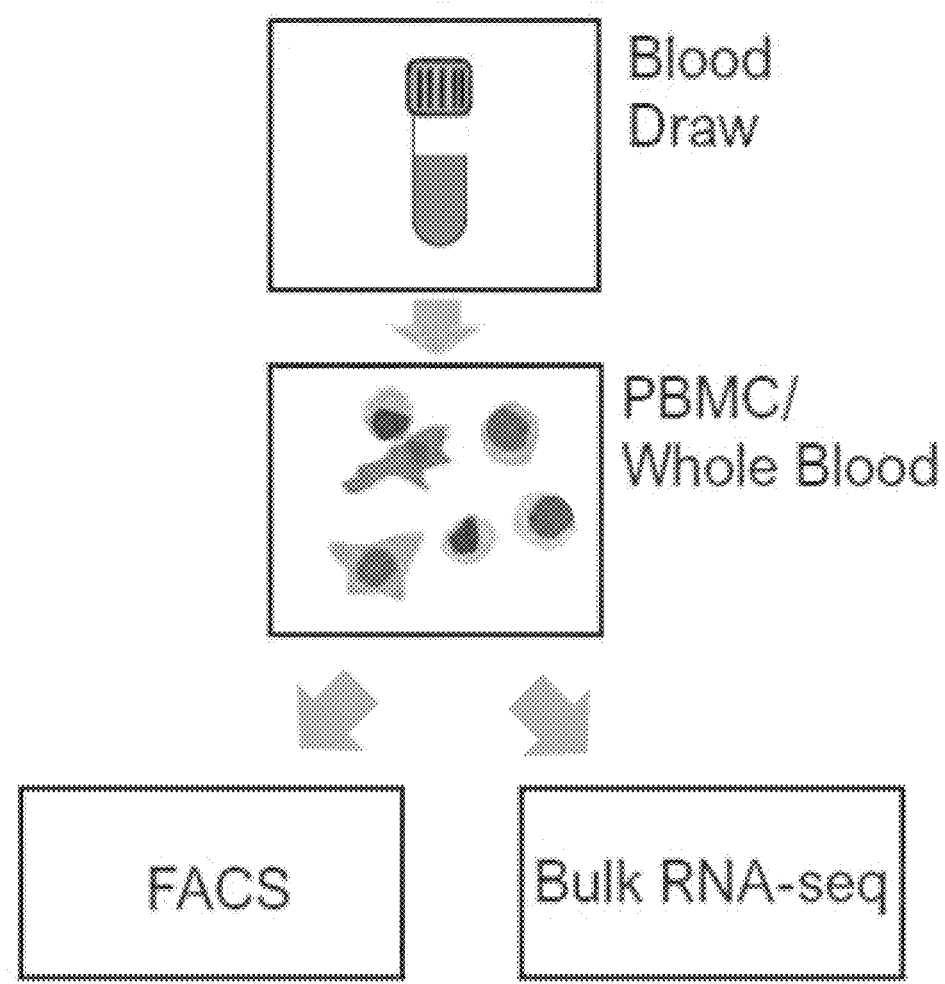

FIG. 14E is a schematic representation of a validation experiment for deconvolution using bulk RNA-seq of PBMC or Whole blood and FACS measurement of the same sample.

Figure 14F:
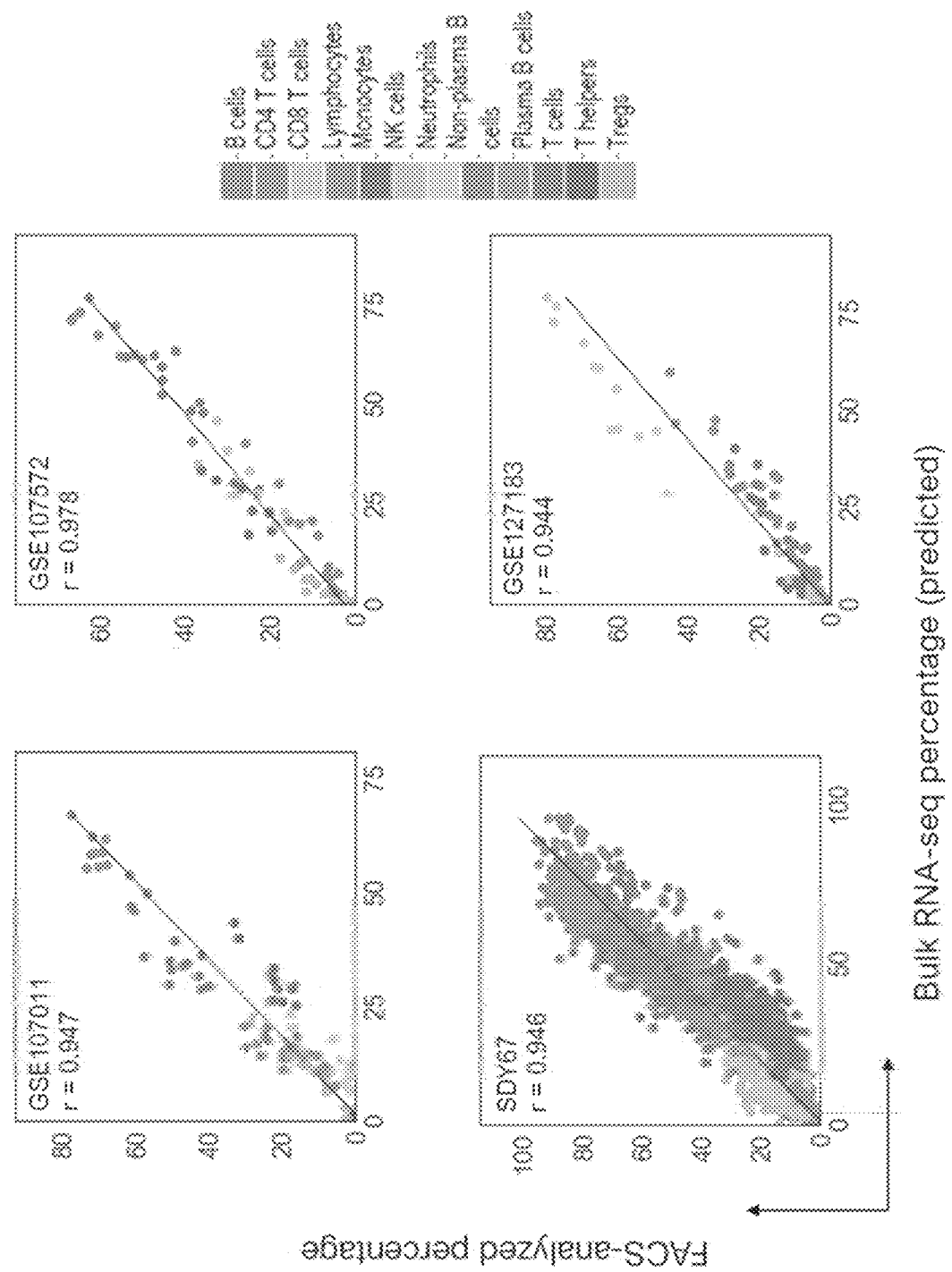
Figure 14G:
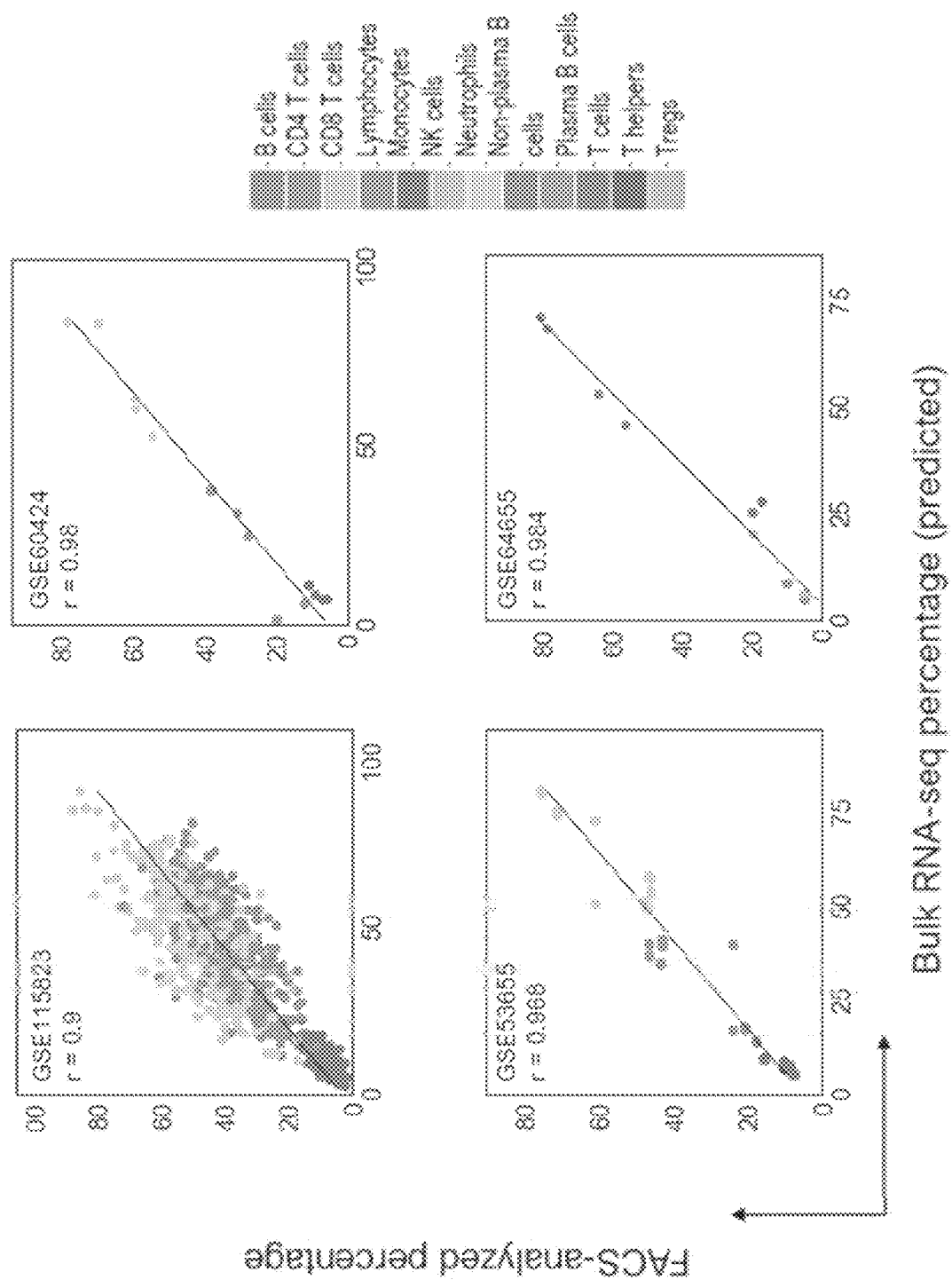

FIGS. 14F-1 and 14F-2 are graphs showing the correlation of predicted cell percentages by the techniques described herein from bulk RNA-seq, and actual cell percentages obtained by flow cytometry measurements for different cell types (CD4+ T cells, CD8+ T cells, NK cells, B cells, monocytes and neutrophils). Datasets that were used for comparison are: GSE107572 (Finotello et al. 2019), GSE115823 (Altman et al. 2019), GSE60424 (Linsley et al. 2014), SDY67 (Zimmermann et al. 2016), GSE127813 (Newman et al. 2019), GSE53655 (Shin et al. 2014), GSE64655 (Hoek et al. 2015). Pearson correlations are shown for all cell types combined.

In this experiment, the inventors applied the techniques described herein to artificial bulk RNA-seq which was built from scRNA-seq datasets derived from peripheral blood mononuclear cells (PBMCs) (FIG. 14A-B). A high correlation value was obtained when aligning the true scRNA-seq percentage with the predicted RNA-seq percentage (FIG. 14C). In this example, when graphing the correlation for each cell type separately, cell types which are present in a high number have the most significant correlation between true and predicted values (FIG. 14D).

Next, the techniques described herein were used to analyze bulk RNA-seq of blood for which FACS analysis was available (FIG. 14E). Eight different PBMC samples were analyzed and for each sample the FACS analysis was compared to the predicted cell composition by the techniques described herein. As shown, all analysis presented with a correlation coefficient ranging from 0.900 to 0.984 (FIGS. 14F-1 and 14F-2).

Example 4—Deconvolution of Microenvironment from Different Cancer Tissues

An experiment was undertaken to perform cellular deconvolution according to the techniques described herein using scRNA-seq data derived from several tumor tissues, including melanoma, head and neck carcinoma, and lung carcinoma. In the figures, the cellular deconvolution techniques developed by the inventors may be referred to as "Kassandra". Specifically, techniques for generating artificial mixes, selecting specific and/or semi-specific genes for cell types and/or subtypes, training multiple non-linear regression models to determine a plurality of cell composition percentages for a plurality of cell types, using the trained non-linear regression models to determine the cell composition percentages, and other pre-processing and post-processing techniques described herein.

Figure 15A:
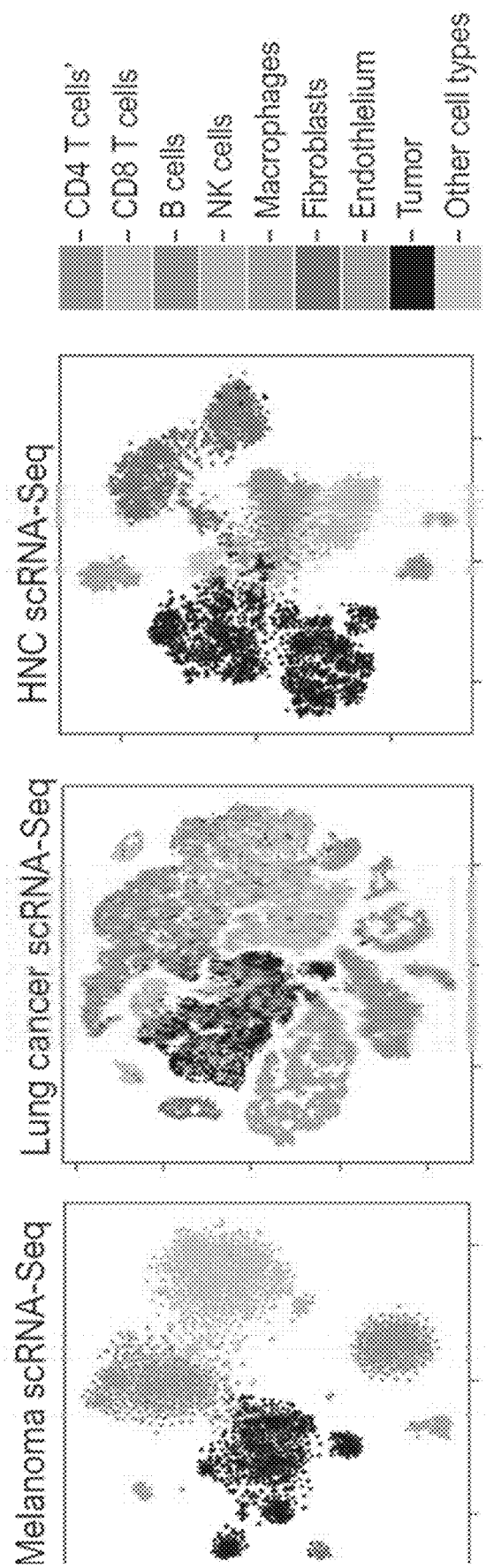
FIGS. 15A-15I are charts and graphs depicting analysis and results from an experiment to deconvolve several different cancer tissues as described in connection with Example 4.

FIG. 15A depicts t-SNE plots of cell phenotyping, from left to right, in melanoma (GSE72056)(Tirosh et al. 2016), lung carcinoma (E-MTAB-6149 and E-MTAB-6653)(Lambrechts et al. 2018) and head and neck carcinoma (HNC) (GSE103322)(Puram et al. 2017) single-cell datasets. The t-SNE plot for lung carcinoma was obtained by the Seurat pipeline including SCTransform normalization, batch correction and preceding PCA (Butler et al. 2018; Stuart et al. 2019). The melanoma and head and neck carcinoma t-SNE plots were obtained by t-SNE transformation of log TPM expression values of cell-type-specific genes.

Figure 15B:
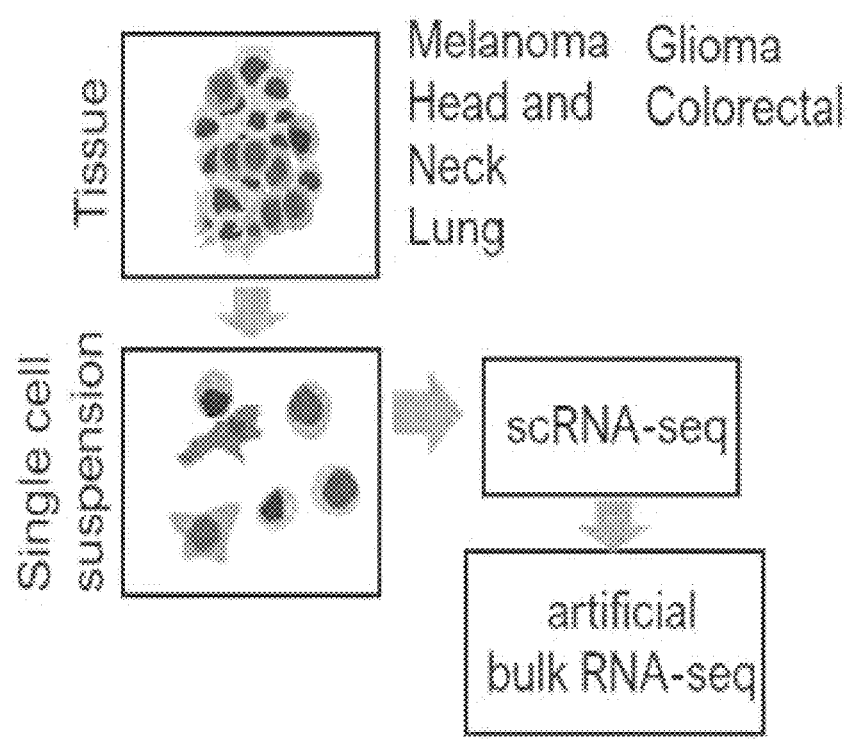
Figure 15C:
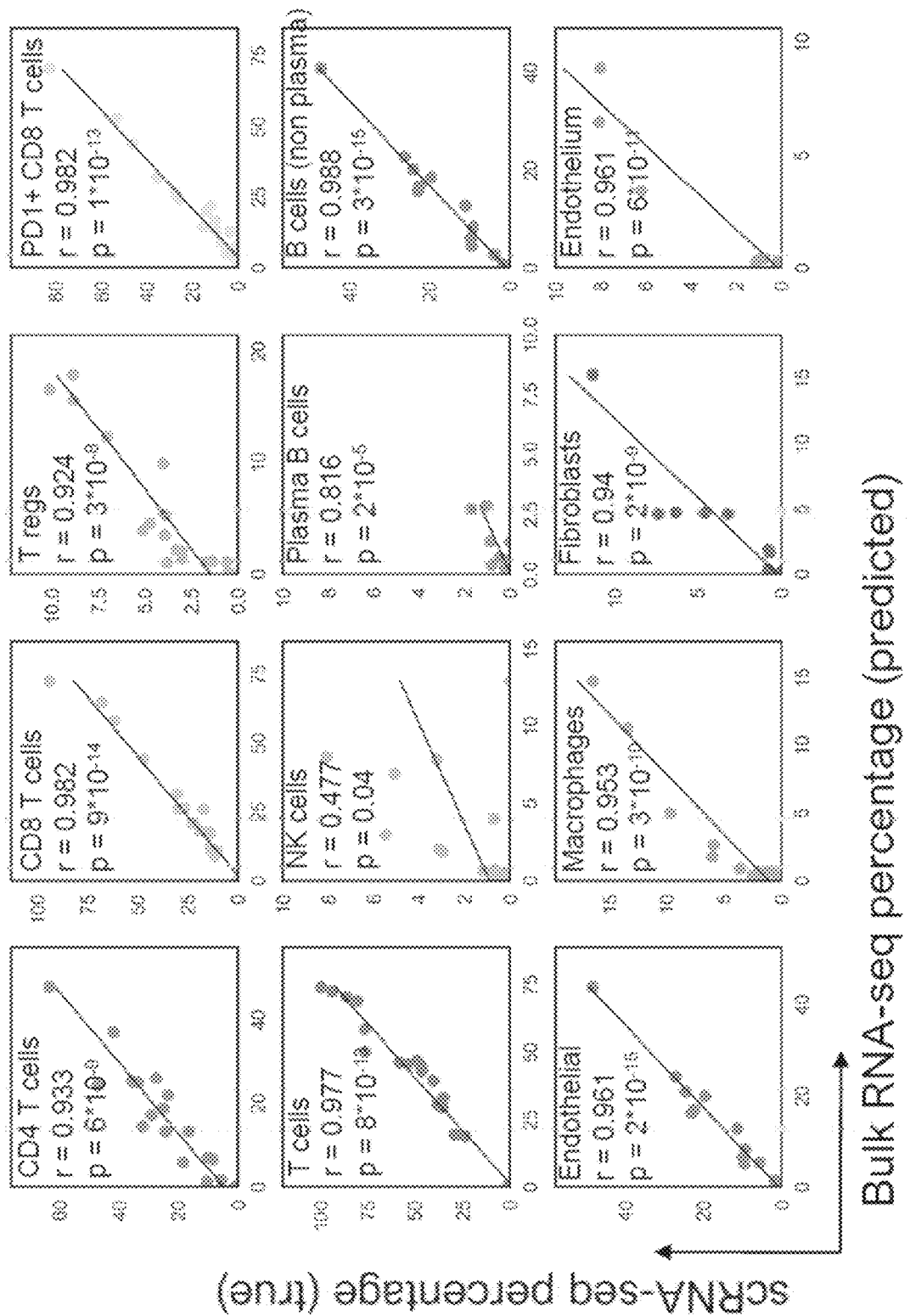
Figure 15:
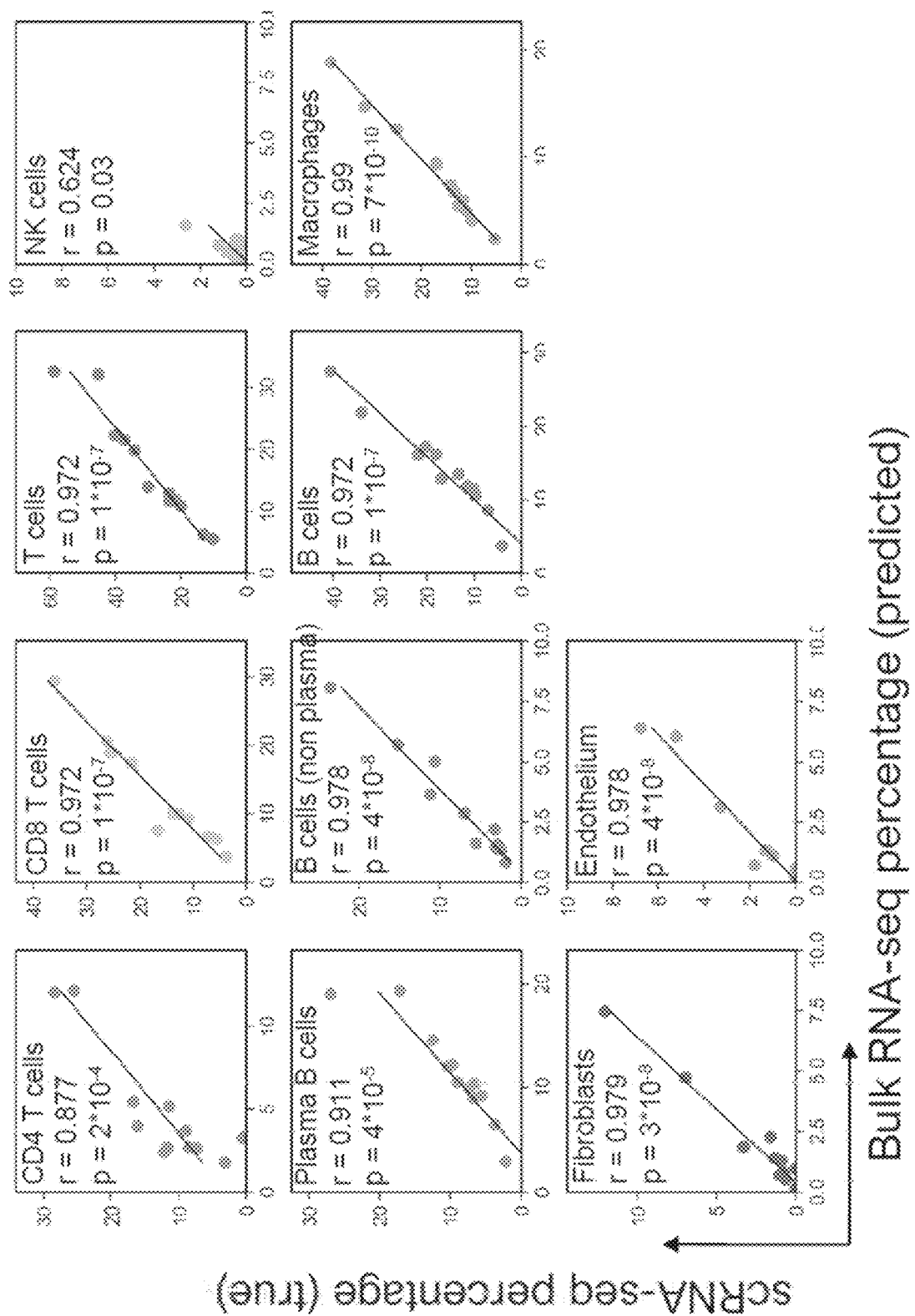
Figure 15E:
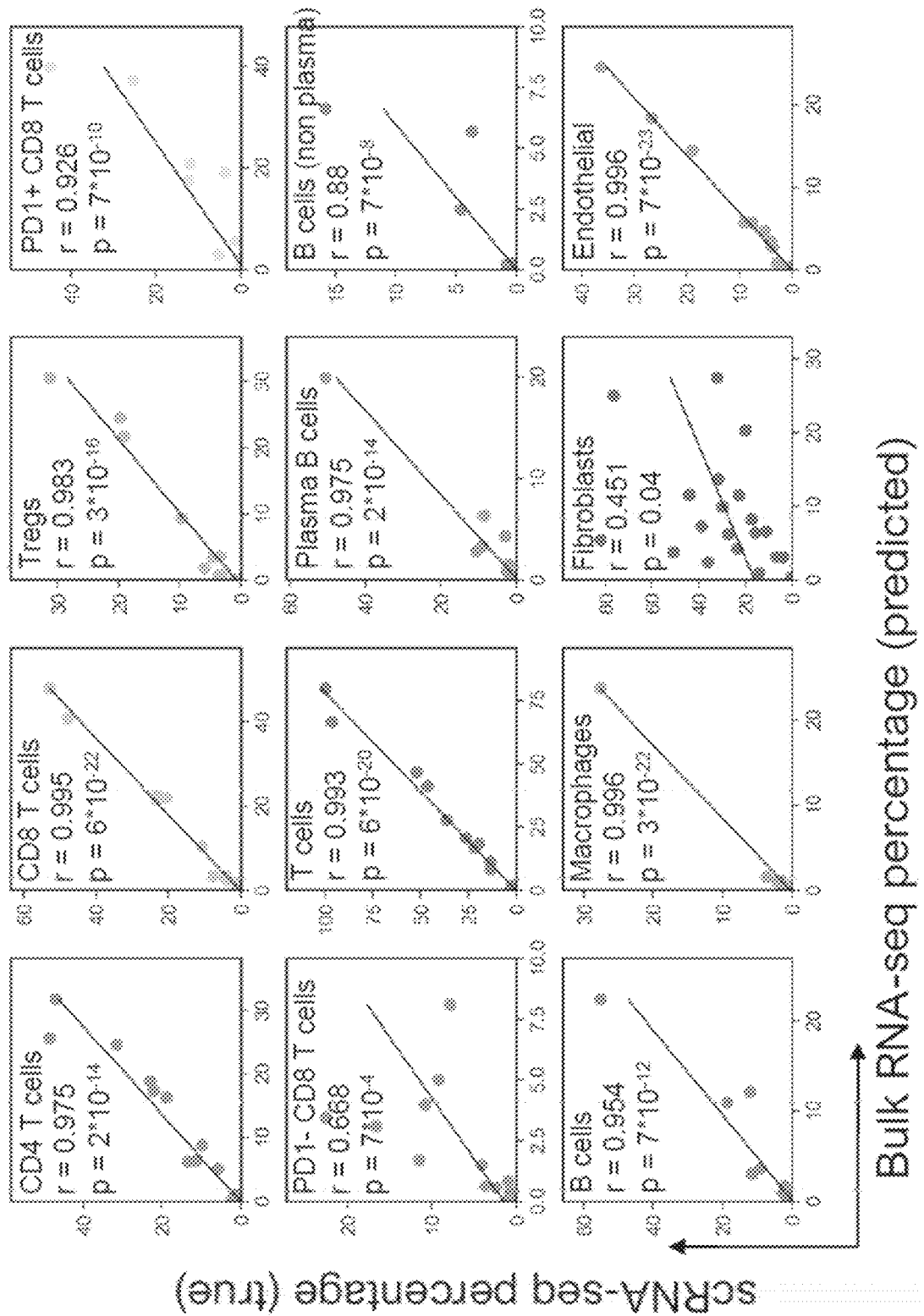
Figure 15F:
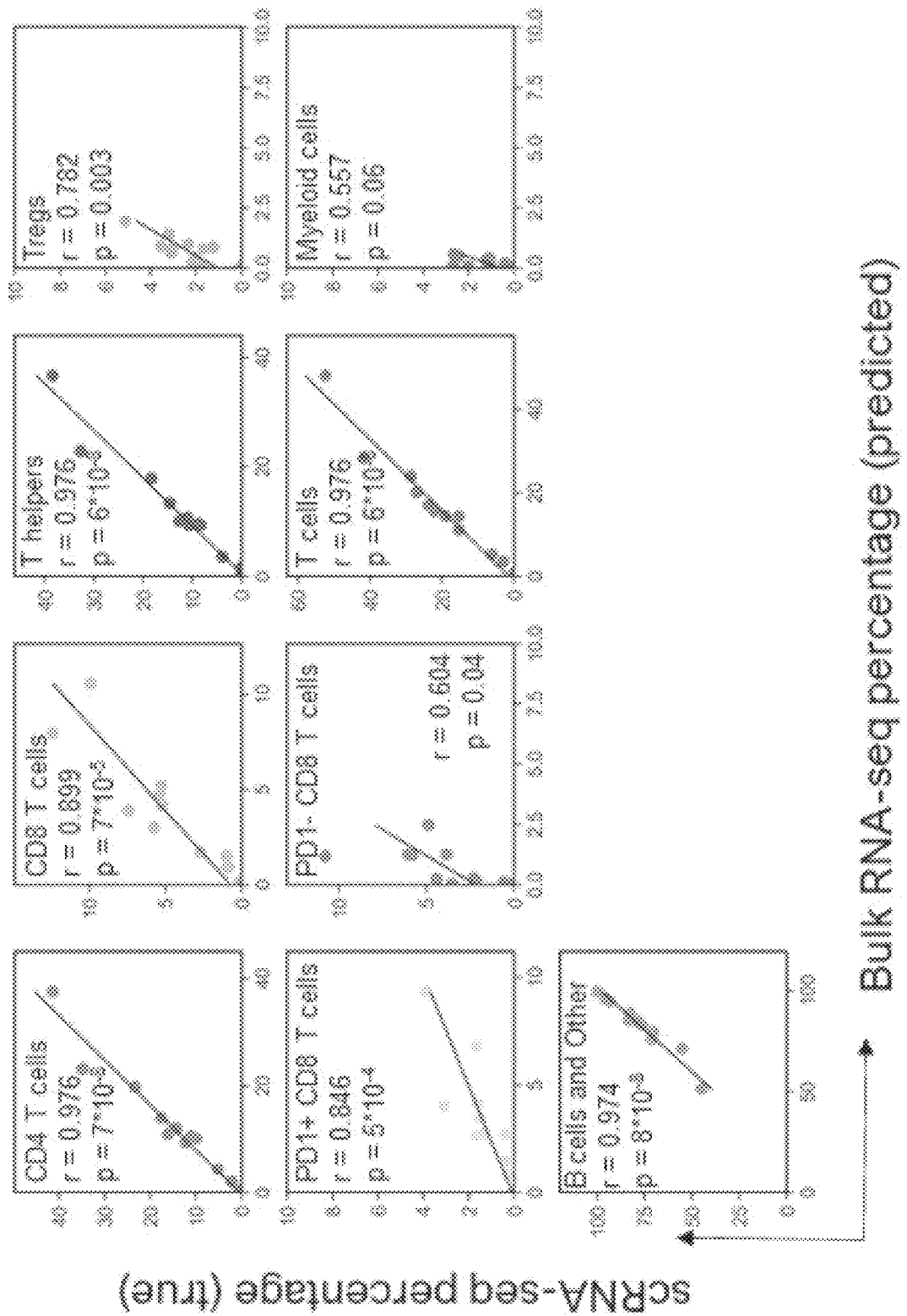

FIG. 15B is a schematic representation of a validation experiment using scRNA-seq data derived from cancer tissues. scRNA-seq data was artificially mixed to create a bulk RNA-seq dataset.

FIGS. 15C, 15D, 15E, and 15F are plots showing the correlation of true cell percentage values derived from scRNA-seq data (FIG. 15A) with deconvolution predictions by the techniques described herein from artificial bulk RNA-seq data. Correlations are shown for different cell subpopulations in melanoma (FIG. 15C)(n=19), lung cancer (FIG. 15D)(n=12), HNC (FIG. 15E) (n=22), and B-cell lymphomas (FIG. 15F)(n=12).

Figure 15G:
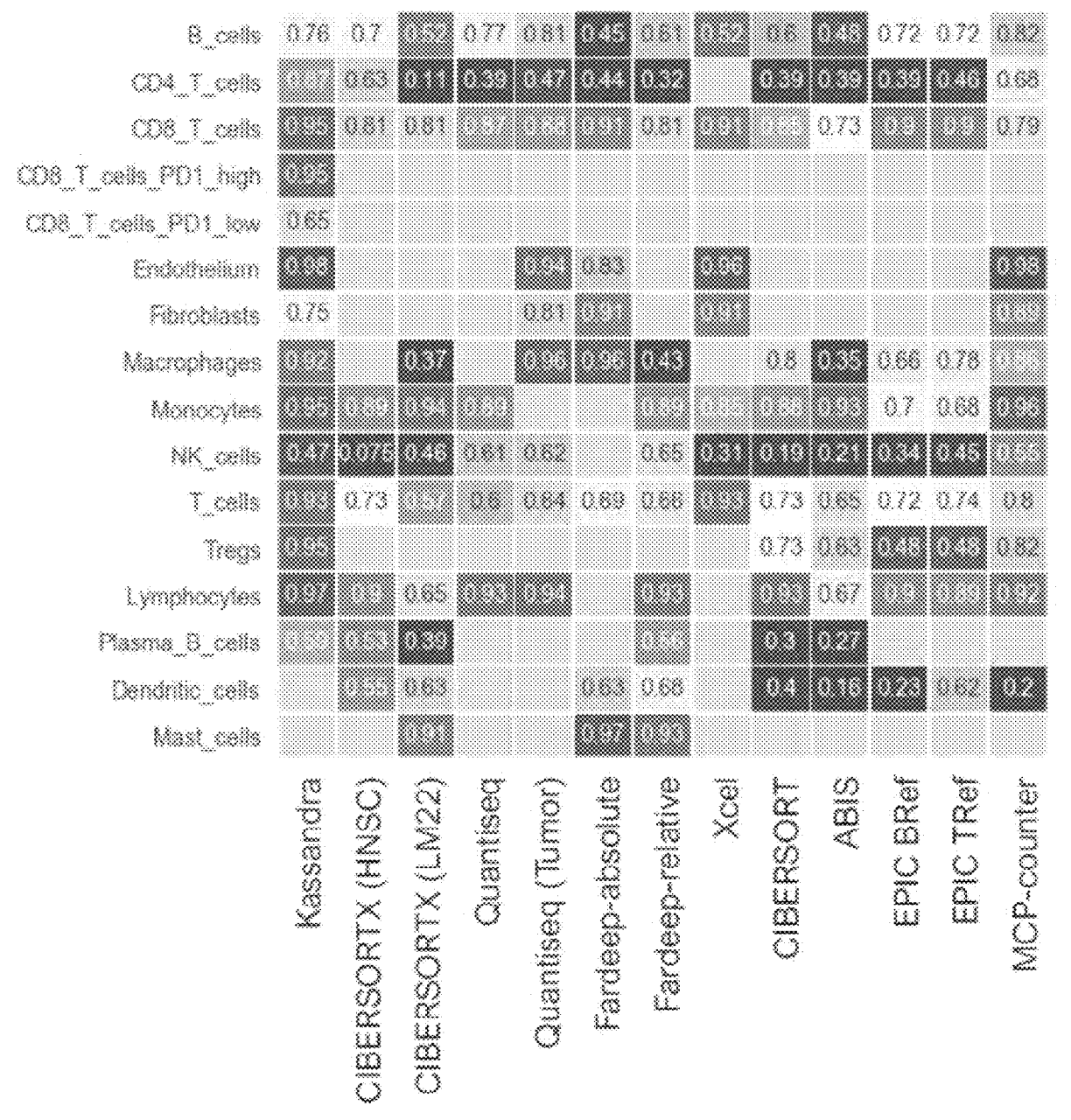
Figure 15H:
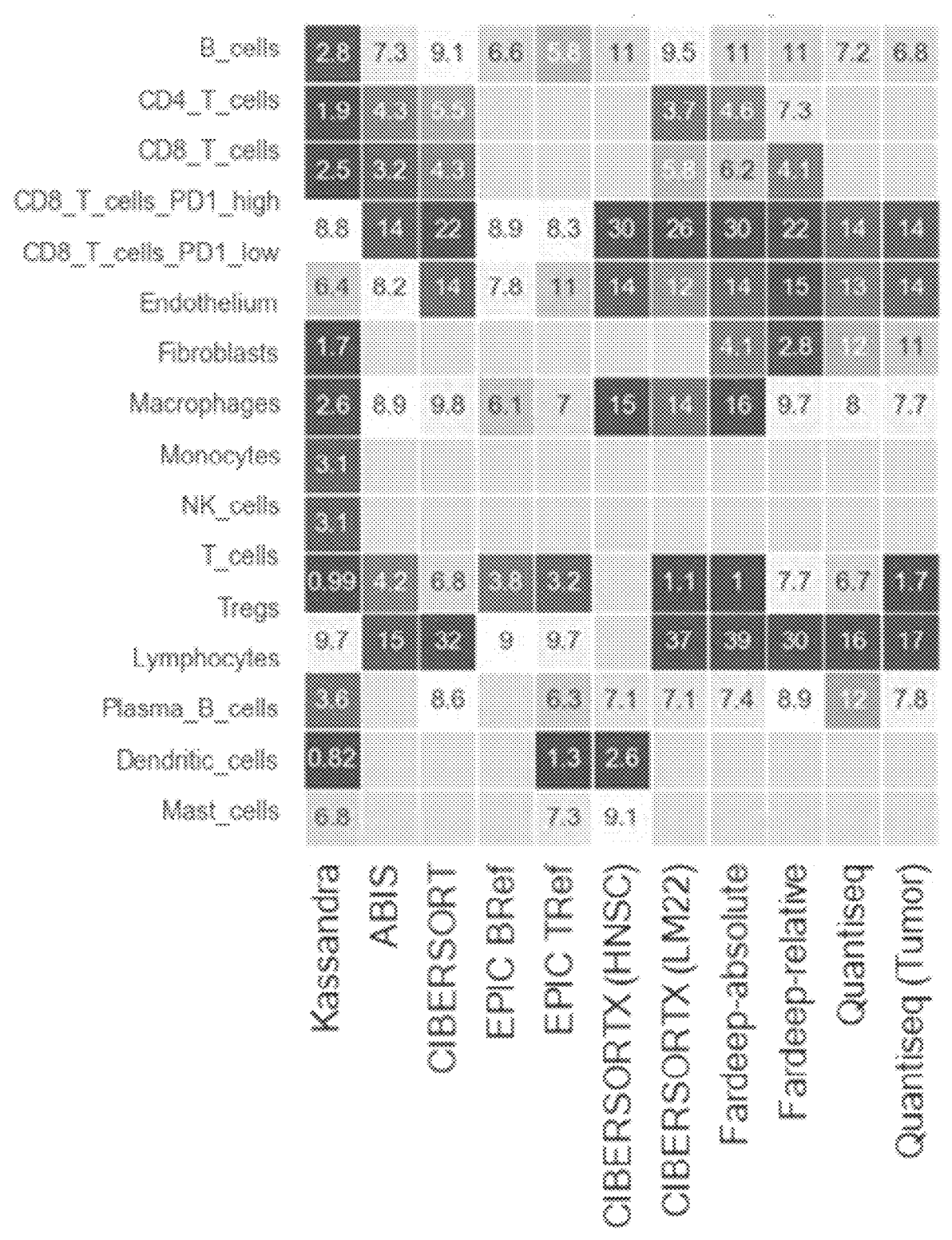

FIGS. 15G and 15H are heatmaps showing mean Pearson correlation values (FIG. 15G) and mean MAE (Mean Average Error) scores (FIG. 15H) between predicted values from artificial bulk RNA-seq data with true values derived from scRNA-seq data for melanoma, lung carcinoma and HNC. In this example, results from the techniques described herein are compared with results from alternative algorithms. Particularly, when compared to conventional techniques for deconvolution, the non-linear regression techniques developed by the inventors are shown to, on average, more accurately predict the cell composition percentages for different cell types with lower mean average error.

Figure 15I:
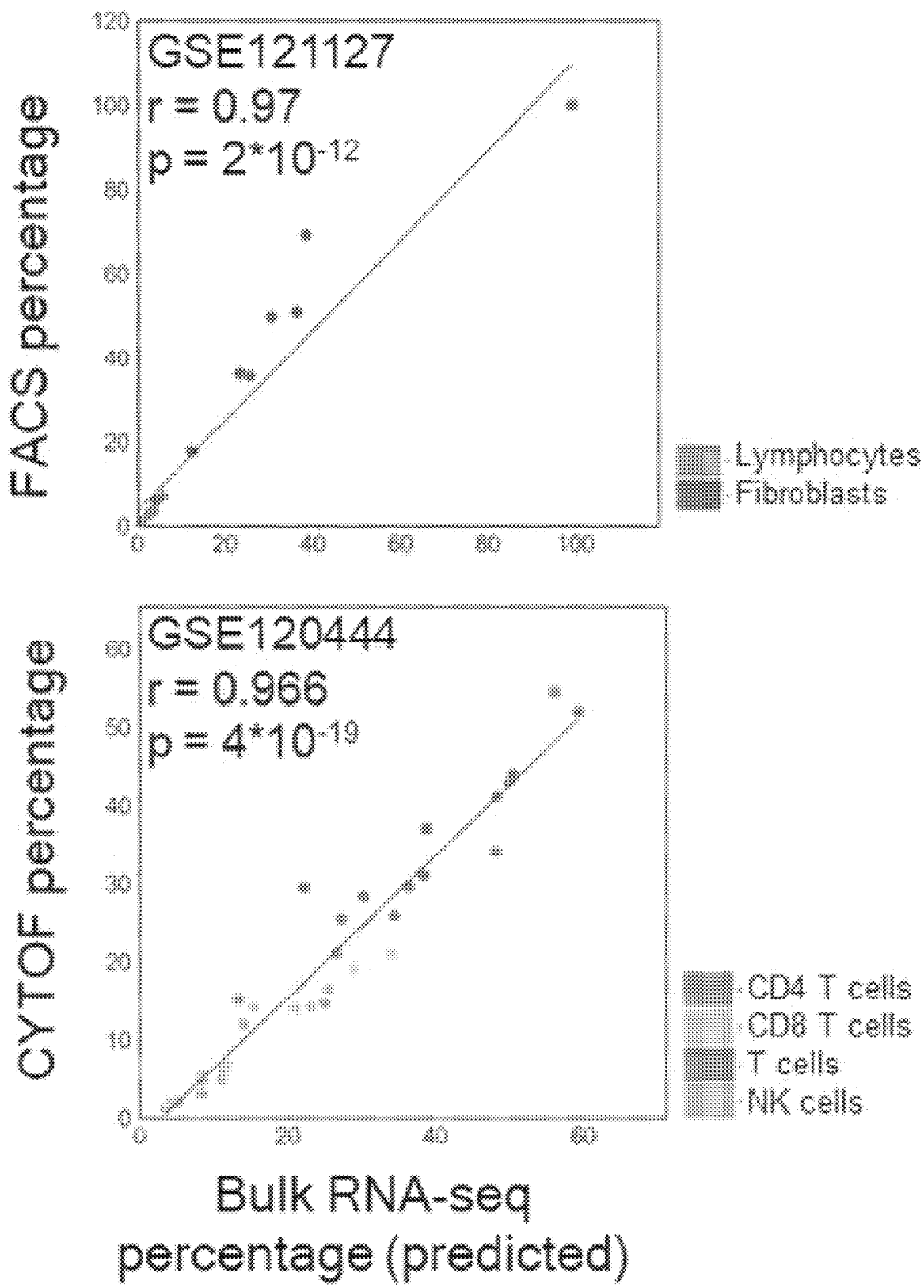

FIG. 15I shows the correlation between predicted cell percentages by the techniques described herein and actual cell percentage obtained by FACS for lymphocytes, fibroblasts and lung adenocarcinoma cell line from dataset GSE121127 (Wang et al. 2018)(top) and CYTOF for bone marrow from dataset GSE120444 (Oetjen et al. 2018)(bottom). The Pearson correlation value (r) represents correlation value for all cell types combined.

In this experiment, cells from scRNA-seq were annotated manually (FIG. 15A) and certain percentages of each cell type were mixed to resemble a bulk-RNA-seq sample (e.g., as described herein above at least with respect to FIG. 6A). Subsequently these cell percentages were compared with predicted values by the techniques described herein. The ability of the techniques described herein to reconstruct cell composition percentages for each cell type was measured (FIGS. 15C-F). The median correlation of cell types reconstruction reached ~0.97 and was the highest among other methods.

When the techniques described herein were compared to alternative techniques in their ability to estimate the absolute cell number in a mixed sample derived from scRNA-seq data, the techniques described herein achieved the most cell types with the highest correlation score (FIG. 15G) and lowest average error (MAE) (FIG. 15H). Only the techniques described herein were accurate in reconstruction of CD4+ T cells and T regs, providing mean Pearson correlation values up to 0.87 and 0.95 (FIG. 15G). Thus, although these cell types have a high number of overlapping genes, the techniques developed by the inventors successfully produce more accurate results than alternative algorithms.

TABLE 11

Exemplary NCBI Accession Numbers for genes mentioned herein. These records are incorporated by reference in their entirety.

| Gene | NCBI Gene ID | NCBI Accession Number (s) |
|---|---|---|
| ACAP1 | 9744 | NM_004288, XM_017005386 |
| ACRBP | 84519 | NM_032415, NM_001324281 |
| ACTA2 | 59 | NM_001141945, NM_001613, NM_001320855 |
| ADAM28 | 10863 | XM_011544370, XM_006716273, XM_011544369, XM_011544371, XR_949375, XM_005273380, XM_006716274, XM_005273382, XM_017012976, XM_017012974, XR_247120, NM_001304351, NM_014265, NR_130710, XM_017012975, NR_130709, XM_011544367, XM_011544368, NM_021777 |
| ADAMTS2 | 9509 | NM_014244, NM_021599 |
| ADAP2 | 55803 | XM_024450832, NM_001346714, XM_024450835, XM_024450834, XM_024450831, NM_001346712, NM_018404, NR_144488, XM_024450833, NM_001346716 |
| ADGRE2 | 30817 | XM_017026727, XR_001753674, NM_152918, XM_011527952, XR_001753675, XM_011527948, NM_001271052, NM_152916, NM_152921, XM_011527951, XR_936174, NM_152919, XM_011527949, XM_011527955, XM_017026726, NM_152920, XM_011527953, XM_011527954, XR_936173, NM_013447, NM_152917 |
| ADGRE3 | 84658 | XM_017027383, NM_001289158, NM_001289159, XM_011528374, XR_001753772, NM_152939, NM_032571 |
| ADGRG3 | 222487 | XM_011522951, XM_011522953, XM_011522954, XR_243399, NM_170776, XM_006721170, XM_005255842, NM_001308360 |
| ADORA3 | 140 | NM_000677, NM_001302678, NM_001302679 |
| AIF1 | 199 | XM_005248870, NM_001318970, NM_001623, XM_017010332, NM_004847, NM_032955 |
| ANGPT2 | 285 | NM_001118887, NM_001147, NM_001118888, XM_017013318 |
| ANKRD55 | 79722 | XM_011543646, XM_017009852, XM_024669, NM_001039935, XM_017009854, XM_017009853 |
| ANXA2R | 389289 | NM_001014279, NM_001382352 |
| AOAH | 313 | XM_011515340, XM_011515334, XM_011515333, XM_011515338, NM_001637, XM_011515336, XM_017012104, NM_001177507, XM_017012106, NM_001177506, XM_011515342, XM_017012102, XM_011515335, XM_011515341, XM_011515339, XM_017012105 |
| APLN | 8862 | NM_017413 |
| APOBEC3D | 140564 | NM_152426, XR_001755169, NM_001363781, XM_017028596, XR_001755170 |
| APOBEC3G | 60489 | XM_017028903, NM_001349437, NM_021822, NR_146179, NM_001349438, XM_017028904, NM_001349436 |
| ARHGAP15 | 55843 | XM_011511479, XR_001738850, XM_024453001, XM_024453000, XM_011511483, XM_011511482, XM_011511484, XM_011511481, XM_017004499, XM_017004500, XM_017004501, NM_018460 |
| ARHGAP30 | 257106 | NM_001287602, XM_017000960, NM_001025598, NM_001287600, XM_005245070, XM_005245073, XM_011509391, NM_181720 |
| ARHGAP9 | 64333 | XR_001748840, NM_032496, XM_005269083, XM_011538657, XR_001748842, NM_001319850, NM_001319851, XM_011538658, XM_011538659, NM_001319852, XM_017019800, NM_001080157, NM_001367422, NM_001367425, XM_005269084, XM_005269085, XM_011538656, XR_001748843, NM_001367424, NM_001367426, NM_001080156, XR_001748841, NM_001367423 |
| ARHGDIB | 397 | NM_001321421, NM_001175, NM_001321423, NR_135637, NM_001321422, XM_024448979, NM_001321420 |
| BANK1 | 55024 | XM_017008337, NM_017935, NM_001127507, NM_001083907 |
| BCL11A | 53335 | XM_011532910, NM_001365609, XM_017004335, XM_024452963, NM_138559, XM_017004336, XM_017004333, XM_024452962, XM_018014, XM_011532909, NM_138553, NM_001363864, NM_022893 |
| BLK | 640 | XM_011543825, XM_011543828, NM_001330465, XM_011543827, XM_011543829, XM_011543824, NM_001715 |
| C15orf48 | 84419 | NM_197955, NM_032413 |
| C1QA | 712 | NM_015991, NM_001347465, NM_001347466 |
| C1QC | 714 | NM_001347619, NM_001347620, NM_001114101, NM_172369 |
| C3AR1 | 719 | NM_001326477, NM_004054, NM_001326475 |
| C5AR1 | 728 | XM_005259190, NM_001736 |
| CAMK4 | 814 | XR_948303, NM_001323377, XR_001742281, NM_001323374, XR_001742282, NM_001323375, NM_001323376, NM_001744 |
| CARD11 | 84433 | NM_032415, NM_001324281 |
| CBLB | 868 | NM_001321786, NM_001321799, NM_001321811, NM_170662, XM_017007399, XM_017007395, XM_017007396, NM_001321789, NM_001321793, NM_001321795, NM_001321796, NM_001321798, NM_001321808, NM_001321820, NR_135808, XM_011513259, NR_135810, NM_001321797, NM_001321806, NM_001321807, NM_001321816, NR_135806, NR_135811, XM_017007400, XR_001740339, NM_001321788, NM_001321791, NR_135807, XM_011513257, XM_017007397, NM_001321790, NM_001321794, NM_001321813, NM_001321822, NR_135812, XM_017007398, XR_001740338, NR_135809 |
| CCDC69 | 26112 | NM_015621 |
| CCL3 | 6348 | NM_002983, NR_168495, NR_168496, NR_168494 |
| CCL3L3 | 6349 | NM_021006, NR_111964 |
| CCL4L2 | 9560 | NM_001291468, NM_001291470, NM_001291473, NM_001291469, NM_001001435, NM_001291475, NM_001291472, NM_001291474, NM_001291471, NR_111970 |
| CCL5 | 6352 | NM_002985, NM_001278736 |
| CCL7 | 6354 | NM_006273 |
| CCR1 | 1230 | NM_001295 |
| CCR2 | 729230 | NM_001123396, NM_001123041, XM_011534069 |
| CCR3 | 1232 | NM_001837, NM_178329, XM_006712960, NM_001164680, XM_017005686, NM_178328, XM_011533335, XM_017005685 |
| CCR4 | 1233 | XM_017005687, NM_005508 |
| CCR7 | 1236 | NM_001301716, NM_001301714, NM_001301717, NM_001301718, NM_001838 |
| CCR8 | 1237 | NM_005201 |
| CD14 | 929 | NM_001174104, NM_001040021, NM_000591, NM_001174105 |

TABLE 11-continued

Exemplary NCBI Accession Numbers for genes mentioned herein. These records are incorporated by reference in their entirety.

| Gene | NCBI Gene ID | NCBI Accession Number (s) |
|---|---|---|
| CD160 | 11126 | NM_007053, XM_011509104, XM_005272929, NR_103845 |
| CD163 | 9332 | XR_002957389, NM_004244, NM_203416, XM_024449278, NM_001370146, NM_001370145, NR_163255 |
| CD19 | 930 | XM_017023893, NM_001770, XM_006721103, XM_011545981, XR_950871, NM_001178098 |
| CD1D | 912 | NM_001371762, NM_001319145, XR_921996, NM_001371763, XM_011510127, NM_001766, XR_921995, NM_001371761, XR_001737534, XM_006711621 |
| CD2 | 914 | NM_001767, NM_001328609 |
| CD209 | 30835 | NM_001144897, NM_001144899, NM_001144894, NM_001144895, NM_001144893, NM_001144896, NR_026692, NM_021155 |
| CD22 | 933 | NM_001185101, NM_001278417, NM_001185100, NM_001771, NM_024916, NM_001185099 |
| CD226 | 10666 | XM_017025525, NM_006566, NM_001303619, XM_006722374, XM_017025526, NM_001303618, XM_005266643, XM_005266642, XM_017025527 |
| CD244 | 51744 | XR_001737229, NM_001166663, XM_011509621, NM_016382, XM_011509623, XM_011509622, NM_001166664 |
| CD247 | 919 | XM_011510145, XM_011510144, NM_001378516, NM_198053, NM_000734, NM_001378515 |
| CD248 | 57124 | NM_020404 |
| CD27 | 939 | XM_017020232, NM_001242, XM_017020233, XM_011521042, XM_017020234 |
| CD28 | 940 | NM_001243078, XM_011512195, NM_001243077, XM_011512194, XM_011512197, NM_006139 |
| CD300A | 11314 | XM_005256990, XM_006721656, NM_001330456, NM_007261, NM_001256841, NM_001330457, XM_005256991 |
| CD300C | 10871 | NM_006678, XM_017024034, XM_017024033 |
| CD300E | 342510 | XM_017024575, NM_181449 |
| CD300LB | 124599 | NM_174892, XM_005257027 |
| CD302 | 9936 | NM_014880, NM_001198763, NM_001198764 |
| CD33 | 945 | XM_017027509, XM_011527531, XM_011527532, NM_001177608, XM_017027510, NM_001082618, XM_017027508, NM_001772 |
| CD37 | 951 | NM_001040031, XM_011527542, XM_011527543, NM_001774, XM_005259436, XM_011527544, XM_017027513, XM_005259435 |
| CD38 | 952 | NM_001775, NR_132660 |
| CD3D | 915 | NM_000732, NM_001040651 |
| CD3E | 916 | NM_000733 |
| CD3G | 917 | XM_006718941, NM_000073, XM_005271724 |
| CD4 | 920 | NM_001195017, NM_001382707, NM_001382705, NM_001382706, NM_001195015, NR_036545, NM_001195016, NM_000616, NM_001195014, NM_001382714 |
| CD40LG | 959 | NM_000074 |
| CD48 | 962 | XM_011510171, NM_001256030, XM_005245625, XM_017002867, NM_001778 |
| CD5 | 921 | NM_014207, NM_001346456 |
| CD53 | 963 | NM_000560, NM_001320638, XM_024451057, NM_001040033 |
| CD6 | 923 | XM_011545362, NM_006725, XM_006718740, XM_011545360, XM_006718739, NM_001254751, NR_045638, XM_006718738, XM_006718741, NM_001254750 |
| CD68 | 968 | NM_001040059, NM_001251 |
| CD69 | 969 | NR_026672, NR_026671, NM_001781 |
| CD7 | 924 | XM_011523608, XM_017025316, XR_001752680, XR_001752681, NM_006137 |
| CD72 | 971 | XM_006716893, NM_001782 |
| CD79A | 973 | NM_021601, NM_001783 |
| CD79B | 974 | NM_000626, NM_001039933, NM_001329050, NM_021602 |
| CD86 | 942 | NM_176892, NM_001206924, NM_006889, NM_175862, NM_001206925 |
| CD8A | 925 | NR_168478, NM_001145873, NM_001382698, NR_168480, NM_001768, NM_171827, NR_027353, NR_168481, NR_168479 |
| CD8B | 926 | NM_172101, NM_172213, NM_172102, NM_001178100, NM_004931, NM_172099, XM_011533164 |
| CD96 | 10225 | NM_001318889, NM_005816, XM_005247063, XM_006713469, XM_006713470, NM_198196, XM_017005521, XR_241462, NR_134917, XR_001739977, XM_017005522, XR_924090 |
| CDH5 | 1003 | NM_001795, XM_011522801, NM_001114117, XM_024450133 |
| CEACAM8 | 1088 | XM_011526342, XM_011526340, XM_017026195, XM_017026194, XM_011526341, XM_017026197, XM_017026196, NM_001816, XM_017026198 |
| CECR1 | 51816 | NM_001282229, NM_001282225, NM_177405, NM_001282227, NM_001282228, NM_001282226, XM_011546133, NM_017424, XM_006724080 |
| CELF2 | 10659 | XM_017015543, XM_017015556, XM_017015557, XM_017015565, XM_017015566, XM_024447778, NM_001326321, NM_001326326, NM_001326327, NM_001326328, NM_001326331, XM_017015546, XM_017015571, XM_024447774, NM_001083591, NM_001326323, NM_001326334, NM_001326342, NM_001326345, NM_006561, XM_006717373, XM_011519297, NM_001326339, XM_017015558, XM_024447775, NM_001025076, NM_001326317, NM_001326318, NM_001326330, NM_001326336, NM_001326338, NM_001326344, XM_017015560, XM_017015569, XM_017015570, XM_024447772, XM_024447776, XM_024447779, NM_001025077, NM_001326335, NM_001326347, NM_001326349, XM_005252357, XM_017015568, XM_024447773, XM_024447777, XM_024447780, NM_001326329, NM_001326332, NM_001326333, NM_001326341, NM_001326346, XM_017015545, XM_017015547, XM_017015550, XM_017015562, XM_017015572, NM_001326325, NM_001326348, XM_017015548, XM_017015552, XM_017015564, NM_001326319, NM_001326320, NM_001326324, NM_001326337, NM_001326340, NM_001326343 |
| CLDND2 | 125875 | NM_152353, XM_011526425, XM_017026246, XM_011526428, XM_017026244, XM_017026247, XM_017026245 |
| CLEC14A | 161198 | NM_175060 |
| CLEC17A | 388512 | XM_017026792, XM_017026786, NM_207390, NR_109785, XM_017026785, XM_017026790, XM_017026793, XM_017026787, XM_017026789, XM_017026791, XM_017026788, NM_001204118, NR_109784, XM_017026794 |

TABLE 11-continued

Exemplary NCBI Accession Numbers for genes mentioned herein. These records are incorporated by reference in their entirety.

| Gene | NCBI Gene ID | NCBI Accession Number (s) |
|---|---|---|
| CLEC2D | 29121 | NM_001197318, NM_013269, NR_036693, NM_001004420, NM_001004419, NM_001197319, NM_001197317 |
| CLEC5A | 23601 | NM_001301167, XM_017011916, NM_013252, XM_017011915, XM_017011917, XM_011515995 |
| CLEC7A | 64581 | NM_022570, XM_017019822, NM_197947, NM_197948, NM_197954, NM_197953, NM_197949, XM_024449132, NM_197951, NM_006719135, XM_017019823, XM_024449133, NM_197950, NR_125336, NM_197952 |
| CMKLR1 | 1240 | NM_001142345, NM_004072, NM_001142343, NM_001142344, XM_017018820 |
| COL16A1 | 1307 | XM_011540726, XM_011540730, XM_011540723, XR_001736982, XM_011540724, XM_011540728, XM_017000340, XM_017000341, XR_001736984, NM_001856, XM_005270481, XM_011540729, XM_017000338, XR_946546, XM_017000339, XR_001736983, XM_011540722, XM_011540727, XR_001736981 |
| COL1A1 | 1277 | NM_000088, XM_005257059, XM_005257058, XM_011524341 |
| COL1A2 | 1278 | NM_000089 |
| COL3A1 | 1281 | NM_000090, NM_001376916 |
| COL4A1 | 1282 | NM_001303110, XM_011521048, NM_001845 |
| COL5A1 | 1289 | XM_017014266, NM_001278074, XR_001746183, NM_000093 |
| COL6A1 | 1291 | NM_001848 |
| COL6A2 | 1292 | XR_937439, NM_058175, NM_058174, XR_937438, NM_001849, XM_011529451 |
| COL6A3 | 1293 | XM_005246065, XM_006712253, NM_057164, XM_017003304, NM_004369, NM_057166, XM_011510574, XM_024452684, NM_057165, NM_057167 |
| CORO1A | 11151 | XM_017022885, NM_001193333, NM_007074, XM_011545714, XM_017022886 |
| CPNE5 | 57699 | XM_011514768, XM_011514771, XR_001743541, NM_001376894, XR_002956291, NM_001314018, NM_001376889, NM_001376890, NM_001314019, XM_011514769, NM_001376892, NM_020939, XM_011514770, XR_002956290, NM_001314017, NR_164866, XM_011514773, NM_001376888, NM_001376891, NM_001376893, XM_005249247, XM_017011139, NM_001314020, NM_001376895, XM_011514772 |
| CR2 | 1380 | NM_001006658, XM_011509206, NM_001877 |
| CRTAM | 56253 | XM_011542900, NM_001304782, NM_019604 |
| CSF1R | 1436 | NM_001288705, NM_001349736, NM_001375320, NR_109969, NR_164679, NM_001375321, NM_005211 |
| CSF2RA | 1438 | XM_011546165, XM_011546175, NM_001161532, NM_001379153, NM_001379155, NM_001379165, NM_001379166, NM_172248, XM_011546167, NM_001161531, NM_001379163, NM_001379164, NM_172245, NM_172249, XM_011545627, NM_001379159, NM_001379167, NR_027760, XM_011545623, XM_011546174, NM_001161530, NM_001379156, NM_001379158, NM_172246, XM_011545620, NM_001161529, NM_001379154, NM_001379160, XM_011545628, NM_001379161, NM_001379169, XM_011545622, XM_011546169, XM_011546170, NM_001379162, NM_001379168, XM_011545618, NM_006140, NM_172247 |
| CSF3R | 1441 | NM_156038, XM_005270493, XM_011540749, XM_017000370, XM_011540750, NM_156039, NM_172313, XM_011540748, NM_000760 |
| CTLA4 | 1493 | NM_001037631, NM_005214 |
| CTSS | 1520 | NM_004079, NM_001199739 |
| CTSW | 1521 | NM_001335 |
| CXCL3 | 2921 | NM_002090 |
| CXCR1 | 3577 | NM_000634 |
| CXCR2 | 3579 | XM_017003992, NM_001557, XM_017003990, NM_001168298, XM_005246530, XM_017003991 |
| CXCR3 | 2833 | NM_001504, XM_005262256, XM_005262257, XM_017029435, XM_017029436, NM_001142797 |
| CXCR5 | 643 | NM_001716, NM_032966 |
| CYBB | 1536 | NM_000397 |
| CYFIP2 | 26999 | XM_017009341, NM_014376, NM_001037332, XM_017009342, NM_001291722, XM_011534516, NM_001291721, XR_001742052, NM_001037333 |
| CYTH4 | 27128 | NM_013385, NM_001318024 |
| CYTIP | 9595 | NM_004288, XM_017005386 |
| DEF6 | 1671 | NM_001926 |
| DENND1C | 79958 | NM_024898, XM_006722905, XM_006722906, NM_001290331, XM_011528318, XM_024451727 |
| DERL3 | 91319 | NM_198440, NM_001002862, XM_017029078, XM_017029080, XM_011530505, XM_017029079, NM_001363072, XM_017029082, NM_001135751 |
| DOCK2 | 1794 | XM_011534451, NM_004946, XM_005265830, XM_011534448, XM_017009190, XM_011534450, XM_017009189, NR_156756, XM_011534449 |
| EAF2 | 55840 | XM_005247618, XM_017006862, NM_001320041, XM_017006861, XM_017006863, NM_018456 |
| ECSCR | 641700 | NR_121659, NM_001293739, NM_001077693 |
| ELF1 | 1997 | NM_001370329, NM_001370331, NM_001370330, NM_172373, NM_001145353, NM_001370332 |
| ELMO1 | 9844 | NM_001039459, NM_001206480, NM_001206482, NR_038120, XM_024447008, XM_017012839, XM_005249919, XM_011515654, NM_130442, XM_006715805, XR_001744894, NM_014800 |
| EMCN | 51705 | XM_017008290, XM_011532024, NM_016242, NM_001159694 |
| EMILIN2 | 84034 | NM_032048, XM_017026038 |
| ENG | 2022 | NM_001114753, NM_001278138, NM_000118 |
| ENTPD1 | 953 | NM_001312654, NM_001320916, XM_011540376, XM_011540377, XM_017016958, NM_001098175, XM_011540372, XM_017016963, XM_017016959, NM_001164181, XM_011540371, XM_011540374, XM_017016960, NM_001164179, NM_001164182, XM_017016961, NM_001164178, XM_011540373, XM_017016964, NM_001164183, NM_001776, XM_011540370, XM_017016962 |
| EOMES | 8320 | NM_005442, NM_001278182, XM_005265510, NM_001278183 |
| ESAM | 90952 | NM_138961 |
| ESM1 | 11082 | NM_007036, NM_001135604 |
| ETS1 | 2113 | XM_017017314, NM_001162422, XM_011542650, NM_005238, XM_017017317, XM_017017315, NM_001143820, NM_001330451 |

TABLE 11-continued

Exemplary NCBI Accession Numbers for genes mentioned herein. These records are incorporated by reference in their entirety.

| Gene | NCBI Gene ID | NCBI Accession Number (s) |
|---|---|---|
| EVI2B | 2124 | XM_005257946, NM_006495 |
| EVL | 51466 | XM_011536828, XR_001750356, XR_001750357, XR_001750366, XM_017021363, XR_001750361, XR_001750360, XR_001750367, NM_016337, XM_005267749, XR_001750362, XR_001750359, XR_001750363, XR_001750364, NM_001330221, XR_001750355, XR_002957557 |
| FAM129C | 199786 | XM_011527786, NM_001321827, XM_011527781, XM_011527789, XM_017026453, NM_001321826, NM_001363609, XM_011527787, XM_017026457, XM_017026456, NM_001098524, NM_173544, XM_005259813, XM_017026454, XM_017026455, NM_001321828 |
| FAM78A | 286336 | XM_011518568, XM_011518567, NM_033387 |
| FAP | 2191 | XM_011510796, XM_011510797, NM_001291807, XM_017003585, NM_004460, XR_001738668, XR_922891 |
| FASLG | 356 | NM_001302746, NM_000639 |
| FBLN2 | 2199 | XM_006713026, NM_001004019, NM_001165035, NM_001998 |
| FBN1 | 2200 | NM_000138 |
| FCER1G | 2207 | NM_004106 |
| FCER2 | 2208 | XM_005272462, NM_001207019, NM_001220500, NM_002002 |
| FCGR1A | 2209 | NM_000566, NM_001378807, NR_166122, NM_001378809, NM_001378805, NM_001378808, NM_001378811, NR_166123, NM_001378804, NM_001378806, NM_001378810, NR_166121 |
| FCGR1B | 2210 | NR_045213, NM_001004340, NM_001017986, NR_164759, NM_001244910, NR_164758, NR_164760 |
| FCGR2A | 2212 | XM_011509287, XM_024454041, XM_011509291, XM_024454040, XR_001737042, NM_001136219, NM_001375297, XM_011509290, XM_017000664, XM_017000665, XM_017000666, NM_021642, NM_001375296, XM_017000663 |
| FCGR3B | 2215 | NM_001271035, NM_001271037, NM_001271036, NM_000570, NM_001244753 |
| FCMR | 9214 | XM_005273351, NM_001193338, NM_005449, XM_005273352, NM_001142472, NM_001142473, XR_921999 |
| FCN1 | 2219 | NM_002003 |
| FCRL1 | 115350 | XM_011509126, XM_011509131, NM_001159397, XM_005244867, XR_921740, XM_005244866, XM_011509128, XM_011509134, XM_011509125, XM_011509137, XM_005244869, XM_011509127, XM_011509133, XR_921739, XM_011509129, XM_011509130, XM_011509135, XM_011509136, XM_011509132, XM_017000227, XR_921738, NM_001159398, NM_052938 |
| FCRL2 | 127943 | NM_001002901, NM_001288830, NM_001288831, NM_001288829, NM_001288832, NM_001320241 |
| FCRL3 | 115352 | NR_135215, NR_135217, NM_001024667, NM_001320333, NR_135214, XM_006711145, NM_052939, NR_135216 |
| FCRL5 | 83416 | XM_011510032, NM_001195388, XM_011510031, NM_031281, XM_011510033, XM_011510030 |
| FCRL6 | 343413 | XM_005245129, XM_011509480, XM_017001177, XM_011509481, XM_005245128, XM_005245131, NM_001284217, XM_017001176, XM_006711292, NM_001004310 |
| FERMT3 | 83706 | NM_001382448, NM_001382361, NM_001382363, NM_001382362, NM_031471, NM_178443, NM_001382364 |
| FFAR2 | 2867 | NM_005306, XM_017026711, NM_001370087 |
| FGF2 | 2247 | NM_002006, NM_001361665 |
| FGFBP2 | 83888 | NM_031950 |
| FGL2 | 10875 | NM_006682 |
| FGR | 2268 | XM_011541011, XM_011541014, NM_001042747, XM_011541012, XM_017000673, XM_011541013, XM_017000674, XR_946583, NM_005248, XM_006710452, XM_011541010, NM_001042729 |
| FHIT | 2272 | NM_001320901, NM_001354589, NM_001354590, NM_001166243, NM_001320899, NM_002012, NR_135491, NM_001320900, NR_148921, NR_148922 |
| FKBP11 | 51303 | NM_001143781, NM_001143782, NM_016594 |
| FKBP15 | 23307 | XM_006717018, NM_015258, XM_006717019, XM_017014552 |
| FLT1 | 2321 | XM_017020485, NM_002019, NM_001160031, XM_011535014, NM_001159920, NM_001160030 |
| FLT3LG | 2323 | XM_011526682, XM_017026534, XM_011526677, XM_017026538, XR_001278638, NM_001459, XM_005258681, XM_005258683, XM_011526678, NM_001278637, XM_006723116, XM_017026532, XM_011526675, XM_017026535, XR_935781, NM_001204503, XM_005258680, XM_011526676, NM_001204502, XM_005258682, XM_011526680 |
| FMNL1 | 752 | XM_006722069, XM_006722064, XM_011525179, XM_006722063, XM_011525180, NM_005892, XM_006722066, XM_006722062, XM_006722065, XM_006722070, XM_011525182 |
| FNBP1 | 23048 | XM_005251830, XM_005251815, XM_005251820, XM_005251823, XM_017014490, XM_005251832, XM_017014493, XM_017014494, NM_001363755, XM_005251831, XM_006717016, XM_011518400, XM_017014492, XM_024447457, XM_005251821, XM_005251828, XM_011518399, XM_017014487, XM_011518488, XM_005251824, XM_005251825, XM_005251834, XM_011518401, XM_005251826, XM_017014489, XM_017014491, XM_005251822, XM_005251827, XM_005251833, XM_011518402, NM_015033 |
| FOXP3 | 50943 | XM_006724533, XM_017029567, NM_001114377, NM_014009 |
| FPR1 | 2357 | NM_002029, NM_001193306 |
| FPR2 | 2358 | NM_001005738, XM_006723120, NM_001462 |
| FPR3 | 2359 | NM_002030, XM_011526687 |
| GADD45G | 10912 | XM_011518163, NM_006705 |
| GLCCI1 | 113263 | NM_138426 |
| GLT1D1 | 144423 | XR_001748587, XR_001748588, XM_011537957, XM_017018855, XR_001748589, NM_001366888, NR_133646, XR_001748590, NM_001366887, NM_144669, NM_001366886, XM_017018859, XR_001748586, XR_001748591, NM_001366889, NR_159493 |
| GPNMB | 10457 | NM_002510, XM_017011676, XM_017011678, NM_001005340, XM_005249578, XM_017011677 |
| GPR174 | 84636 | NM_032553 |
| GPR18 | 2841 | XM_006719946, NM_005292, XM_024449339, NM_001098200 |
| GRAMD1A | 57655 | XM_011527155, XM_017027034, NM_001320036, XM_011527154, XM_024451623, NM_001320035, NM_001320034, XM_011527153, XM_017027035, XM_024451622, XM_011527149, XM_011527156, NM_001136199, NM_020895 |

TABLE 11-continued

Exemplary NCBI Accession Numbers for genes mentioned herein. These records are incorporated by reference in their entirety.

| Gene | NCBI Gene ID | NCBI Accession Number (s) |
|---|---|---|
| GRAP2 | 9402 | NM_001291826, NM_001291825, XM_006724376, NM_004810, NM_001291824, NM_001291828 |
| GZMA | 3001 | NM_006144 |
| GZMB | 3002 | NM_001346011, NR_144343, NM_004131 |
| GZMH | 2999 | NM_033423, NM_001270781, NM_001270780, XM_011536683 |
| GZMK | 3003 | NM_002104 |
| GZMM | 3004 | NM_005317, NM_001258351 |
| HAVCR2 | 84868 | NM_032782 |
| HCK | 3055 | NM_001172133, NM_002110, NM_001172129, NM_001172131, NM_001172132, NM_001172130 |
| HCLS1 | 3059 | NM_001292041, NM_005335 |
| HHIP | 64399 | XM_006714288, NM_022475, XM_005263178 |
| HK3 | 3101 | XR_941101, XR_941102, XM_011534540, XM_017009411, NM_002115 |
| HLA-DOB | 3112 | NM_002120 |
| HMHA1 | 23526 | NM_001282335, XM_006722713, XM_011527858, NM_001321232, NM_012292, XM_024451435, NM_001282334, NM_001258328 |
| ICAM3 | 3385 | NM_001320606, NM_001320608, NM_002162, NM_001320605 |
| ICOS | 29851 | NM_012092 |
| IFI30 | 10437 | NM_006332 |
| IFITM2 | 10581 | NM_006435 |
| IGFLR1 | 79713 | NM_001346006, NM_024660, NR_144338, NR_144339, NR_144340, NM_001346003, NM_001346005, NM_001346004, NR_144341, NR_144342 |
| IGHG1 | 3500 | _001019.6 |
| IGKC | 3514 | _000834.1 |
| IGLL5 | 100423062 | NM_001256296, NM_001178126 |
| IGSF6 | 10261 | NM_005849 |
| IKZF1 | 10320 | XM_011515063, XM_011515067, XM_011515074, XM_011515075, XM_011515077, XM_017011669, NM_001220765, XM_011515060, XM_011515073, NM_001291839, NM_001291846, NM_001220774, XM_011515076, NM_001220771, XM_011515058, XM_011515065, XM_011515066, XM_011515072, XM_011515078, XM_011515070, NM_001291837, NM_001291838, NM_001291842, NM_001291845, NM_001291847, NM_001220766, NM_001220775, XM_011515070, NM_001220770, NM_001291843, NM_001291844, XM_011515059, XM_011515069, XM_017011667, XM_017011668, XM_017011670, NM_001291840, NM_001220773, NM_001220776, XM_011515062, XM_011515064, XM_011515068, XM_011515071, NM_001220768, NM_001220769, NM_001220772, XM_011515061, NM_001220767, NM_001291841, NM_006060 |
| IKZF2 | 22807 | XM_005246385, XM_011510818, NM_001371277, XM_011510809, XM_005246386, XM_011510810, XM_011510803, XM_011510804, XM_011510812, XM_011510815, XM_011510817, XM_017003592, NM_001371275, XM_011510808, NM_001371274, NM_016260, XM_011510802, XM_011510807, XM_011510819, NM_001371276, XM_005246384, XM_011510805, XM_011510811, XM_017003591, XM_011510816, NM_001079526 |
| IKZF3 | 22806 | NM_001257408, NM_183232, NM_001257412, NM_012481, NM_001257409, NM_001284514, NM_183230, NM_001257413, NM_001284515, NM_183231, NM_001257410, NM_183228, NM_001257411, NM_001284516, NM_183229, NM_001257414 |
| IKZF4 | 64375 | XM_005269089, XM_017019813, XM_017019815, XM_024449128, XM_024449129, NM_001351090, XM_017019807, XM_017019812, XM_024449131, NM_001351089, XM_011538664, XM_011538669, XM_017019814, XM_017019808, XM_024449130, NM_001351092, XM_017019806, XM_017019809, XM_017019810, NM_022465, XM_005269086, XM_017019811, XM_017019816, NM_001351091 |
| IL10 | 3586 | NM_001382624, NM_000572, NR_168466, NR_168467 |
| IL12B | 3593 | NM_002187 |
| IL15RA | 3601 | XM_011519472, XM_017016198, XM_011519476, XM_017016196, NM_001351095, XM_011519461, XM_011519468, XM_011519469, XM_024447981, XM_024447982, XM_011519475, XM_017016197, XM_017016199, NM_001351096, NM_172200, XM_011519465, XM_011519467, XM_011519470, XM_024447983, XM_011519464, XM_011519466, XM_011519471, XM_011519474, NM_001351097, NR_046362, XM_011519462, XM_011519463, XM_011519477, XM_017016200, NM_001256765, NM_002189, XM_017016195, NM_001243539 |
| IL16 | 3603 | NR_148035, NM_001172128, NM_001352685, NM_004513, NM_001352686, NM_172217, NM_001352684 |
| IL1RN | 3557 | NM_173843, NM_000577, NM_173841, NM_173842, NM_001318914, NM_001379360, XM_011511121 |
| IL21R | 50615 | NM_181078, XM_011545857, XM_017023257, XM_011545858, NM_021798, NM_181079 |
| IL27 | 246778 | XM_011545780, NM_145659 |
| IL2RA | 3559 | NM_000417, NM_001308242, NM_001308243 |
| IL2RB | 3560 | NM_001346222, NM_000878, NM_001346223 |
| IL2RG | 3561 | NM_000206 |
| IL4I1 | 259307 | NM_001258017, NM_001258018, NM_152899, NR_047577, NM_172374 |
| IL7R | 3575 | XM_005248299, NR_120485, NM_002185 |
| IL9 | 3578 | NM_000590 |
| INPP5D | 3635 | NM_001017915, NM_005541, XM_017004004 |
| IRF4 | 3662 | NR_036585, XM_006715090, NM_002460, NM_001195286, NR_046000 |
| IRF5 | 3663 | XM_011516158, NM_001242452, NM_001364314, NM_032643, XM_006715974, NM_001098627, NM_001098629, NM_001098630, XM_011516159, NM_001347928, XM_011516160 |
| ITGAE | 3682 | XM_011523827, NM_002208, XM_011523825, XM_017024587, XM_017024586, XM_011523828, XM_024450740 |
| ITGAL | 3683 | XM_005255313, XR_950794, NM_001114380, XM_011545849, XM_006721044, XM_024450262, NM_002209 |
| ITGAM | 3684 | XM_006721045, NM_000632, XM_011545850, XM_017023216, NM_001145808, XM_011545851, XR_950796 |

TABLE 11-continued

Exemplary NCBI Accession Numbers for genes mentioned herein. These records are incorporated by reference in their entirety.

| Gene | NCBI Gene ID | NCBI Accession Number (s) |
|---|---|---|
| ITGAX | 3687 | NM_001286375, NM_000887, XM_024450263, XR_950797, XM_011545852, XM_011545854 |
| ITGB2 | 3689 | NM_001303238, XM_006724001, NM_001127491, NM_000211 |
| ITGB7 | 3695 | NM_000889, XR_429099, XM_005268851, XM_005268852, NR_104181, XR_001748685, XM_006719376 |
| ITK | 3702 | XM_017009443, NM_005546 |
| ITM2A | 9452 | NM_004867, NM_001171581 |
| KCNA3 | 3738 | NR_109845, NM_002232, NR_109846 |
| KCNAB2 | 8514 | XM_017002619, XM_017002621, XM_011542321, NM_001199861, XM_011542322, NM_172130, XM_017002618, XM_017002620, NM_001199860, NM_001199862, NM_001199863, NM_003636, XM_005263514 |
| KCNJ15 | 3772 | NM_001276435, NM_001276439, XM_005260975, XM_017028344, NM_002243, XM_017028343, XM_017028345, NM_001276436, NM_001276437, NM_170737, XM_011529560, NM_170736, XM_006724002, NM_001276438, XM_011529561 |
| KDR | 3791 | NM_002253 |
| KIR2DL1 | 3802 | XM_011526939, XM_017026782, XM_017026783, NM_014218 |
| KIR2DL2 | 3803 | NM_014219 |
| KIR2DL3 | 3804 | NM_015868, NM_014511 |
| KIR2DL4 | 3805 | NM_001080772, NM_001258383, NM_001080770, NM_002255 |
| KIR2DS2 | 100132285 | NM_012312, NM_001291696, NM_001291700, NM_001291695, XM_017030275, NM_001291701 |
| KIR3DL1 | 3811 | NM_013289, XM_017030274, NM_001322168 |
| KIR3DL2 | 3812 | XM_017026784, NM_001242867, NM_006737, XM_011526940 |
| KLRB1 | 3820 | NM_002258 |
| KLRC1 | 3821 | NM_001304448, NM_007328, NM_213657, NM_213658, XM_024448973, NM_002259 |
| KLRC2 | 3822 | NM_002260 |
| KLRC3 | 3823 | NM_007333, NM_002261 |
| KLRC4 | 8302 | NM_013431 |
| KLRD1 | 3824 | NM_007334, XM_006719067, XR_001748697, XM_017019289, NM_001351062, NR_147038, XM_017019287, NM_001351063, XM_011520650, XM_017019286, XM_024448974, XR_001748696, NR_147040, XM_017019285, NM_001114396, NM_001351060, NR_147039, XM_011520651, XM_017019288, NM_002262 |
| KLRF1 | 51348 | NM_001291822, NR_120305, NR_159359, NM_016523, NM_001366534, NR_159360, XR_931301, XM_017019415, NM_001291823, NR_159361 |
| KLRG1 | 10219 | NM_001329101, XM_017018683, NR_137428, NM_005810, NM_001329102, NR_137427, XM_017018682, XM_017018684, XM_017018685, NM_001329099, NR_137426, NM_001329103 |
| KLRK1 | 22914 | NM_007360 |
| LACC1 | 144811 | NM_001350645, NM_153218, NM_001128303, NM_001350642, XM_024449319, XM_024449320, NM_001350639, NM_001350640, NM_001350648, XM_006719766, XM_024449321, NM_001350643, NM_001350644, NM_001350641, NM_001350646, NM_001350647, XM_011534935, NM_001350638 |
| LAG3 | 3902 | XM_011520956, NM_002286 |
| LAIR1 | 3903 | NM_001289025, NM_001289027, NM_021706, NR_110279, NR_110280, NM_001289026, NM_021708, NM_002287, XM_017026803, NM_001289023 |
| LAPTM5 | 7805 | NM_006762, XM_011542098 |
| LAT | 27040 | NM_001014988, NM_001014987, NM_001014989, NM_014387 |
| LAX1 | 54900 | NM_001136190, NM_001282878, XM_006711397, NM_017773 |
| LCK | 3932 | XM_024447047, NM_001042771, NM_001330468, NM_005356, XM_011541453, XM_024447046 |
| LCP1 | 3936 | XM_005266374, NM_002298 |
| LEF1 | 51176 | XM_006714233, XM_005263047, NM_016269, NM_001130714, NM_001166119, XM_005263046, XM_005263048, NM_001130713 |
| LILRA3 | 11026 | NM_006865, NM_001172654 |
| LILRA5 | 353514 | NM_181879, NM_021250, NM_181985, NM_181986 |
| LILRA6 | 79168 | NM_001360167, NR_104098, XR_001756516, XM_011547130, NM_024318 |
| LILRB2 | 10288 | NM_001080978, NM_005874, NM_001278403, NM_001278404, NM_001278405, NM_001278406, NR_103521 |
| LILRB3 | 107987425 | XM_006726280, XM_006726278, XM_011547050, XM_011547051, XM_011547058, XR_952182 |
| LILRB4 | 11006 | XR_002958246, XM_017026217, XM_017026215, NM_001278428, XM_024451331, NM_001278426, NM_001278429, NM_001278430, NM_001278427, NM_006847, XM_017026216, NM_001081438 |
| LIM2 | 3982 | NM_001161748, NM_030657 |
| LIPA | 3988 | NM_001127605, NR_110233, NM_000235, NM_001288979, XM_024448023 |
| LOXL1 | 4016 | XR_931824, XM_011521555, XM_017022179, NM_005576 |
| LRRC25 | 126364 | XM_005259739, NM_145256, XR_001753602 |
| LRRN3 | 54674 | NM_001099660, NM_001099658, NM_018334 |
| LSP1 | 4046 | NM_001013255, NM_001013253, NM_001242932, NM_002339, NM_001013254, NM_001289005 |
| LTA | 4049 | XM_011514615, NM_001514617, XM_011514618, XM_011514616, NM_000595, NM_001159740 |
| LTB | 4050 | NM_002341, NM_009588 |
| LY9 | 4063 | XM_011509549, XM_011509560, NM_001261457, XM_011509548, XM_011509552, XM_017001297, XM_017001301, XM_017001303, NM_002348, XM_017001304, NM_001033667, NM_001261456, XM_017001300, XM_011509550, XM_011509556, XM_017001302, XM_017001298, XM_017001299 |
| LYN | 4067 | NM_002350, XM_011517529, NM_001111097, XM_017013416, XM_017013415 |
| LYZ | 4069 | NM_000239 |
| MAFB | 9935 | NM_005461 |
| MAP4K1 | 11184 | XM_017026231, XM_011526404, NM_001042600, NM_007181, XM_011526403 |
| MEFV | 4210 | XR_001751903, NM_001198536, XM_017023236, NM_000243 |
| MFAP5 | 8076 | NM_001297710, NM_001297711, NM_001297712, NM_003480, NR_123733, NR_123734, NM_001297709 |

TABLE 11-continued

Exemplary NCBI Accession Numbers for genes mentioned herein. These records are incorporated by reference in their entirety.

| Gene | NCBI Gene ID | NCBI Accession Number (s) |
|---|---|---|
| MMP19 | 4327 | XM_017019308, XR_429102, NM_001272101, XM_017019309, XM_011538359, XM_006719401, XR_944553, NM_022792, NM_022790, NM_002429, NM_001032360, NR_073606 |
| MMP25 | 79148 | NM_001032278, NM_032950, XM_011525230, XM_017025062, XM_024450943, XM_011525225, NR_111988, XM_011525226, XM_017025063, NM_024302, XM_011525228, XM_011525229, XM_011525231, XM_017025061, XM_017025064, XM_011525227, XM_011525232 |
| MMRN1 | 22915 | XM_005262856, NM_007351, NM_001371403 |
| MMRN2 | 79812 | XM_006717970, XM_005270153, NM_024756 |
| MNDA | 4332 | NM_002432 |
| MPP1 | 4354 | NM_001166462, XM_011531167, XM_011531169, NM_001166460, NM_001166461, XM_024452385, NM_002436 |
| MRC1 | 4360 | NM_002438, NM_001009567 |
| MS4A1 | 931 | NM_152867, NM_152866, NM_021950 |
| MS4A4A | 51338 | NM_024021, NM_001243266, NM_148975, XM_017017909 |
| MS4A6A | 64231 | XM_005274177, XM_011545209, XM_006718661, XM_024448654, NM_001247999, XM_024448652, XM_024448655, NM_001330275, NM_022349, NM_152851, XM_006718660, XM_024448653, XM_017018125, NM_152852 |
| MS4A7 | 58475 | NM_206938, NM_206939, NM_206940, NM_021201 |
| MSR1 | 4481 | NM_138715, NM_001363744, NM_002445, XM_024447161, NM_138716 |
| MYO1F | 4542 | XR_936180, XR_936182, XM_011528025, NM_012335, XR_001753692, XM_011528026, XM_011528028, XM_011528027, XM_024451522, NM_001348355, XM_011528024, XR_936181 |
| MYO1G | 64005 | NM_033054, XM_017012504, XM_017012503, XR_926943 |
| MZB1 | 51237 | NM_016459 |
| NCAM1 | 4684 | NM_001076682, NM_001242607, NM_001242608, NM_181351, NM_000615 |
| NCF2 | 4688 | XM_011509580, XM_005245207, XM_011509581, NM_000433, NM_001190789, NM_001190794, NM_001127651 |
| NCKAP1L | 3071 | NM_001184976, NM_005337 |
| NCR1 | 9437 | XM_011527529, NM_001145457, XM_011527528, XR_001753801, NM_001242357, NM_004829, NM_001242356, XM_011527530, NM_001145458 |
| NCR3 | 259197 | XM_011514459, XM_006715049, NM_001145466, NM_001145467, NM_147130 |
| NELL2 | 4753 | NM_006159, XM_011538396, XM_017019342, NM_001145108, XM_017019344, NM_001145107, XM_017019341, XM_017019343, NM_001145109, NM_001145110, XM_005268905 |
| NFATC2 | 4773 | NM_001136021, NM_001258296, NM_001258295, NM_173091, NM_012340, XM_017027851, NM_001258292, XM_011528826, XM_017027850, XM_011528825, NM_001258294, NM_001258297, XM_011528824 |
| NINJ1 | 4814 | XM_011518716, NM_004148 |
| NKG7 | 4818 | XM_005258955, NM_005601, XM_006723228, NM_001363693 |
| NLRC3 | 197358 | XM_017023029, XM_017023031, XM_017023036, XM_017023027, NM_178844, XM_017023033, XM_017023037, XM_017023039, XM_017023035, XM_017023030, NR_075083, XM_017023038, XM_017023028, XM_017023034 |
| NMUR1 | 10316 | XM_006712195, XM_011510487, XM_011510488, XM_011510489, XM_006712196, NM_006056 |
| NOS3 | 4846 | NM_001160109, NM_001160110, NM_000603, NM_001160111 |
| NPL | 80896 | NM_001200050, NM_001200051, NM_001200056, NM_001200052, NM_030769 |
| OSCAR | 126014 | NM_130771, NM_133168, NM_133169, NM_206818, NM_206817, NM_001282350, NM_001282349 |
| P2RX1 | 5023 | XM_006721529, XM_011523897, XM_011523898, XM_011523899, XM_011523896, XR_934030, XR_934029, NM_002558, XM_011523900 |
| P2RY10 | 27334 | NM_001324218, NM_001324221, NM_198333, NM_001324225, NM_014499 |
| P2RY13 | 53829 | XM_006713664, NM_176894, NM_023914 |
| P2RY8 | 64109 | XM_011546182, XM_011545634, XM_011545635, XM_011546181, NM_001012288, NM_022148, NR_110830 |
| PADI2 | 11240 | NM_007365, XR_001736944, XM_017000148 |
| PADI4 | 23569 | XM_011541156, XM_011541157, NM_012387, XM_011541152, XM_011541155, XM_011541154, XM_011541150, XM_011541153, XM_011541151 |
| PARP15 | 165631 | XM_011512477, NM_001308321, NM_152615, XM_011512475, XM_005247160, XM_017005792, XM_011512480, XM_017005791, NM_001308320, XM_005247159, XM_011512478, XM_011512476, XM_011512479, NM_001113523 |
| PARVG | 64098 | XM_011530302, XM_017028907, XM_017028908, NM_001254743, NM_001254742, NM_001137606, NM_022141, XM_005261702, NM_001254741, NM_001137605 |
| PAX5 | 5079 | NM_001280549, NR_104000, NM_001280550, NM_001280551, NM_016734, NM_001280555, NM_001280556, NM_001280548, NM_001280552, NM_001280554, NM_001280547, NM_001280553, NR_103999 |
| PCOLCE | 5118 | NM_002593, XM_024446785 |
| PDCD1 | 5133 | NM_005018, XM_006712573, XM_017004293 |
| PDGFRA | 5156 | NM_001347828, XM_017008281, XM_005265743, NM_006206, XM_006714041, NM_001347827, NM_001347829, NM_001347830 |
| PDGFRB | 5159 | NR_149150, NM_001355017, NM_002609, NM_001355016 |
| PECAM1 | 5175 | XM_011524890, XM_017024739, NM_000442, XM_005276881, XM_017024738, XM_017024741, XM_005276880, XM_005276882, XM_011524889, XM_005276883, XM_017024740 |
| PFKFB3 | 5209 | NM_001323016, XM_017016327, XM_017016328, NM_001282630, NM_004566, XM_017016329, XM_024448037, NM_001323017, NM_001145443, NM_001363545, XM_011519493, XM_005252464, NM_001314063, NR_136554, XM_017016326 |
| PGLYRP1 | 8993 | NM_005091 |
| PHOSPHO1 | 162466 | NM_001143804, NM_178500, XM_017024271 |
| PIK3AP1 | 118788 | NM_152309, XM_011539249, XM_005269498, XM_005269499, XM_011539248 |
| PIK3IP1 | 113791 | NM_052880, NM_001135911 |
| PILRA | 29992 | XM_024446739, NM_013439, NM_178272, NM_178273 |

TABLE 11-continued

Exemplary NCBI Accession Numbers for genes mentioned herein. These records are incorporated by reference in their entirety.

| Gene | NCBI Gene ID | NCBI Accession Number (s) |
|---|---|---|
| PLA2G7 | 7941 | NM_001168357, XR_001743639, NM_005084, XR_002956305, XM_005249408 |
| PLCB2 | 5330 | XM_024449951, NM_001284297, XM_024449952, XR_001751317, XM_024449950, XR_001751315, NM_001284298, XM_017022314, XM_017022319, XM_017022317, NM_001284299, XM_024449948, XR_001751316, NM_004573, XM_024449949 |
| PLEK | 5341 | NM_002664 |
| POU2AF1 | 5450 | XM_006718859, NM_006235, XM_005271594, XM_005271593, XM_017017932, XM_006718860 |
| PPP1R16B | 26051 | XM_011528768, NM_001172735, NM_015568, XM_017027785, XM_011528769 |
| PPP3CC | 5533 | XR_001745553, NM_005605, XM_017013611, XR_001745556, XR_001745557, XR_001745558, XR_001745559, NM_001243974, NM_001243975, XR_001745555, XR_001745554 |
| PRDM1 | 639 | XM_017011187, XM_011536064, NM_182907, XM_011536063, XM_011536062, NM_001198, XM_006715550 |
| PRF1 | 5551 | NM_001083116, NM_005041 |
| PRKCB | 5579 | NM_002738, NM_212535 |
| PRKCD | 5580 | XR_002959550, NM_212539, NM_001316327, NM_001354679, NM_006254, NM_001354680, NM_001354676, NM_001354678 |
| PRKCQ | 5588 | NM_001242413, XM_005252496, XM_024448077, NM_001323265, NM_001323267, NM_001282645, NM_001323266, NM_001282644, XM_005252497, XM_024448076, NM_006257 |
| PSAP | 5660 | NM_001042465, NM_002778, NM_001042466 |
| PTGDR | 5729 | NM_001281469, NM_000953, XM_005267891 |
| PTPN22 | 26191 | XM_011541221, NM_001193431, XM_011541222, XM_017001005, NM_015967, XM_017001006, NM_001308297, NM_012411, XM_011541223, XM_017001004, XM_011541225 |
| PTPN6 | 5777 | XM_011520988, XM_006718994, NM_002831, XM_024449106, NM_080548, NM_080549 |
| PTPRB | 5787 | NM_001330204, XM_006719528, XM_017019724, NM_001206972, XM_011538614, NM_001109754, XR_944651, NM_001206971, NM_002837, XM_006719529 XM_006711473, XM_006711474, NM_080921, NM_080922, NM_001267798, NM_002838, |
| PTPRC | 5788 | XM_006711472, NR_052021 |
| PTPRCAP | 5790 | NM_005608 |
| PVRIG | 79037 | XM_011516575, NM_024070 |
| PYHIN1 | 149628 | XM_011509243, NM_198928, NM_198929, NM_152501, XM_011509242, XM_017000463, XM_005244930, NM_198930 |
| RAB42 | 115273 | NM_001193532, NM_152304, XM_017000226 |
| RAB7B | 338382 | NM_177403, NM_001164522, NM_001304839, XM_006711288 |
| RAC2 | 5880 | NM_002872, XM_006724286 |
| RALGPS2 | 55103 | XM_006711411, XM_006711410, NM_001286247, XM_011509688, NM_152663, NM_018037, XM_017001591 |
| RASAL3 | 64926 | XM_011528187, NM_022904, XR_001753737, NM_001348028, XM_024451656, NM_001348027, XM_011528185, XM_011528186, XR_936202, XR_936203 |
| RASGRP1 | 10125 | XM_011521151, NM_001128602, XM_005254114, XM_017021860, NM_005739, NM_001306086 |
| RASGRP2 | 10235 | XM_011544718, XM_017017084, XM_017017085, XM_017017086, XM_011544723, NM_001098670, NM_001318398, XM_011544721, XM_011544722, NM_153819, XM_011544720, XM_011544725, XM_017017082, NM_005825, XR_001747719, XM_017017083, NM_001098671 |
| RASGRP4 | 115727 | NM_001146205, NM_001146206, NM_170604, NM_052949, NM_170602, NM_001146203, NM_001146202, NM_170603, XR_935732, NM_001146204, NM_001146207 |
| RASIP1 | 54922 | NM_017805 |
| RASSF5 | 83593 | NM_182665, NM_182664, NM_182663, NM_031437 |
| RCSD1 | 92241 | NR_136519, NM_001322923, NM_001322924, NM_052862 |
| RHOH | 399 | NM_001278359, NM_001278369, NM_001278361, XM_017008189, XM_024454042, NM_001278365, XM_011513692, NM_001278360, NM_004310, NM_001278362, NM_001278366, NM_001278364, XM_017008188, NM_001278363, NM_001278367, NM_001278368 |
| RLTPR | 146206 | XM_011522875, XM_017022953, XR_001751843, NM_001317026, XM_011522874, NM_001013838 |
| RNASE6 | 6039 | NM_005615, XM_017021566, XM_017021567 |
| ROBO4 | 54538 | NM_019055, XM_006718861, XM_011542875, NM_001301088 |
| RP2 | 6102 | NM_006915 |
| S1PR5 | 53637 | NM_030760, NM_001166215 |
| SAMD3 | 154075 | XM_024446333, XM_024446336, XR_001743171, XM_024446334, XR_001743172, XM_024446337, XM_017010305, XM_017010307, XM_017010308, NM_001017373, NM_152552, NM_001258275, XM_017010310, NM_001277185, XM_017010309, XR_001743173, XR_001743174, XM_024446335 |
| SAMSN1 | 64092 | XM_011529686, NM_022136, NM_001256370, XM_017028427, NM_001286523, XM_011529684, XM_011529685 |
| SASH3 | 54440 | XM_006724763, NM_018990 |
| SEC11C | 90701 | NM_001307941, XM_011526260, NM_033280, XM_017026073 |
| SELE | 6401 | NM_000450 |
| SH2D1A | 4068 | NM_002351, NM_001114937 |
| SH2D1B | 117157 | NM_053282 |
| SIGLEC1 | 6614 | NM_001367089, NM_023068 |
| SIGLEC14 | 100049587 | XM_017026113, NM_001098612, XR_001753563 |
| SIGLEC5 | 8778 | XM_011527438, XM_017027419, NM_003830 |
| SIGLEC7 | 27036 | XR_002958297, NM_014385, XM_011526721, NM_016543, NR_102350, XR_001753662, NM_001277201, XR_001753660, XR_001753661 |
| SIGLEC9 | 27180 | XM_006723146, XM_011526730, XM_017026595, NM_014441, XR_001753663, XM_011526732, XM_017026596, XR_001753664, NM_001198558 |
| SIRPB2 | 284759 | XM_005260708, XM_011529223, NM_001134836, XM_005260709, XM_011529224, XM_011529225, XM_011529221, NM_001122962, NR_021484 |
| SIT1 | 54716 | NM_020208, XM_011533847, XM_011533848, NM_022405 |

TABLE 11-continued

Exemplary NCBI Accession Numbers for genes mentioned herein. These records are incorporated by reference in their entirety.

| Gene | NCBI Gene ID | NCBI Accession Number (s) |
|---|---|---|
| SKAP1 | 8631 | NM_001075099, XM_017025259, XM_017025257, XM_017025258, NM_003726, XM_017025260, XM_024451012, XM_005257755 |
| SLA2 | 84174 | XM_017028098, NM_032214, NM_175077 |
| SLAMF6 | 114836 | XM_017000215, NM_001184715, XM_017000216, NM_052931, XM_017000217, NM_001184714, NM_001184716 |
| SLAMF7 | 57823 | XM_011509828, XM_011509829, NM_001282590, NM_001282589, NM_001282591, NM_001282592, NM_001282593, NM_001282595, XM_024448757, NM_001282588, NM_021181, NM_001282594, NM_001282596 |
| SLC38A6 | 145389 | XM_017021020, XM_017021021, XM_024449490, XM_024449492, XM_024449497, XR_002957534, XM_024449494, XM_017021024, XM_024449493, XM_017021022, XM_017021023, XM_017021025, XM_024449487, XR_001750163, XM_024449488, XM_011536469, XM_024449495, XR_001750164, NM_001172702, NR_033344, XM_024449486, XM_024449496, NM_153811, XM_006720050, XM_017021026, XM_024449489, XM_024449491 |
| SNX20 | 124460 | NM_153337, NM_182854, NM_001144972 |
| SOCS3 | 9021 | NM_001378932, NM_003955, NM_001378933 |
| SOD2 | 6648 | NM_001024466, NM_001322815, NM_001322817, NM_001322814, NM_001322819, NM_001322820, NM_001322816, NM_000636, NM_001024465 |
| SP140 | 11262 | XM_005246256, XM_017003242, XM_017003243, XM_017003250, XM_017003252, XM_011510516, XR_001738595, NM_001278453, XM_005246255, XM_017003244, XM_017003245, NM_001005176, XM_005246253, NM_001278452, XM_006712223, XM_017003239, XM_017003240, XM_017003241, XM_017003249, XM_017003251, XM_005246252, XM_011510519, XM_011510520, XM_017003246, XR_001738596, NM_007237, XM_011510517, XM_011510518, XM_017003247, XM_017003248, XM_017003253, XM_005246254, XM_011510515, NM_001278451 |
| SPHK1 | 8877 | NM_001142602, NM_182965, NM_001142601, NM_021972, NM_001355139 |
| SPI1 | 6688 | XM_011520307, NM_003120, XM_017018173, NM_001080547 |
| SPIB | 6689 | NM_003121, NM_001243998, NM_001244000, NM_001243999 |
| SPN | 6693 | NM_001030288, NM_003123 |
| SSR4 | 6748 | XM_024452428, NM_006280, NR_037927, XM_017029757, NM_001204526, NM_001204527, XM_017029756 |
| STAB1 | 23166 | XM_017005998, XM_017006004, XM_017006003, XM_017006000, XM_017005999, XR_001740064, NM_015136, XM_005264974, XM_017006001, XM_005264973, XM_006713065, XM_017006002 |
| STAP1 | 26228 | NM_001317769, NM_012108, XM_017008018 |
| STAT5A | 6776 | NM_001288720, NM_001288719, XM_005257624, NM_001288718, NM_003152 |
| STK4 | 6789 | XM_005260532, XM_017028032, XM_011529020, NM_001352385, XM_005260530, XM_005260531, XM_017028029, NR_147974, XM_011529018, XM_017028033, XM_017028030, NR_147975, XM_017028031, NM_006282 |
| STX11 | 8676 | XM_011536213, XR_001743702, XR_942613, XM_011536217, XM_011536214, XM_011536218, NM_003764, XM_017011400 |
| TAGAP | 117289 | NM_001278733, NM_138810, NM_054114, NM_152133 |
| TAGLN | 6876 | NM_003186, NM_001001522 |
| TBC1D10C | 374403 | NR_046266, XM_006718539, NM_001369492, NM_001369496, XM_006718538, XM_006718541, NM_001369497, XM_011545002, NM_001256508, NM_001369494, NM_001369495, NM_198517, XM_006718542, XM_006718543, NM_001369498 |
| TBX21 | 30009 | NM_013351 |
| TCF7 | 6932 | XM_006714682, XM_011543607, XM_011543613, NM_001134851, NM_003202, NM_213648, XM_006714685, NM_001346450, NR_033449, XM_006714686, NM_001366502, XM_011543604, XM_011543606, NM_201634, NM_001134852, XM_011543608, XM_017009790, XM_006714679, XM_006714684, XR_001742232, XR_948292, XM_006714678, XM_011543609, XR_948294, XR_001742231, NM_001346425, NM_201632 |
| TEK | 7010 | NM_001290078, NM_001290077, NM_001375476, NM_001375475, NM_000459 |
| TESPA1 | 9840 | XM_011539037, NM_001351149, NM_001351151, NM_001351155, XM_017020262, NM_001098815, XR_001748931, NM_001351153, NR_147062, NR_147063, NR_147065, XM_005269247, XM_006719715, NM_011539035, NM_001261844, NR_147066, NM_001351148, NM_001351154, NM_014796, NR_147064, NR_147072, XM_017020263, NM_001136030, NR_147068, NR_147069, NR_147070, XM_024449286, XR_001748928, NM_001351150, NM_001351152, NR_147067, NR_147071, NR_147073 |
| THBS2 | 7058 | NM_001381940, NM_001381941, NR_167745, NM_001381942, NM_001381939, NM_003247, NR_167744 |
| THEMIS | 387357 | XM_017010848, XM_011535816, XM_011535814, XM_024446434, NM_001318531, NM_001010923, NM_001164687, NM_024446433, NM_001164685, XM_017010849 |
| THY1 | 7070 | NM_001372050, NM_001311160, NM_001311162, NM_006288, NR_164077 |
| TIE1 | 7075 | XM_006710869, NM_005424, XM_017002207, XM_005271163, XR_946751, NM_001253357 |
| TIGIT | 201633 | XM_024453388, XR_002959502, NM_173799 |
| TLR2 | 7097 | XM_017008576, NM_001318796, XM_011532215, XM_011532216, NM_001318787, NM_001318791, NM_001318793, NM_001318795, XM_017008574, XM_017008575, NM_001318790, NM_003264, XM_017008573, NM_001318789 |
| TMC6 | 11322 | NM_001375353, NM_001375354, XM_011524256, NM_001374596, NM_007267, XR_243632, NM_001374593, XM_011524257, XM_024450557, NM_001321185, NM_001374594, XM_011524255, XM_011524258, XM_024450556, XR_001752420, NM_001127198 |
| TMC8 | 147138 | XM_017024244, XR_002957973, XR_002957979, NM_152468, XM_024450621, XM_024450623, XM_024450624, XM_024450627, XM_024450617, XM_024450620, XM_024450625, XM_024450626, XR_002957978, XM_024450622, XR_002957974, XR_002957975, XR_002957977, XM_017024242, XM_017024243, XM_024450618, XM_024450619, XR_002957976 |
| TMIGD2 | 126259 | XM_017026284, NM_001308232, NM_144615, XM_024451359, NM_001169126 |
| TNF | 7124 | NM_000594 |

TABLE 11-continued

Exemplary NCBI Accession Numbers for genes mentioned herein. These records are incorporated by reference in their entirety.

| Gene | NCBI Gene ID | NCBI Accession Number (s) |
|---|---|---|
| TNFAIP6 | 7130 | NM_007115 |
| TNFAIP8 | 25816 | NM_001286815, NM_001286817, XM_017009327, NM_014350, XM_017009328, NM_001077654, NM_001286813, NM_001286814 |
| TNFAIP8L2 | 79626 | NM_024575 |
| TNFRSF10C | 8794 | NM_003841 |
| TNFRSF13B | 23495 | NM_012452 |
| TNFRSF13C | 115650 | NM_052945 |
| TNFRSF17 | 608 | NM_001192 |
| TNFRSF18 | 8784 | NM_148902, NM_148901, XM_017002722, NM_004195 |
| TNFRSF4 | 7293 | XM_011542075, XM_011542076, XM_011542074, XM_011542077, XM_017002231, XM_017002232, NM_003327 |
| TNFRSF8 | 943 | NM_152942, XM_011542443, NM_001281430, XM_011542441, NM_001243 |
| TNFRSF9 | 3604 | XM_006710618, NM_001561 |
| TNFSF13 | 8741 | NR_073490, NM_001198624, NM_172087, NM_001198622, NM_003808, NM_001198623, NM_172088 |
| TNIP3 | 79931 | NM_024873, XM_011532256, XM_017008624, XM_017008623, XM_017008621, XM_011532257, XM_017008620, NM_001244764, XM_017008619, NM_001128843, XM_017008622, XM_017008625 |
| TRAC | 28755 | _001332.3 |
| TRAF3IP3 | 80342 | NM_001320144, XR_001737438, NM_001320143, XM_005273280, XM_024449954, XR_001737440, XR_247044, XM_011510018, NM_025228, NR_109871, XM_011510019, NM_001287754, XM_017002400, XR_001737439, XM_005273279, XM_017002399 |
| TRAT1 | 50852 | NM_016388, NM_001317747 |
| TRBC2 | 28638 | _001333.2 |
| TREM2 | 54209 | NM_001271821, NM_018965 |
| TRGC1 | 6966 | _001336.2 |
| TXNDC11 | 51061 | XM_011522515, NR_136674, NM_001303447, NR_136673, NR_136671, XM_011522516, NM_001324024, NM_001324025, NM_015914, NR_136672, NM_001324022, XM_017023268 |
| TXNDC5 | 81567 | NM_001145549, NM_030810, NM_022085 |
| TYROBP | 7305 | NM_003332, NM_001173514, NR_033390, NM_198125, NM_001173515 |
| UBASH3A | 53347 | XM_011529609, XM_011529606, NM_018961, XM_006724013, XM_011529607, NM_001243467, NM_001001895, XM_011529605, XM_011529610, XR_244316 |
| VAV1 | 7409 | NM_001258206, XM_005259642, NM_005428, NM_001258207 |
| VEGFC | 7424 | NM_005429 |
| VNN2 | 8875 | XR_002956311, NR_110145, XM_006715593, XM_011536231, XM_017011409, NR_110144, NM_078488, NR_110143, NR_110146, NR_034174, NM_004665, XM_017011408, NM_001242350, NR_034173 |
| VNN3 | 55350 | NM_001368149, NM_001291702, NM_001368150, NM_001368152, NM_078625, NM_001368156, NM_001291703, NM_001368151, NM_018399, NM_001368154, NM_001368155 |
| VPREB3 | 29802 | NM_013378 |
| VSIG4 | 11326 | NM_001184831, NM_001257403, XM_017029251, NM_007268, NM_001100431, NM_001184830 |
| VWF | 7450 | NM_000552 |
| WAS | 7454 | XM_017029786, NM_000377, XM_011543977 |
| XCL2 | 6846 | NM_003175 |
| ZAP70 | 7535 | XM_017004868, XR_001738926, XR_001738927, NM_001378594, NM_207519, XM_017004867, XR_001738925, NM_001079, XM_017004869, XM_017004870 |
| ZBED2 | 79413 | NM_024508 |
| ZNF101 | 94039 | NM_001300949, XM_024451787, XM_024451786, NM_033204, XM_024451785 |

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize or be able to ascertain using no more than routine experimentation many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone, a tablet, or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "approximately," "substantially," and "about" may be used to mean within ±20% of a target value in some embodiments, within ±10% of a target value in some embodiments, within ±5% of a target value in some embodiments, within ±2% of a target value in some embodiments. The terms "approximately," "substantially," and "about" may include the target value.

What is claimed is:

1. A method, comprising:
using at least one computer hardware processor to perform:
obtaining RNA expression data for a biological sample, the biological sample previously obtained from a subject having, suspected of having, or at risk of having cancer,
wherein the RNA expression data includes first RNA expression data associated with a first set of genes associated with a first cell type and second RNA expression data associated with a second set of genes associated with a second cell type, wherein the second cell type is different from the first cell type,
wherein the first RNA expression data consists of expression data for at least 10 genes selected from the group of genes for the first cell type listed in Table 2,
wherein the second RNA expression data consists of expression data for at least 10 genes selected from the group of genes for the second cell type listed in the Table 2,
wherein the first cell type and the second cell type are each selected from the group consisting of B cells, CD4+ T cells, CD8+ T cells, endothelial cells, fibroblasts, lymphocytes, macrophages, monocytes, NK cells, neutrophils, and T cells;
determining a first cell composition percentage for the first cell type, using the first RNA expression data, the first cell composition percentage indicating an estimated percentage of cells of the first cell type in the biological sample, wherein determining the first cell composition percentage for the first cell type comprises:
providing only the first RNA expression data as input to a first non-linear regression model to obtain a corresponding output representing an estimated percentage of RNA from the first cell type, wherein the first non-linear regression model comprises a first ensemble of prediction models trained using gradient boosting; and
determining, based on the estimated percentage of RNA from the first cell type, the first cell composition percentage for the first cell type; and
determining a second cell composition percentage for the second cell type, using the second RNA expression data, the second cell composition percentage indicating an estimated percentage of cells of the second cell type in the biological sample, wherein determining the second cell composition percentage for the second cell type comprises:
providing only the second RNA expression data as input to a second non-linear regression model to obtain a corresponding output representing an estimated percentage of RNA from the second cell type, wherein the second non-linear regression model comprises a second ensemble of prediction models trained using gradient boosting; and
determining, based on the estimated percentage of RNA from the second cell type, the second cell composition percentage for the second cell type wherein the Table 2 is:

| Cell group name | Gene set |
| --- | --- |
| Immune_cells | ADAP2, ADGRE3, ADGRG3, ADORA3, AIF1, AOAH, APOBEC3D, ARHGAP15, ARHGAP30, ARHGAP9, ARHGDIB, BANK1, BLK, C1QA, C1QC, C3AR1, C5AR1, CAMK4, CBLB, CCDC69, CCL5, CCL7, CCR1, CCR2, CCR3, CD14, CD160, CD163, CD19, CD1D, CD2, CD22, CD226, CD244, CD247, CD27, CD300A, CD300C, CD300E, CD300LB, CD302, CD33, CD37, CD3D, CD3E, CD3G, CD4, CD48, CD5, CD53, CD6, CD68, CD69, CD7, CD79A, CD79B, CD86, CEACAM8, CECR1, CELF2, CLDND2, CLEC17A, CLEC2D, CLEC5A, CLEC7A, CMKLR1, CORO1A, CPNE5, CR2, CSF1R, CSF2RA, CSF3R, CTSS, CTSW, CXCR1, CXCR2, CXCR5, CYBB, CYFIP2, CYTH4, CYTIP, DENND1C, DERL3, DOCK2, EAF2, ELF1, ELMO1, EVI2B, FAM129C, FAM78A, FCER1G, FCGR1A, FCGR1B, FCGR2A, FCGR3B, FCMR, FCN1, FCRL1, FCRL2, FCRL3, FCRL5, FCRLA, FERMT3, FFAR2, FGR, FKBP11, FLT3LG, FMNL1, FNBP1, FPR1, FPR2, FPR3, GLCCI1, GLT1D1, GPR174, GZMM, HCK, HCLS1, HLA-DOB, HMHA1 ICAM3, IFI30, IFITM2, IGFLR1, IGHG1, IGHG3, IGHM, IGKC, IGLL5, IKZF1, IKZF3, IL10, IL16, IL2RB, IL2RG, IL4I1, INPP5D, IRF5, ITGAL, ITGAX, ITGB2, ITGB7, ITK, KCNA3, KCNAB2, KCNJ15, KIR2DL1, KIR2DL2, KIR2DL3, KIR2DL4, KIR2DS2, KIR3DL1, KIR3DL2, KLRB1, KLRC2, KLRC3, KLRD1, KLRF1, KLRK1, LAG3, LAIR1, LAPTM5, LAT, LAX1, LCK, LCP1, LIM2, LRRC25, LSP1, LTA, LY9, MAP4K1, MEFV, MMP25, MNDA, MRC1, MS4A1, MS4A4A, MS4A6A, MSR1, MYO1F, MYO1G, MZB1, NCAM1, NCF2, NCKAP1L, NCR1, NCR3, NFATC2, NKG7, NLRC3, NMUR1, P2RY10, P2RY13, P2RY8, PADI2, PADI4, PARVG, PAX5, PGLYRP1, PHOSPHO1, PIK3AP1, PILRA, PLA2G7, PLCB2, POU2AF1, PPP1R16B, PRF1, PRKCB, PTGDR, PTPN22, PTPN6, PTPRC, PTPRCAP, PVRIG, PYHIN1, RAB7B, RAC2, RASGRP1, RASGRP2, RASGRP4, RASSF5, RCSD1, RHOH, RLTPR, S1PR5, SAMD3, |

-continued

| Cell group name | Gene set |
|---|---|
| | SAMSN1, SASH3, SEC11C, SH2D1B, SIGLEC1, SIGLEC5, SIGLEC7, SIGLEC9, SIRPB2, SIRPG, SIT1, SLA2, SLAMF6, SNX20, SP140, SPI1, SPIB, SPN, SSR4, STAP1, STAT5A, STK4, TAGAP, TBC1D10C, TBX21, TCF7, TESPA1, TLR2, TMC 8, TMIGD2, TNFAIP8, TNFAIP8L2, TNFRSF10C, TNFRSF13B, TNFRSF13C, TNFRSF17, TRAC, TRAF3IP3, TRAT1, TRBC2, TRDC, TREM2, TRGC1, TRGC2, TXNDC11, TXNDC5, TYROBP, UBASH3A, VAV1, VNN2, VNN3, VPREB3, VSIG4, WAS, XCL2, ZBED2 |
| B_cells | BANK1, BLK, CD19, CD22, CD37, CD79A, CD79B, CLEC17A, CPNE5, CR2, CXCR5, DERL3, EAF2, FAM129C, FCRL1, FCRL2, FCRL3, FCRL5, FCRLA, FKBP11, GLCCI1, HLA-DOB, IGHG1, IGHG3, IGHM, IGKC, IGLL5, MS4A1, MZB1, PAX5, POU2AF1, SEC11C, SPIB, SSR4, STAP1, TNFRSF13B, TNFRSF13C, TNFRSF17, TXNDC11, TXNDC5, VPREB3 |
| Plasma_B_cells | BANK1, BLK, CD19, CD22, CD37, CD79A, CD79B, CLEC17A, CPNE5, CR2, DERL3, EAF2, FAM129C, FCRL1, FCRL2, FCRL3, FCRL5, FCRLA, FKBP11, GLCCI1, HLA-DOB, IGHG1, IGHG3, IGHM, IGKC, IGLL5, MZB1, POU2AF1, SEC11C, SPIB, SSR4, STAP1, TNFRSF13B, TNFRSF13C, TNFRSF17, TXNDC11, TXNDC5 |
| Non_plasma_B_cells | ADAM28, BANK1, BCL11A, BLK, CD19, CD22, CD37, CD72, CD79A, CD79B, CLEC17A, CPNE5, CR2, CXCR5, FAM129C, FCER2, FCRL1, FCRL2, FCRL3, FCRL5, FCRLA, HLA-DOB, MS4A1, PAX5, POU2AF1, RALGPS2, SPIB, STAP1, TNFRSF13B, TNFRSF13C, VPREB3 |
| T_cells | CAMK4, CBLB, CD2, CD226, CD3D, CD3E, CD3G, CD48, CD5, CD6, CD7, FLT3LG, ITK, KCNA3, KLRB1, LAG3, LAT, LCK, LTA, SIRPG, SIT1, SLA2, TBX21, TCF7, TESPA1, TRAC, TRAF3IP3, TRAT1, TRBC2, TRDC, TRGC1, TRGC2, UBASH3A, ZBED2 |
| CD4_T_cells | ANKRD55, CCR4, CD2, CD27, CD28, CD3D, CD3E, CD3G, CD4, CD40LG, CD5, CD6, FHIT, FLT3LG, ICOS, IKZFL IL2RA, IL9, IRF4, ITK, LCK, LEF1, LTA, TESPA1, TNFRSF4, TRAC, TRAT1, TRBC2, UBASH3A |
| Tregs | CCR4, CCR8, CD2, CD27, CD4, CTLA4, ENTPD1, FOXP3, HAVCR2, IKZF2, IKZF4, IL21R, IL2RA, IL2RB, IL2RG, ITGAE, ITK, LAG3, LTB, SIRPG, TIGIT, TNFRSF18, TNFRSF4, TNFRSF8, TNFRSF9, TRAC |
| T_helpers | ANKRD55, CD2, CD28, CD40LG, CD5, CD6, FHIT, FLT3LG, IL7R, ITK, ITM2A, KLRB1, LCK, LEF1, LRRN3, NELL2, P2RY8, TCF7, TESPA1, THEMIS, TRAF3IP3, TRAT1 |
| CD8_T_cells | CCL5, CD2, CD3D, CD3E, CD3G, CD6, CD7, CD8A, CD8B, CD96, CRTAM, CXCR3, EOMES, FCRL6, FLT3LG, GZMA, GZMB, GZMH, GZMK, ITK, KLRC2, KLRC4, KLRK1, PRF1, PRKCQ, PTGDR, PVRIG, SH2D1A, TBX21, TCF7, THEMIS, TIGIT, TRAC, TRAT1, TRBC2, UBASH3A, XCL2, ZAP70, ZBED2 |
| CD8_T_cells_PD1_low | CCR7, CD160, CD28, CD5, CD8A, CD8B, CRTAM, EOMES, FCRL6, FGFBP2, GZMK, GZMM, IL7R, KCNA3, KLRF1, KLRG1, KLRK1, PRKCQ, PTGDR, PVRIG, S1PR5, SH2D1A, TCF7, ZAP70 |
| CD8_T_cells_PD1_high | CBLB, CD2, CD226, CD244, CD27, CD38, CD8A, CD8B, CRTAM, CTLA4, ENTPD1, FASLG, HAVCR2, ICOS, IL2RA, IL2RB, IRF4, ITGAE, KLRC1, KLRK1, LAG3, LTA, PDCD1, PRDM1, PRKCQ, PVRIG, SH2D1A, SIRPG, TIGIT, TMIGD2, TNFRSF9 |
| NK_cells | CCL5, CD160, CD244, CD247, CD7, CLDND2, CTSW, GZMM, IL2RB, KIR2DL1, KIR2DL2, KIR2DL3, KIR2DL4, KIR2DS2, KIR3DL1, KIR3DL2, KLRB1, KLRC2, KLRC3, KLRD1, KLRF1, KLRK1, LIM2, NCAM1, NCR1, NCR3, NKG7, NMUR1, PRF1, PTGDR, PYHIN1, S1PR5, SAMD3, SH2D1B, TMIGD2, XCL2 |
| Monocytes | AOAH, CCR1, CCR2, CD1D, CD300C, CD300E, CD300LB, CD302, CD33, CECR1, CSF1R, CTSS, CYBB, FCN1, IRF5, MEFV, MS4A6A, PADI4 |
| Macrophages | ADAP2, ADORA3, C1QA, C1QC, C3AR1, C5AR1, CCL7, CCR1, CD14, CD163, CD33, CD4, CD68, CLEC5A, CMKLR1, CSF1R, CYBB, FPR3, IL10, IL4I1, MRC1, MS4A4A, MS4A7, MSR1, PLA2G7, RAB7B, SIGLEC1, TREM2, VSIG4 |
| Macrophages_M1 | C15orf48, C1QC, C3AR1, CCL3, CCL3L3, CCL4L2, CCL7, CD14, CD68, CLEC5A, CSF1R, CXCL3, CYBB, GADD45G, GRAMD1A, IL10, IL12B, IL15RA, TURN, IL27, IL4I1, LILRB4, MMP19, PFKFB3, PLA2G7, SIGLEC1, SLAMF7, |

-continued

| Cell group name | Gene set |
| --- | --- |
| | SOCS3, SOD2, SPHK1, TNF, TNFAIP6, TNIP3, VSIG4 |
| Macrophages_M2 | ADAP2, C1QC, CCR1, CD14, CD163, CD209, CD4, CD68, CLEC5A, CMKLR1, CSF1R, CYBB, FKBP15, FPR3, GPNMB, LACC1, LIPA, MRC1, MS4A4A, MSR1, NPL, PLA2G7, RAB42, SIGLEC1, SLC38A6, STAB1, TREM2, VSIG4 |
| Neutrophils | ADGRE3, ADGRG3, C5AR1, CCR3, CEACAM8, CLEC7A, CSF3R, CXCR1, CXCR2, EVI2B, FCGR2A, FCGR3B, FFAR2, FPR1, FPR2, GLT1D1, IFITM2, KCNJ15, LILRB3, MEFV, MMP25, MNDA, P2RY13, PADI2, PADI4, PGLYRP1, PHOSPHO1, RASGRP4, SIGLEC5, TNFRSF10C, VNN2, VNN3, WAS |
| Fibroblasts | ACTA2, ADAMTS2, CD248, COL16A1, COL1A1, COL1A2, COL3A1, COL4A1, COL5A1, COL6A1, COL6A2, COL6A3, FAP, FBLN2, FBN1, FGF2, LOXL1, MFAP5, PCOLCE, PDGFRA, PDGFRB, TAGLN, THBS2, THY1, VEGFC |
| Endothelium | ANGPT2, APLN, CDH5, CLEC14A, ECSCR, EMCN, ENG, ESAM, ESM1, FLT1, HHIP, KDR, MMRN1, MMRN2, NOS3, PECAM1, PTPRB, RASIP1, ROBO4, SELE, TEK, TIE1, VWF |
| Myeloid_cells | ACRBP, ADAP2, ADGRE2, ADGRE3, ADGRG3, ADORA3, AIF1, AOAH, C1QA, C1QC, C3AR1, C5AR1, CCL7, CCR1, CCR2, CCR3, CD14, CD163, CD1D, CD300A, CD300C, CD300E, CD300LB, CD302, CD33, CD4, CD68, CD86, CEACAM8, CECR1, CLEC5A, CLEC7A, CMKLR1, CSF1R, CSF2RA, CSF3R, CTSS, CXCR1, CXCR2, CYBB, EMILIN2, EVI2B, FCER1G, FCGR1A, FCGR1B, FCGR2A, FCGR3B, FCN1, FFAR2, FGL2, FPR1, FPR2, FPR3, GLT1D1, HCK, HK3, IFI30, IFITM2, IGSF6, IL10, IL4I1, IRF5, ITGAM, ITGAX, KCNJ15, LILRA3, LILRA5, LILRA6, LILRB2, LRRC25, LYN, LYZ, MAFB, MEFV, MMP25, MNDA, MPP1, MRC1, MS4A4A, MS4A6A, MSR1, NCF2, NINJ1, OSCAR, P2RX1, P2RY13, PADI2, PADI4, PGLYRP1, PHOSPHO1, PILRA, PLA2G7, PLEK, PRKCD, PSAP, RAB7B, RASGRP4, RNASE6, RP2, SIGLEC1, SIGLEC14, SIGLEC5, SIGLEC9, SIRPB2, SPI1, STX11, TLR2, TNFRSF10C, TNFSF13, TREM2, TYROBP, VNN2, VNN3, VSIG4, WAS |
| Lymphocytes | ACAP1, ANXA2R, APOBEC3D, APOBEC3G, BANK1, BLK, CAMK4, CARD11, CBLB, CCL5, CD160, CD19, CD2, CD22, CD226, CD244, CD247, CD27, CD37, CD3D, CD3E, CD3G, CD48, CD5, CD6, CD69, CD7, CD79A, CD79B, CLDND2, CLEC17A, CLEC2D, CPNE5, CR2, CTSW, CXCR5, CYFIP2, DEF6, DERL3, EAF2, ETS1, EVL, FAM129C, FCMR, FCRL1, FCRL2, FCRL3, FCRL5, FCRLA, FKBP11, FLT3LG, GLCCI1, GPR174, GPR18, GRAP2, GZMM, HLA-DOB, IGHG1, IGHG3, IGHM, IGKC, IGLL5, IKZF1, IKZF3, IL16, IL2RB, IL2RG, ITGB7, ITK, KCNA3, KIR2DL1, KIR2DL2, KIR2DL3, KIR2DL4, KIR2DS2, KIR3DL1, KIR3DL2, KLRB1, KLRC2, KLRC3, KLRD1, KLRF1, KLRK1, LAG3, LAT, LAX1, LCK, LIM2, LTA, LY9, MAP4K1, MS4A1, MZB1, NCAM1, NCR1, NCR3, NFATC2, NKG7, NLRC3, NMUR1, P2RY10, P2RY8, PARP15, PAX5, PIK3IP1, POU2AF1, PPP1R16B, PPP3CC, PRF1, PTGDR, PTPRCAP, PVRIG, PYHIN1, RASAL3, RASGRP1, RASGRP2, RHOH, RLTPR, S1PR5, SAMD3, SEC11C, SH2D1B, SIRPG, SIT1, SKAP1, SLA2, SLAMF6, SP140, SPIB, SSR4, STAP1, TBC1D10C, TBX21, TCF7, TESPA1, TMC6, TMC8, TMIGD2, TNFRSF13B, TNFRSF13C, TNFRSF17, TRAC, TRAF3IP3, TRAT1, TRBC2, TRDC, TRGC1, TRGC2, TXNDC11, TXNDC5, UBASH3A, VPREB3, XCL2, ZBED2, ZNF101. |

2. The method of claim 1, wherein:
the RNA expression data includes third RNA expression data associated with the first set of genes associated with the first cell type; and
the first non-linear regression model comprises:
a first sub-model configured to generate, using the first RNA expression data as input, a first value for the estimated percentage of RNA from the first cell type; and
a second sub-model configured to generate, using the third RNA expression data and the first value for the estimated percentage of RNA from the first cell type as input, a second value for the estimated percentage of RNA from the first cell type.

3. The method of claim 1,
wherein the RNA expression data includes RNA expression data associated with a plurality of gene sets associated with a respective plurality of cell types, the plurality of gene sets including the first set of genes and the plurality of cell types including the first cell type;
wherein the method further comprises determining a plurality of cell composition percentages for the plurality of cell types using the RNA expression data associated with the plurality of gene sets, the plurality of cell composition percentages including the first cell composition percentage, wherein determining the plurality of cell composition percentages comprises:

for each cell type of the plurality of cell types, determining a respective cell composition percentage for the cell type at least in part by processing RNA expression data associated with a set of genes associated with the cell type using a respective non-linear regression model to determine the cell composition percentage for the cell type.

4. The method of claim 1, wherein the first non-linear regression model was trained at least in part by generating training data comprising simulated RNA expression data, wherein generating the training data comprises:

obtaining a set of RNA expression data from one or more biological samples, the set of RNA expression data comprising microenvironment cell RNA expression data and malignant cell RNA expression data;

generating simulated microenvironment cell RNA expression data using the microenvironment cell RNA expression data;

generating simulated malignant cell RNA expression data using the malignant cell RNA expression data; and combining the simulated microenvironment cell RNA expression data and the simulated malignant cell RNA expression data to produce at least a part of the simulated RNA expression data.

5. The method of claim 1, further comprising:

determining a malignancy expression profile using an RNA expression profile for the first cell type and the first cell composition percentage for the first cell type.

6. The method of claim 1, wherein the first RNA expression data consists of expression data for at least 25 genes selected from the group of genes for the first cell type listed in the Table 2.

7. The method of claim 1, wherein the first RNA expression data consists of expression data for at least 50 genes selected from the group of genes for the first cell type listed in the Table 2.

8. The method of claim 1, wherein the first RNA expression data consists of expression data for at least 100 genes selected from the group of genes for the first cell type listed in the Table 2.

9. The method of claim 1, wherein the first non-linear regression model has been trained by:

obtaining training data comprising simulated RNA expression data, the simulated RNA expression data including third RNA expression data for the first set of genes associated with the first cell type;

training the first non-linear regression model to estimate a percentage of RNA from the first cell type, the training comprising:

generating, using the first non-linear regression-model and the third RNA expression data, an estimated percentage of RNA from the first cell type; and updating parameters of the first non-linear regression-model using the estimated percentage of RNA from the first cell type.

10. A system, comprising:

at least one hardware processor; and at least one non-transitory computer-readable storage medium storing processor-executable instructions that, when executed by the at least one hardware processor, cause the at least one hardware processor to perform:

obtaining RNA expression data for a biological sample, the biological sample previously obtained from a subject having, suspected of having, or at risk of having cancer, wherein the RNA expression data includes first RNA expression data associated with a first set of genes associated with a first cell type and second RNA expression data associated with a second set of genes associated with a second cell type, wherein the second cell type is different from the first cell type, wherein the first RNA expression data consists of expression data for at least 10 genes selected from the group of genes for the first cell type listed in Table 2, wherein the second RNA expression data consists of expression data for at least 10 genes selected from the group of genes for the second cell type listed in the Table 2, wherein the first cell type and the second cell type are each selected from the group consisting of B cells, CD4+ T cells, CD8+ T cells, endothelial cells, fibroblasts, lymphocytes, macrophages, monocytes, NK cells, neutrophils, and T cells;

determining a first cell composition percentage for the first cell type, using the first RNA expression data, the first cell composition percentage indicating an estimated percentage of cells of the first cell type in the biological sample, wherein determining the first cell composition percentage for the first cell type comprises:

providing only the first RNA expression data as input to a first non-linear regression model to obtain a corresponding output representing an estimated percentage of RNA from the first cell type, wherein the first non-linear regression model comprises a first ensemble of prediction models trained using gradient boosting; and determining, based on the estimated percentage of RNA from the first cell type, the first cell composition percentage for the first cell type; and determining a second cell composition percentage for the second cell type, using the second RNA expression data, the second cell composition percentage indicating an estimated percentage of cells of the second cell type in the biological sample, wherein determining the second cell composition percentage for the second cell type comprises:

providing only the second RNA expression data as input to a second non-linear regression model to obtain a corresponding output representing an estimated percentage of RNA from the second cell type, wherein the second non-linear regression model comprises a second ensemble of prediction models trained using gradient boosting; and determining, based on the estimated percentage of RNA from the second cell type, the second cell composition percentage for the second cell type wherein the Table 2 is:

| Cell group name | Gene set |
| --- | --- |
| Immune_cells | ADAP2, ADGRE3, ADGRG3, ADORA3, AIF1, AOAH, APOBEC3D, ARHGAP15, ARHGAP30, ARHGAP9, ARHGDIB, BANK1, BLK, C1QA, C1QC, C3AR1, C5AR1, CAMK4, CBLB, CCDC69, CCL5, CCL7, CCR1, CCR2, CCR3, CD14, CD160, CD163, CD19, CD1D, CD2, CD22, CD226, CD244, CD247, CD27, CD300A, CD300C, CD300E, CD300LB, CD302, CD33, CD37, CD3D, CD3E, CD3G, CD4, CD48, CD5, CD53, CD6, CD68, CD69, CD7, CD79A, CD79B, CD86, CEACAM8, CECR1, CELF2, CLDND2, CLEC17A, CLEC2D, CLEC5A, CLEC7A, CMKLR1, CORO1A, CPNE5, CR2, CSF1R, CSF2RA, CSF3R, CTSS, CTSW, CXCR1, CXCR2, CXCR5, CYBB, CYFIP2, CYTH4, CYTIP, DENND1C, DERL3, DOCK2, EAF2, ELF1, ELMO1, EVI2B, FAM129C, FAM78A, FCER1G, FCGR1A, FCGR1B, FCGR2A, FCGR3B, FCMR, FCN1, FCRL1, FCRL2, FCRL3, FCRL5, FCRLA, FERMT3, FFAR2, FGR, FKBP11, FLT3LG, FMNL1, FNBP1, FPR1, FPR2, FPR3, GLCCI1, GLT1D1, GPR174, GZMM, HCK, HCLS1, HLA-DOB, HMHA1, ICAM3, IFI30, IFITM2, IGFLR1, IGHG1, IGHG3, IGHM, IGKC, IGLL5, IKZF1, IKZF3, IL10, IL16, IL2RB, IL2RG, IL4I1, INPP5D, IRF5, ITGAL, ITGAX, ITGB2, ITGB7, ITK, KCNA3, KCNAB2, KCNJ15, KIR2DL1, KIR2DL2, KIR2DL3, KIR2DL4, KIR2DS2, KIR3DL1, KIR3DL2, KLRB1, KLRC2, KLRC3, KLRD1, KLRF1, KLRK1, LAG3, LAIR1, LAPTM5, LAT, LAX1, LCK, LCP1, LIM2, LRRC25, LSP1, LTA, LY9, MAP4K1, MEFV, MMP25, MNDA, MRC1, MS4A1, MS4A4A, MS4A6A, MSR1, MYO1F, MYO1G, MZB1, NCAM1, NCF2, NCKAP1L, NCR1, NCR3, NFATC2, NKG7, NLRC3, NMUR1, P2RY10, P2RY13, P2RY8, PADI2, PADI4, PARVG, PAX5, PGLYRP1, PHOSPHO1, PIK3AP1, PILRA, PLA2G7, PLCB2, POU2AF1, PPP1R16B, PRF1, PRKCB, PTGDR, PTPN22, PTPN6, PTPRC, PTPRCAP, PVRIG, PYHIN1, RAB7B, RAC2, RASGRP1, RASGRP2, RASGRP4, RASSF5, RCSD1, RHOH, RLTPR, S1PR5, SAMD3, SAMSN1, SASH3, SEC11C, SH2D1B, SIGLEC1, SIGLEC5, SIGLEC7, SIGLEC9, SIRPB2, SIRPG, SIT1, SLA2, SLAMF6, SNX20, SP140, SPI1, SPIB, SPN, SSR4, STAP1, STAT5A, STK4, TAGAP, TBC1D10C, TBX21, TCF7, TESPA1, TLR2, TMC8, TMIGD2, TNFAIP8, TNFAIP8L2, TNFRSF10C, TNFRSF13B, TNFRSF13C, TNFRSF17, TRAC, TRAF3IP3, TRAT1, TRBC2, TRDC, TREM2, TRGC1, TRGC2, TXNDC11, TXNDC5, TYROBP, UBASH3A, VAV1, VNN2, VNN3, VPREB3, VSIG4, WAS, XCL2, ZBED2 |
| B_cells | BANK1, BLK, CD19, CD22, CD37, CD79A, CD79B, CLEC17A, CPNE5, CR2, CXCR5, DERL3, EAF2, FAM129C, FCRL1, FCRL2, FCRL3, FCRL5, FCRLA, FKBP11, GLCCI1, HLA-DOB, IGHG1, IGHG3, IGHM, IGKC, IGLL5, MS4A1, MZB1, PAX5, POU2AF1, SEC11C, SPIB, SSR4, STAP1, TNFRSF13B, TNFRSF13C, TNFRSF17, TXNDC11, TXNDC5, VPREB3 |
| Plasma_B_cells | BANK1, BLK, CD19, CD22, CD37, CD79A, CD79B, CLEC17A, CPNE5, CR2, DERL3, EAF2, FAM129C, FCRL1, FCRL2, FCRL3, FCRL5, FCRLA, FKBP11, GLCCI1, HLA-DOB, IGHG1, IGHG3, IGHM, IGKC, IGLL5, MZB1, POU2AF1, SEC11C, SPIB, SSR4, STAP1, TNFRSF13B, TNFRSF13C, TNFRSF17, TXNDC11, TXNDC5 |
| Non_plasma_B_cells | ADAM28, BANK1, BCL11A, BLK, CD19, CD22, CD37, CD72, CD79A, CD79B, CLEC17A, CPNE5, CR2, CXCR5, FAM129C, FCER2, FCRL1, FCRL2, FCRL3, FCRL5, FCRLA, HLA-DOB, MS4A1, PAX5, POU2AF1, RALGPS2, SPIB, STAP1, TNFRSF13B, TNFRSF13C, VPREB3 |
| T_cells | CAMK4, CBLB, CD2, CD226, CD3D, CD3E, CD3G, CD48, CD5, CD6, CD7, FLT3LG, ITK, KCNA3, KLRB1, LAG3, LAT, LCK, LTA, SIRPG, SIT1, SLA2, TBX21, TCF7, TESPA1, TRAC, TRAF3IP3, TRAT1, TRBC2, TRDC, TRGC1, TRGC2, UBASH3A, ZBED2 |
| CD4_T_cells | ANKRD55, CCR4, CD2, CD27, CD28, CD3D, CD3E, CD3G, CD4, CD40LG, CD5, CD6, FHIT, FLT3LG, ICOS, IKZF1, IL2RA, IL9, IRF4, ITK, LCK, LEF1, LTA, TESPA1, TNFRSF4, TRAC, TRAT1, TRBC2, UBASH3A |
| Tregs | CCR4, CCR8, CD2, CD27, CD4, CTLA4, ENTPD1, FOXP3, HAVCR2, IKZF2, IKZF4, IL21R, IL2RA, IL2RB, IL2RG, ITGAE, ITK, LAG3, LTB, SIRPG, TIGIT, TNFRSF18, TNFRSF4, TNFRSF8, TNFRSF9, TRAC |
| T_helpers | ANKRD55, CD2, CD28, CD40LG, CD5, CD6, FHIT, FLT3LG, IL7R, ITK, ITM2A, KLRB1, LCK, LEF1, LRRN3, NELL2, P2RY8, TCF7, TESPA1, THEMIS, TRAF3IP3, TRAT1 |
| CD8_T_cells | CCL5, CD2, CD3D, CD3E, CD3G, CD6, CD7, CD8A, CD8B, CD96, CRTAM, CXCR3, EOMES, FCRL6, FLT3LG, GZMA, |

-continued

| Cell group name | Gene set |
|---|---|
| | GZMB, GZMH, GZMK, ITK, KLRC2, KLRC4, KLRK1, PRF1, PRKCQ, PTGDR, PVRIG, SH2D1A, TBX21, TCF7, THEMIS, TIGIT, TRAC, TRAT1, TRBC2, UBASH3A, XCL2, ZAP70, ZBED2 |
| CD8_T_cells_PD1_low | CCR7, CD160, CD28, CD5, CD8A, CD8B, CRTAM, EOMES, FCRL6, FGFBP2, GZMK, GZMM, IL7R, KCNA3, KLRF1, KLRG1, KLRK1, PRKCQ, PTGDR, PVRIG, S1PR5, SH2D1A, TCF7, ZAP70 |
| CD8_T_cells_PD1_high | CBLB, CD2, CD226, CD244, CD27, CD38, CD8A, CD8B, CRTAM, CTLA4, ENTPD1, FASLG, HAVCR2, ICOS, IL2RA, IL2RB, IRF4, ITGAE, KLRC1, KLRK1, LAG3, LTA, PDCD1, PRDM1, PRKCQ, PVRIG, SH2D1A, SIRPG, TIGIT, TMIGD2, TNFRSF9 |
| NK_cells | CCL5, CD160, CD244, CD247, CD7, CLDND2, CTSW, GZMM, IL2RB, KIR2DL1, KIR2DL2, KIR2DL3, KIR2DL4, KIR2DS2, KIR3DL1, KIR3DL2, KLRB1, KLRC2, KLRC3, KLRD1, KLRF1, KLRK1, LIM2, NCAM1, NCR1, NCR3, NKG7, NMUR1, PRF1, PTGDR, PYHIN1, S1PR5, SAMD3, SH2D1B, TMIGD2, XCL2 |
| Monocytes | AOAH, CCR1, CCR2, CD1D, CD300C, CD300E, CD300LB, CD302, CD33, CECR1, CSF1R, CTSS, CYBB, FCN1, IRF5, MEFV, MS4A6A, PADI4 |
| Macrophages | ADAP2, ADORA3, C1QA, C1QC, C3AR1, C5AR1, CCL7, CCR1, CD14, CD163, CD33, CD4, CD68, CLEC5A, CMKLR1, CSF1R, CYBB, FPR3, IL10, IL4I1, MRC1, MS4A4A, MS4A7, MSR1, PLA2G7, RAB7B, SIGLEC1, TREM2, VSIG4 |
| Macrophages_M1 | C15orf48, C1QC, C3AR1, CCL3, CCL3L3, CCL4L2, CCL7, CD14, CD68, CLEC5A, CSF1R, CXCL3, CYBB, GADD45G, GRAMD1A, IL10, IL12B, IL15RA, TURN, IL27, IL4I1, LILRB4, MMP19, PFKFB3, PLA2G7, SIGLEC1, SLAMF7, SOCS3, SOD2, SPHK1, TNF, TNFAIP6, TNIP3, VSIG4 |
| Macrophages_M2 | ADAP2, C1QC, CCR1, CD14, CD163, CD209, CD4, CD68, CLEC5A, CMKLR1, CSF1R, CYBB, FKBP15, FPR3, GPNMB, LACC1, LIPA, MRC1, MS4A4A, MSR1, NPL, PLA2G7, RAB42, SIGLEC1, SLC38A6, STAB1, TREM2, VSIG4 |
| Neutrophils | ADGRE3, ADGRG3, C5AR1, CCR3, CEACAM8, CLEC7A, CSF3R, CXCR1, CXCR2, EVI2B, FCGR2A, FCGR3B, FFAR2, FPR1, FPR2, GLT1D1, IFITM2, KCNJ15, LILRB3, MEFV, MMP25, MNDA, P2RY13, PADI2, PADI4, PGLYRP1, PHOSPHO1, RASGRP4, SIGLEC5, TNFRSF10C, VNN2, VNN3, WAS |
| Fibroblasts | ACTA2, ADAMTS2, CD248, COL16A1, COL1A1, COL1A2, COL3A1, COL4A1, COL5A1, COL6A1, COL6A2, COL6A3, FAP, FBLN2, FBN1, FGF2, LOXL1, MFAP5, PCOLCE, PDGFRA, PDGFRB, TAGLN, THBS2, THY1, VEGFC |
| Endothelium | ANGPT2, APLN, CDH5, CLEC14A, ECSCR, EMCN, ENG, ESAM, ESM1, FLT1, HHIP, KDR, MMRN1, MMRN2, NOS3, PECAM1, PTPRB, RASIP1, ROBO4, SELE, TEK, TIE1, VWF |
| Myeloid_cells | ACRBP, ADAP2, ADGRE2, ADGRE3, ADGRG3, ADORA3, AIF1, AOAH, C1QA, C1QC, C3AR1, C5AR1, CCL7, CCR1, CCR2, CCR3, CD14, CD163, CD1D, CD300A, CD300C, CD300E, CD300LB, CD302, CD33, CD4, CD68, CD86, CEACAM8, CECR1, CLEC5A, CLEC7A, CMKLR1, CSF1R, CSF2RA, CSF3R, CTSS, CXCR1, CXCR2, CYBB, EMILIN2, EVI2B, FCER1G, FCGR1A, FCGR1B, FCGR2A, FCGR3B, FCN1, FFAR2, FGL2, FPR1, FPR2, FPR3, GLT1D1, HCK, HK3, IFI30, IFITM2, IGSF6, IL10, IL4I1, IRF5, ITGAM, ITGAX, KCNJ15, LILRA3, LILRA5, LILRA6, LILRB2, LRRC25, LYN, LYZ, MAFB, MEFV, MMP25, MNDA, MPP1, MRC1, MS4A4A, MS4A6A, MSR1, NCF2, NINJ1, OSCAR, P2RX1, P2RY13, PADI2, PADI4, PGLYRP1, PHOSPHO1, PILRA, PLA2G7, PLEK, PRKCD, PSAP, RAB7B, RASGRP4, RNASE6, RP2, SIGLEC1, SIGLEC14, SIGLEC5, SIGLEC9, SIRPB2, SPI1, STX11, TLR2, TNFRSF10C, TNFSF13, TREM2, TYROBP, VNN2, VNN3, VSIG4, WAS |
| Lymphocytes | ACAP1, ANXA2R, APOBEC3D, APOBEC3G, BANK1, BLK, CAMK4, CARD11, CBLB, CCL5, CD160, CD19, CD2, CD22, CD226, CD244, CD247, CD27, CD37, CD3D, CD3E, CD3G, CD48, CD5, CD6, CD69, CD7, CD79A, CD79B, CLDND2, CLEC17A, CLEC2D, CPNE5, CR2, CTSW, CXCR5, CYFIP2, DEF6, DERL3, EAF2, ETS1, EVL, FAM129C, FCMR, FCRL1, FCRL2, FCRL3, FCRL5, FCRLA, FKBP11, FLT3LG, GLCCI1, GPR174, GPR18, GRAP2, GZMM, HLA-DOB, IGHG1, IGHG3, IGHM, IGKC, IGLL5, IKZF1, IKZF3, IL16, IL2RB, |

| Cell group name | Gene set |
|---|---|
| | 1L2RG, ITGB7, ITK, KCNA3, KIR2DL1, KIR2DL2, KIR2DL3, KIR2DL4, KIR2DS2, KIR3DL1, KIR3DL2, KLRB1, KLRC2, KLRC3, KLRD1, KLRF1, KLRK1, LAG3, LAT, LAX1, LCK, LIM2, LTA, LY9, MAP4K1, MS4A1, MZB1, NCAM1, NCR1, NCR3, NFATC2, NKG7, NLRC3, NMUR1, P2RY10, P2RY8, PARP15, PAX5, PIK3IP1, POU2AF1, PPP1R16B, PPP3CC, PRF1, PTGDR, PTPRCAP, PVRIG, PYHIN1, RASAL3, RASGRP1, RASGRP2, RHOH, RLTPR, S1PR5, SAMD3, SEC11C, SH2D1B, SIRPG, SIT1, SKAP1, SLA2, SLAMF6, SP140, SPIB, SSR4, STAP1, TBC1D10C, TBX21, TCF7, TESPA1, TMC6, TMC8, TMIGD2, TNFRSF13B, TNFRSF13C, TNFRSF17, TRAC, TRAF3IP3, TRAT1, TRBC2, TRDC, TRGC1, TRGC2, TXNDC11, TXNDC5, UBASH3A, VPREB3, XCL2, ZBED2, ZNF101. |

11. The system of claim 10, wherein:
the RNA expression data includes third RNA expression data associated with the first set of genes associated with the first cell type; and
the first non-linear regression model comprises:
   a first sub-model configured to generate, using the first RNA expression data as input, a first value for the estimated percentage of RNA from the first cell type; and
   a second sub-model configured to generate, using the third RNA expression data and the first value for the estimated percentage of RNA from the first cell type as input, a second value for the estimated percentage of RNA from the first cell type.

12. The system of claim 10,
wherein the RNA expression data includes RNA expression data associated with a plurality of gene sets associated with a respective plurality of cell types, the plurality of gene sets including the first set of genes and the plurality of cell types including the first cell type;
wherein the method further comprises determining a plurality of cell composition percentages for the plurality of cell types using the RNA expression data associated with the plurality of gene sets, the plurality of cell composition percentages including the first cell composition percentage, wherein determining the plurality of cell composition percentages comprises:
   for each cell type of the plurality of cell types, determining a respective cell composition percentage for the cell type at least in part by processing RNA expression data associated with a set of genes associated with the cell type using a respective non-linear regression model to determine the cell composition percentage for the cell type.

13. At least one non-transitory computer-readable storage medium storing processor-executable instructions that, when executed by at least one hardware processor, cause the at least one hardware processor to perform:
obtaining RNA expression data for a biological sample, the biological sample previously obtained from a subject having, suspected of having, or at risk of having cancer,
   wherein the RNA expression data includes first RNA expression data associated with a first set of genes associated with a first cell type and second RNA expression data associated with a second set of genes associated with a second cell type, wherein the second cell type is different from the first cell type,
   wherein the first RNA expression data consists of expression data for at least 10 genes selected from the group of genes for the first cell type listed in Table 2,
   wherein the second RNA expression data consists of expression data for at least 10 genes selected from the group of genes for the second cell type listed in the Table 2,
   wherein the first cell type and the second cell type are each selected from the group consisting of B cells, CD4+ T cells, CD8+ T cells, endothelial cells, fibroblasts, lymphocytes, macrophages, monocytes, NK cells, neutrophils, and T cells;
determining a first cell composition percentage for the first cell type, using the first RNA expression data, the first cell composition percentage indicating an estimated percentage of cells of the first cell type in the biological sample, wherein determining the first cell composition percentage for the first cell type comprises:
   providing only the first RNA expression data as input to a first non-linear regression model to obtain a corresponding output representing an estimated percentage of RNA from the first cell type, wherein the first non-linear regression model comprises a first ensemble of prediction models trained using gradient boosting; and
   determining, based on the estimated percentage of RNA from the first cell type, the first cell composition percentage for the first cell type; and
determining a second cell composition percentage for the second cell type, using the second RNA expression data, the second cell composition percentage indicating an estimated percentage of cells of the second cell type in the biological sample, wherein determining the second cell composition percentage for the second cell type comprises:
   providing only the second RNA expression data as input to a second non-linear regression model to obtain a corresponding output representing an estimated percentage of RNA from the second cell type, wherein the second non-linear regression model comprises a second ensemble of prediction models trained using gradient boosting; and
   determining, based on the estimated percentage of RNA from the second cell type, the second cell composition percentage for the second cell type
wherein the Table 2 is:

| Cell group name | Gene set |
| --- | --- |
| Immune_cells | ADAP2, ADGRE3, ADGRG3, ADORA3, AIF1, AOAH, APOBEC3D, ARHGAP15, ARHGAP30, ARHGAP9, ARHGDIB, BANK1, BLK, C1QA, C1QC, C3AR1, C5AR1, CAMK4, CBLB, CCDC69, CCL5, CCL7, CCR1, CCR2, CCR3, CD14, CD160, CD163, CD19, CD1D, CD2, CD22, CD226, CD244, CD247, CD27, CD300A, CD300C, CD300E, CD300LB, CD302, CD33, CD37, CD3D, CD3E, CD3G, CD4, CD48, CD5, CD53, CD6, CD68, CD69, CD7, CD79A, CD79B, CD86, CEACAM8, CECR1, CELF2, CLDND2, CLEC17A, CLEC2D, CLEC5A, CLEC7A, CMKLR1, CORO1A, CPNE5, CR2, CSF1R, CSF2RA, CSF3R, CTSS, CTSW, CXCR1, CXCR2, CXCR5, CYBB, CYFIP2, CYTH4, CYTIP, DENND1C, DERL3, DOCK2, EAF2, ELF1, ELMO1, EVI2B, FAM129C, FAM78A, FCER1G, FCGR1A, FCGR1B, FCGR2A, FCGR3B, FCMR, FCN1, FCRL1, FCRL2, FCRL3, FCRL5, FCRLA, FERMT3, FFAR2, FGR, FKBP11, FLT3LG, FMNL1, FNBP1, FPR1, FPR2, FPR3, GLCCI1, GLT1D1, GPR174, GZMM, HCK, HCLS1, HLA-DOB, HMHA1, ICAM3, IFI30, IFITM2, IGFLR1, IGHG1, IGHG3, IGHM, IGKC, IGLL5, IKZF1, IKZF3, IL10, IL16, IL2RB, IL2RG, IL4I1, INPP5D, IRF5, ITGAL, ITGAX, ITGB2, ITGB7, ITK, KCNA3, KCNAB2, KCNJ15, KIR2DL1, KIR2DL2, KIR2DL3, KIR2DL4, KIR2DS2, KIR3DL1, KIR3DL2, KLRB1, KLRC2, KLRC3, KLRD1, KLRF1, KLRK1, LAG3, LAIR1, LAPTM5, LAT, LAX1, LCK, LCP1, LIM2, LRRC25, LSP1, LTA, LY9, MAP4K1, MEFV, MMP25, MNDA, MRC1, MS4A1, MS4A4A, MS4A6A, MSR1, MYO1F, MYO1G, MZB1, NCAM1, NCF2, NCKAP1L, NCR1, NCR3, NFATC2, NKG7, NLRC3, NMUR1, P2RY10, P2RY13, P2RY8, PADI2, PADI4, PARVG, PAX5, PGLYRP1, PHOSPHO1, PIK3AP1, PILRA, PLA2G7, PLCB2, POU2AF1, PPP1R16B, PRF1, PRKCB, PTGDR, PTPN22, PTPN6, PTPRC, PTPRCAP, PVRIG, PYHIN1, RAB7B, RAC2, RASGRP1, RASGRP2, RASGRP4, RASSF5, RCSD1, RHOH, RLTPR, S1PR5, SAMD3, SAMSN1, SASH3, SEC11C, SH2D1B, SIGLEC1, SIGLEC5, SIGLEC7, SIGLEC9, SIRPB2, SIRPG, SIT1, SLA2, SLAMF6, SNX20, SP140, SPI1, SPIB, SPN, SSR4, STAP1, STAT5A, STK4, TAGAP, TBC1D10C, TBX21, TCF7, TESPA1, TLR2, TMC8, TMIGD2, TNFAIP8, TNFAIP8L2, TNFRSF10C, TNFRSF13B, TNFRSF13C, TNFRSF17, TRAC, TRAF3IP3, TRAT1, TRBC2, TRDC, TREM2, TRGC1, TRGC2, TXNDC11, TXNDC5, TYROBP, UBASH3A, VAV1, VNN2, VNN3, VPREB3, VSIG4, WAS, XCL2, ZBED2 |
| B_cells | BANK1, BLK, CD19, CD22, CD37, CD79A, CD79B, CLEC17A, CPNE5, CR2, CXCR5, DERL3, EAF2, FAM129C, FCRL1, FCRL2, FCRL3, FCRL5, FCRLA, FKBP11, GLCCI1, HLA-DOB, IGHG1, IGHG3, IGHM, IGKC, IGLL5, MS4A1, MZB1, PAX5, POU2AF1, SEC11C, SPIB, SSR4, STAP1, TNFRSF13B, TNFRSF13C, TNFRSF17, TXNDC11, TXNDC5, VPREB3 |
| Plasma_B_cells | BANK1, BLK, CD19, CD22, CD37, CD79A, CD79B, CLEC17A, CPNE5, CR2, DERL3, EAF2, FAM129C, FCRL1, FCRL2, FCRL3, FCRL5, FCRLA, FKBP11, GLCCI1, HLA-DOB, IGHG1, IGHG3, IGHM, IGKC, IGLL5, MZB1, POU2AF1, SEC11C, SPIB, SSR4, STAP1, TNFRSF13B, TNFRSF13C, TNFRSF17, TXNDC11, TXNDC5 |
| Non_plasma_B_cells | ADAM28, BANK1, BCL11A, BLK, CD19, CD22, CD37, CD72, CD79A, CD79B, CLEC17A, CPNE5, CR2, CXCR5, FAM129C, FCER2, FCRL1, FCRL2, FCRL3, FCRL5, FCRLA, HLA-DOB, MS4A1, PAX5, POU2AF1, RALGPS2, SPIB, STAP1, TNFRSF13B, TNFRSF13C, VPREB3 |
| T_cells | CAMK4, CBLB, CD2, CD226, CD3D, CD3E, CD3G, CD48, CD5, CD6, CD7, FLT3LG, ITK, KCNA3, KLRB1, LAG3, LAT, LCK, LTA, SIRPG, SIT1, SLA2, TBX21, TCF7, TESPA1, TRAC, TRAF3IP3, TRAT1, TRBC2, TRDC, TRGC1, TRGC2, UBASH3A, ZBED2 |
| CD4_T_cells | ANKRD55, CCR4, CD2, CD27, CD28, CD3D, CD3E, CD3G, CD4, CD40LG, CD5, CD6, FHIT, FLT3LG, ICOS, IKZF1, IL2RA, IL9, IRF4, ITK, LCK, LEF1, LTA, TESPA1, TNFRSF4, TRAC, TRAT1, TRBC2, UBASH3A |
| Tregs | CCR4, CCR8, CD2, CD27, CD4, CTLA4, ENTPD1, FOXP3, HAVCR2, IKZF2, IKZF4, IL21R, IL2RA, IL2RB, IL2RG, ITGAE, ITK, LAG3, LTB, SIRPG, TIGIT, TNFRSF18, TNFRSF4, TNFRSF8, TNFRSF9, TRAC |
| T_helpers | ANKRD55, CD2, CD28, CD40LG, CD5, CD6, FHIT, FLT3LG, IL7R, ITK, ITM2A, KLRB1, LCK, LEF1, LRRN3, NELL2, P2RY8, TCF7, TESPA1, THEMIS, TRAF3IP3, TRAT1 |
| CD8_T_cells | CCL5, CD2, CD3D, CD3E, CD3G, CD6, CD7, CD8A, CD8B, CD96, CRTAM, CXCR3, EOMES, FCRL6, FLT3LG, GZMA, |

| Cell group name | Gene set |
|---|---|
| | GZMB, GZMH, GZMK, ITK, KLRC2, KLRC4, KLRK1, PRF1, PRKCQ, PTGDR, PVRIG, SH2D1A, TBX21, TCF7, THEMIS, TIGIT, TRAC, TRAT1, TRBC2, UBASH3A, XCL2, ZAP70, ZBED2 |
| CD8_T_cells_PD1_low | CCR7, CD160, CD28, CD5, CD8A, CD8B, CRTAM, EOMES, FCRL6, FGFBP2, GZMK, GZMM, IL7R, KCNA3, KLRF1, KLRG1, KLRK1, PRKCQ, PTGDR, PVRIG, S1PR5, SH2D1A, TCF7, ZAP70 |
| CD8_T_cells_PD1_high | CBLB, CD2, CD226, CD244, CD27, CD38, CD8A, CD8B, CRTAM, CTLA4, ENTPD1, FASLG, HAVCR2, ICOS, IL2RA, IL2RB, IRF4, ITGAE, KLRC1, KLRK1, LAG3, LTA, PDCD1, PRDM1, PRKCQ, PVRIG, SH2D1A, SIRPG, TIGIT, TMIGD2, TNFRSF9 |
| NK_cells | CCL5, CD160, CD244, CD247, CD7, CLDND2, CTSW, GZMM, IL2RB, KIR2DL1, KIR2DL2, KIR2DL3, KIR2DL4, KIR2DS2, KIR3DL1, KIR3DL2, KLRB1, KLRC2, KLRC3, KLRD1, KLRF1, KLRK1, LIM2, NCAM1, NCR1, NCR3, NKG7, NMUR1, PRF1, PTGDR, PYHIN1, S1PR5, SAMD3, SH2D1B, TMIGD2, XCL2 |
| Monocytes | AOAH, CCR1, CCR2, CD1D, CD300C, CD300E, CD300LB, CD302, CD33, CECR1, CSF1R, CTSS, CYBB, FCN1, IRF5, MEFV, MS4A6A, PADI4 |
| Macrophages | ADAP2, ADORA3, C1QA, C1QC, C3AR1, C5AR1, CCL7, CCR1, CD14, CD163, CD33, CD4, CD68, CLEC5A, CMKLR1, CSF1R, CYBB, FPR3, IL10, IL4I1, MRC1, MS4A4A, MS4A7, MSR1, PLA2G7, RAB7B, SIGLEC1, TREM2, VSIG4 |
| Macrophages_M1 | C15orf48, C1QC, C3AR1, CCL3, CCL3L3, CCL4L2, CCL7, CD14, CD68, CLEC5A, CSF1R, CXCL3, CYBB, GADD45G, GRAMD1A, IL10, IL12B, IL15RA, TURN, IL27, IL4I1, LILRB4, MMP19, PFKFB3, PLA2G7, SIGLEC1, SLAMF7, SOCS3, SOD2, SPHK1, TNF, TNFAIP6, TNIP3, VSIG4 |
| Macrophages_M2 | ADAP2, C1QC, CCR1, CD14, CD163, CD209, CD4, CD68, CLEC5A, CMKLR1, CSF1R, CYBB, FKBP15, FPR3, GPNMB, LACC1, LIPA, MRC1, MS4A4A, MSR1, NPL, PLA2G7, RAB42, SIGLEC1, SLC38A6, STAB1, TREM2, VSIG4 |
| Neutrophils | ADGRE3, ADGRG3, C5AR1, CCR3, CEACAM8, CLEC7A, CSF3R, CXCR1, CXCR2, EVI2B, FCGR2A, FCGR3B, FFAR2, FPR1, FPR2, GLT1D1, IFITM2, KCNJ15, LILRB3, MEFV, MMP25, MNDA, P2RY13, PADI2, PADI4, PGLYRP1, PHOSPHO1, RASGRP4, SIGLEC5, TNFRSF10C, VNN2, VNN3, WAS |
| Fibroblasts | ACTA2, ADAMTS2, CD248, COL16A1, COL1A1, COL1A2, COL3A1, COL4A1, COL5A1, COL6A1, COL6A2, COL6A3, FAP, FBLN2, FBN1, FGF2, LOXL1, MFAP5, PCOLCE, PDGFRA, PDGFRB, TAGLN, THBS2, THY1, VEGFC |
| Endothelium | ANGPT2, APLN, CDH5, CLEC14A, ECSCR, EMCN, ENG, ESAM, ESM1, FLT1, HHIP, KDR, MMRN1, MMRN2, NOS3, PECAM1, PTPRB, RASIP1, ROBO4, SELE, TEK, TIE1, VWF |
| Myeloid_cells | ACRBP, ADAP2, ADGRE2, ADGRE3, ADGRG3, ADORA3, AIF1, AOAH, C1QA, C1QC, C3AR1, C5AR1, CCL7, CCR1, CCR2, CCR3, CD14, CD163, CD1D, CD300A, CD300C, CD300E, CD300LB, CD302, CD33, CD4, CD68, CD86, CEACAM8, CECR1, CLEC5A, CLEC7A, CMKLR1, CSF1R, CSF2RA, CSF3R, CTSS, CXCR1, CXCR2, CYBB, EMILIN2, EVI2B, FCER1G, FCGR1A, FCGR1B, FCGR2A, FCGR3B, FCN1, FFAR2, FGL2, FPR1, FPR2, FPR3, GLT1D1, HCK, HK3, IFI30, IFITM2, IGSF6, IL10, IL4I1, IRF5, ITGAM, ITGAX, KCNJ15, LILRA3, LILRA5, LILRA6, LILRB2, LRRC25, LYN, LYZ, MAFB, MEFV, MMP25, MNDA, MPP1, MRC1, MS4A4A, MS4A6A, MSR1, NCF2, NINJ1, OSCAR, P2RX1, P2RY13, PADI2, PADI4, PGLYRP1, PHOSPHO1, PILRA, PLA2G7, PLEK, PRKCD, PSAP, RAB7B, RASGRP4, RNASE6, RP2, SIGLEC1, SIGLEC14, SIGLEC5, SIGLEC9, SIRPB2, SPI1, STX11, TLR2, TNFRSF10C, TNFSF13, TREM2, TYROBP, VNN2, VNN3, VSIG4, WAS |
| Lymphocytes | ACAP1, ANXA2R, APOBEC3D, APOBEC3G, BANK1, BLK, CAMK4, CARD11, CBLB, CCL5, CD160, CD19, CD2, CD22, CD226, CD244, CD247, CD27, CD37, CD3D, CD3E, CD3G, CD48, CD5, CD6, CD69, CD7, CD79A, CD79B, CLDND2, CLEC17A, CLEC2D, CPNE5, CR2, CTSW, CXCR5, CYFIP2, DEF6, DERL3, EAF2, ETS1, EVL, FAM129C, FCMR, FCRL1, FCRL2, FCRL3, FCRL5, FCRLA, FKBP11, FLT3LG, GLCCI1, GPR174, GPR18, GRAP2, GZMM, HLA-DOB, IGHG1, IGHG3, IGHM, IGKC, IGLL5, IKZF1, IKZF3, IL16, IL2RB, IL2RG, ITGB7, ITK, KCNA3, KIR2DL1, KIR2DL2, KIR2DL3, KIR2DL4, KIR2DS2, KIR3DL1, KIR3DL2, KLRB1, KLRC2, KLRC3, KLRD1, KLRF1, KLRK1, LAG3, LAT, LAX1, LCK, |

-continued

| Cell group name | Gene set |
| --- | --- |
| | LIM2, LTA, LY9, MAP4K1, MS4A1, MZB1, NCAM1, NCR1, NCR3, NFATC2, NKG7, NLRC3, NMUR1, P2RY10, P2RY8, PARP15, PAX5, PIK3IP1, POU2AF1, PPP1R16B, PPP3CC, PRF1, PTGDR, PTPRCAP, PVRIG, PYHIN1, RASAL3, RASGRP1, RASGRP2, RHOH, RLTPR, S1PR5, SAMD3, SEC11C, SH2D1B, SIRPG, SIT1, SKAP1, SLA2, SLAMF6, SP140, SPIB, SSR4, STAP1, TBC1D10C, TBX21, TCF7, TESPA1, TMC6, TMC8, TMIGD2, TNFRSF13B, TNFRSF13C, TNFRSF17, TRAC, TRAF3IP3, TRAT1, TRBC2, TRDC, TRGC1, TRGC2, TXNDC11, TXNDC5, UBASH3A, VPREB3, XCL2, ZBED2, ZNF101. |

14. The at least one non-transitory computer-readable storage medium of claim 13, wherein:
the RNA expression data includes third RNA expression data associated with the first set of genes associated with the first cell type; and
the first non-linear regression model comprises:
a first sub-model configured to generate, using the first RNA expression data as input, a first value for the estimated percentage of RNA from the first cell type; and
a second sub-model configured to generate, using the third RNA expression data and the first value for the estimated percentage of RNA from the first cell type as input, a second value for the estimated percentage of RNA from the first cell type.

15. The at least one non-transitory computer-readable storage medium of claim 13,
wherein the RNA expression data includes RNA expression data associated with a plurality of gene sets associated with a respective plurality of cell types, the plurality of gene sets including the first set of genes and the plurality of cell types including the first cell type;
wherein the method further comprises determining a plurality of cell composition percentages for the plurality of cell types using the RNA expression data associated with the plurality of gene sets, the plurality of cell composition percentages including the first cell composition percentage, wherein determining the plurality of cell composition percentages comprises:
for each cell type of the plurality of cell types, determining a respective cell composition percentage for the cell type at least in part by processing RNA expression data associated with a set of genes associated with the cell type using a respective non-linear regression model to determine the cell composition percentage for the cell type.

* * * * *